United States Patent
Foltz et al.

(10) Patent No.: US 9,315,577 B2
(45) Date of Patent: Apr. 19, 2016

(54) ANTI-HEPCIDIN ANTIBODIES AND METHODS OF USE

(75) Inventors: Ian Foltz, Burnaby (CA); Michael Gallo, North Vancouver (CA); Keegan Cooke, Ventura, CA (US); Randal R. Ketchem, Snohomish, WA (US); Christopher Mehlin, Seattle, WA (US)

(73) Assignee: AMGEN INC., Thousand Oaks, CA (US)

( * ) Notice: Subject to any disclaimer, the term of this patent is extended or adjusted under 35 U.S.C. 154(b) by 357 days.

(21) Appl. No.: 12/990,137

(22) PCT Filed: Apr. 28, 2009

(86) PCT No.: PCT/US2009/002606
§ 371 (c)(1),
(2), (4) Date: Feb. 11, 2011

(87) PCT Pub. No.: WO2009/139822
PCT Pub. Date: Nov. 19, 2009

(65) Prior Publication Data
US 2011/0150888 A1    Jun. 23, 2011

Related U.S. Application Data

(60) Provisional application No. 61/049,687, filed on May 1, 2008.

(51) Int. Cl.
*C07K 16/26* (2006.01)
*A61K 38/18* (2006.01)
*A61K 39/395* (2006.01)
*A61K 39/00* (2006.01)
*C07K 19/00* (2006.01)

(52) U.S. Cl.
CPC ............ *C07K 16/26* (2013.01); *A61K 38/1816* (2013.01); *A61K 39/3955* (2013.01); *A61K 2039/505* (2013.01); *C07K 2317/21* (2013.01); *C07K 2317/56* (2013.01); *C07K 2317/565* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,859,205 | A | * | 1/1999 | Adair et al. ................. 530/387.3 |
| 2005/0032114 | A1 | * | 2/2005 | Hinton et al. .................. 435/7.1 |
| 2006/0141456 | A1 | * | 6/2006 | Edwards et al. .................. 435/6 |
| 2007/0148164 | A1 | * | 6/2007 | Farrington et al. ......... 424/133.1 |
| 2009/0136495 | A1 | * | 5/2009 | Gately et al. ............... 424/133.1 |

FOREIGN PATENT DOCUMENTS

WO     WO 2008097461 A2 * 8/2008

OTHER PUBLICATIONS

Eduardo Padlan, "Anatomy of the antibody molecule" Molecular Immun. 31(3) (1994), pp. 169-217.*
William E. Paul, M.D. "Fundamental Immunology" 3rd Edition, 1993, 292-295.*
Rudikoff et al. "Single amino acid substitution altering antigen-binding specificity" Proc. Natl. Acad. Sci. USA, 79 (Mar. 1982), pp. 1979-1983.*
Adams et al. "Prolonged in vivo tumour retention of a human diabody targeting the extracellular domain of human HER2/neu" British J Cancer (1998) 77(9), 1405-1412.*

* cited by examiner

*Primary Examiner* — Daniel E Kolker
*Assistant Examiner* — James Rogers
(74) *Attorney, Agent, or Firm* — Susan Lingenfelter; Jonathan M. Dermott

(57) ABSTRACT

The invention relates to monoclonal antibodies that bind hepcidin and methods of making and using such antibodies. Also provided are methods of treating hepcidin-related disorders.

2 Claims, 26 Drawing Sheets

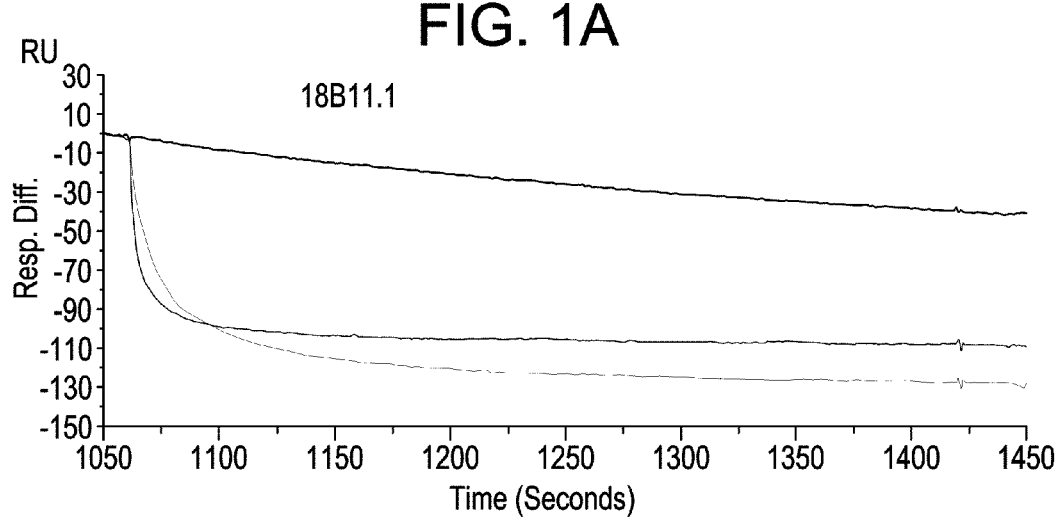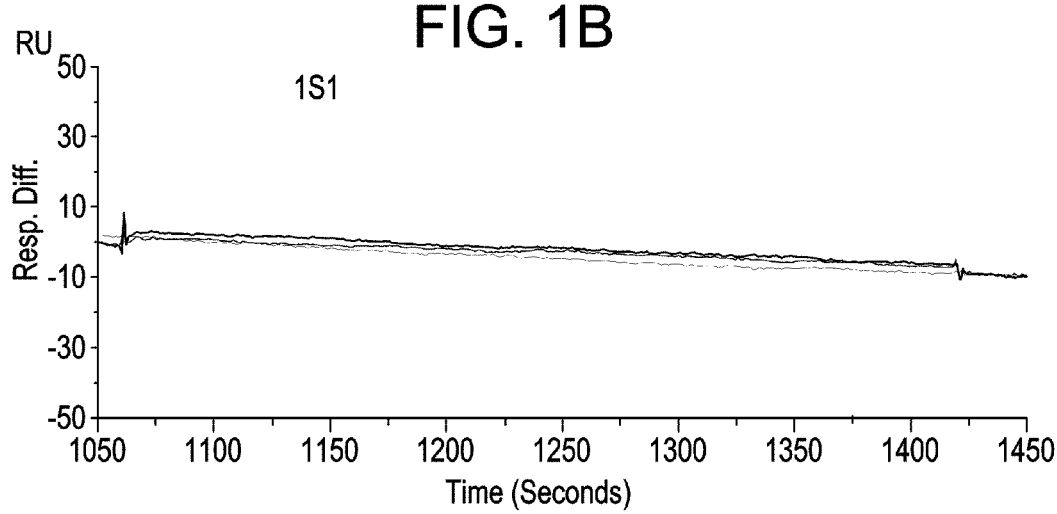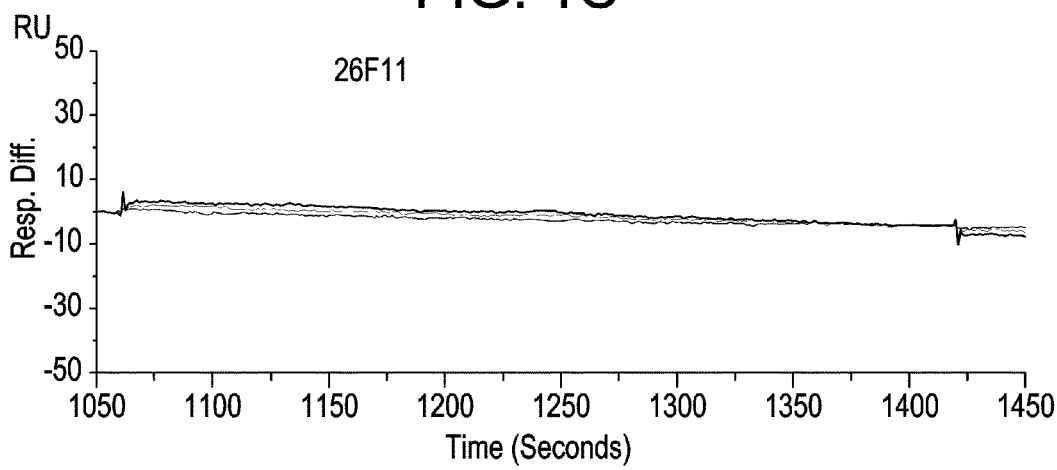

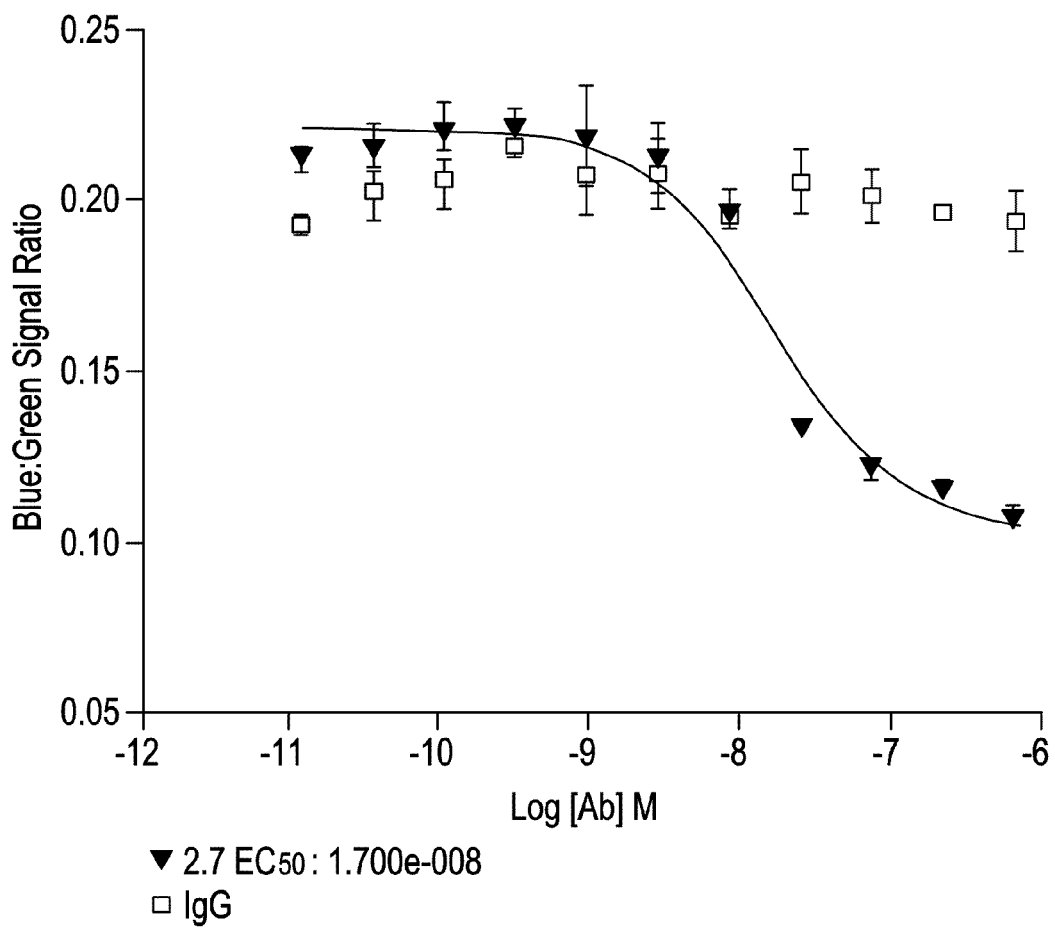

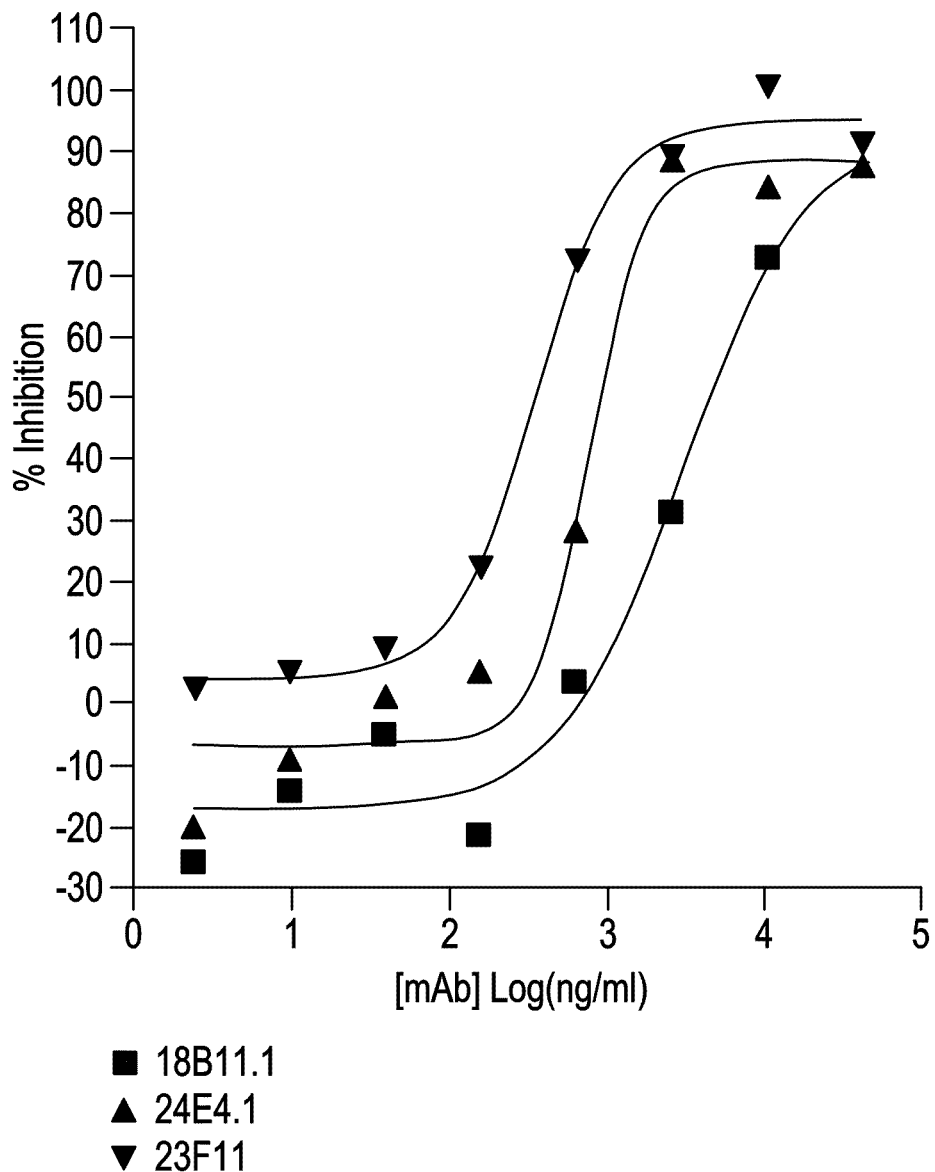

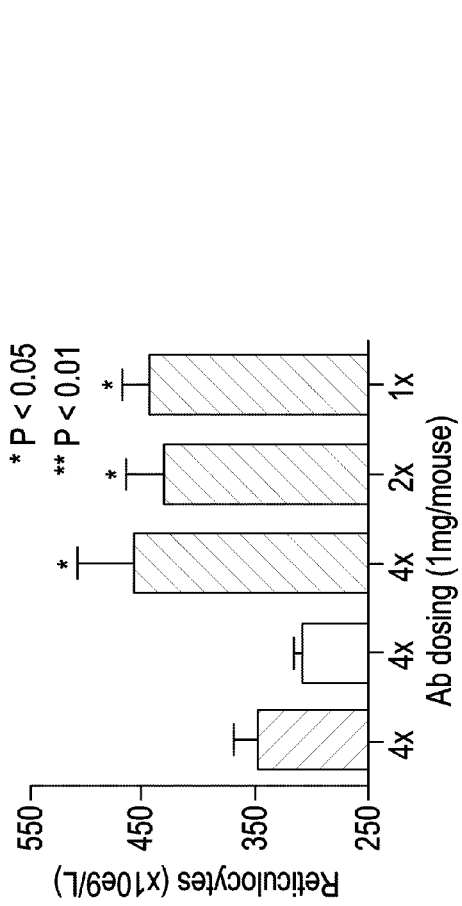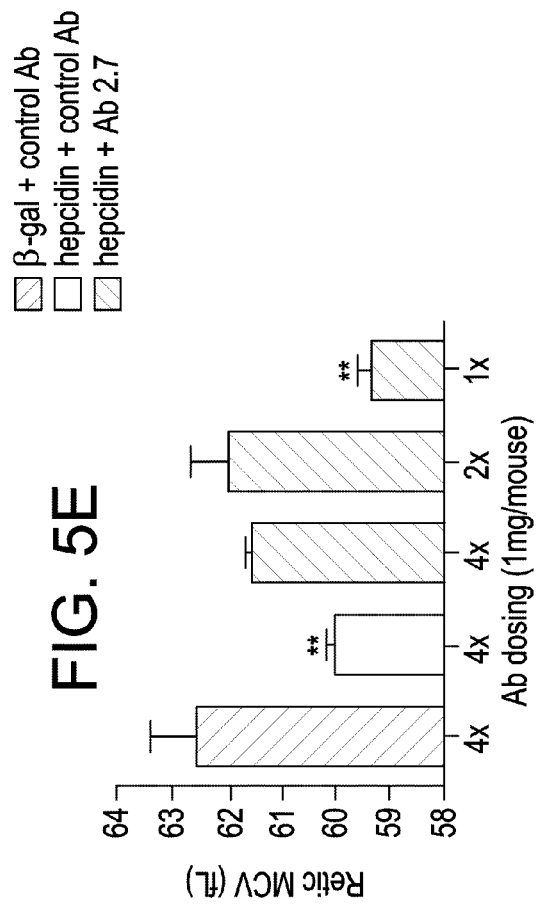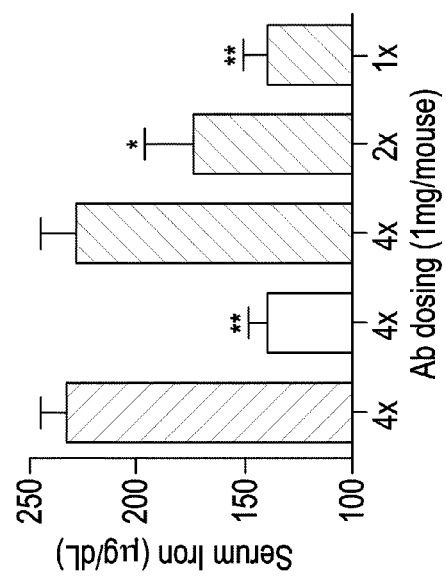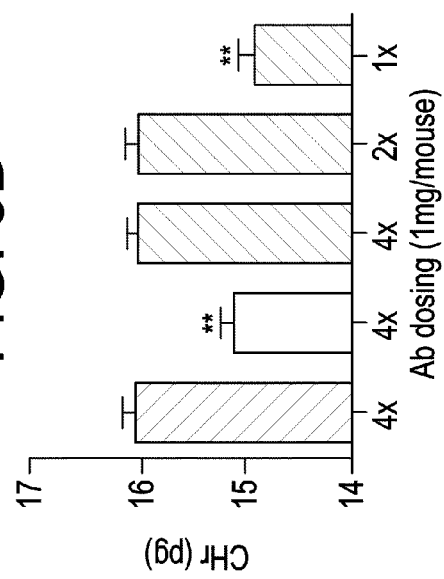

▨ AAV-GFP + isotype
☐ AAV-hHepc + isotype
▨ AAV-hHepc + Ab 1S1
▨ AAV-hHepc + Ab18B11
▨ AAV-hHepc + Ab 24E4

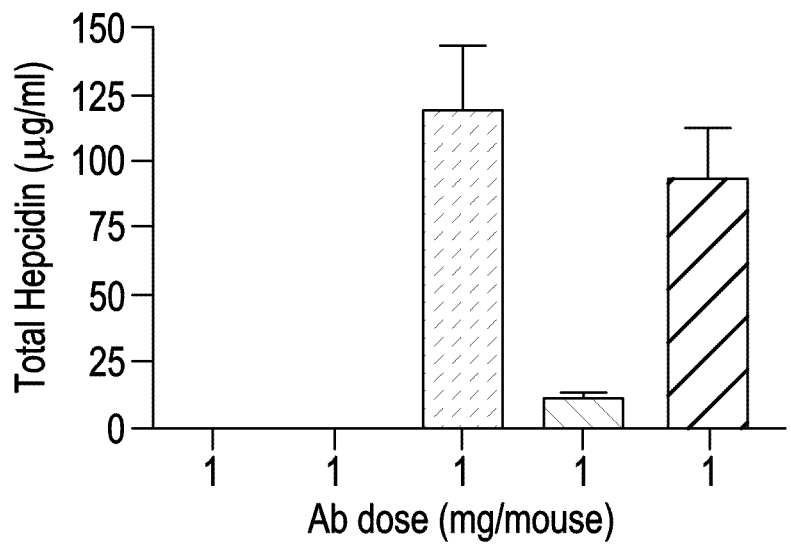
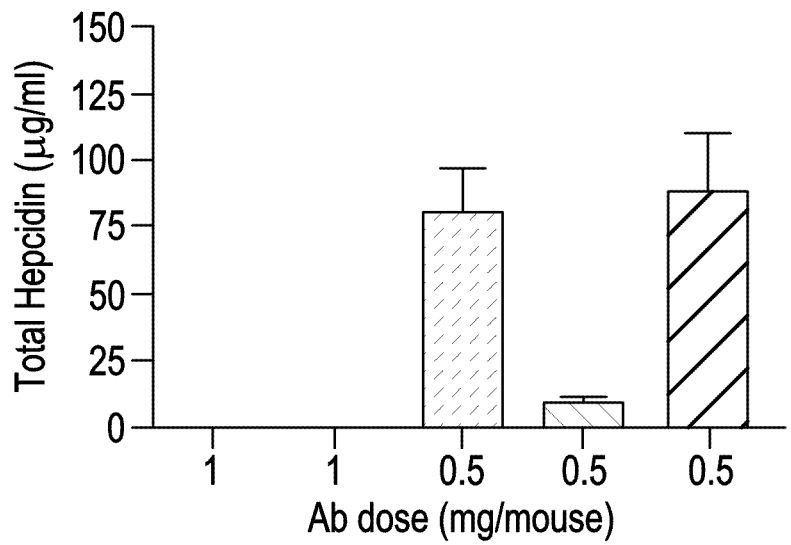

FIG. 11A

Week: 0 — 6 — 7 — 8 — 9 — 13 pre-bleed ↓ (week 6), Aranesp® ↓ (week 7)

↑ Brucella abortus (week 0); ↑ Ab (week 6); ↑ Ab (week 7); ↑ Ab (week 8); ↑ Ab (week 9); (harvest) (week 13)

FIG. 11B

Hemoglobin (g/dL) vs Day (6, 13)

FIG. 11C

Hemoglobin (g/dL) vs Day (6, 13)

▲ control Ab + saline
◆ Ab 2.7 + saline
● control Ab + Aranesp®
□ Ab 2.7 + Aranesp®

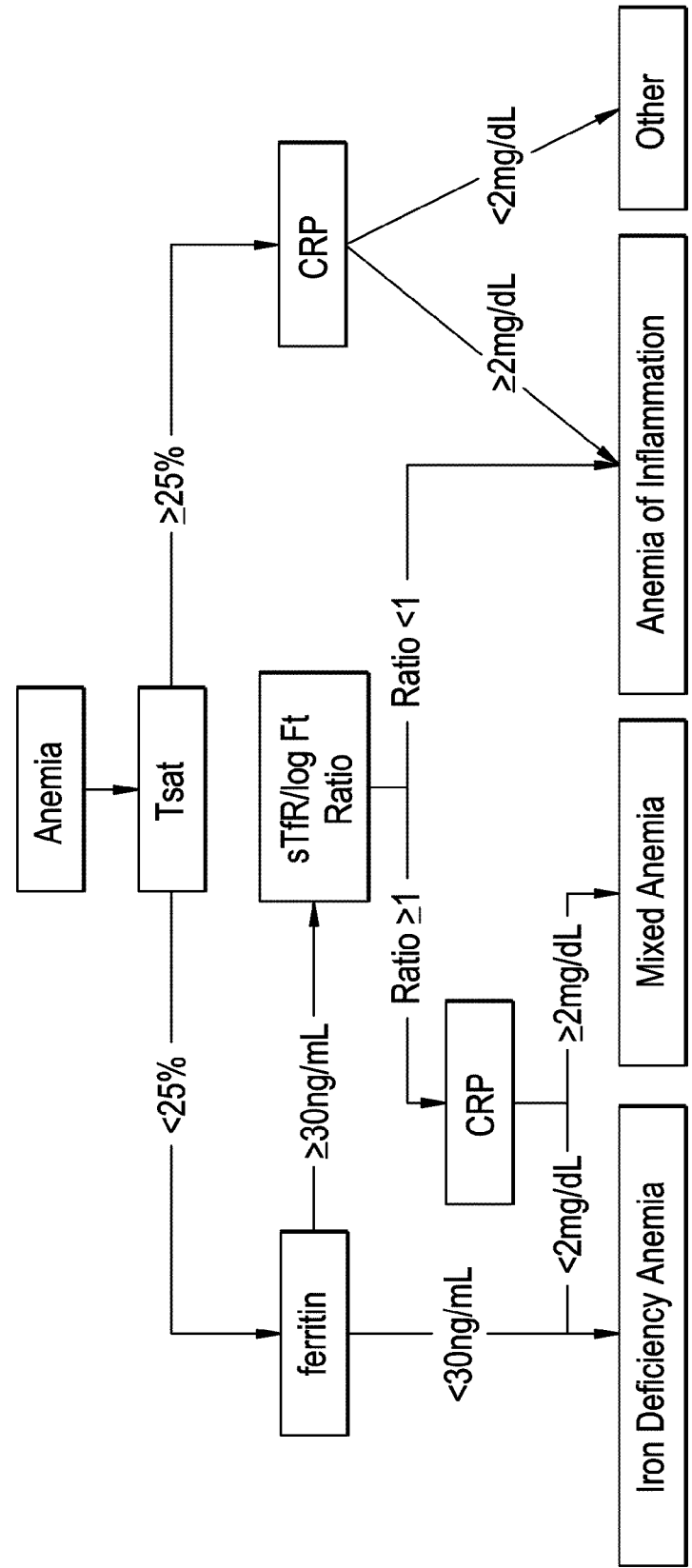

Proposed Stratification Scheme 21-016K07 Serum Total Hepcidin

→ 1S1, N=3
→ 18B11, N=3
→ IgG2/k, N=3

Hepcidin cellular association

☐ extracellular Hepcidin
☐ total Hepcidin

SEQUENCE LISTING

```
<160> NUMBER OF SEQ ID NOS: 416

<210> SEQ ID NO 1
<211> LENGTH: 249
<212> TYPE: DNA
<213> ORGANISM: Mus musculus

<400> SEQUENCE: 1
atggcactca gcactcggac ccaggctgcc tgtctcctgc ttctcctcct tgccagcctg      60
agcagcacca cctatctcca tcaacagatg agacagacta cagagctgca gcctttgcac     120
ggggaagaaa gcagggcaga cattgcgata ccaatgcaga agagaaggaa gagagacacc     180
aacttcccca tctgcatctt ctgctgtaaa tgctgtaaca attcccagtg tggtatctgt     240
tgcaaaaca                                                             249

<210> SEQ ID NO 2
<211> LENGTH: 83
<212> TYPE: PRT
<213> ORGANISM: Mus musculus

<400> SEQUENCE: 2

Met Ala Leu Ser Thr Arg Thr Gln Ala Ala Cys Leu Leu Leu Leu Leu
1               5                   10                  15

Leu Ala Ser Leu Ser Ser Thr Thr Tyr Leu His Gln Gln Met Arg Gln
            20                  25                  30

Thr Thr Glu Leu Gln Pro Leu His Gly Glu Glu Ser Arg Ala Asp Ile
        35                  40                  45

Ala Ile Pro Met Gln Lys Arg Arg Lys Arg Asp Thr Asn Phe Pro Ile
    50                  55                  60

Cys Ile Phe Cys Cys Lys Cys Cys Asn Asn Ser Gln Cys Gly Ile Cys
```

Cys Lys Thr

<210> SEQ ID NO 3
<211> LENGTH: 252
<212> TYPE: DNA
<213> ORGANISM: Rattus norvegicus

<400> SEQUENCE: 3

```
atggcactaa gcactcggat ccaggctgcc tgtctcctgc ttctcctcct ggccagcctg      60
agcagcggtg cctatctccg gcaacagacg agacagacta cggctctgca gccttggcat     120
ggggcagaaa gcaagactga tgacagtgcg ctgctgatgc tgaagcgaag gaagcgagac     180
accaacttcc ccatatgcct cttctgctgt aaatgctgta agaattcctc ctgtggtctc     240
tgttgcataa ca                                                        252
```

<210> SEQ ID NO 4
<211> LENGTH: 84
<212> TYPE: PRT
<213> ORGANISM: Rattus norvegicus

<400> SEQUENCE: 4

Met Ala Leu Ser Thr Arg Ile Gln Ala Ala Cys Leu Leu Leu Leu Leu
1               5                   10                  15

Leu Ala Ser Leu Ser Ser Gly Ala Tyr Leu Arg Gln Gln Thr Arg Gln
            20                  25                  30

Thr Thr Ala Leu Gln Pro Trp His Gly Ala Glu Ser Lys Thr Asp Asp
        35                  40                  45

Ser Ala Leu Leu Met Leu Lys Arg Arg Lys Arg Asp Thr Asn Phe Pro
    50                  55                  60

Ile Cys Leu Phe Cys Cys Lys Cys Cys Lys Asn Ser Ser Cys Gly Leu
65                  70                  75                  80

Cys Cys Ile Thr

<210> SEQ ID NO 5
<211> LENGTH: 78
<212> TYPE: DNA
<213> ORGANISM: Macaca fascicularis

<400> SEQUENCE: 5

```
gacacccact tccccatctg cattttctgc tgcggctgct gtcatcgatc aaagtgtggg      60
atgtgctgca ggacgtag                                                   78
```

<210> SEQ ID NO 6
<211> LENGTH: 25
<212> TYPE: PRT
<213> ORGANISM: Macaca fascicularis

<400> SEQUENCE: 6

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 7
<211> LENGTH: 252
<212> TYPE: DNA
<213> ORGANISM: Homo sapiens

<400> SEQUENCE: 7

```
atggcactga gctcccagat ctgggccgct tgcctcctgc tcctcctcct cctcgccagc      60
ctgaccagtg gctctgtttt cccacaacag acgggacaac ttgcagagct gcaaccccag     120
gacagagctg agccagggc cagctggatg cccatgttcc agaggcgaag gaggcgagac     180
acccacttcc ccatctgcat tttctgctgc ggctgctgtc atcgatcaaa gtgtgggatg     240
tgctgcaaga cg                                                         252
```

<210> SEQ ID NO 8
<211> LENGTH: 84
<212> TYPE: PRT
<213> ORGANISM: Homo sapiens

<400> SEQUENCE: 8

```
Met Ala Leu Ser Ser Gln Ile Trp Ala Ala Cys Leu Leu Leu Leu Leu
1               5                   10                  15
Leu Leu Ala Ser Leu Thr Ser Gly Ser Val Phe Pro Gln Gln Thr Gly
            20                  25                  30
Gln Leu Ala Glu Leu Gln Pro Gln Asp Arg Ala Gly Ala Arg Ala Ser
        35                  40                  45
Trp Met Pro Met Phe Gln Arg Arg Arg Arg Asp Thr His Phe Pro
    50                  55                  60
Ile Cys Ile Phe Cys Cys Gly Cys Cys His Arg Ser Lys Cys Gly Met
65                  70                  75                  80
Cys Cys Lys Thr
```

<210> SEQ ID NO 9
<211> LENGTH: 25
<212> TYPE: PRT
<213> ORGANISM: Homo sapiens

<400> SEQUENCE: 9

```
Asp Thr His Phe Pro Ile Cys Ile Phe Cys Cys Gly Cys Cys His Arg
1               5                   10                  15
Ser Lys Cys Gly Met Cys Cys Lys Thr
            20                  25
```

<210> SEQ ID NO 10

<400> SEQUENCE: 10

000

<210> SEQ ID NO 11

<400> SEQUENCE: 11

000

<210> SEQ ID NO 12
<211> LENGTH: 330
<212> TYPE: DNA
<213> ORGANISM: Homo sapiens

<400> SEQUENCE: 12

```
aacatcgtgc tgacccaatc tccagcttct ttggctgtgt ctctagggca gagggccacc      60
atatcctgca gagccagtga aagtgttgat agttatggca atagttttat gcactggtac     120
cagcagaaac aggacagcc acccaaactc ctcatctatc ttgcatccaa cctagaatct     180
```

```
ggggtccctg ccaggttcag tggcagtggg tctaggacag acttcaccct caccattgat      240
cctgtggagg ctgatgatgc tgcaacctat tactgtcagc aaaataatga ggatcggacg      300
ttcggtggag gcaccaagct ggaaatcaaa                                        330
```

<210> SEQ ID NO 13
<211> LENGTH: 110
<212> TYPE: PRT
<213> ORGANISM: Homo sapiens

<400> SEQUENCE: 13

```
Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Arg Thr Phe Gly Gly Gly Thr Lys Leu Glu Ile Lys
            100                 105                 110
```

<210> SEQ ID NO 14
<211> LENGTH: 357
<212> TYPE: DNA
<213> ORGANISM: Homo sapiens

<400> SEQUENCE: 14

```
cagatccagt tggtacagtc tggacctgag ctgaagaagc ctggagagac agtcaagatc       60
tcctgcaagg cttctgggta taccttcaca acctatggaa tgagctgggt gaaacaggct      120
ccaggaaagg gtttaaagtg gatgggctgg ataaacacct actctggagt gccaacatat      180
gctgatgact caagggacg gtttgccttc tctttggaaa cctctgccag cactgcctat      240
ttgcagatca caaacctcaa aaatgaggac acggctacat atttctgtgc aagcttatgg      300
tactacggta gggcctttga ctactggggc caaggcacca ctctcacagt ctcctca        357
```

<210> SEQ ID NO 15
<211> LENGTH: 119
<212> TYPE: PRT
<213> ORGANISM: Homo sapiens

<400> SEQUENCE: 15

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
```

```
                85                  90                  95
Ala Ser Leu Trp Tyr Tyr Gly Arg Ala Phe Asp Tyr Trp Gly Gln Gly
            100                 105                 110

Thr Thr Leu Thr Val Ser Ser
        115
```

<210> SEQ ID NO 16
<211> LENGTH: 15
<212> TYPE: PRT
<213> ORGANISM: Homo sapiens

<400> SEQUENCE: 16

```
Arg Ala Ser Glu Ser Val Asp Ser Tyr Gly Asn Ser Phe Met His
1               5                   10                  15
```

<210> SEQ ID NO 17
<211> LENGTH: 7
<212> TYPE: PRT
<213> ORGANISM: Homo sapiens

<400> SEQUENCE: 17

```
Leu Ala Ser Asn Leu Glu Ser
1               5
```

<210> SEQ ID NO 18
<211> LENGTH: 8
<212> TYPE: PRT
<213> ORGANISM: Homo sapiens

<400> SEQUENCE: 18

```
Gln Gln Asn Asn Glu Asp Arg Thr
1               5
```

<210> SEQ ID NO 19
<211> LENGTH: 5
<212> TYPE: PRT
<213> ORGANISM: Homo sapiens

<400> SEQUENCE: 19

```
Thr Tyr Gly Met Ser
1               5
```

<210> SEQ ID NO 20
<211> LENGTH: 17
<212> TYPE: PRT
<213> ORGANISM: Homo sapiens

<400> SEQUENCE: 20

```
Trp Ile Asn Thr Tyr Ser Gly Val Pro Thr Tyr Ala Asp Asp Phe Lys
1               5                   10                  15

Gly
```

<210> SEQ ID NO 21
<211> LENGTH: 10
<212> TYPE: PRT
<213> ORGANISM: Homo sapiens

<400> SEQUENCE: 21

```
Leu Trp Tyr Tyr Gly Arg Ala Phe Asp Tyr
1               5                   10
```

<210> SEQ ID NO 22

```
<400> SEQUENCE: 22

000

<210> SEQ ID NO 23
<400> SEQUENCE: 23

000

<210> SEQ ID NO 24
<211> LENGTH: 330
<212> TYPE: DNA
<213> ORGANISM: Homo sapiens

<400> SEQUENCE: 24
gacattgtgc tgacccaatc tccagcttct ttggctgtgt ctctagggca gagggccacc      60
atatcctgca gagccagtga aagtgttgat agttatggca atagttttat gcactggtac     120
cagcagaaac aggacagcc acccaaactc ctcatctatc gtgcatccaa cctagaatct      180
gggatccctg ccaggttcag tggcagtggg tctaggacag acttcaccct caccattaat     240
cctgtggagg ctgatgatgt tgcaacctat tactgtcacc aaagtaatga ggagtacacg     300
ttcggagggg ggaccaagct ggaaataaaa                                      330

<210> SEQ ID NO 25
<211> LENGTH: 110
<212> TYPE: PRT
<213> ORGANISM: Homo sapiens

<400> SEQUENCE: 25

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys His Gln Ser Asn
                85                  90                  95

Glu Glu Tyr Thr Phe Gly Gly Gly Thr Lys Leu Glu Ile Lys
            100                 105                 110

<210> SEQ ID NO 26
<211> LENGTH: 354
<212> TYPE: DNA
<213> ORGANISM: Homo sapiens

<400> SEQUENCE: 26
cagatccagt tggtacagtc tggacctgag ctgaagaagc ctggagagac agtcaagatc      60
tcctgcaagg cttctgggta taccttcaca acctatggaa tgagctgggt gaaacaggct     120
ccaggaaagg gtttaaagtg gatgggctgg ataaatacct actctggagt gccaacatat     180
gctgatgact tcaagggacg gtttgccttc tctttggaaa cctctgccag cactgcctat     240
ttgcagatca caaacctcaa aaatgaggac acggctacat atttctgtgg aagagaccac     300
tactacgggg aggttgctta ctggggccaa gggactctgg tcactgtctc tgca           354
```

```
<210> SEQ ID NO 27
<211> LENGTH: 118
<212> TYPE: PRT
<213> ORGANISM: Homo sapiens

<400> SEQUENCE: 27

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Gly Arg Asp His Tyr Tyr Gly Glu Val Ala Tyr Trp Gly Gln Gly Thr
            100                 105                 110

Leu Val Thr Val Ser Ala
        115

<210> SEQ ID NO 28
<211> LENGTH: 15
<212> TYPE: PRT
<213> ORGANISM: Homo sapiens

<400> SEQUENCE: 28

Arg Ala Ser Glu Ser Val Asp Ser Tyr Gly Asn Ser Phe Met His
1               5                   10                  15

<210> SEQ ID NO 29
<211> LENGTH: 7
<212> TYPE: PRT
<213> ORGANISM: Homo sapiens

<400> SEQUENCE: 29

Arg Ala Ser Asn Leu Glu Ser
1               5

<210> SEQ ID NO 30
<211> LENGTH: 8
<212> TYPE: PRT
<213> ORGANISM: Homo sapiens

<400> SEQUENCE: 30

His Gln Ser Asn Glu Glu Tyr Thr
1               5

<210> SEQ ID NO 31
<211> LENGTH: 5
<212> TYPE: PRT
<213> ORGANISM: Homo sapiens

<400> SEQUENCE: 31

Thr Tyr Gly Met Ser
1               5

<210> SEQ ID NO 32
```

```
<211> LENGTH: 17
<212> TYPE: PRT
<213> ORGANISM: Homo sapiens

<400> SEQUENCE: 32

Trp Ile Asn Thr Tyr Ser Gly Val Pro Thr Tyr Ala Asp Asp Phe Lys
1               5                   10                  15
Gly

<210> SEQ ID NO 33
<211> LENGTH: 9
<212> TYPE: PRT
<213> ORGANISM: Homo sapiens

<400> SEQUENCE: 33

Asp His Tyr Tyr Gly Glu Val Ala Tyr
1               5

<210> SEQ ID NO 34

<400> SEQUENCE: 34

000

<210> SEQ ID NO 35

<400> SEQUENCE: 35

000

<210> SEQ ID NO 36
<211> LENGTH: 330
<212> TYPE: DNA
<213> ORGANISM: Homo sapiens

<400> SEQUENCE: 36
gacattgtgc tgacccaatc tccagcttct ttggctgtgt ctctagggca gagggccacc     60
atatcctgca gagccagtga aagtgttgat agttttggca atagtttat gcactggtac    120
cagctgaaac caggacagcc acccaaactc ctcatctatc gtgcatccaa cctagaatct    180
gggatccctg ccaggttcag tggcagtggg tctaggacag acttcaccct caccattaat    240
cctgtggagg ctgatgatgt tgcaatttat tactgtcagc aaagtaatga ggagtacacg    300
ttcggagggg ggaccaagct ggaaataaaa                                      330

<210> SEQ ID NO 37
<211> LENGTH: 110
<212> TYPE: PRT
<213> ORGANISM: Homo sapiens

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Phe
            20                  25                  30

Gly Asn Ser Phe Met His Trp Tyr Gln Leu Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80
```

Pro Val Glu Ala Asp Asp Val Ala Ile Tyr Tyr Cys Gln Gln Ser Asn
            85                  90                  95

Glu Glu Tyr Thr Phe Gly Gly Gly Thr Lys Leu Glu Ile Lys
            100                 105                 110

<210> SEQ ID NO 38
<211> LENGTH: 354
<212> TYPE: DNA
<213> ORGANISM: Homo sapiens

<400> SEQUENCE: 38
cagatccagt tggtacagtc tggacctgag ctgaagaagc ctggagagac agtcaagatc      60
tcctgcaagg cttctgggta taccttcaca acctatggaa tgagctgggt gaaacaggct     120
ccaggaaagg gtttaaagtg gatgggctgg ataaacacct cctctggagt gccaacatat     180
gctgatgact tcatgggacg gtttgccttc tctttggaaa cctctgccag cactgcctat     240
ttgcagatca acaacctcaa aaatgaggac acggctacgt atttctgtgc aagagaccgc     300
tactacgggg aggttgctta ctggggccaa gggactctgg tcaccgtctc tgca           354

<210> SEQ ID NO 39
<211> LENGTH: 118
<212> TYPE: PRT
<213> ORGANISM: Homo sapiens

<400> SEQUENCE: 39

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Ser Ser Gly Val Pro Thr Tyr Ala Asp Asp Phe
    50                  55                  60

Met Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Arg Tyr Tyr Gly Glu Val Ala Tyr Trp Gly Gln Gly Thr
            100                 105                 110

Leu Val Thr Val Ser Ala
        115

<210> SEQ ID NO 40
<211> LENGTH: 15
<212> TYPE: PRT
<213> ORGANISM: Homo sapiens

<400> SEQUENCE: 40

Arg Ala Ser Glu Ser Val Asp Ser Phe Gly Asn Ser Phe Met His
1               5                   10                  15

<210> SEQ ID NO 41
<211> LENGTH: 7
<212> TYPE: PRT
<213> ORGANISM: Homo sapiens

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Homo sapiens

<400> SEQUENCE: 42

Gln Gln Ser Asn Glu Glu Tyr Thr
1               5

<210> SEQ ID NO 43
<211> LENGTH: 5
<212> TYPE: PRT
<213> ORGANISM: Homo sapiens

<400> SEQUENCE: 43

Thr Tyr Gly Met Ser
1               5

<210> SEQ ID NO 44
<211> LENGTH: 17
<212> TYPE: PRT
<213> ORGANISM: Homo sapiens

<400> SEQUENCE: 44

Trp Ile Asn Thr Ser Ser Gly Val Pro Thr Tyr Ala Asp Asp Phe Met
1               5                   10                  15

Gly

<210> SEQ ID NO 45
<211> LENGTH: 9
<212> TYPE: PRT
<213> ORGANISM: Homo sapiens

<400> SEQUENCE: 45

Asp Arg Tyr Tyr Gly Glu Val Ala Tyr
1               5

<210> SEQ ID NO 46

<400> SEQUENCE: 46

000

<210> SEQ ID NO 47

<400> SEQUENCE: 47

000

<210> SEQ ID NO 48
<211> LENGTH: 317
<212> TYPE: DNA
<213> ORGANISM: Homo sapiens

<400> SEQUENCE: 48
acatccagat gacccagtct ccttcactcc tgtcagcatc tgtgggagac agagtcactc      60
tcagctgcaa agcaagtcag aatatttaca gtacttaaa ctggtatcag caaaagcttg     120
gagaagctcc caaactcctg atatattata caaacagttt gcaaacgggc atcccatcaa     180
ggttcagtgg cagtggatct ggtacagatt tcacttac catcagcagc ctgcagcctg     240
aagatgttgc cacatattac tgctatcagt ataacagtgg gcccacgttt ggagctggga     300
ccaagctgga actgaaa                                                       317

<210> SEQ ID NO 49
<211> LENGTH: 106
<212> TYPE: PRT
<213> ORGANISM: Homo sapiens

<400> SEQUENCE: 49

Asp Ile Gln Met Thr Gln Ser Pro Ser Leu Leu Ser Ala Ser Val Gly
1               5                   10                  15

Asp Arg Val Thr Leu Ser Cys Lys Ala Ser Gln Asn Ile Tyr Lys Tyr
            20                  25                  30

Leu Asn Trp Tyr Gln Gln Lys Leu Gly Glu Ala Pro Lys Leu Leu Ile
        35                  40                  45

Tyr Tyr Thr Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Asn Ser Gly Pro Thr
                85                  90                  95

Phe Gly Ala Gly Thr Lys Leu Glu Leu Lys
            100                 105

<210> SEQ ID NO 50
<211> LENGTH: 372
<212> TYPE: DNA
<213> ORGANISM: Homo sapiens

<400> SEQUENCE: 50
caggttactc tgaaagagtc tggccctggg atattgcagc cttcccagac cctcagtctg      60
acttgctctt tctctgggtt ttcactgagc acttctggta tatgtgtgag ctggattcgt     120
cagccttcag ggaagggtct ggagtggctg gcaactattt gttgggagga tagtaagggc     180
tacaacccct ctctgaagaa ccggctcaca atctccaagg acacctccaa caaccaagca     240
ttcctcaaga tcaccagtgt ggacactgca gataccgcca tatactctg tgctcggccc      300
cttaactacg agggtatag tgagctagaa ttggattact ggggccaagg agtcatggtc     360
acagtctcct ca                                                        372

<210> SEQ ID NO 51
<211> LENGTH: 124
<212> TYPE: PRT
<213> ORGANISM: Homo sapiens

<400> SEQUENCE: 51

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Ile Cys Val Ser Trp Ile Arg Gln Pro Ser Gly Lys Gly Leu Glu
        35                  40                  45

Trp Leu Ala Thr Ile Cys Trp Glu Asp Ser Lys Gly Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Ser Val Asp Thr Ala Asp Thr Ala Ile Tyr Tyr
                85                  90                  95

```
Cys Ala Arg Pro Leu Asn Tyr Gly Gly Tyr Ser Glu Leu Glu Leu Asp
            100                 105                 110

Tyr Trp Gly Gln Gly Val Met Val Thr Val Ser Ser
        115                 120
```

<210> SEQ ID NO 52
<211> LENGTH: 11
<212> TYPE: PRT
<213> ORGANISM: Homo sapiens

<400> SEQUENCE: 52

```
Lys Ala Ser Gln Asn Ile Tyr Lys Tyr Leu Asn
1               5                   10
```

<210> SEQ ID NO 53
<211> LENGTH: 7
<212> TYPE: PRT
<213> ORGANISM: Homo sapiens

<400> SEQUENCE: 53

```
Tyr Thr Asn Ser Leu Gln Thr
1               5
```

<210> SEQ ID NO 54
<211> LENGTH: 8
<212> TYPE: PRT
<213> ORGANISM: Homo sapiens

<400> SEQUENCE: 54

```
Tyr Gln Tyr Asn Ser Gly Pro Thr
1               5
```

<210> SEQ ID NO 55
<211> LENGTH: 7
<212> TYPE: PRT
<213> ORGANISM: Homo sapiens

<400> SEQUENCE: 55

```
Thr Ser Gly Ile Cys Val Ser
1               5
```

<210> SEQ ID NO 56
<211> LENGTH: 16
<212> TYPE: PRT
<213> ORGANISM: Homo sapiens

<400> SEQUENCE: 56

```
Thr Ile Cys Trp Glu Asp Ser Lys Gly Tyr Asn Pro Ser Leu Lys Asn
1               5                   10                  15
```

<210> SEQ ID NO 57
<211> LENGTH: 14
<212> TYPE: PRT
<213> ORGANISM: Homo sapiens

<400> SEQUENCE: 57

```
Pro Leu Asn Tyr Gly Gly Tyr Ser Glu Leu Glu Leu Asp Tyr
1               5                   10
```

<210> SEQ ID NO 58
<211> LENGTH: 19
<212> TYPE: RNA
<213> ORGANISM: Homo sapiens

<400> SEQUENCE: 58

| | |
|---|---|
| uguaaaugcu guaacaauu | 19 |

<210> SEQ ID NO 59
<211> LENGTH: 19
<212> TYPE: RNA
<213> ORGANISM: Homo sapiens

<400> SEQUENCE: 59

| | |
|---|---|
| gcuguaaaug cuguaacaa | 19 |

<210> SEQ ID NO 60
<211> LENGTH: 19
<212> TYPE: RNA
<213> ORGANISM: Homo sapiens

<400> SEQUENCE: 60

| | |
|---|---|
| guguggauc uguugcaaa | 19 |

<210> SEQ ID NO 61
<211> LENGTH: 19
<212> TYPE: RNA
<213> ORGANISM: Homo sapiens

<400> SEQUENCE: 61

| | |
|---|---|
| gcagacauug cgauaccaa | 19 |

<210> SEQ ID NO 62
<211> LENGTH: 19
<212> TYPE: RNA
<213> ORGANISM: Homo sapiens

<400> SEQUENCE: 62

| | |
|---|---|
| auaccaaugc agaagagaa | 19 |

<210> SEQ ID NO 63
<211> LENGTH: 19
<212> TYPE: RNA
<213> ORGANISM: Homo sapiens

<400> SEQUENCE: 63

| | |
|---|---|
| cuacagagcu gcagccuuu | 19 |

<210> SEQ ID NO 64
<211> LENGTH: 19
<212> TYPE: RNA
<213> ORGANISM: Homo sapiens

<400> SEQUENCE: 64

| | |
|---|---|
| gaagagagac accaacuuc | 19 |

<210> SEQ ID NO 65
<211> LENGTH: 19
<212> TYPE: RNA
<213> ORGANISM: Homo sapiens

<400> SEQUENCE: 65

| | |
|---|---|
| acuucccau cugcaucuu | 19 |

<210> SEQ ID NO 66
<211> LENGTH: 19
<212> TYPE: RNA
<213> ORGANISM: Homo sapiens

```
<400> SEQUENCE: 66
cugagcagca ccaccuauc                                                    19

<210> SEQ ID NO 67
<211> LENGTH: 19
<212> TYPE: RNA
<213> ORGANISM: Homo sapiens

<400> SEQUENCE: 67
acagaugaga cagacuaca                                                    19

<210> SEQ ID NO 68
<211> LENGTH: 19
<212> TYPE: RNA
<213> ORGANISM: Homo sapiens

<400> SEQUENCE: 68
caaugcagaa gagaaggaa                                                    19

<210> SEQ ID NO 69
<211> LENGTH: 19
<212> TYPE: RNA
<213> ORGANISM: Homo sapiens

<400> SEQUENCE: 69
aauucccagu gugguaucu                                                    19

<210> SEQ ID NO 70

<400> SEQUENCE: 70

000

<210> SEQ ID NO 71

<400> SEQUENCE: 71

000

<210> SEQ ID NO 72
<211> LENGTH: 193
<212> TYPE: PRT
<213> ORGANISM: Homo sapiens

<400> SEQUENCE: 72
```

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

```
Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 73
<211> LENGTH: 193
<212> TYPE: PRT
<213> ORGANISM: Homo sapiens

<400> SEQUENCE: 73

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
                35                  40                  45

Ala Glu Asn Ile Thr Thr Gly Cys Ala Glu His Cys Ser Leu Asn Glu
            50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 74
<211> LENGTH: 7
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 74

Xaa Ala Ser Asn Leu Glu Ser
1               5

<210> SEQ ID NO 75
<211> LENGTH: 6
```

```
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 75

Xaa Gln Ser Asn Glu Glu
1               5

<210> SEQ ID NO 76
<211> LENGTH: 6
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 76

Gln Gln Xaa Asn Glu Xaa
1               5

<210> SEQ ID NO 77
<211> LENGTH: 17
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 77

Trp Ile Asn Thr Xaa Ser Gly Val Pro Thr Tyr Ala Asp Asp Phe Xaa
1               5                   10                  15
Gly

<210> SEQ ID NO 78
<211> LENGTH: 10
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 78

Xaa Xaa Tyr Tyr Gly Xaa Xaa Ala Xaa Tyr
1               5                   10

<210> SEQ ID NO 79
<211> LENGTH: 75
<212> TYPE: DNA
```

```
<213> ORGANISM: Mus musculus

<400> SEQUENCE: 79
gacaccaact tccccatctg catcttctgc tgtaaatgct gtaacaattc ccagtgtggt    60
atctgttgca aaaca                                                    75

<210> SEQ ID NO 80
<211> LENGTH: 25
<212> TYPE: PRT
<213> ORGANISM: Mus musculus

<400> SEQUENCE: 80

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 81
<211> LENGTH: 75
<212> TYPE: DNA
<213> ORGANISM: Rattus norvegicus

<400> SEQUENCE: 81
gacaccaact tccccatatg cctcttctgc tgtaaatgct gtaagaattc ctcctgtggt    60
ctctgttgca taaca                                                    75

<210> SEQ ID NO 82
<211> LENGTH: 25
<212> TYPE: PRT
<213> ORGANISM: Rattus norvegicus

<400> SEQUENCE: 82

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 83
<211> LENGTH: 78
<212> TYPE: DNA
<213> ORGANISM: Cercopithecus aethiops

<400> SEQUENCE: 83
gacacccact tccccatctg cattttctgc tgcggctgct gtcatcgatc aaagtgtggg    60
atgtgctgca ggacgtag                                                 78

<210> SEQ ID NO 84
<211> LENGTH: 25
<212> TYPE: PRT
<213> ORGANISM: Cercopithecus aethiops

<400> SEQUENCE: 84

Asp Thr His Phe Pro Ile Cys Ile Phe Cys Cys Gly Cys Cys His Arg
1               5                   10                  15

Ser Lys Cys Gly Met Cys Cys Arg Thr
            20                  25

<210> SEQ ID NO 85
<211> LENGTH: 75
<212> TYPE: DNA
<213> ORGANISM: Oryctolagus cuniculus
```

<400> SEQUENCE: 85
gacacccact tccccatctg catcttctgc tgcagctgct gtaggaattc aaaatgtggg    60
atctgctgca agacc                                                    75

<210> SEQ ID NO 86
<211> LENGTH: 25
<212> TYPE: PRT
<213> ORGANISM: Oryctolagus cuniculus

<400> SEQUENCE: 86

Asp Thr His Phe Pro Ile Cys Ile Phe Cys Cys Ser Cys Cys Arg Asn
1               5                   10                  15

Ser Lys Cys Gly Ile Cys Cys Lys Thr
            20                  25

<210> SEQ ID NO 87
<211> LENGTH: 75
<212> TYPE: DNA
<213> ORGANISM: Canis familiaris

<400> SEQUENCE: 87
gacacccact tccccatctg catattctgc tgtggctgct gtaaacacc gaagtgtggg     60 ctctgctgca taaca                                                    75

<210> SEQ ID NO 88
<211> LENGTH: 25
<212> TYPE: PRT
<213> ORGANISM: Canis familiaris

<400> SEQUENCE: 88

Asp Thr His Phe Pro Ile Cys Ile Phe Cys Cys Gly Cys Cys Lys Thr
1               5                   10                  15

Pro Lys Cys Gly Leu Cys Cys Ile Thr
            20                  25

<210> SEQ ID NO 89
<211> LENGTH: 75
<212> TYPE: DNA
<213> ORGANISM: Canis familiaris

<400> SEQUENCE: 89
gacacccact tccccatctg catattctgc tgtggctgct gtaaacacc gaagtgtggg     60 ttctgctgca ggacg                                                    75

<210> SEQ ID NO 90
<211> LENGTH: 25
<212> TYPE: PRT
<213> ORGANISM: Canis familiaris

<400> SEQUENCE: 90

Asp Thr His Phe Pro Ile Cys Ile Phe Cys Cys Gly Cys Cys Lys Thr
1               5                   10                  15

Pro Lys Cys Gly Phe Cys Cys Arg Thr
            20                  25

<210> SEQ ID NO 91
<211> LENGTH: 75
<212> TYPE: DNA
<213> ORGANISM: Canis familiaris

<400> SEQUENCE: 91

```
gacacccact tccccatctg catattctgc tgtggctgct gtaaaacacc gaagtgtggg      60
ttgtgctgca agacg                                                       75
```

<210> SEQ ID NO 92
<211> LENGTH: 25
<212> TYPE: PRT
<213> ORGANISM: Canis familiaris

<400> SEQUENCE: 92

```
Asp Thr His Phe Pro Ile Cys Ile Phe Cys Cys Gly Cys Cys Lys Thr
1               5                   10                  15

Pro Lys Cys Gly Leu Cys Cys Lys Thr
            20                  25
```

<210> SEQ ID NO 93
<211> LENGTH: 180
<212> TYPE: DNA
<213> ORGANISM: Homo sapiens

<400> SEQUENCE: 93

```
tctgttttcc cacaacagac gggacaactt gcagagctgc aaccccagga cagagctgga      60
gccagggcca gctggatgcc catgttccag aggcgaagga ggcgagacac ccacttcccc     120
atctgcattt tctgctgcgg ctgctgtcat cgatcaaagt gtgggatgtg ctgcaagacg     180
```

<210> SEQ ID NO 94
<211> LENGTH: 60
<212> TYPE: PRT
<213> ORGANISM: Homo sapiens

<400> SEQUENCE: 94

```
Ser Val Phe Pro Gln Gln Thr Gly Gln Leu Ala Glu Leu Gln Pro Gln
1               5                   10                  15

Asp Arg Ala Gly Ala Arg Ala Ser Trp Met Pro Met Phe Gln Arg Arg
            20                  25                  30

Arg Arg Arg Asp Thr His Phe Pro Ile Cys Ile Phe Cys Cys Gly Cys
        35                  40                  45

Cys His Arg Ser Lys Cys Gly Met Cys Cys Lys Thr
    50                  55                  60
```

<210> SEQ ID NO 95
<211> LENGTH: 60
<212> TYPE: DNA
<213> ORGANISM: Homo sapiens

<400> SEQUENCE: 95

```
atctgcattt tctgctgcgg ctgctgtcat cgatcaaagt gtgggatgtg ctgcaagacg      60
```

<210> SEQ ID NO 96
<211> LENGTH: 20
<212> TYPE: PRT
<213> ORGANISM: Homo sapiens

<400> SEQUENCE: 96

```
Ile Cys Ile Phe Cys Cys Gly Cys Cys His Arg Ser Lys Cys Gly Met
1               5                   10                  15

Cys Cys Lys Thr
            20
```

```
<210> SEQ ID NO 97
<211> LENGTH: 66
<212> TYPE: DNA
<213> ORGANISM: Homo sapiens

<400> SEQUENCE: 97
ttccccatct gcattttctg ctgcggctgc tgtcatcgat caaagtgtgg gatgtgctgc     60
aagacg                                                               66

<210> SEQ ID NO 98
<211> LENGTH: 22
<212> TYPE: PRT
<213> ORGANISM: Homo sapiens

<400> SEQUENCE: 98

Phe Pro Ile Cys Ile Phe Cys Cys Gly Cys Cys His Arg Ser Lys Cys
1               5                   10                  15

Gly Met Cys Cys Lys Thr
            20

<210> SEQ ID NO 99
<211> LENGTH: 1650
<212> TYPE: DNA
<213> ORGANISM: Mus musculus

<400> SEQUENCE: 99
agtccttaga ctgcacagca gaacagaagg catgatggca ctcagcactc ggacccaggc     60
tgcctgtctc ctgcttctcc tccttgccag cctgagcagc accacctatc tccatcaaca    120
ggtgagcacc ccaggcccat gtggtggga gagccaggtc ccaggcaggc aggagctgct    180
caccactgag tagttagaat ggctcaggag tgatggcagc tgctgacaag gaagagggtg    240
gtccttagtg ggagctggga agctgcacag gtgtccttga atagctactc tgttgtccta    300
ctgtggaaaa tgaagcatgg tgggagccaa acaaaagtgt tccttggctg tcccaccccg    360
tcagggcatt cttttaagcag cctttacatg agtattttat aaagaattac tgtggatagt    420
acaaaagaca atgggcagaa aaactctaat gaggaaggac cagaggtggg gctaagaggc    480
tgacagccag gcaaagtatt ctatgagaaa atgatacaga agtcgggcag tggtggcaca    540
tgcctttaat cccagcattt gggaggcaga ggcaggtgga tttctgagtt tgaatccagc    600
ctggtctaca aagtgagttt caagacagcc agggctacac agaaaatcc tgtctgaaaa    660 aaaaaaaaa acaaaaaaag aaaaaaaaaa tgatacagaa gggtctggag agatggctta    720
gctgttagga acatttgatg cttgtgcata ggacctagtg tcagttccca gcacccatgt    780
ggtggatcac aaccatcctg aactctactt ccagggtacc tgatgccttc tgccctagat    840
ggcagtcagt agtaagcatg catatgatac acataggcac tcaaggcaat cacaagaccc    900
ttggggactg tagggtctga taagtgaagc cagtgttggc aataaagggc tgtagaggtt    960
ctgctgtgcc gagctttgtg acagctgtg cagatgatga tctgtcctgg aaagccacaa   1020
tccagatgaa tgtgctataa gcctttgtgc tatggggtga cctggttata agagataaga   1080
tgcagggaaa actgtccgga gtgtgcaaaa gcaaagaaag tgggtgcttt taggagcatc   1140
caaggaatgg tgaggggaca cagggcagta ggagcccttc tagaaattct gtctaagcac   1200
agtccctaaa tctctgggga gaagctggca gagaaaagtc aggaagctat gccgggtact   1260
ccacaagatt caatacctct tctgctttca cagatgagac agactacaga gctgcagcct   1320
ttgcacgggg aagaaagcag ggcagacatt gcggtaagag catctgggac tccctcctg   1380
```

-continued

| | |
|---|---|
| atccccagcc tctcccatgc ccaagctagg ctgcttacct ctctttcttt acacagatac | 1440 |
| caatgcagaa gagaaggaag agagacacca acttccccat ctgcatcttc tgctgtaaat | 1500 |
| gctgtaacaa ttcccagtgt ggtatctgtt gcaaaacata gcctagagcc acatcctgac | 1560 |
| ctctctacac ccctgcagcc cctcaacccc attatttatt cctgccctcc ccaccaatga | 1620 |
| ccttgaaata aagacgattt tattttcaaa | 1650 |

<210> SEQ ID NO 100
<211> LENGTH: 2637
<212> TYPE: DNA
<213> ORGANISM: Homo sapiens

<400> SEQUENCE: 100

| | |
|---|---|
| gactgtcact cggtcccaga caccagagca agctcaagac ccagcagtgg gacagccaga | 60 |
| cagacggcac gatggcactg agctcccaga tctgggccgc ttgcctcctg ctcctcctcc | 120 |
| tcctcgccag cctgaccagt ggctctgttt cccacaaca ggtgagagcc cagtggcctg | 180 |
| ggtccttagc agggcagcag ggatgggaga gccaggcctc agcctagggc actggagaca | 240 |
| cccgagcact gagcagagct caggacgtct caggagtact ggcagctgaa caggaaccag | 300 |
| gacaggcacg gtggctcatg cctgtaatcc cagcactttg ggaggttgag gcaggcagcc | 360 |
| cacttgaggt cagtttgaga ccagcctggc caacatggta aaaccccgtc tctactaaaa | 420 |
| atacaaaagt tagccaggct tggtggcagg tgcctgtaat cccagctact cgggagactg | 480 |
| aggcaggaga attgcttgaa cccgcaaggt ggaggttgca cagtgagctg agattgcacc | 540 |
| actgcactcc agcctggcaa cagagcaaga ctccatctcc aaaaaagaac agaaatcaat | 600 |
| gaagcaccga gtgacaggga ctggaaggtc ctaattccat gggtatttac ggaacccta | 660 |
| cgccgtgtgg agtcttattc tagacagtgg ggacgaggcc atgaacaagg tagatgagag | 720 |
| aggagatttc tccatcctgg tcagggaatt tgttaaagac tgatgaaaac atgaataaat | 780 |
| aattgtgtct agtacattct attcgtgaat ctcataacag acagtggtag agtgaccgtg | 840 |
| acccattcgc cacacagtag agtcactttt ttggtttgtt ttttagagac agggtcttcc | 900 |
| tctgttgctg aggctggagt gcagtggtgc agtcatagtt cactgcagcc tcaacctcct | 960 |
| gtgctcaagc aatcctccca cctcagcgtc ccaagtagct gggacagcag gcacatgcca | 1020 |
| cgggttgggg gaccacaggc atggtcaagg ggctggcagt caagcaagtg tttcatgaga | 1080 |
| aagtgacagt tgaccttcgt cttggagggt gagagatgga ggcagcaaag acctaaggag | 1140 |
| aggacaagcc agcatagccc agggtcaggc tgaacaagag gagatggtgg gacttgggga | 1200 |
| taaggctgag gggtgggcag tccctaagtc ttgtgggcaa ccatgcagac actgattttt | 1260 |
| ccttggaata aagaggaagc ccccataagc ttttttttt ttttctgaga tagggtctcg | 1320 |
| ctctgtcgtt caggctggtg tgcagtggca tcatctgggc tcactgcaac ctccgcctcc | 1380 |
| cgggttcaag caattctcct gcctcagctt cccgagcagc tgggattaca gcggctgcc | 1440 |
| accacgcccg gctaattttt gtttttttag tagagacagg gtttcaccat gttggccaga | 1500 |
| ctggtcttga actcctgacc tcaggtgatt ctcccacctc ggcttcccaa agtgctggga | 1560 |
| ttacaggcgt gagccactgc gcccagcctc ctgtaggttt ttaaaatgga gaaaaccaca | 1620 |
| atctcactgg ccatgtttta aaaaacttaa tctgccagtc aggcaccatg gctcacacct | 1680 |
| gtaatcccag agttttggga ggccaaggta ggaagatcag ttgagcccag gagttcaaga | 1740 |
| ccagcttggg caacacaacc agaccccacc tctacaaaaa attaaaaaat tagccgggtg | 1800 |
| tggtggcgtg cacctgctgt cccagctact cgggaagctg aggcgggagc atcgcttgag | 1860 |

```
cacaggaggt caaggctgca gggagctatg actgtgccac tgcactctgg cctgggcaac    1920
agaggaagac tctgtctaaa aaacaaacaa aaaaagtgac tctgctgtgt ggcaaatgga    1980
ttgaggggca agaatgcagg gaggtgtgtt aggaggctgg cactggcatc caggcagggg    2040
aaggtgatat cccaaagaag agtagcagct gtggaaagag gaggaggcgg atctgggagg    2100
tttttttttt taggaaaagc cgcccatggg aaggtgagca aagcaagaa agcaaggccc     2160 ctcctaagag tccatttgag ctctgggttt aaaccacttg gagaggagca ggttgccggg    2220
agccagtctc agaggtccac tgggcccccct gccatcctct gcaccccctt ctgctttcac    2280
agacgggaca acttgcagag ctgcaacccc aggacagagc tggagccagg ccagctgga    2340 tggtgagcgc aacagtgatg cctttcctag cccctgctc cctccccatg ctaaggccgg     2400
ttccctgctc acattccctt ccttcccaca gccatgttc cagaggcgaa ggaggcgaga     2460
cacccacttc cccatctgca ttttctgctg cggctgctgt catcgatcaa agtgtgggat    2520
gtgctgcaag acgtagaacc tacctgccct gcccccgtcc cctcccttcc ttatttattc    2580
ctgctgcccc agaacatagg tcttggaata aaatggctgg ttcttttgtt ttccaaa      2637
```

<210> SEQ ID NO 101
<211> LENGTH: 180
<212> TYPE: DNA
<213> ORGANISM: Homo sapiens

<400> SEQUENCE: 101

```
tctgttttcc cacaacagac gggacaactt gcagagctgc aacccagga cagagctgga     60 gccagggcca gctggatgcc catgttccag aggcgaagga ggcgagacac ccacttcccc   120
atctgcattt tctgctgcgg ctgctgtcat cgatcaaagt gtgggatgtg ctgcaagacg   180
```

<210> SEQ ID NO 102
<211> LENGTH: 61
<212> TYPE: PRT
<213> ORGANISM: Homo sapiens

<400> SEQUENCE: 102

```
Gly Ser Val Phe Pro Gln Gln Thr Gly Gln Leu Ala Glu Leu Gln Pro
1               5                   10                  15

Gln Asp Arg Ala Gly Ala Arg Ala Ser Trp Met Pro Met Phe Gln Arg
            20                  25                  30

Arg Arg Arg Arg Asp Thr His Phe Pro Ile Cys Ile Phe Cys Cys Gly
        35                  40                  45

Cys Cys His Arg Ser Lys Cys Gly Met Cys Cys Lys Thr
    50                  55                  60
```

<210> SEQ ID NO 103
<211> LENGTH: 301
<212> TYPE: DNA
<213> ORGANISM: Homo sapiens

<400> SEQUENCE: 103

```
tcggccccgc ctcctgccac cgcagattgg ccgctagccc tccccgagcg ccctgcctcc     60
gagggccggc gcaccataaa agaagccgcc ctagccacgt cccctcgcag ttcggcggtc    120
ccgcgggtct gtctcttgct tcaacagtgt ttggacggaa cagatccggg gactctcttc    180
cagcctccga ccgccctccg atttcctctc cgcttgcaac ctcgggacc atcttctcgg    240 ccatctcctg cttctgggac ctgccagcac cgttttttgtg gttagctcct tcttgccaac    300
``` c                                                                           301

<210> SEQ ID NO 104
<211> LENGTH: 75
<212> TYPE: DNA
<213> ORGANISM: Homo sapiens

<400> SEQUENCE: 104
gacacccact tccccatctg cattttctgc tgcggctgct gtcatcgatc aaagtgtggg    60
atgtgctgca agacg                                                     75

<210> SEQ ID NO 105
<211> LENGTH: 66
<212> TYPE: DNA
<213> ORGANISM: Homo sapiens

<400> SEQUENCE: 105
ggggacaagt ttgtacaaaa aagcaggctt agatctgaat tcaatttacg cgtgggatcc    60
aaggtc                                                               66

<210> SEQ ID NO 106

<400> SEQUENCE: 106

000

<210> SEQ ID NO 107
<211> LENGTH: 336
<212> TYPE: DNA
<213> ORGANISM: Homo sapiens

<400> SEQUENCE: 107
gatattgtga tgacccagtc tccactctcc ctgcccgtca cccctggaga gccggcctcc    60
atctcctgca ggtctagtca gagcctcctg catagtgatg gatacaacta tttggattgg   120
tacctgcaga agtcagggca gtctccacag cgcctgatct atatgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccg   300
ctcactatcg gcggagggac caaggtggag atcaaa                             336

<210> SEQ ID NO 108
<211> LENGTH: 112
<212> TYPE: PRT
<213> ORGANISM: Homo sapiens

<400> SEQUENCE: 108

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Ser Gly Gln Ser
        35                  40                  45

Pro Gln Arg Leu Ile Tyr Met Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

```
Leu Gln Thr Pro Leu Thr Ile Gly Gly Gly Thr Lys Val Glu Ile Lys
            100                 105                 110
```

<210> SEQ ID NO 109
<211> LENGTH: 366
<212> TYPE: DNA
<213> ORGANISM: Homo sapiens

<400> SEQUENCE: 109

```
caggtgcagc tggtggagtc tgggggaggc gtggtccagc ctggggaggtc cctgagactc    60
tcctgtgcag cctctggatt caccttcagt agttatggca tgcactgggt ccgtcaggct   120
ccaggcaagg ggctggagtg ggtggcagtt atttcatatg atggaagtaa tgaatactat   180
gcagactccg tgaagggccg attcaccatc tccagagaca attccaagaa cacgctgtat   240
ctgcaaatga acagcctgag agctgaggac acggctgtat attactgtgt gagagatgtg   300
tggttcgggg agtccctcca cggtttggac gtctggggcc aagggaccac ggtcaccgtc   360
tcctca                                                              366
```

<210> SEQ ID NO 110
<211> LENGTH: 122
<212> TYPE: PRT
<213> ORGANISM: Homo sapiens

<400> SEQUENCE: 110

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Glu Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Val Arg Asp Val Trp Phe Gly Glu Ser Leu His Gly Leu Asp Val Trp
            100                 105                 110
Gly Gln Gly Thr Thr Val Thr Val Ser Ser
        115                 120
```

<210> SEQ ID NO 111
<211> LENGTH: 16
<212> TYPE: PRT
<213> ORGANISM: Homo sapiens

<400> SEQUENCE: 111

```
Arg Ser Ser Gln Ser Leu Leu His Ser Asp Gly Tyr Asn Tyr Leu Asp
1               5                   10                  15
```

<210> SEQ ID NO 112
<211> LENGTH: 7
<212> TYPE: PRT
<213> ORGANISM: Homo sapiens

<400> SEQUENCE: 112

```
Met Gly Ser Asn Arg Ala Ser
1               5
```

<210> SEQ ID NO 113
<211> LENGTH: 9
<212> TYPE: PRT
<213> ORGANISM: Homo sapiens

<400> SEQUENCE: 113

Met Gln Ala Leu Gln Thr Pro Leu Thr
1               5

<210> SEQ ID NO 114
<211> LENGTH: 5
<212> TYPE: PRT
<213> ORGANISM: Homo sapiens

<400> SEQUENCE: 114

Ser Tyr Gly Met His
1               5

<210> SEQ ID NO 115
<211> LENGTH: 17
<212> TYPE: PRT
<213> ORGANISM: Homo sapiens

<400> SEQUENCE: 115

Val Ile Ser Tyr Asp Gly Ser Asn Glu Tyr Tyr Ala Asp Ser Val Lys
1               5                   10                  15

Gly

<210> SEQ ID NO 116
<211> LENGTH: 13
<212> TYPE: PRT
<213> ORGANISM: Homo sapiens

<400> SEQUENCE: 116

Asp Val Trp Phe Gly Glu Ser Leu His Gly Leu Asp Val
1               5                   10

<210> SEQ ID NO 117
<211> LENGTH: 333
<212> TYPE: DNA
<213> ORGANISM: Homo sapiens

<400> SEQUENCE: 117

```
cagtctgtgt tgacgcagcc gccctcactg tctggggccc cagggcagag ggtcaccatc      60
tcctgcactg ggggcagctc caacatcggg tcaggttttg ctatatactg gtaccagcag     120
cttccaggaa cagcccccaa actcctcatc tttggtgaca acattcggcc ctcaggggtc     180
cctgaccgat tctctggctc caagtctggc acctccgcct ccctggccat cactgggctc     240
caggctgagg atgaggctga ttattactgc cagtcctatg acagcagcct gagtggttcg     300
gttttcggcg agggaccaa gctgaccgtc cta                                   333
```

<210> SEQ ID NO 118
<211> LENGTH: 111
<212> TYPE: PRT
<213> ORGANISM: Homo sapiens

<400> SEQUENCE: 118

Gln Ser Val Leu Thr Gln Pro Pro Ser Leu Ser Gly Ala Pro Gly Gln
1               5                   10                  15

Arg Val Thr Ile Ser Cys Thr Gly Gly Ser Ser Asn Ile Gly Ser Gly
            20                  25                  30

```
Phe Ala Ile Tyr Trp Tyr Gln Gln Leu Pro Gly Thr Ala Pro Lys Leu
         35                  40                  45

Leu Ile Phe Gly Asp Asn Ile Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Gly Thr Lys Leu Thr Val Leu
                100                 105                 110
```

<210> SEQ ID NO 119
<211> LENGTH: 351
<212> TYPE: DNA
<213> ORGANISM: Homo sapiens

<400> SEQUENCE: 119

```
caggttcagc tggtgcagtc tggagctgag gtgaagaagc ctggggcctc agtgaaggtc    60
tcctgcaagg cttctggtta ccctttacc agctatggta tcagctgggt gcgacaggcc   120
cctggacaag gcttgagtg gatgggatgg atcagcgctt acaatggtga aaaaacact    180
gcacagaaac tccagggcag agtcaccatg accacagaca catccacgag cacagcctac   240
atggagctga ggagcctgag atctgacgac acggccgtgt attactgtgc gagagaggaa   300
ctaggggctt ttgatatctg gggccaaggg acaatggtca ccgtctcttc a            351
```

<210> SEQ ID NO 120
<211> LENGTH: 117
<212> TYPE: PRT
<213> ORGANISM: Homo sapiens

<400> SEQUENCE: 120

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Glu Lys Asn Thr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Glu Leu Gly Ala Phe Asp Ile Trp Gly Gln Gly Thr Met
                100                 105                 110

Val Thr Val Ser Ser
            115
```

<210> SEQ ID NO 121
<211> LENGTH: 14
<212> TYPE: PRT
<213> ORGANISM: Homo sapiens

<400> SEQUENCE: 121

```
Thr Gly Gly Ser Ser Asn Ile Gly Ser Gly Phe Ala Ile Tyr
 1               5                  10
```

<210> SEQ ID NO 122
<211> LENGTH: 7
<212> TYPE: PRT
<213> ORGANISM: Homo sapiens

<400> SEQUENCE: 122

Gly Asp Asn Ile Arg Pro Ser
1               5

<210> SEQ ID NO 123
<211> LENGTH: 11
<212> TYPE: PRT
<213> ORGANISM: Homo sapiens

<400> SEQUENCE: 123

Gln Ser Tyr Asp Ser Ser Leu Ser Gly Ser Val
1               5                   10

<210> SEQ ID NO 124
<211> LENGTH: 5
<212> TYPE: PRT
<213> ORGANISM: Homo sapiens

<400> SEQUENCE: 124

Ser Tyr Gly Ile Ser
1               5

<210> SEQ ID NO 125
<211> LENGTH: 17
<212> TYPE: PRT
<213> ORGANISM: Homo sapiens

<400> SEQUENCE: 125

Trp Ile Ser Ala Tyr Asn Gly Glu Lys Asn Thr Ala Gln Lys Leu Gln
1               5                   10                  15

Gly

<210> SEQ ID NO 126
<211> LENGTH: 8
<212> TYPE: PRT
<213> ORGANISM: Homo sapiens

<400> SEQUENCE: 126

Glu Glu Leu Gly Ala Phe Asp Ile
1               5

<210> SEQ ID NO 127
<211> LENGTH: 321
<212> TYPE: DNA
<213> ORGANISM: Homo sapiens

<400> SEQUENCE: 127
gaaattgtgt tgacgcagtc tccaggcacc ctgtctttgt ctccagggga aagagccacc    60
ctctcctgca gggccagtca gagtgttagc agcaactact tagcctggta ccagcagaaa   120
cctggccagg ctcccaggct cctcatctat ggtgcatcca gcagggccac tggcatccca   180
gacaggttca gtggcagtgg gtctgggaca gacttcactc tcatcatcag cagactggag   240
cctgaagatt ttgtagtgta ttactgtcag cagtatggta gctcactcac tttcggcgga   300
gggaccaagg tggagatcaa a                                             321

<210> SEQ ID NO 128

```
<211> LENGTH: 107
<212> TYPE: PRT
<213> ORGANISM: Homo sapiens

<400> SEQUENCE: 128

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Ile Ile Ser Arg Leu Glu
65                  70                  75                  80

Pro Glu Asp Phe Val Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 129
<211> LENGTH: 366
<212> TYPE: DNA
<213> ORGANISM: Homo sapiens

<400> SEQUENCE: 129
caggttcagc tggtgcagtc tggagatgag gtgaagaagc ctggggcctc agtgaaggtc      60
tcctgcaagg cttctggtta cacctttatc aagtatggaa tcagttgggt gcgacaggcc     120
cctggacaag gcttgagtg gatgggatgg atcggcgctt tcaatggtaa cacagactat     180
gcacggaacc tccaggccag agtcaccatg accacagaca catccacgag cacagcctac     240
atggagctga ggagcctgag atctgacgac acggccgtat attactgtgc gagagagggc     300
tggaacgacg actacttctg cggtttggac gtctggggcc aagggaccac ggtcaccgtc     360
tcctca                                                                 366

<210> SEQ ID NO 130
<211> LENGTH: 122
<212> TYPE: PRT
<213> ORGANISM: Homo sapiens

<400> SEQUENCE: 130

Gln Val Gln Leu Val Gln Ser Gly Asp Glu Val Lys Lys Pro Gly Ala
1               5                   10                  15

Ser Val Lys Val Ser Cys Lys Ala Ser Gly Tyr Thr Phe Ile Lys Tyr
            20                  25                  30

Gly Ile Ser Trp Val Arg Gln Ala Pro Gly Gln Gly Leu Glu Trp Met
        35                  40                  45

Gly Trp Ile Gly Ala Phe Asn Gly Asn Thr Asp Tyr Ala Arg Asn Leu
    50                  55                  60

Gln Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Trp Asn Asp Asp Tyr Phe Cys Gly Leu Asp Val Trp
            100                 105                 110

Gly Gln Gly Thr Thr Val Thr Val Ser Ser
        115                 120
```

<210> SEQ ID NO 131
<211> LENGTH: 12
<212> TYPE: PRT
<213> ORGANISM: Homo sapiens

<400> SEQUENCE: 131

Arg Ala Ser Gln Ser Val Ser Ser Asn Tyr Leu Ala
1               5                   10

<210> SEQ ID NO 132
<211> LENGTH: 7
<212> TYPE: PRT
<213> ORGANISM: Homo sapiens

<400> SEQUENCE: 132

Gly Ala Ser Ser Arg Ala Thr
1               5

<210> SEQ ID NO 133
<211> LENGTH: 8
<212> TYPE: PRT
<213> ORGANISM: Homo sapiens

<400> SEQUENCE: 133

Gln Gln Tyr Gly Ser Ser Leu Thr
1               5

<210> SEQ ID NO 134
<211> LENGTH: 5
<212> TYPE: PRT
<213> ORGANISM: Homo sapiens

<400> SEQUENCE: 134

Lys Tyr Gly Ile Ser
1               5

<210> SEQ ID NO 135
<211> LENGTH: 17
<212> TYPE: PRT
<213> ORGANISM: Homo sapiens

<400> SEQUENCE: 135

Trp Ile Gly Ala Phe Asn Gly Asn Thr Asp Tyr Ala Arg Asn Leu Gln
1               5                   10                  15

Ala

<210> SEQ ID NO 136
<211> LENGTH: 13
<212> TYPE: PRT
<213> ORGANISM: Homo sapiens

<400> SEQUENCE: 136

Glu Gly Trp Asn Asp Asp Tyr Phe Cys Gly Leu Asp Val
1               5                   10

<210> SEQ ID NO 137
<211> LENGTH: 318
<212> TYPE: DNA
<213> ORGANISM: Homo sapiens

<400> SEQUENCE: 137
tatgagctga ctcagccacc ctcagtgtcc gtgtccccag gacagacagc cagcctcacc      60

```
tgctctggag ataaattggg ggatagatat gcttcctggt atcagcagaa gccaggccag    120 tccccctgtgc tggtcatcta tcaagatagc aagcggccct cagggatccc tgagcgattc   180
tctggctcca actctgggaa cacagccact ctgaccatca gcgggaccca ggctatggat    240
gaggctgact attactgtca ggcgtgggac agcagcactg catgtgtctt cggaactggg    300
accaaggtca ccgtccta                                                  318
```

```
<210> SEQ ID NO 138
<211> LENGTH: 106
<212> TYPE: PRT
<213> ORGANISM: Homo sapiens

<400> SEQUENCE: 138
```

Tyr Glu Leu Thr Gln Pro Pro Ser Val Ser Val Ser Pro Gly Gln Thr
1               5                   10                  15

Ala Ser Leu Thr Cys Ser Gly Asp Lys Leu Gly Asp Arg Tyr Ala Ser
            20                  25                  30

Trp Tyr Gln Gln Lys Pro Gly Gln Ser Pro Val Leu Val Ile Tyr Gln
        35                  40                  45

Asp Ser Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Asp Ser Ser Thr Ala Cys Val
                85                  90                  95

Phe Gly Thr Gly Thr Lys Val Thr Val Leu
            100                 105

```
<210> SEQ ID NO 139
<211> LENGTH: 363
<212> TYPE: DNA
<213> ORGANISM: Homo sapiens

<400> SEQUENCE: 139
caggtgcagc tggtggagtc tgggggaggc gtggtccagc ctgggaggtc cctgagactc    60
tcctgtgcag cgtctggatt caccctcagt agctatggca tgcactgggt ccgccaggct   120
ccaggcaagg ggctggagtg ggtggcagtt atatggtatg atgaaagtaa taaatactat    180
gcagactccg tgaagggccg attcaccatc tccagagaca attccaagaa cacgttgaat    240
ctgcaaatga acagcctgag agccgaggac acggctttgt attactgtgc gagagccggt    300
atagcagcag cccttgatgc ttttgatatc tggggccaag gacaatggt caccgtctct    360 tca                                                                  363
```

```
<210> SEQ ID NO 140
<211> LENGTH: 121
<212> TYPE: PRT
<213> ORGANISM: Homo sapiens

<400> SEQUENCE: 140
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Glu Ser Asn Lys Tyr Tyr Ala Asp Ser Val
            50                  55                  60

Lys Gly Arg Phe Thr Ile Ser Arg Asp Asn Ser Lys Asn Thr Leu Asn
 65                  70                  75                  80

Leu Gln Met Asn Ser Leu Arg Ala Glu Asp Thr Ala Leu Tyr Tyr Cys
                 85                  90                  95

Ala Arg Ala Gly Ile Ala Ala Ala Leu Asp Ala Phe Asp Ile Trp Gly
            100                 105                 110

Gln Gly Thr Met Val Thr Val Ser Ser
            115                 120

<210> SEQ ID NO 141
<211> LENGTH: 11
<212> TYPE: PRT
<213> ORGANISM: Homo sapiens

<400> SEQUENCE: 141

Ser Gly Asp Lys Leu Gly Asp Arg Tyr Ala Ser
 1               5                  10

<210> SEQ ID NO 142
<211> LENGTH: 7
<212> TYPE: PRT
<213> ORGANISM: Homo sapiens

<400> SEQUENCE: 142

Gln Asp Ser Lys Arg Pro Ser
 1               5

<210> SEQ ID NO 143
<211> LENGTH: 10
<212> TYPE: PRT
<213> ORGANISM: Homo sapiens

<400> SEQUENCE: 143

Gln Ala Trp Asp Ser Ser Thr Ala Cys Val
 1               5                  10

<210> SEQ ID NO 144
<211> LENGTH: 5
<212> TYPE: PRT
<213> ORGANISM: Homo sapiens

<400> SEQUENCE: 144

Ser Tyr Gly Met His
 1               5

<210> SEQ ID NO 145
<211> LENGTH: 17
<212> TYPE: PRT
<213> ORGANISM: Homo sapiens

<400> SEQUENCE: 145

Val Ile Trp Tyr Asp Glu Ser Asn Lys Tyr Tyr Ala Asp Ser Val Lys
 1               5                  10                  15

Gly

<210> SEQ ID NO 146
<211> LENGTH: 12
<212> TYPE: PRT
<213> ORGANISM: Homo sapiens

<400> SEQUENCE: 146

Ala Gly Ile Ala Ala Ala Leu Asp Ala Phe Asp Ile
1               5                   10

<210> SEQ ID NO 147
<211> LENGTH: 333
<212> TYPE: DNA
<213> ORGANISM: Homo sapiens

<400> SEQUENCE: 147
cagtctgtgt tgacgcagcc gccctcactg tctggggccc cagggcagag ggtcaccatc    60
tcctgcactg ggggcagctc caacatcggg tcaggttttg ctatatactg gtaccagcag   120
cttccaggaa cagcccccaa actcctcatc tatggtgaca cattcggcc ctcaggggtc    180 cctgaccgat tctctggctc caagtctggc acctccgcct ccctggccat cactgggctc   240
caggctgagg atgaggctga ttattactgc cagtcctatg acagcagcct gagtggttcg   300
gtattcggcg gagggaccaa gctgaccgtc cta                                333

<210> SEQ ID NO 148
<211> LENGTH: 111
<212> TYPE: PRT
<213> ORGANISM: Homo sapiens

<400> SEQUENCE: 148

Gln Ser Val Leu Thr Gln Pro Pro Ser Leu Ser Gly Ala Pro Gly Gln
1               5                   10                  15

Arg Val Thr Ile Ser Cys Thr Gly Gly Ser Ser Asn Ile Gly Ser Gly
                20                  25                  30

Phe Ala Ile Tyr Trp Tyr Gln Gln Leu Pro Gly Thr Ala Pro Lys Leu
            35                  40                  45

Leu Ile Tyr Gly Asp Asn Ile Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 149
<211> LENGTH: 351
<212> TYPE: DNA
<213> ORGANISM: Homo sapiens

<400> SEQUENCE: 149
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtga aacaaacact    180
gcacagaaac tccagggcag agtcaccatg accacagaca catccacgag cacagcctac   240
atggagctga ggagcctgag atctgacgac acggccgtgt attactgtgc gagagaggaa   300 ctagggggctt ttgatatctg gggccaaggg acaatggtca ccgtctcttc a           351

<210> SEQ ID NO 150
<211> LENGTH: 117
<212> TYPE: PRT
<213> ORGANISM: Homo sapiens

<400> SEQUENCE: 150

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Glu Thr Asn Thr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Glu Glu Leu Gly Ala Phe Asp Ile Trp Gly Gln Gly Thr Met
            100                 105                 110
Val Thr Val Ser Ser
        115

<210> SEQ ID NO 151
<211> LENGTH: 14
<212> TYPE: PRT
<213> ORGANISM: Homo sapiens

<400> SEQUENCE: 151

Thr Gly Gly Ser Ser Asn Ile Gly Ser Gly Phe Ala Ile Tyr
1               5                   10

<210> SEQ ID NO 152
<211> LENGTH: 7
<212> TYPE: PRT
<213> ORGANISM: Homo sapiens

<400> SEQUENCE: 152

Gly Asp Asn Ile Arg Pro Ser
1               5

<210> SEQ ID NO 153
<211> LENGTH: 11
<212> TYPE: PRT
<213> ORGANISM: Homo sapiens

<400> SEQUENCE: 153

Gln Ser Tyr Asp Ser Ser Leu Ser Gly Ser Val
1               5                   10

<210> SEQ ID NO 154
<211> LENGTH: 5
<212> TYPE: PRT
<213> ORGANISM: Homo sapiens

<400> SEQUENCE: 154

Ser Tyr Gly Ile Ser
1               5

<210> SEQ ID NO 155
<211> LENGTH: 17
<212> TYPE: PRT
<213> ORGANISM: Homo sapiens

<400> SEQUENCE: 155

Trp Ile Ser Ala Tyr Asn Gly Glu Thr Asn Thr Ala Gln Lys Leu Gln

Gly

<210> SEQ ID NO 156
<211> LENGTH: 8
<212> TYPE: PRT
<213> ORGANISM: Homo sapiens

<400> SEQUENCE: 156

Glu Glu Leu Gly Ala Phe Asp Ile
1               5

<210> SEQ ID NO 157
<211> LENGTH: 321
<212> TYPE: DNA
<213> ORGANISM: Homo sapiens

<400> SEQUENCE: 157

```
tcctatgagc tgactcagcc accctcagtg tccgtgtccc caggacagac agccaccatc      60
acctgctctg gagataaatt gggggaaaga tatgcgtgtt ggtatcagca gaggccaggc     120
cagtcccctg tactggtcat ctatcaagat atcaagcggc cctcaggat  ccctgagcga     180
ttctctggct ccaactctgg gaacacagcc actctgacca tcagcgggac ccaggctatg     240
gatgaggctg actatttctg tcaggcgtgg tacagcagca ccaatgtgct tttcggcgga     300
gggaccaagc tgaccgtcct a                                               321
```

<210> SEQ ID NO 158
<211> LENGTH: 107
<212> TYPE: PRT
<213> ORGANISM: Homo sapiens

<400> SEQUENCE: 158

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Glu Arg Tyr Ala
            20                  25                  30

Cys Trp Tyr Gln Gln Arg Pro Gly Gln Ser Pro Val Leu Val Ile Tyr
        35                  40                  45

Gln Asp Ile Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Tyr Ser Ser Thr Asn Val
                85                  90                  95

Leu Phe Gly Gly Gly Thr Lys Leu Thr Val Leu
            100                 105

<210> SEQ ID NO 159
<211> LENGTH: 363
<212> TYPE: DNA
<213> ORGANISM: Homo sapiens

<400> SEQUENCE: 159

```
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg ctgaaagtaa taaatactac     180
gcagactccg tgaagggccg attcaccatc tccagagaca attccaagaa cacgctgtat     240
```

```
ctgcaaatga acagcctgag agccgaggac acggctgtgt attactgtgc gagagcccag    300
gagggtatag cccctgacgc ttttgatatc tggggccaag gaacaatggt caccgtctct    360
tca                                                                  363
```

<210> SEQ ID NO 160
<211> LENGTH: 121
<212> TYPE: PRT
<213> ORGANISM: Homo sapiens

<400> SEQUENCE: 160

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Glu Gly Ile Ala Pro Asp Ala Phe Asp Ile Trp Gly
            100                 105                 110

Gln Gly Thr Met Val Thr Val Ser Ser
        115                 120

<210> SEQ ID NO 161
<211> LENGTH: 11
<212> TYPE: PRT
<213> ORGANISM: Homo sapiens

<400> SEQUENCE: 161

Ser Gly Asp Lys Leu Gly Glu Arg Tyr Ala Cys
1               5                   10

<210> SEQ ID NO 162
<211> LENGTH: 7
<212> TYPE: PRT
<213> ORGANISM: Homo sapiens

<400> SEQUENCE: 162

Gln Asp Ile Lys Arg Pro Ser
1               5

<210> SEQ ID NO 163
<211> LENGTH: 10
<212> TYPE: PRT
<213> ORGANISM: Homo sapiens

<400> SEQUENCE: 163

Gln Ala Trp Tyr Ser Ser Thr Asn Val Leu
1               5                   10

<210> SEQ ID NO 164
<211> LENGTH: 5
<212> TYPE: PRT
<213> ORGANISM: Homo sapiens

<400> SEQUENCE: 164

```
Ser Tyr Gly Met His
1               5
```

```
<210> SEQ ID NO 165
<211> LENGTH: 17
<212> TYPE: PRT
<213> ORGANISM: Homo sapiens

<400> SEQUENCE: 165
```

```
Val Ile Trp Tyr Ala Glu Ser Asn Lys Tyr Tyr Ala Asp Ser Val Lys
1               5                  10                  15

Gly
```

```
<210> SEQ ID NO 166
<211> LENGTH: 12
<212> TYPE: PRT
<213> ORGANISM: Homo sapiens

<400> SEQUENCE: 166
```

```
Ala Gln Glu Gly Ile Ala Pro Asp Ala Phe Asp Ile
1               5                  10
```

```
<210> SEQ ID NO 167
<211> LENGTH: 321
<212> TYPE: DNA
<213> ORGANISM: Homo sapiens

<400> SEQUENCE: 167
tcctatgagc tgactcagcc acccctcagtg tccgtgtccc caggacagac agccaccatc    60
acctgctctg gagataaatt gggggaaaga tatgcgtgtt ggtatcagca gaggccaggc   120 cagtccctg tactggtcat ctatcaagat agcaagcggc cctcagggat ccctgagcga   180
ttctctggct ccaactctgg gaacacagcc actctgacca tcagcgggac ccaggctatg   240
gatgaggctg actatttctg tcaggcgtgg tacagcagca ccaatgtgct tttcggcgga   300
gggaccaagc tgaccgtcct a                                             321
```

```
<210> SEQ ID NO 168
<211> LENGTH: 107
<212> TYPE: PRT
<213> ORGANISM: Homo sapiens

<400> SEQUENCE: 168
```

```
Ser Tyr Glu Leu Thr Gln Pro Pro Ser Val Ser Val Ser Pro Gly Gln
1               5                  10                  15

Thr Ala Thr Ile Thr Cys Ser Gly Asp Lys Leu Gly Glu Arg Tyr Ala
            20                  25                  30

Cys Trp Tyr Gln Gln Arg Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Phe Cys Gln Ala Trp Tyr Ser Ser Thr Asn Val
                85                  90                  95

Leu Phe Gly Gly Gly Thr Lys Leu Thr Val Leu
            100                 105
```

```
<210> SEQ ID NO 169
```

```
<211> LENGTH: 363
<212> TYPE: DNA
<213> ORGANISM: Homo sapiens

<400> SEQUENCE: 169
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatggtatg ctgaaagtaa taaatactac   180
gcagactccg tgaagggccg attcaccatc tccagagaca attccaagaa cacgctgtat   240
ctgcaaatga acagcctgag agccgaggac acggctgtgt attactgtgc gagagcccag   300
gagggtatag cccctgacgc ttttgatatc tggggccaag gaacaatggt caccgtctct   360
tca                                                                 363

<210> SEQ ID NO 170
<211> LENGTH: 121
<212> TYPE: PRT
<213> ORGANISM: Homo sapiens

<400> SEQUENCE: 170

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ala Glu Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Glu Gly Ile Ala Pro Asp Ala Phe Asp Ile Trp Gly
            100                 105                 110

Gln Gly Thr Met Val Thr Val Ser Ser
        115                 120

<210> SEQ ID NO 171
<211> LENGTH: 11
<212> TYPE: PRT
<213> ORGANISM: Homo sapiens

<400> SEQUENCE: 171

Ser Gly Asp Lys Leu Gly Glu Arg Tyr Ala Cys
1               5                   10

<210> SEQ ID NO 172
<211> LENGTH: 7
<212> TYPE: PRT
<213> ORGANISM: Homo sapiens

<400> SEQUENCE: 172

Gln Asp Ser Lys Arg Pro Ser
1               5

<210> SEQ ID NO 173
<211> LENGTH: 10
<212> TYPE: PRT
<213> ORGANISM: Homo sapiens
```

<400> SEQUENCE: 173

Gln Ala Trp Tyr Ser Ser Thr Asn Val Leu
1               5                   10

<210> SEQ ID NO 174
<211> LENGTH: 5
<212> TYPE: PRT
<213> ORGANISM: Homo sapiens

<400> SEQUENCE: 174

Ser Tyr Gly Met His
1               5

<210> SEQ ID NO 175
<211> LENGTH: 17
<212> TYPE: PRT
<213> ORGANISM: Homo sapiens

<400> SEQUENCE: 175

Val Ile Trp Tyr Ala Glu Ser Asn Lys Tyr Tyr Ala Asp Ser Val Lys
1               5                   10                  15

Gly

<210> SEQ ID NO 176
<211> LENGTH: 12
<212> TYPE: PRT
<213> ORGANISM: Homo sapiens

<400> SEQUENCE: 176

Ala Gln Glu Gly Ile Ala Pro Asp Ala Phe Asp Ile
1               5                   10

<210> SEQ ID NO 177
<211> LENGTH: 330
<212> TYPE: DNA
<213> ORGANISM: Homo sapiens

<400> SEQUENCE: 177
aattttatgc tgactcagcc ccactctgtg tcggagtctc cggggaagac ggtaaccatc      60
tcctgcaccc gcagcagtgg cagcattgcc agctactatg tgcagtggta ccagcagcgc     120
ccgggcagtt cccccaccac tgtgatctat gaggatagcc agagaccctc tggggtccct     180
gatcggttct ctggctccat cgacagctcc tccaactctg cctccctcac catctctgga     240
ctgaagactg aggacgaggc tgactattat tgtcagtctt atgatagcag caatgtggta     300
ttcggcggag ggaccaagct gaccgtccta                                      330

<210> SEQ ID NO 178
<211> LENGTH: 110
<212> TYPE: PRT
<213> ORGANISM: Homo sapiens

<400> SEQUENCE: 178

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Tyr
                20                  25                  30

Tyr Val Gln Trp Tyr Gln Gln Arg Pro Gly Ser Ser Pro Thr Thr Val
            35                  40                  45

Ile Tyr Glu Asp Ser Gln Arg Pro Ser Gly Val Pro Asp Arg Phe Ser

```
                    50                  55                  60
Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn Val Val Phe Gly Gly Gly Thr Lys Leu Thr Val Leu
                100                 105                 110
```

<210> SEQ ID NO 179
<211> LENGTH: 366
<212> TYPE: DNA
<213> ORGANISM: Homo sapiens

<400> SEQUENCE: 179

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg gaaggacat actacaggtc caagtggttt    180
aatgattatg cagtatctgt gcaaagtcga ataaccatca cccagacac atccaagaac   240
cagttctccc tgcagctgaa ctctgtgact cccgaggaca cggctgtgta ttactgtgca   300
agagggattg tcttctccta cgctatggac gtctggggcc aagggaccac ggtcaccgtc   360
tcctca                                                              366
```

<210> SEQ ID NO 180
<211> LENGTH: 122
<212> TYPE: PRT
<213> ORGANISM: Homo sapiens

<400> SEQUENCE: 180

```
Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30

Ser Ala Ala Trp Asn Trp Ile Arg Gln Ser Pro Ser Arg Gly Leu Glu
             35                  40                  45

Trp Leu Gly Arg Thr Tyr Tyr Arg Ser Lys Trp Phe Asn Asp Tyr Ala
         50                  55                  60

Val Ser Val Gln Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gly Ile Val Phe Ser Tyr Ala Met Asp Val Trp
                100                 105                 110

Gly Gln Gly Thr Thr Val Thr Val Ser Ser
            115                 120
```

<210> SEQ ID NO 181
<211> LENGTH: 13
<212> TYPE: PRT
<213> ORGANISM: Homo sapiens

<400> SEQUENCE: 181

```
Thr Arg Ser Ser Gly Ser Ile Ala Ser Tyr Tyr Val Gln
  1               5                  10
```

<210> SEQ ID NO 182
<211> LENGTH: 7

<212> TYPE: PRT
<213> ORGANISM: Homo sapiens

<400> SEQUENCE: 182

Glu Asp Ser Gln Arg Pro Ser
1               5

<210> SEQ ID NO 183
<211> LENGTH: 9
<212> TYPE: PRT
<213> ORGANISM: Homo sapiens

<400> SEQUENCE: 183

Gln Ser Tyr Asp Ser Ser Asn Val Val
1               5

<210> SEQ ID NO 184
<211> LENGTH: 7
<212> TYPE: PRT
<213> ORGANISM: Homo sapiens

<400> SEQUENCE: 184

Ser Asn Ser Ala Ala Trp Asn
1               5

<210> SEQ ID NO 185
<211> LENGTH: 18
<212> TYPE: PRT
<213> ORGANISM: Homo sapiens

<400> SEQUENCE: 185

Arg Thr Tyr Tyr Arg Ser Lys Trp Phe Asn Asp Tyr Ala Val Ser Val
1               5                   10                  15

Gln Ser

<210> SEQ ID NO 186
<211> LENGTH: 10
<212> TYPE: PRT
<213> ORGANISM: Homo sapiens

<400> SEQUENCE: 186

Gly Ile Val Phe Ser Tyr Ala Met Asp Val
1               5                   10

<210> SEQ ID NO 187
<211> LENGTH: 321
<212> TYPE: DNA
<213> ORGANISM: Homo sapiens

<400> SEQUENCE: 187
tcctatgagc tgactcagcc cccctcagtg tccgtgtccc caggacagac agccagcatc      60
acctgttctg gagataaaat gggggaaaga tatgcttgct ggtatcagca gaagccaggc     120
cagtccccta tactggtcat ctatcaagat accaagcggc cctcagggat ccctgagcga     180
ttctctggct ccaactctgg gaacacagcc actctgacca tcagcgggac ccaggctatg     240
gatgaggctg actattactg tcaggcgtgg tacagcagca ccaatgtggt attcggcgga     300
gggaccaagc tgaccgtcct a                                                321

<210> SEQ ID NO 188
<211> LENGTH: 107
<212> TYPE: PRT
<213> ORGANISM: Homo sapiens

<400> SEQUENCE: 188

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Met Gly Glu Arg Tyr Ala
            20                  25                  30

Cys Trp Tyr Gln Gln Lys Pro Gly Gln Ser Pro Ile Leu Val Ile Tyr
        35                  40                  45

Gln Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Tyr Ser Ser Thr Asn Val
                85                  90                  95

Val Phe Gly Gly Gly Thr Lys Leu Thr Val Leu
            100                 105

<210> SEQ ID NO 189
<211> LENGTH: 363
<212> TYPE: DNA
<213> ORGANISM: Homo sapiens

<400> SEQUENCE: 189
caggtgcagc tggtggagtc tgggggaggc gtggtccagc ctggggaggtc cctgagactc        60 tcctgtgcag cgtctggatt caccttcagt aactatggca tgcactgggt ccgccaggct       120
ccaggcaagg ggctggagtg gtggcagtt atatggtatg ttggaagtaa taaatactat       180
gcagactccg tgaagggccg attcaccatc tccagagaca attccaagaa cacgctgtat       240
ctgcaaatga acagcctgag agccgaggac acggctgtgt attactgtgc gagagcccag       300
gagggtatgg cccctgatgc ttttgatatc tggggccaag ggacaatggt caccgtctct       360
tca                                                                     363

<210> SEQ ID NO 190
<211> LENGTH: 121
<212> TYPE: PRT
<213> ORGANISM: Homo sapiens

<400> SEQUENCE: 190

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Val Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Glu Gly Met Ala Pro Asp Ala Phe Asp Ile Trp Gly
            100                 105                 110

Gln Gly Thr Met Val Thr Val Ser Ser
        115                 120

```
<210> SEQ ID NO 191
<211> LENGTH: 11
<212> TYPE: PRT
<213> ORGANISM: Homo sapiens

<400> SEQUENCE: 191

Ser Gly Asp Lys Met Gly Glu Arg Tyr Ala Cys
1               5                   10

<210> SEQ ID NO 192
<211> LENGTH: 7
<212> TYPE: PRT
<213> ORGANISM: Homo sapiens

<400> SEQUENCE: 192

Gln Asp Thr Lys Arg Pro Ser
1               5

<210> SEQ ID NO 193
<211> LENGTH: 10
<212> TYPE: PRT
<213> ORGANISM: Homo sapiens

<400> SEQUENCE: 193

Gln Ala Trp Tyr Ser Ser Thr Asn Val Val
1               5                   10

<210> SEQ ID NO 194
<211> LENGTH: 5
<212> TYPE: PRT
<213> ORGANISM: Homo sapiens

<400> SEQUENCE: 194

Asn Tyr Gly Met His
1               5

<210> SEQ ID NO 195
<211> LENGTH: 17
<212> TYPE: PRT
<213> ORGANISM: Homo sapiens

<400> SEQUENCE: 195

Val Ile Trp Tyr Val Gly Ser Asn Lys Tyr Tyr Ala Asp Ser Val Lys
1               5                   10                  15

Gly

<210> SEQ ID NO 196
<211> LENGTH: 12
<212> TYPE: PRT
<213> ORGANISM: Homo sapiens

<400> SEQUENCE: 196

Ala Gln Glu Gly Met Ala Pro Asp Ala Phe Asp Ile
1               5                   10

<210> SEQ ID NO 197
<211> LENGTH: 717
<212> TYPE: DNA
<213> ORGANISM: Homo sapiens

<400> SEQUENCE: 197
atgaggctcc ctgctcagct cctggggctg ctaatgctct ggtctctgg atccagtggg      60 gatattgtga tgacccagtc tccactctcc ctgcccgtca cccctggaga gccggcctcc     120
```

```
atctcctgca ggtctagtca gagcctcctg catagtgatg gatacaacta tttggattgg    180
tacctgcaga agtcagggca gtctccacag cgcctgatct atatgggttc taatcgggcc    240
tccggggtcc ctgacaggtt cagtggcagt ggatcaggca cagattttac actgaaaatc    300
agcagagtgg aggctgagga tgttggggtt tattactgca tgcaagctct acaaactccg    360
ctcactatcg gcggagggac caaggtggag atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct caacaggggg agagtgt      717
```

<210> SEQ ID NO 198
<211> LENGTH: 239
<212> TYPE: PRT
<213> ORGANISM: Homo sapiens

<400> SEQUENCE: 198

```
Met Arg Leu Pro Ala Gln Leu Leu Gly Leu Leu Met Leu Trp Val Ser
1               5                   10                  15

Gly Ser Ser Gly Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Leu Leu His Ser Asp Gly Tyr Asn Tyr Leu Asp Trp Tyr Leu Gln Lys
    50                  55                  60

Ser Gly Gln Ser Pro Gln Arg Leu Ile Tyr Met Gly Ser Asn Arg Ala
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Leu Gln Thr Pro Leu Thr Ile Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 199
<211> LENGTH: 1401
<212> TYPE: DNA
<213> ORGANISM: Homo sapiens

<400> SEQUENCE: 199

```
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcct ctggattcac cttcagtagt tatggcatgc actgggtccg tcaggctcca     180
ggcaagggc tggagtgggt ggcagttatt tcatatgatg gaagtaatga atactatgca     240
gactccgtga agggccgatt caccatctcc agagacaatt ccaagaacac gctgtatctg     300
caaatgaaca gcctgagagc tgaggacacg gctgtatatt actgtgtgag agatgtgtgg     360
ttcggggagt ccctccacgg tttggacgtc tggggccaag ggaccacggt caccgtctcc     420
tcagcctcca ccaagggccc atcggtcttc ccctggcgc cctgctccag gagcacctcc     480
gagagcacag cggccctggg ctgcctggtc aaggactact ccccgaacc ggtgacggtg     540
tcgtggaact caggcgctct gaccagcggc gtgcacacct tcccagctgt cctacagtcc     600
tcaggactct actccctcag cagcgtggtg accgtgccct ccagcaactt cggcacccag     660
acctacacct gcaacgtaga tcacaagccc agcaacacca aggtggacaa gacagttgag     720
cgcaaatgtt gtgtcgagtg cccaccgtgc ccagcaccac ctgtggcagg accgtcagtc     780
ttcctcttcc cccaaaacc caaggacacc ctcatgatct cccggacccc tgaggtcacg     840
tgcgtggtgg tggacgtgag ccacgaagac cccgaggtcc agttcaactg gtacgtggac     900
ggcgtggagg tgcataatgc caagacaaag ccacgggagg agcagttcaa cagcacgttc     960
cgtgtggtca gcgtcctcac cgttgtgcac caggactggc tgaacggcaa ggagtacaag    1020
tgcaaggtct ccaacaaagg cctcccagcc cccatcgaga aaccatctc caaaaccaaa    1080
gggcagcccc gagaaccaca ggtgtacacc ctgcccccat cccgggagga tgaccaag    1140
aaccaggtca gcctgacctg cctggtcaaa ggcttctacc ccagcgacat cgccgtggag    1200
tgggagagca atgggcagcc ggagaacaac tacaagacca cacctcccat gctggactcc    1260
gacggctcct tcttcctcta cagcaagctc accgtggaca gagcaggtg gcagcagggg    1320
aacgtcttct catgctccgt gatgcatgag gctctgcaca accactacac gcagaagagc    1380
ctctccctgt ctccgggtaa a                                              1401
```

<210> SEQ ID NO 200
<211> LENGTH: 467
<212> TYPE: PRT
<213> ORGANISM: Homo sapiens

<400> SEQUENCE: 200

```
Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Ser Tyr Gly Met His Trp Val Arg Gln Ala Pro Gly Lys Gly Leu
     50                  55                  60

Glu Trp Val Ala Val Ile Ser Tyr Asp Gly Ser Asn Glu Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110
```

| | | | | | | | | | | | |
|---|---|---|---|---|---|---|---|---|---|---|---|
|Tyr|Tyr|Cys|Val|Arg|Asp|Val|Trp|Phe|Gly|Glu|Ser|Leu|His|Gly|Leu|
| | |115| | | |120| | | |125| |
|Asp|Val|Trp|Gly|Gln|Gly|Thr|Thr|Val|Thr|Val|Ser|Ser|Ala|Ser|Thr|
| |130| | | |135| | | |140| | |
|Lys|Gly|Pro|Ser|Val|Phe|Pro|Leu|Ala|Pro|Cys|Ser|Arg|Ser|Thr|Ser|
|145| | | |150| | | |155| | | |160|
|Glu|Ser|Thr|Ala|Ala|Leu|Gly|Cys|Leu|Val|Lys|Asp|Tyr|Phe|Pro|Glu|
| | |165| | | |170| | | |175| |
|Pro|Val|Thr|Val|Ser|Trp|Asn|Ser|Gly|Ala|Leu|Thr|Ser|Gly|Val|His|
| |180| | | |185| | | |190| | |
|Thr|Phe|Pro|Ala|Val|Leu|Gln|Ser|Ser|Gly|Leu|Tyr|Ser|Leu|Ser|Ser|
| |195| | | |200| | | |205| | |
|Val|Val|Thr|Val|Pro|Ser|Ser|Asn|Phe|Gly|Thr|Gln|Thr|Tyr|Thr|Cys|
| |210| | | |215| | | |220| | |
|Asn|Val|Asp|His|Lys|Pro|Ser|Asn|Thr|Lys|Val|Asp|Lys|Thr|Val|Glu|
|225| | | |230| | | |235| | | |240|
|Arg|Lys|Cys|Cys|Val|Glu|Cys|Pro|Pro|Cys|Pro|Ala|Pro|Pro|Val|Ala|
| | |245| | | |250| | | |255| |
|Gly|Pro|Ser|Val|Phe|Leu|Phe|Pro|Pro|Lys|Pro|Lys|Asp|Thr|Leu|Met|
| | |260| | | |265| | | |270| |
|Ile|Ser|Arg|Thr|Pro|Glu|Val|Thr|Cys|Val|Val|Val|Asp|Val|Ser|His|
| |275| | | |280| | | |285| | |
|Glu|Asp|Pro|Glu|Val|Gln|Phe|Asn|Trp|Tyr|Val|Asp|Gly|Val|Glu|Val|
|290| | | |295| | | |300| | | |
|His|Asn|Ala|Lys|Thr|Lys|Pro|Arg|Glu|Glu|Gln|Phe|Asn|Ser|Thr|Phe|
|305| | | |310| | | |315| | | |320|
|Arg|Val|Val|Ser|Val|Leu|Thr|Val|Val|His|Gln|Asp|Trp|Leu|Asn|Gly|
| | |325| | | |330| | | |335| |
|Lys|Glu|Tyr|Lys|Cys|Lys|Val|Ser|Asn|Lys|Gly|Leu|Pro|Ala|Pro|Ile|
| | |340| | | |345| | | |350| |
|Glu|Lys|Thr|Ile|Ser|Lys|Thr|Lys|Gly|Gln|Pro|Arg|Glu|Pro|Gln|Val|
| | |355| | | |360| | | |365| |
|Tyr|Thr|Leu|Pro|Pro|Ser|Arg|Glu|Glu|Met|Thr|Lys|Asn|Gln|Val|Ser|
| |370| | | |375| | | |380| | |
|Leu|Thr|Cys|Leu|Val|Lys|Gly|Phe|Tyr|Pro|Ser|Asp|Ile|Ala|Val|Glu|
|385| | | |390| | | |395| | | |400|
|Trp|Glu|Ser|Asn|Gly|Gln|Pro|Glu|Asn|Asn|Tyr|Lys|Thr|Thr|Pro|Pro|
| | | |405| | | |410| | | |415| |
|Met|Leu|Asp|Ser|Asp|Gly|Ser|Phe|Phe|Leu|Tyr|Ser|Lys|Leu|Thr|Val|
| | | |420| | | |425| | | |430| |
|Asp|Lys|Ser|Arg|Trp|Gln|Gln|Gly|Asn|Val|Phe|Ser|Cys|Ser|Val|Met|
| | |435| | | |440| | | |445| |
|His|Glu|Ala|Leu|His|Asn|His|Tyr|Thr|Gln|Lys|Ser|Leu|Ser|Leu|Ser|
| |450| | | |455| | | |460| | |
|Pro|Gly|Lys|
|465|

<210> SEQ ID NO 201
<211> LENGTH: 366
<212> TYPE: DNA
<213> ORGANISM: Homo sapiens
<400> SEQUENCE: 201
caggttcagc tggtgcagtc tggagatgag gtgaagaagc ctggggcctc agtgaaggtc    60

```
tcctgcaagg cttctggtta cacctttatc aagtatggaa tcagttgggt gcgacaggcc    120
cctggacaag ggcttgagtg gatgggatgg atcggcgctt tcaatggtaa cacagactat    180
gcacggaacc tccaggccag agtcaccatg accacagaca catccacgag cacagcctac    240
atggagctga ggagcctgag atctgacgac acggccgtat attactgtgc gagagagggc    300
tggaacgacg actacttctc cggtttggac gtctggggcc aagggaccac ggtcaccgtc    360
tcctca                                                               366
```

<210> SEQ ID NO 202
<211> LENGTH: 122
<212> TYPE: PRT
<213> ORGANISM: Homo sapiens

<400> SEQUENCE: 202

Gln Val Gln Leu Val Gln Ser Gly Asp Glu Val Lys Lys Pro Gly Ala
1               5                   10                  15

Ser Val Lys Val Ser Cys Lys Ala Ser Gly Tyr Thr Phe Ile Lys Tyr
            20                  25                  30

Gly Ile Ser Trp Val Arg Gln Ala Pro Gly Gln Gly Leu Glu Trp Met
        35                  40                  45

Gly Trp Ile Gly Ala Phe Asn Gly Asn Thr Asp Tyr Ala Arg Asn Leu
    50                  55                  60

Gln Ala Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Gly Trp Asn Asp Asp Tyr Phe Ser Gly Leu Asp Val Trp
            100                 105                 110

Gly Gln Gly Thr Thr Val Thr Val Ser Ser
        115                 120

<210> SEQ ID NO 203
<211> LENGTH: 5
<212> TYPE: PRT
<213> ORGANISM: Homo sapiens

<400> SEQUENCE: 203

Lys Tyr Gly Ile Ser
1               5

<210> SEQ ID NO 204
<211> LENGTH: 17
<212> TYPE: PRT
<213> ORGANISM: Homo sapiens

<400> SEQUENCE: 204

Trp Ile Gly Ala Phe Asn Gly Asn Thr Asp Tyr Ala Arg Asn Leu Gln
1               5                   10                  15

Ala

<210> SEQ ID NO 205
<211> LENGTH: 13
<212> TYPE: PRT
<213> ORGANISM: Homo sapiens

<400> SEQUENCE: 205

Glu Gly Trp Asn Asp Asp Tyr Phe Ser Gly Leu Asp Val
1               5                   10

<210> SEQ ID NO 206
<211> LENGTH: 1401
<212> TYPE: DNA
<213> ORGANISM: Homo sapiens

<400> SEQUENCE: 206

```
atggactgga cctggagcat ccttttcttg gtggcagcag caacaggtgc ccactcccag    60
gttcagctgg tgcagtctgg agatgaggtg aagaagcctg ggcctcagt gaaggtctcc    120
tgcaaggctt ctggttacac ctttatcaag tatggaatca gttgggtgcg acaggcccct   180
ggacaagggc ttgagtggat gggatggatc ggcgctttca atggtaacac agactatgca   240
cggaacctcc aggccagagt caccatgacc acagacacat ccacgagcac agcctacatg   300
gagctgagga gcctgagatc tgacgacacg gccgtatatt actgtgcgag agagggctgg   360
aacgacgact acttctccgg tttggacgtc tggggccaag ggaccacggt caccgtctcc   420
tcagcctcca ccaagggccc atcggtcttc cccctggcgc cctgctccag gagcacctcc   480
gagagcacag cggccctggg ctgcctggtc aaggactact ccccgaacc ggtgacggtg    540
tcgtggaact caggcgctct gaccagcggc gtgcacacct tcccagctgt cctacagtcc   600
tcaggactct actccctcag cagcgtggtg accgtgccct ccagcaactt cggcacccag   660
acctacacct gcaacgtaga tcacaagccc agcaacacca aggtggacaa gacagttgag   720
cgcaaatgtt gtgtcgagtg cccaccgtgc ccagcaccac ctgtggcagg accgtcagtc   780
ttcctcttcc ccccaaaacc caaggacacc ctcatgatct cccggacccc tgaggtcacg   840
tgcgtggtgg tggacgtgag ccacgaagac cccgaggtcc agttcaactg gtacgtggac   900
ggcgtggagg tgcataatgc caagacaaag ccacgggagg agcagttcaa cagcacgttc   960
cgtgtggtca gcgtcctcac cgttgtgcac caggactggc tgaacggcaa ggagtacaag   1020
tgcaaggtct ccaacaaagg cctcccagcc cccatcgaga aaaccatctc caaaaccaaa   1080
gggcagcccc gagaaccaca ggtgtacacc ctgcccccat cccgggagga tgaccaag    1140
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctcccctgt ctccgggtaa a                                              1401
```

<210> SEQ ID NO 207
<211> LENGTH: 467
<212> TYPE: PRT
<213> ORGANISM: Homo sapiens

<400> SEQUENCE: 207

```
Met Asp Trp Thr Trp Ser Ile Leu Phe Leu Val Ala Ala Ala Thr Gly
1               5                   10                  15

Ala His Ser Gln Val Gln Leu Val Gln Ser Gly Asp Glu Val Lys Lys
            20                  25                  30

Pro Gly Ala Ser Val Lys Val Ser Cys Lys Ala Ser Gly Tyr Thr Phe
        35                  40                  45

Ile Lys Tyr Gly Ile Ser Trp Val Arg Gln Ala Pro Gly Gln Gly Leu
    50                  55                  60

Glu Trp Met Gly Trp Ile Gly Ala Phe Asn Gly Asn Thr Asp Tyr Ala
65                  70                  75                  80
```

Arg Asn Leu Gln Ala Arg Val Thr Met Thr Thr Asp Thr Ser Thr Ser
                85                  90                  95

Thr Ala Tyr Met Glu Leu Arg Ser Leu Arg Ser Asp Thr Ala Val
            100                 105                 110

Tyr Tyr Cys Ala Arg Glu Gly Trp Asn Asp Asp Tyr Phe Ser Gly Leu
            115                 120                 125

Asp Val Trp Gly Gln Gly Thr Thr Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
            165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
            210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 208
<211> LENGTH: 708
<212> TYPE: DNA

<213> ORGANISM: Homo sapiens

<400> SEQUENCE: 208

```
atggcctggt ctcctctcct cctcactctc ctcgctcact gcacagggtc ctgggcccag      60
tctgtgttga cgcagccgcc ctcactgtct ggggccccag ggcagagggt caccatctcc     120
tgcactgggg gcagctccaa catcgggtca ggttttgcta tatactggta ccagcagctt     180
ccaggaacag cccccaaact cctcatcttt ggtgacaaca ttcggccctc agggtccct      240
gaccgattct ctggctccaa gtctggcacc tccgcctccc tggccatcac tgggctccag     300
gctgaggatg aggctgatta ttactgccag tcctatgaca gcagcctgag tggttcggtt     360
ttcggcggag ggaccaagct gaccgtccta agtcagccca aggctgcccc ctcggtcact     420
ctgttcccgc cctcctctga ggagcttcaa gccaacaagg ccacactggt gtgtctcata     480
agtgacttct acccgggagc cgtgacagtg gcctggaagg cagatagcag ccccgtcaag     540
gcgggagtgg agaccaccac accctccaaa caaagcaaca acaagtacgc ggccagcagc     600
tatctgagcc tgacgcctga gcagtggaag tcccacagaa gctacagctg ccaggtcacg     660
catgaaggga gcaccgtgga agacagtg gcccctacag aatgttca                    708
```

<210> SEQ ID NO 209
<211> LENGTH: 236
<212> TYPE: PRT
<213> ORGANISM: Homo sapiens

<400> SEQUENCE: 209

```
Met Ala Trp Ser Pro Leu Leu Leu Thr Leu Leu Ala His Cys Thr Gly
1               5                   10                  15

Ser Trp Ala Gln Ser Val Leu Thr Gln Pro Pro Ser Leu Ser Gly Ala
            20                  25                  30

Pro Gly Gln Arg Val Thr Ile Ser Cys Thr Gly Gly Ser Ser Asn Ile
        35                  40                  45

Gly Ser Gly Phe Ala Ile Tyr Trp Tyr Gln Gln Leu Pro Gly Thr Ala
    50                  55                  60

Pro Lys Leu Leu Ile Phe Gly Asp Asn Ile Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala Asp Tyr Tyr Cys Gln Ser Tyr
            100                 105                 110

Asp Ser Ser Leu Ser Gly Ser Val Phe Gly Gly Gly Thr Lys Leu Thr
        115                 120                 125

Val Leu Ser Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
```

<210> SEQ ID NO 210
<211> LENGTH: 1386
<212> TYPE: DNA
<213> ORGANISM: Homo sapiens

<400> SEQUENCE: 210

| | | | | | |
|---|---|---|---|---|---|
| atggactgga | cctggagcat | ccttttcttg | gtggcagcag | caacaggtgc | ccactcccag | 60 |
| gttcagctgg | tgcagtctgg | agctgaggtg | aagaagcctg | ggcctcagt | gaaggtctcc | 120 |
| tgcaaggctt | ctggttacac | ctttaccagc | tatggtatca | gctgggtgcg | acaggccct | 180 |
| ggacaagggc | ttgagtggat | gggatggatc | agcgcttaca | atggtgaaaa | aaacactgca | 240 |
| cagaaactcc | agggcagagt | caccatgacc | acagacacat | ccacgagcac | agcctacatg | 300 |
| gagctgagga | gcctgagatc | tgacgacacg | gccgtgtatt | actgtgcgag | agaggaacta | 360 |
| ggggcttttg | atatctgggg | ccaagggaca | atggtcaccg | tctcttcagc | ctccaccaag | 420 |
| ggcccatcgg | tcttccccct | ggcgccctgc | tccaggagca | cctccgagag | cacagcggcc | 480 |
| ctgggctgcc | tggtcaagga | ctacttcccc | gaaccggtga | cggtgtcgtg | gaactcaggc | 540 |
| gctctgacca | gcggcgtgca | caccttccca | gctgtcctac | agtcctcagg | actctactcc | 600 |
| ctcagcagcg | tggtgaccgt | gccctccagc | aacttcggca | cccagaccta | cacctgcaac | 660 |
| gtagatcaca | agcccagcaa | caccaaggtg | gacaagacag | ttgagcgcaa | atgttgtgtc | 720 |
| gagtgcccac | cgtgcccagc | accacctgtg | gcaggaccgt | cagtcttcct | cttccccca | 780 |
| aaacccaagg | acaccctcat | gatctcccgg | accctgagg | tcacgtgcgt | ggtggtggac | 840 |
| gtgagccacg | aagaccccga | ggtccagttc | aactggtacg | tggacggcgt | ggaggtgcat | 900 |
| aatgccaaga | caaagccacg | ggaggagcag | ttcaacagca | cgttccgtgt | ggtcagcgtc | 960 |
| ctcaccgttg | tgcaccagga | ctggctgaac | ggcaaggagt | acaagtgcaa | ggtctccaac | 1020 |
| aaaggcctcc | cagcccccat | cgagaaaacc | atctccaaaa | ccaaagggca | gccccgagaa | 1080 |
| ccacaggtgt | acaccctgcc | cccatcccgg | gaggagatga | ccaagaacca | ggtcagcctg | 1140 |
| acctgcctgg | tcaaaggctt | ctaccccagc | gacatcgccg | tggagtggga | gagcaatggg | 1200 |
| cagccggaga | acaactacaa | gaccacacct | cccatgctgg | actccgacgg | ctccttcttc | 1260 |
| ctctacagca | agctcaccgt | ggacaagagc | aggtggcagc | aggggaacgt | cttctcatgc | 1320 |
| tccgtgatgc | atgaggctct | gcacaaccac | tacacgcaga | agagcctctc | cctgtctccg | 1380 |
| ggtaaa | | | | | | 1386 |

<210> SEQ ID NO 211
<211> LENGTH: 462
<212> TYPE: PRT
<213> ORGANISM: Homo sapiens

<400> SEQUENCE: 211

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Glu Lys Asn Thr Ala

```
                65                  70                  75                  80
        Gln Lys Leu Gln Gly Arg Val Thr Met Thr Thr Asp Thr Ser Thr Ser
                        85                  90                  95

Thr Ala Tyr Met Glu Leu Arg Ser Leu Arg Ser Asp Asp Thr Ala Val
                        100                 105                 110

Tyr Tyr Cys Ala Arg Glu Glu Leu Gly Ala Phe Asp Ile Trp Gly Gln
                        115                 120                 125

Gly Thr Met Val Thr Val Ser Ser Ala Ser Thr Lys Gly Pro Ser Val
                    130                 135                 140

Phe Pro Leu Ala Pro Cys Ser Arg Ser Thr Ser Glu Ser Thr Ala Ala
        145                 150                 155                 160

Leu Gly Cys Leu Val Lys Asp Tyr Phe Pro Glu Pro Val Thr Val Ser
                        165                 170                 175

Trp Asn Ser Gly Ala Leu Thr Ser Gly Val His Thr Phe Pro Ala Val
                        180                 185                 190

Leu Gln Ser Ser Gly Leu Tyr Ser Leu Ser Ser Val Val Thr Val Pro
                        195                 200                 205

Ser Ser Asn Phe Gly Thr Gln Thr Tyr Thr Cys Asn Val Asp His Lys
                210                 215                 220

Pro Ser Asn Thr Lys Val Asp Lys Thr Val Glu Arg Lys Cys Cys Val
        225                 230                 235                 240

Glu Cys Pro Pro Cys Pro Ala Pro Pro Val Ala Gly Pro Ser Val Phe
                        245                 250                 255

Leu Phe Pro Pro Lys Pro Lys Asp Thr Leu Met Ile Ser Arg Thr Pro
                        260                 265                 270

Glu Val Thr Cys Val Val Val Asp Val Ser His Glu Asp Pro Glu Val
                    275                 280                 285

Gln Phe Asn Trp Tyr Val Asp Gly Val Glu Val His Asn Ala Lys Thr
                        290                 295                 300

Lys Pro Arg Glu Glu Gln Phe Asn Ser Thr Phe Arg Val Val Ser Val
        305                 310                 315                 320

Leu Thr Val Val His Gln Asp Trp Leu Asn Gly Lys Glu Tyr Lys Cys
                        325                 330                 335

Lys Val Ser Asn Lys Gly Leu Pro Ala Pro Ile Glu Lys Thr Ile Ser
                        340                 345                 350

Lys Thr Lys Gly Gln Pro Arg Glu Pro Gln Val Tyr Thr Leu Pro Pro
                    355                 360                 365

Ser Arg Glu Glu Met Thr Lys Asn Gln Val Ser Leu Thr Cys Leu Val
                370                 375                 380

Lys Gly Phe Tyr Pro Ser Asp Ile Ala Val Glu Trp Glu Ser Asn Gly
        385                 390                 395                 400

Gln Pro Glu Asn Asn Tyr Lys Thr Thr Pro Pro Met Leu Asp Ser Asp
                        405                 410                 415

Gly Ser Phe Phe Leu Tyr Ser Lys Leu Thr Val Asp Lys Ser Arg Trp
                        420                 425                 430

Gln Gln Gly Asn Val Phe Ser Cys Ser Val Met His Glu Ala Leu His
                    435                 440                 445

Asn His Tyr Thr Gln Lys Ser Leu Ser Leu Ser Pro Gly Lys
                450                 455                 460

<210> SEQ ID NO 212
<211> LENGTH: 318
<212> TYPE: DNA
<213> ORGANISM: Homo sapiens
```

<400> SEQUENCE: 212

```
tatgagctga ctcagccacc ctcagtgtcc gtgtccccag gacagacagc cagcctcacc    60
tgctctggag ataaattggg ggatagatat gcttcctggt atcagcagaa gccaggccag   120
tcccctgtgc tggtcatcta tcaagatagc aagcggccct cagggatccc tgagcgattc   180
tctggctcca actctgggaa cacagccact ctgaccatca gcgggaccca ggctatggat   240
gaggctgact attactgtca ggcgtgggac agcagcactg catctgtctt cggaactggg   300
accaaggtca ccgtccta                                                 318
```

<210> SEQ ID NO 213
<211> LENGTH: 106
<212> TYPE: PRT
<213> ORGANISM: Homo sapiens

<400> SEQUENCE: 213

```
Tyr Glu Leu Thr Gln Pro Pro Ser Val Ser Val Ser Pro Gly Gln Thr
1               5                   10                  15

Ala Ser Leu Thr Cys Ser Gly Asp Lys Leu Gly Asp Arg Tyr Ala Ser
            20                  25                  30

Trp Tyr Gln Gln Lys Pro Gly Gln Ser Pro Val Leu Val Ile Tyr Gln
        35                  40                  45

Asp Ser Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Asp Ser Ser Thr Ala Ser Val
                85                  90                  95

Phe Gly Thr Gly Thr Lys Val Thr Val Leu
            100                 105
```

<210> SEQ ID NO 214
<211> LENGTH: 11
<212> TYPE: PRT
<213> ORGANISM: Homo sapiens

<400> SEQUENCE: 214

```
Ser Gly Asp Lys Leu Gly Asp Arg Tyr Ala Ser
1               5                   10
```

<210> SEQ ID NO 215
<211> LENGTH: 7
<212> TYPE: PRT
<213> ORGANISM: Homo sapiens

<400> SEQUENCE: 215

```
Gln Asp Ser Lys Arg Pro Ser
1               5
```

<210> SEQ ID NO 216
<211> LENGTH: 10
<212> TYPE: PRT
<213> ORGANISM: Homo sapiens

<400> SEQUENCE: 216

```
Gln Ala Trp Asp Ser Ser Thr Ala Ser Val
1               5                   10
```

<210> SEQ ID NO 217

<211> LENGTH: 702
<212> TYPE: DNA
<213> ORGANISM: Homo sapiens

<400> SEQUENCE: 217

```
atggacatga gggtgcccgc tcagctcctg gggctcctgc tgctgtggct gagaggtgcc      60
agatgttatg agctgactca gccaccctca gtgtccgtgt ccccaggaca gacagccagc    120
ctcacctgct ctggagataa attgggggat agatatgctt cctggtatca gcagaagcca    180
ggccagtccc ctgtgctggt catctatcaa gatagcaagc ggccctcagg gatccctgag    240
cgattctctg gctccaactc tgggaacaca gccactctga ccatcagcgg gacccaggct    300
atggatgagg ctgactatta ctgtcaggcg tgggacagca gcactgcatc tgtcttcgga    360
actgggacca aggtcaccgt cctaggtcag cccaaggcca accccactgt cactctgttc    420
ccgccctcct ctgaggagct ccaagccaac aaggccacac tagtgtgtct gatcagtgac    480
ttctacccgg gagctgtgac agtggcctgg aaggcagatg gcagcccgt caaggcggga    540
gtggagacca ccaaaccctc aaacagagc aacaacaagt acgcggccag cagctacctg    600
agcctgacgc ccgagcagtg gaagtcccac agaagctaca gctgccaggt cacgcatgaa    660
gggagcaccg tggagaagac agtggcccct acagaatgtt ca                      702
```

<210> SEQ ID NO 218
<211> LENGTH: 234
<212> TYPE: PRT
<213> ORGANISM: Homo sapiens

<400> SEQUENCE: 218

```
Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Ser Leu Thr Cys Ser Gly Asp Lys Leu
        35                  40                  45

Gly Asp Arg Tyr Ala Ser Trp Tyr Gln Gln Lys Pro Gly Gln Ser Pro
    50                  55                  60

Val Leu Val Ile Tyr Gln Asp Ser Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Tyr Cys Gln Ala Trp Asp
            100                 105                 110

Ser Ser Thr Ala Ser Val Phe Gly Thr Gly Thr Lys Val Thr Val Leu
        115                 120                 125

Gly Gln Pro Lys Ala Asn Pro Thr Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Gly Ser Pro
                165                 170                 175

Val Lys Ala Gly Val Glu Thr Thr Lys Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220
```

```
Glu Lys Thr Val Ala Pro Thr Glu Cys Ser
225                 230
```

<210> SEQ ID NO 219
<211> LENGTH: 702
<212> TYPE: DNA
<213> ORGANISM: Homo sapiens

<400> SEQUENCE: 219

```
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcaactact tagcctggta ccagcagaaa     180
cctggccagg ctcccaggct cctcatctat ggtgcatcca gcagggccac tggcatccca     240
gacaggttca gtggcagtgg gtctgggaca gacttcactc tcatcatcag cagactggag     300
cctgaagatt ttgtagtgta ttactgtcag cagtatggta gctcactcac tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gt                        702
```

<210> SEQ ID NO 220
<211> LENGTH: 234
<212> TYPE: PRT
<213> ORGANISM: Homo sapiens

<400> SEQUENCE: 220

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Asn Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Ile Ile
                85                  90                  95

Ser Arg Leu Glu Pro Glu Asp Phe Val Val Tyr Tyr Cys Gln Gln Tyr
            100                 105                 110

Gly Ser Ser Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 221
<211> LENGTH: 1401
<212> TYPE: DNA
<213> ORGANISM: Homo sapiens

<400> SEQUENCE: 221

| | | | | | |
|---|---|---|---|---|---|
| atggactgga | cctggagcat | ccttttcttg | gtggcagcag | caacaggtgc | ccactcccag | 60 |
| gttcagctgg | tgcagtctgg | agatgaggtg | aagaagcctg | gggcctcagt | gaaggtctcc | 120 |
| tgcaaggctt | ctggttacac | ctttatcaag | tatggaatca | gttgggtgcg | acaggcccct | 180 |
| ggacaagggc | ttgagtggat | gggatggatc | ggcgctttca | atggtaacac | agactatgca | 240 |
| cggaacctcc | aggccagagt | caccatgacc | acagacacat | ccacgagcac | agcctacatg | 300 |
| gagctgagga | gcctgagatc | tgacgacacg | gccgtatatt | actgtgcgag | agagggctgg | 360 |
| aacgacgact | acttctgcgg | tttggacgtc | tggggccaag | ggaccacggt | caccgtctcc | 420 |
| tcagcctcca | ccaagggccc | atcggtcttc | cccctggcgc | cctgctccag | gagcacctcc | 480 |
| gagagcacag | cggccctggg | ctgcctggtc | aaggactact | tccccgaacc | ggtgacggtg | 540 |
| tcgtggaact | caggcgctct | gaccagcggc | gtgcacacct | tcccagctgt | cctacagtcc | 600 |
| tcaggactct | actccctcag | cagcgtggtg | accgtgccct | ccagcaactt | cggcacccag | 660 |
| acctacacct | gcaacgtaga | tcacaagccc | agcaacacca | aggtggacaa | gacagttgag | 720 |
| cgcaaatgtt | gtgtcgagtg | cccaccgtgc | ccagcaccac | ctgtggcagg | accgtcagtc | 780 |
| ttcctcttcc | ccccaaaacc | caaggacacc | ctcatgatct | cccggacccc | tgaggtcacg | 840 |
| tgcgtggtgg | tggacgtgag | ccacgaagac | cccgaggtcc | agttcaactg | gtacgtggac | 900 |
| ggcgtggagg | tgcataatgc | caagacaaag | ccacgggagg | agcagttcaa | cagcacgttc | 960 |
| cgtgtggtca | gcgtcctcac | cgttgtgcac | caggactggc | tgaacggcaa | ggagtacaag | 1020 |
| tgcaaggtct | ccaacaaagg | cctcccagcc | cccatcgaga | aaaccatctc | caaaaccaaa | 1080 |
| gggcagcccc | gagaaccaca | ggtgtacacc | ctgcccccat | cccgggagga | gatgaccaag | 1140 |
| aaccaggtca | gcctgacctg | cctggtcaaa | ggcttctacc | ccagcgacat | cgccgtggag | 1200 |
| tgggagagca | atgggcagcc | ggagaacaac | tacaagacca | cacctcccat | gctggactcc | 1260 |
| gacggctcct | tcttcctcta | cagcaagctc | accgtggaca | agagcaggtg | gcagcagggg | 1320 |
| aacgtcttct | catgctccgt | gatgcatgag | gctctgcaca | accactacac | gcagaagagc | 1380 |
| ctctccctgt | ctccgggtaa | a | | | | 1401 |

<210> SEQ ID NO 222
<211> LENGTH: 467
<212> TYPE: PRT
<213> ORGANISM: Homo sapiens

<400> SEQUENCE: 222

Met Asp Trp Thr Trp Ser Ile Leu Phe Leu Val Ala Ala Ala Thr Gly
1               5                   10                  15

Ala His Ser Gln Val Gln Leu Val Gln Ser Gly Asp Glu Val Lys Lys
            20                  25                  30

```
Pro Gly Ala Ser Val Lys Val Ser Cys Lys Ala Ser Gly Tyr Thr Phe
            35                  40                  45

Ile Lys Tyr Gly Ile Ser Trp Val Arg Gln Ala Pro Gly Gln Gly Leu
    50                  55                  60

Glu Trp Met Gly Trp Ile Gly Ala Phe Asn Gly Asn Thr Asp Tyr Ala
65                  70                  75                  80

Arg Asn Leu Gln Ala Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Gly Trp Asn Asp Asp Tyr Phe Cys Gly Leu
            115                 120                 125

Asp Val Trp Gly Gln Gly Thr Thr Val Thr Val Ser Ser Ala Ser Thr
            130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
            210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Gln Phe Asn Trp Tyr Val Asp Gly Val Glu Val
            290                 295                 300

His Asn Ala Lys Thr Lys Pro Arg Glu Glu Gln Phe Asn Ser Thr Phe
305                 310                 315                 320

Arg Val Val Ser Val Leu Thr Val His Gln Asp Trp Leu Asn Gly
                325                 330                 335

Lys Glu Tyr Lys Cys Lys Val Ser Asn Lys Gly Leu Pro Ala Pro Ile
                340                 345                 350

Glu Lys Thr Ile Ser Lys Thr Lys Gly Gln Pro Arg Glu Pro Gln Val
                355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445
```

His Glu Ala Leu His Asn His Tyr Thr Gln Lys Ser Leu Ser Leu Ser
     450                 455                 460

Pro Gly Lys
465

<210> SEQ ID NO 223
<211> LENGTH: 318
<212> TYPE: DNA
<213> ORGANISM: Homo sapiens

<400> SEQUENCE: 223

```
tatgagctga ctcagccacc ctcagtgtcc gtgtcccag  gacagacagc caccatcacc    60
tgctctggag ataaattggg ggaaagatat gcgtcttggt atcagcagag gccaggccag   120
tcccctgtac tggtcatcta tcaagatatc aagcggccct cagggatccc tgagcgattc   180
tctggctcca actctgggaa cacagccact ctgaccatca gcgggaccca ggctatggat   240
gaggctgact atttctgtca ggcgtggtac agcagcacca atgtgctttt cggcggaggg   300
accaagctga ccgtccta                                                 318
```

<210> SEQ ID NO 224
<211> LENGTH: 106
<212> TYPE: PRT
<213> ORGANISM: Homo sapiens

<400> SEQUENCE: 224

Tyr Glu Leu Thr Gln Pro Pro Ser Val Ser Val Ser Pro Gly Gln Thr
1               5                   10                  15

Ala Thr Ile Thr Cys Ser Gly Asp Lys Leu Gly Glu Arg Tyr Ala Ser
            20                  25                  30

Trp Tyr Gln Gln Arg Pro Gly Gln Ser Pro Val Leu Val Ile Tyr Gln
        35                  40                  45

Asp Ile Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Phe Cys Gln Ala Trp Tyr Ser Ser Thr Asn Val Leu
                85                  90                  95

Phe Gly Gly Gly Thr Lys Leu Thr Val Leu
            100                 105

<210> SEQ ID NO 225
<211> LENGTH: 11
<212> TYPE: PRT
<213> ORGANISM: Homo sapiens

<400> SEQUENCE: 225

Ser Gly Asp Lys Leu Gly Glu Arg Tyr Ala Ser
1               5                   10

<210> SEQ ID NO 226
<211> LENGTH: 7
<212> TYPE: PRT
<213> ORGANISM: Homo sapiens

<400> SEQUENCE: 226

Gln Asp Ile Lys Arg Pro Ser
1               5

<210> SEQ ID NO 227

```
<211> LENGTH: 10
<212> TYPE: PRT
<213> ORGANISM: Homo sapiens

<400> SEQUENCE: 227

Gln Ala Trp Tyr Ser Ser Thr Asn Val Leu
1               5                   10

<210> SEQ ID NO 228
<211> LENGTH: 702
<212> TYPE: DNA
<213> ORGANISM: Homo sapiens

<400> SEQUENCE: 228
atggacatga gggtgcccgc tcagctcctg gggctcctgc tgctgtggct gagaggtgcc      60
agatgttatg agctgactca gccaccctca gtgtccgtgt ccccaggaca gacagccacc     120
atcacctgct ctggagataa attgggggaa agatatgcgt cttggtatca gcagaggcca     180
ggccagtccc ctgtactggt catctatcaa gatatcaagc ggccctcagg gatccctgag     240
cgattctctg gctccaactc tgggaacaca gccactctga ccatcagcgg acccaggct     300
atggatgagg ctgactattt ctgtcaggcg tggtacagca gcaccaatgt gcttttcggc     360
ggagggacca agctgaccgt cctaggtcag cccaaggctg cccctcggt cactctgttc      420
ccgccctcct ctgaggagct tcaagccaac aaggccacac tggtgtgtct cataagtgac     480
ttctacccgg agccgtgac agtggcctgg aaggcagata gcagcccgt caaggcggga      540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702

<210> SEQ ID NO 229
<211> LENGTH: 234
<212> TYPE: PRT
<213> ORGANISM: Homo sapiens

<400> SEQUENCE: 229

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Thr Ile Thr Cys Ser Gly Asp Lys Leu
        35                  40                  45

Gly Glu Arg Tyr Ala Ser Trp Tyr Gln Gln Arg Pro Gly Gln Ser Pro
    50                  55                  60

Val Leu Val Ile Tyr Gln Asp Ile Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Phe Cys Gln Ala Trp Tyr
            100                 105                 110

Ser Ser Thr Asn Val Leu Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160
```

```
Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 230
<211> LENGTH: 696
<212> TYPE: DNA
<213> ORGANISM: Homo sapiens

<400> SEQUENCE: 230

```
atggcatgga tccctctctt cctcggcgtc cttgcttact gcacaggatc cgtggcctcc      60
tatgagctga ctcagccacc ctcagtgtcc gtgtccccag acagacagc cagcctcacc     120
tgctctggag ataaaattgg ggatagatat gcttcctggt atcagcagaa gccaggccag     180
tcccctgtgc tggtcatcta tcaagatagc aagcggccct cagggatccc tgagcgattc     240
tctggctcca actctgggaa cacagccact ctgaccatca gcgggaccca ggctatggat     300
gaggctgact attactgtca ggcgtgggac agcagcactg catgtgtctt cggaactggg     360
accaaggtca ccgtcctagg tcagcccaag gccaaccca ctgtcactct gttcccgccc     420
tcctctgagg agctccaagc caacaaggcc acactagtgt gtctgatcag tgacttctac     480
ccgggagctg tgacagtggc ctggaaggca gatggcagcc ccgtcaaggc gggagtggag     540
accaccaaac cctccaaaca gagcaacaac aagtacgcgg ccagcagcta cctgagcctg     600
acgcccgagc agtggaagtc ccacagaagc tacagctgcc aggtcacgca tgaagggagc     660
accgtggaga agacagtggc ccctacagaa tgttca                              696
```

<210> SEQ ID NO 231
<211> LENGTH: 232
<212> TYPE: PRT
<213> ORGANISM: Homo sapiens

<400> SEQUENCE: 231

```
Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Ser Leu Thr Cys Ser Gly Asp Lys Leu Gly Asp
        35                  40                  45

Arg Tyr Ala Ser Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110

Thr Ala Cys Val Phe Gly Thr Gly Thr Lys Val Thr Val Leu Gly Gln
        115                 120                 125
```

```
Pro Lys Ala Asn Pro Thr Val Thr Leu Phe Pro Pro Ser Ser Glu Glu
        130                 135                 140
Leu Gln Ala Asn Lys Ala Thr Leu Val Cys Leu Ile Ser Asp Phe Tyr
145                 150                 155                 160
Pro Gly Ala Val Thr Val Ala Trp Lys Ala Asp Gly Ser Pro Val Lys
                165                 170                 175
Ala Gly Val Glu Thr Thr Lys Pro Ser Lys Gln Ser Asn Asn Lys Tyr
            180                 185                 190
Ala Ala Ser Ser Tyr Leu Ser Leu Thr Pro Glu Gln Trp Lys Ser His
        195                 200                 205
Arg Ser Tyr Ser Cys Gln Val Thr His Glu Gly Ser Thr Val Glu Lys
    210                 215                 220
Thr Val Ala Pro Thr Glu Cys Ser
225                 230

<210> SEQ ID NO 232
<211> LENGTH: 1398
<212> TYPE: DNA
<213> ORGANISM: Homo sapiens

<400> SEQUENCE: 232
atggagtttg ggctgagctg ggttttcctc gttgctcttt taagaggtgt ccagtgtcag      60
gtgcagctgg tggagtctgg gggaggcgtg gtccagcctg gaggtccct  gagactctcc    120
tgtgcagcgt ctggattcac cctcagtagc tatggcatgc actgggtccg ccaggctcca    180
ggcaaggggc tggagtgggt ggcagttata tggtatgatg aaagtaataa atactatgca    240
gactccgtga agggccgatt caccatctcc agagacaatt ccaagaacac gttgaatctg    300
caaatgaaca gcctgagagc cgaggacacg gctttgtatt actgtgcgag agccggtata    360
gcagcagccc ttgatgcttt tgatatctgg ggccaaggga caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcacccctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                 1398

<210> SEQ ID NO 233
```

```
<211> LENGTH: 466
<212> TYPE: PRT
<213> ORGANISM: Homo sapiens

<400> SEQUENCE: 233

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Leu
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Asn Leu Gln Met Asn Ser Leu Arg Ala Glu Asp Thr Ala Leu
            100                 105                 110

Tyr Tyr Cys Ala Arg Ala Gly Ile Ala Ala Leu Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
```

385                 390                 395                 400
Glu Ser Asn Gly Gln Pro Glu Asn Asn Tyr Lys Thr Thr Pro Pro Met
                    405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
        450                 455                 460

Gly Lys
465

<210> SEQ ID NO 234
<211> LENGTH: 318
<212> TYPE: DNA
<213> ORGANISM: Homo sapiens

<400> SEQUENCE: 234
tatgagctga ctcagccacc ctcagtgtcc gtgtccccag gacagacagc caccatcacc      60
tgctctggag ataaattggg ggaaagatat gcgtcttggt atcagcagag gccaggccag     120
tcccctgtac tggtcatcta tcaagatagc aagcggccct cagggatccc tgagcgattc     180
tctggctcca actctgggaa cacagccact ctgaccatca gcgggaccca ggctatggat     240
gaggctgact atttctgtca ggcgtggtac agcagcacca atgtgctttt cggcggaggg     300
accaagctga ccgtccta                                                   318

<210> SEQ ID NO 235
<211> LENGTH: 106
<212> TYPE: PRT
<213> ORGANISM: Homo sapiens

<400> SEQUENCE: 235

Tyr Glu Leu Thr Gln Pro Pro Ser Val Ser Val Ser Pro Gly Gln Thr
1               5                   10                  15

Ala Thr Ile Thr Cys Ser Gly Asp Lys Leu Gly Glu Arg Tyr Ala Ser
            20                  25                  30

Trp Tyr Gln Gln Arg Pro Gly Gln Ser Pro Val Leu Val Ile Tyr Gln
        35                  40                  45

Asp Ser Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Phe Cys Gln Ala Trp Tyr Ser Ser Thr Asn Val Leu
                85                  90                  95

Phe Gly Gly Gly Thr Lys Leu Thr Val Leu
            100                 105

<210> SEQ ID NO 236
<211> LENGTH: 11
<212> TYPE: PRT
<213> ORGANISM: Homo sapiens

<400> SEQUENCE: 236

Ser Gly Asp Lys Leu Gly Glu Arg Tyr Ala Ser
1               5                   10

<210> SEQ ID NO 237

```
<211> LENGTH: 7
<212> TYPE: PRT
<213> ORGANISM: Homo sapiens

<400> SEQUENCE: 237

Gln Asp Ser Lys Arg Pro Ser
1               5

<210> SEQ ID NO 238
<211> LENGTH: 10
<212> TYPE: PRT
<213> ORGANISM: Homo sapiens

<400> SEQUENCE: 238

Gln Ala Trp Tyr Ser Ser Thr Asn Val Leu
1               5                   10

<210> SEQ ID NO 239
<211> LENGTH: 702
<212> TYPE: DNA
<213> ORGANISM: Homo sapiens

<400> SEQUENCE: 239
```

| | | | | | |
|---|---|---|---|---|---|
| atggacatga | gggtgcccgc | tcagctcctg | gggctcctgc | tgctgtggct | gagaggtgcc    60 |
| agatgttatg | agctgactca | gccaccctca | gtgtccgtgt | ccccaggaca | gacagccacc   120 |
| atcacctgct | ctggagataa | attgggggaa | agatatgcgt | cttggtatca | gcagaggcca   180 |
| ggccagtccc | ctgtactggt | catctatcaa | gatagcaagc | ggccctcagg | gatccctgag   240 |
| cgattctctg | gctccaactc | tgggaacaca | gccactctga | ccatcagcgg | gacccaggct   300 |
| atggatgagg | ctgactattt | ctgtcaggcg | tggtacagca | gcaccaatgt | gcttttcggc   360 |
| ggagggacca | agctgaccgt | cctaggtcag | cccaaggctg | ccccctcggt | cactctgttc   420 |
| ccgccctcct | ctgaggagct | tcaagccaac | aaggccacac | tggtgtgtct | cataagtgac   480 |
| ttctacccgg | gagccgtgac | agtggcctgg | aaggcagata | gcagccccgt | caaggcggga   540 |
| gtggagacca | ccacaccctc | caaacaaagc | aacaacaagt | acgcggccag | cagctatctg   600 |
| agcctgacgc | ctgagcagtg | gaagtcccac | agaagctaca | gctgccaggt | cacgcatgaa   660 |
| gggagcaccg | tggagaagac | agtggcccct | acagaatgtt | ca         702 |

```
<210> SEQ ID NO 240
<211> LENGTH: 234
<212> TYPE: PRT
<213> ORGANISM: Homo sapiens

<400> SEQUENCE: 240

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
                20                  25                  30

Val Ser Pro Gly Gln Thr Ala Thr Ile Thr Cys Ser Gly Asp Lys Leu
            35                  40                  45

Gly Glu Arg Tyr Ala Ser Trp Tyr Gln Gln Arg Pro Gly Gln Ser Pro
        50                  55                  60

Val Leu Val Ile Tyr Gln Asp Ser Lys Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Gly Thr Gln Ala Met Asp Glu Ala Asp Tyr Phe Cys Gln Ala Trp Tyr
```

```
                        100                 105                 110
Ser Ser Thr Asn Val Leu Phe Gly Gly Thr Lys Leu Thr Val Leu
        115                 120                 125

Gly Gln Pro Lys Ala Ala Pro Ser Val Thr Leu Phe Pro Pro Ser Ser
130                 135                 140

Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
        180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

<210> SEQ ID NO 241
<211> LENGTH: 708
<212> TYPE: DNA
<213> ORGANISM: Homo sapiens

<400> SEQUENCE: 241

```
atggcctggt ctcctctcct cctcactctc ctcgctcact gcacagggtc ctgggcccag    60
tctgtgttga cgcagccgcc ctcactgtct ggggccccag gcagagggt caccatctcc    120
tgcactgggg gcagctccaa catcgggtca ggttttgcta tatactggta ccagcagctt    180
ccaggaacag cccccaaact cctcatctat ggtgacaaca tcggccctc aggggtccct    240
gaccgattct ctggctccaa gtctggcacc tccgcctccc tggccatcac tgggctccag    300
gctgaggatg aggctgatta ttactgccag tcctatgaca gcagcctgag tggttcggta    360
ttcggcggag ggaccaagct gaccgtccta agtcagccca aggctgcccc ctcggtcact    420
ctgttcccgc cctcctctga ggagcttcaa gccaacaagg ccacactggt gtgtctcata    480
agtgacttct acccgggagc cgtgacagtg gcctggaagg cagatagcag ccccgtcaag    540
gcgggagtgg agaccaccac accctccaaa caaagcaaca acaagtacgc ggccagcagc    600
tatctgagcc tgacgcctga gcagtggaag tcccacagaa gctacagctg ccaggtcacg    660
catgaaggga gcaccgtgga agacagtg ccccctacag aatgttca                    708
```

<210> SEQ ID NO 242
<211> LENGTH: 236
<212> TYPE: PRT
<213> ORGANISM: Homo sapiens

<400> SEQUENCE: 242

```
Met Ala Trp Ser Pro Leu Leu Leu Thr Leu Leu Ala His Cys Thr Gly
1               5                   10                  15

Ser Trp Ala Gln Ser Val Leu Thr Gln Pro Pro Ser Leu Ser Gly Ala
            20                  25                  30

Pro Gly Gln Arg Val Thr Ile Ser Cys Thr Gly Gly Ser Ser Asn Ile
        35                  40                  45

Gly Ser Gly Phe Ala Ile Tyr Trp Tyr Gln Gln Leu Pro Gly Thr Ala
    50                  55                  60

Pro Lys Leu Leu Ile Tyr Gly Asp Asn Ile Arg Pro Ser Gly Val Pro
```

```
                65                  70                  75                  80
Asp Arg Phe Ser Gly Ser Lys Ser Gly Thr Ser Ala Ser Leu Ala Ile
                    85                  90                  95

Thr Gly Leu Gln Ala Glu Asp Glu Ala Asp Tyr Tyr Cys Gln Ser Tyr
                100                 105                 110

Asp Ser Ser Leu Ser Gly Ser Val Phe Gly Gly Gly Thr Lys Leu Thr
                115                 120                 125

Val Leu Ser Gln Pro Lys Ala Ala Pro Ser Val Thr Leu Phe Pro Pro
        130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
                180                 185                 190

Asn Asn Lys Tyr Ala Ala Ser Ser Tyr Leu Ser Leu Thr Pro Glu Gln
                195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser
225                 230                 235

<210> SEQ ID NO 243
<211> LENGTH: 1329
<212> TYPE: DNA
<213> ORGANISM: Homo sapiens

<400> SEQUENCE: 243
caggttcagc tggtgcagtc tggagctgag gtgaagaagc tggggcctc  agtgaaggtc      60 tcctgcaagg cttctggtta cacctttacc agctatggta tcagctgggt gcgacaggcc    120
cctggacaag gcttgagtg gatgggatgg atcagcgctt acaatggtga  acaaacact     180 gcacagaaac tccagggcag agtcaccatg accacagaca catccacgag cacagcctac    240
atggagctga ggagcctgag atctgacgac acggccgtgt attactgtgc gagagaggaa    300
ctaggggctt ttgatatctg gggccaaggg acaatggtca ccgtctcttc agcctccacc    360
aagggcccat cggtcttccc cctggcgccc tgctccagga gcacctccga gagcacagcg    420
gccctgggct gcctggtcaa ggactacttc cccgaaccgg tgacggtgtc gtggaactca    480
ggcgctctga ccagcggcgt gcacaccttc ccagctgtcc tacagtcctc aggactctac    540
tccctcagca gcgtggtgac cgtgccctcc agcaacttcg gcacccagac ctacacctgc    600
aacgtagatc acaagcccag caacaccaag gtggacaaga cagttgagcg caaatgttgt    660
gtcgagtgcc caccgtgccc agcaccacct gtggcaggac cgtcagtctt cctcttcccc    720
ccaaaaccca aggacaccct catgatctcc cggacccctg aggtcacgtg cgtggtggtg    780
gacgtgagcc acgaagaccc cgaggtccag ttcaactggt acgtggacgg cgtggaggtg    840
cataatgcca agacaaagcc acgggaggag cagttcaaca gcacgttccg tgtggtcagc    900
gtcctcaccg ttgtgcacca ggactggctg aacggcaagg agtacaagtg caaggtctcc    960
aacaaaggcc tcccagcccc catcgagaaa accatctcca aaccaaagg  gcagccccga   1020 gaaccacagg tgtacaccct gcccccatcc cgggaggaga tgaccaagaa  ccaggtcagc   1080
ctgacctgcc tggtcaaagg cttctacccc agcgacatcg ccgtggagtg ggagagcaat    1140
gggcagccgg agaacaacta caagaccaca cctcccatgc tggactccga cggctccttc    1200
```

```
ttcctctaca gcaagctcac cgtggacaag agcaggtggc agcagggaa cgtcttctca    1260 tgctccgtga tgcatgaggc tctgcacaac cactacacgc agaagagcct ctccctgtct    1320
ccgggtaaa                                                              1329
```

<210> SEQ ID NO 244
<211> LENGTH: 443
<212> TYPE: PRT
<213> ORGANISM: Homo sapiens

<400> SEQUENCE: 244

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Glu Thr Asn Thr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Glu Glu Leu Gly Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
```

```
            340              345                350
Glu Met Thr Lys Asn Gln Val Ser Leu Thr Cys Leu Val Lys Gly Phe
           355                  360              365

Tyr Pro Ser Asp Ile Ala Val Glu Trp Glu Ser Asn Gly Gln Pro Glu
       370                  375              380

Asn Asn Tyr Lys Thr Thr Pro Pro Met Leu Asp Ser Asp Gly Ser Phe
385                  390              395                  400

Phe Leu Tyr Ser Lys Leu Thr Val Asp Lys Ser Arg Trp Gln Gln Gly
               405                  410              415

Asn Val Phe Ser Cys Ser Val Met His Glu Ala Leu His Asn His Tyr
                   420              425              430

Thr Gln Lys Ser Leu Ser Leu Ser Pro Gly Lys
               435                  440

<210> SEQ ID NO 245
<211> LENGTH: 318
<212> TYPE: DNA
<213> ORGANISM: Homo sapiens

<400> SEQUENCE: 245
tatgagctga ctcagccccc ctcagtgtcc gtgtccccag gacagacagc cagcatcacc      60
tgttctggag ataaaatggg ggaaagatat gcttcctggt atcagcagaa gccaggccag     120
tcccctatac tggtcatcta tcaagatacc aagcggccct cagggatccc tgagcgattc     180
tctggctcca actctgggaa cacagccact ctgaccatca gcgggaccca ggctatggat     240
gaggctgact attactgtca ggcgtggtac agcagcacca atgtggtatt cggcggaggg     300
accaagctga ccgtccta                                                   318

<210> SEQ ID NO 246
<211> LENGTH: 106
<212> TYPE: PRT
<213> ORGANISM: Homo sapiens

<400> SEQUENCE: 246

Tyr Glu Leu Thr Gln Pro Pro Ser Val Ser Val Ser Pro Gly Gln Thr
1               5                  10                  15

Ala Ser Ile Thr Cys Ser Gly Asp Lys Met Gly Glu Arg Tyr Ala Ser
            20                  25                  30

Trp Tyr Gln Gln Lys Pro Gly Gln Ser Pro Ile Leu Val Ile Tyr Gln
        35                  40                  45

Asp Thr Lys Arg Pro Ser Gly Ile Pro Glu Arg Phe Ser Gly Ser Asn
    50                  55                  60

Ser Gly Asn Thr Ala Thr Leu Thr Ile Ser Gly Thr Gln Ala Met Asp
65                  70                  75                  80

Glu Ala Asp Tyr Tyr Cys Gln Ala Trp Tyr Ser Ser Thr Asn Val Val
                85                  90                  95

Phe Gly Gly Gly Thr Lys Leu Thr Val Leu
            100                 105

<210> SEQ ID NO 247
<211> LENGTH: 11
<212> TYPE: PRT
<213> ORGANISM: Homo sapiens

<400> SEQUENCE: 247

Ser Gly Asp Lys Met Gly Glu Arg Tyr Ala Ser
1               5                  10
```

<210> SEQ ID NO 248
<211> LENGTH: 7
<212> TYPE: PRT
<213> ORGANISM: Homo sapiens

<400> SEQUENCE: 248

Gln Asp Thr Lys Arg Pro Ser
1               5

<210> SEQ ID NO 249
<211> LENGTH: 10
<212> TYPE: PRT
<213> ORGANISM: Homo sapiens

<400> SEQUENCE: 249

Gln Ala Trp Tyr Ser Ser Thr Asn Val Val
1               5                   10

<210> SEQ ID NO 250
<211> LENGTH: 702
<212> TYPE: DNA
<213> ORGANISM: Homo sapiens

<400> SEQUENCE: 250

```
atggacatga gggtgcccgc tcagctcctg gggctcctgc tgctgtggct gagaggtgcc      60
agatgttatg agctgactca gccccctca gtgtccgtgt ccccaggaca gacagccagc     120
atcacctgtt ctggagataa aatgggggaa agatatgctt cctggtatca gcagaagcca     180
ggccagtccc ctatactggt catctatcaa gataccaagc ggccctcagg gatccctgag     240
cgattctctg gctccaactc tgggaacaca gccactctga ccatcagcgg gacccaggct     300
atggatgagg ctgactatta ctgtcaggcg tggtacagca caccaatgt ggtattcggc      360
ggagggacca gcctgaccgt cctaggtcag cccaaggctg cccccctcggt cactctgttc     420
ccgccctcct ctgaggagct tcaagccaac aaggccacac tggtgtgtct cataagtgac     480
ttctacccgg gagccgtgac agtggcctgg aaggcagata gcagcccgt caaggcggga     540
gtggagacca ccacaccctc caaacaaagc aacaacaagt acgcggccag cagctatctg     600
agcctgacgc ctgaacagtg gaagtcccac agaagctaca gctgccaggt cacgcatgaa     660
gggagcaccg tggagaagac agtggcccct acagaatgtt ca                       702
```

<210> SEQ ID NO 251
<211> LENGTH: 234
<212> TYPE: PRT
<213> ORGANISM: Homo sapiens

<400> SEQUENCE: 251

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
            20                  25                  30

Val Ser Pro Gly Gln Thr Ala Ser Ile Thr Cys Ser Gly Asp Lys Met
        35                  40                  45

Gly Glu Arg Tyr Ala Ser Trp Tyr Gln Gln Lys Pro Gly Gln Ser Pro
    50                  55                  60

Ile Leu Val Ile Tyr Gln Asp Thr Lys Arg Pro Ser Gly Ile Pro Glu
65                  70                  75                  80

Arg Phe Ser Gly Ser Asn Ser Gly Asn Thr Ala Thr Leu Thr Ile Ser

```
                    85                  90                  95

Gly Thr Gln Ala Met Asp Glu Ala Asp Tyr Tyr Cys Gln Ala Trp Tyr
            100                 105                 110

Ser Ser Thr Asn Val Val Phe Gly Gly Gly Thr Lys Leu Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 252
<211> LENGTH: 696
<212> TYPE: DNA
<213> ORGANISM: Homo sapiens

<400> SEQUENCE: 252

```
atggcatgga tccctctctt cctcggcgtc cttgcttact gcacaggatc cgtggcctcc    60
tatgagctga ctcagccacc ctcagtgtcc gtgtccccag acagacagc caccatcacc     120
tgctctggag ataaattggg ggaaagatat gcgtgttggt atcagcagag gccaggccag    180
tcccctgtac tggtcatcta tcaagatatc aagcggccct cagggatccc tgagcgattc    240
tctggctcca actctgggaa cacagccact ctgaccatca gcgggaccca ggctatggat    300
gaggctgact atttctgtca ggcgtggtac agcagcacca atgtgctttt cggcggaggg    360
accaagctga ccgtcctagg tcagcccaag gctgccccct cggtcactct gttcccgccc    420
tcctctgagg agcttcaagc caacaaggcc acactggtgt gtctcataag tgacttctac    480
ccgggagccg tgacagtggc ctggaaggca gatagcagcc ccgtcaaggc gggagtggag    540
accaccacac cctccaaaca aagcaacaac aagtacgcgg ccagcagcta tctgagcctg    600
acgcctgagc agtggaagtc ccacagaagc tacagctgcc aggtcacgca tgaagggagc    660
accgtggaga agacagtggc ccctacagaa tgttca                              696
```

<210> SEQ ID NO 253
<211> LENGTH: 232
<212> TYPE: PRT
<213> ORGANISM: Homo sapiens

<400> SEQUENCE: 253

```
Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Thr Ile Thr Cys Ser Gly Asp Lys Leu Gly Glu
        35                  40                  45

Arg Tyr Ala Cys Trp Tyr Gln Gln Arg Pro Gly Gln Ser Pro Val Leu
```

```
              50                  55                  60
Val Ile Tyr Gln Asp Ile Lys Arg Pro Ser Gly Ile Pro Glu Arg Phe
 65                  70                  75                  80

Ser Gly Ser Asn Ser Gly Asn Thr Ala Thr Leu Thr Ile Ser Gly Thr
                 85                  90                  95

Gln Ala Met Asp Glu Ala Asp Tyr Phe Cys Gln Ala Trp Tyr Ser Ser
            100                 105                 110

Thr Asn Val Leu Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 254
<211> LENGTH: 1398
<212> TYPE: DNA
<213> ORGANISM: Homo sapiens

<400> SEQUENCE: 254
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120 tgtgcagcgt ctggattcac cttcagtagc tatggcatgc actgggtccg ccaggctcca     180 ggcaagggc tggagtgggt ggcagttata tggtatgctg aaagtaataa atactacgca     240
gactccgtga agggccgatt caccatctcc agagacaatt ccaagaacac gctgtatctg     300
caaatgaaca gcctgagagc cgaggacacg gctgtgtatt actgtgcgag agcccaggag     360
ggtatagccc tgacgctttt tgatatctgg ggccaaggaa caatggtcac cgtctcttca     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgccctcca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggacccctga ggtcacgtgc     840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggcct cccagccccc atcgagaaaa ccatctccaa aaccaaaggg    1080
```

```
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                  1398

<210> SEQ ID NO 255
<211> LENGTH: 466
<212> TYPE: PRT
<213> ORGANISM: Homo sapiens

<400> SEQUENCE: 255

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Ile Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320
```

```
Val Val Ser Val Leu Thr Val His Gln Asp Trp Leu Asn Gly Lys
            325                 330                 335

Glu Tyr Lys Cys Lys Val Ser Asn Lys Gly Leu Pro Ala Pro Ile Glu
        340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 256
<211> LENGTH: 696
<212> TYPE: DNA
<213> ORGANISM: Homo sapiens

<400> SEQUENCE: 256
atggcatgga tccctctctt cctcggcgtc cttgcttact gcacaggatc cgtggcctcc      60
tatgagctga ctcagccacc ctcagtgtcc gtgtccccag gacagacagc caccatcacc     120
tgctctggag ataaaattgg ggaaagatat gcgtgttggt atcagcagag gccaggccag     180
tcccctgtac tggtcatcta tcaagatagc aagcggccct cagggatccc tgagcgattc     240
tctggctcca actctgggaa cacagccact ctgaccatca gcgggaccca ggctatggat     300
gaggctgact atttctgtca ggcgtggtac agcagcacca atgtgctttt cggcggaggg     360
accaagctga ccgtcctagg tcagcccaag gctgccccct cggtcactct gttcccgccc     420
tcctctgagg agcttcaagc caacaaggcc acactggtgt gtctcataag tgacttctac     480
ccgggagccg tgacagtggc ctggaaggca gatagcagcc cgtcaaggc gggagtggag     540 accaccacac cctccaaaca aagcaacaac aagtacgcgg ccagcagcta tctgagcctg     600
acgcctgagc agtggaagtc ccacagaagc tacagctgcc aggtcacgca tgaagggagc     660
accgtggaga agacagtggc ccctacagaa tgttca                              696

<210> SEQ ID NO 257
<211> LENGTH: 232
<212> TYPE: PRT
<213> ORGANISM: Homo sapiens

<400> SEQUENCE: 257

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
            20                  25                  30

Pro Gly Gln Thr Ala Thr Ile Thr Cys Ser Gly Asp Lys Leu Gly Glu
        35                  40                  45
```

Arg Tyr Ala Cys Trp Tyr Gln Gln Arg Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Phe Cys Gln Ala Trp Tyr Ser Ser
            100                 105                 110

Thr Asn Val Leu Phe Gly Gly Gly Thr Lys Leu Thr Val Leu Gly Gln
            115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 258
<211> LENGTH: 1398
<212> TYPE: DNA
<213> ORGANISM: Homo sapiens

<400> SEQUENCE: 258

```
atggagtttg ggctgagctg ggttttcctc gttgctcttt taagaggtgt ccagtgtcag    60
gtgcagctgg tggagtctgg gggaggcgtg gtccagcctg gaggtccct gagactctcc    120 tgtgcagcgt ctggattcac cttcagtagc tatggcatgc actgggtccg ccaggctcca    180
ggcaaggggc tggagtgggt ggcagttata tggtatgctg aaagtaataa atactacgca    240
gactccgtga agggccgatt caccatctcc agagacaatt ccaagaacac gctgtatctg    300
caaatgaaca gcctgagagc cgaggacacg gctgtgtatt actgtgcgag agcccaggag    360
ggtatagccc ctgacgcttt tgatatctgg ggccaaggaa caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tgcaggacc gtcagtcttc    780 ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc    1020
```

-continued

```
aaggtctcca acaaaggcct cccagccccc atcgagaaaa ccatctccaa aaccaaaggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                  1398
```

<210> SEQ ID NO 259
<211> LENGTH: 466
<212> TYPE: PRT
<213> ORGANISM: Homo sapiens

<400> SEQUENCE: 259

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Ile Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300
```

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 260
<211> LENGTH: 705
<212> TYPE: DNA
<213> ORGANISM: Homo sapiens

<400> SEQUENCE: 260
atggcctggg ctccactact ctcaccctc ctcgctcact gcacaggttc ttgggccaat    60
tttatgctga ctcagcccca ctctgtgtcg gagtctccgg ggaagacggt aaccatctcc   120
tgcacccgca gcagtggcag cattgccagc tactatgtgc agtggtacca gcagcgcccg   180
ggcagttccc ccaccactgt gatctatgag gatagccaga ccctctgggg gtccctgat   240 cggttctctg gctccatcga cagctcctcc aactctgcct ccctcaccat ctctggactg   300
aagactgagg acgaggctga ctattattgt cagtcttatg atagcagcaa tgtggtattc   360
ggcggaggga ccaagctgac cgtcctaggt cagcccaagg ctgccccctc ggtcactctg   420
ttcccgccct cctctgagga gcttcaagcc aacaaggcca cactggtgtg tctcataagt   480
gacttctacc cgggagccgt gacagtggcc tggaaggcag atagcagccc cgtcaaggcg   540
ggagtggaga ccaccacacc ctccaaacaa agcaacaaca gtacgcggc cagcagctat   600 ctgagcctga cgcctgagca gtggaagtcc cacagaagct acagctgcca ggtcacgcat   660
gaagggagca ccgtggagaa gacagtggcc cctacagaat gttca              705

<210> SEQ ID NO 261
<211> LENGTH: 235
<212> TYPE: PRT
<213> ORGANISM: Homo sapiens

<400> SEQUENCE: 261

Met Ala Trp Ala Pro Leu Leu Leu Thr Leu Leu Ala His Cys Thr Gly
1               5                   10                  15

Ser Trp Ala Asn Phe Met Leu Thr Gln Pro His Ser Val Ser Glu Ser
            20                  25                  30

Pro Gly Lys Thr Val Thr Ile Ser Cys Thr Arg Ser Ser Gly Ser Ile
            35                  40                  45

Ala Ser Tyr Tyr Val Gln Trp Tyr Gln Gln Arg Pro Gly Ser Ser Pro
 50                  55                  60

Thr Thr Val Ile Tyr Glu Asp Ser Gln Arg Pro Ser Gly Val Pro Asp
65                  70                  75                  80

Arg Phe Ser Gly Ser Ile Asp Ser Ser Ser Asn Ser Ala Ser Leu Thr
                85                  90                  95

Ile Ser Gly Leu Lys Thr Glu Asp Glu Ala Asp Tyr Tyr Cys Gln Ser
            100                 105                 110

Tyr Asp Ser Ser Asn Val Val Phe Gly Gly Gly Thr Lys Leu Thr Val
            115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
            195                 200                 205

Lys Ser His Arg Ser Tyr Ser Cys Gln Val Thr His Glu Gly Ser Thr
            210                 215                 220

Val Glu Lys Thr Val Ala Pro Thr Glu Cys Ser
225                 230                 235

<210> SEQ ID NO 262
<211> LENGTH: 1404
<212> TYPE: DNA
<213> ORGANISM: Homo sapiens

<400> SEQUENCE: 262
atgtctgtct ccttcctcat cttcctgccc gtgctgggcc tcccatgggg tgtcctgtca      60
caggtacagc tgcagcagtc aggtccagga ctggtgaagc cctcgcagac cctctcactc     120
acctgtgcca tctccgggga cagtgtctct agcaacagtg ctgcttggaa ctggatcagg     180
cagtccccat cgagaggcct tgagtggctg gaaggacat actacaggtc caagtggttt      240
aatgattatg cagtatctgt gcaaagtcga ataaccatca cccagacac atccaagaac      300 cagttctccc tgcagctgaa ctctgtgact cccgaggaca cggctgtgta ttactgtgca     360
agagggattg tcttctccta cgctatggac gtctggggcc aagggaccac ggtcaccgtc     420
tcctcagcct ccaccaaggg cccatcggtc ttccccctgg cgccctgctc caggagcacc     480
tccgagagca gcgcggccct gggctgcctg gtcaaggact acttccccga accggtgacg     540
gtgtcgtgga actcaggcgc tctgaccagc ggcgtgcaca ccttcccagc tgtcctacag     600
tcctcaggac tctactccct cagcagcgtg gtgaccgtgc cctccagcaa cttcggcacc     660
cagacctaca cctgcaacgt agatcacaag cccagcaaca ccaaggtgga caagacagtt     720
gagcgcaaat gttgtgtcga gtgcccaccg tgcccagcac cacctgtggc aggaccgtca     780
gtcttcctct tccccccaaa acccaaggac accctcatga tctcccggac ccctgaggtc     840
acgtgcgtgg tggtggacgt gagccacgaa gaccccgagg tccagttcaa ctggtacgtg     900
gacggcgtgg aggtgcataa tgccaagaca aagccacggg aggagcagtt caacagcacg     960

```
ttccgtgtgg tcagcgtcct caccgttgtg caccaggact ggctgaacgg caaggagtac      1020
aagtgcaagg tctccaacaa aggcctccca gcccccatcg agaaaaccat ctccaaaacc      1080
aaagggcagc cccgagaacc acaggtgtac accctgcccc catcccggga ggagatgacc      1140
aagaaccagg tcagcctgac ctgcctggtc aaaggcttct accccagcga catcgccgtg      1200
gagtgggaga gcaatgggca gccggagaac aactacaaga ccacacctcc catgctggac      1260
tccgacggct ccttcttcct ctacagcaag ctcaccgtgg acaagagcag gtggcagcag      1320
gggaacgtct tctcatgctc cgtgatgcat gaggctctgc acaaccacta cacgcagaag      1380
agcctctccc tgtctccggg taaa                                             1404
```

<210> SEQ ID NO 263
<211> LENGTH: 468
<212> TYPE: PRT
<213> ORGANISM: Homo sapiens

<400> SEQUENCE: 263

```
Met Ser Val Ser Phe Leu Ile Phe Leu Pro Val Leu Gly Leu Pro Trp
 1               5                  10                  15

Gly Val Leu Ser Gln Val Gln Leu Gln Gln Ser Gly Pro Gly Leu Val
             20                  25                  30

Lys Pro Ser Gln Thr Leu Ser Leu Thr Cys Ala Ile Ser Gly Asp Ser
         35                  40                  45

Val Ser Ser Asn Ser Ala Ala Trp Asn Trp Ile Arg Gln Ser Pro Ser
     50                  55                  60

Arg Gly Leu Glu Trp Leu Gly Arg Thr Tyr Tyr Arg Ser Lys Trp Phe
 65                  70                  75                  80

Asn Asp Tyr Ala Val Ser Val Gln Ser Arg Ile Thr Ile Asn Pro Asp
                 85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Gly Ile Val Phe Ser Tyr Ala
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
```

```
                290                 295                 300
Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
                340                 345                 350

Ile Glu Lys Thr Ile Ser Lys Thr Lys Gly Gln Pro Arg Glu Pro Gln
                355                 360                 365

Val Tyr Thr Leu Pro Pro Ser Arg Glu Glu Met Thr Lys Asn Gln Val
                370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys
465

<210> SEQ ID NO 264
<211> LENGTH: 696
<212> TYPE: DNA
<213> ORGANISM: Homo sapiens

<400> SEQUENCE: 264
atggcatgga tccctctctt cctcggcgtc cttgcttact gcacaggatc cgtggcctcc      60
tatgagctga ctcagccccc ctcagtgtcc gtgtccccag acagacagc cagcatcacc     120
tgttctggag ataaaatggg ggaaagatat gcttgctggt atcagcagaa gccaggccag     180
tcccctatac tggtcatcta tcaagatacc aagcggccct cagggatccc tgagcgattc     240
tctggctcca actctgggaa cacagccact ctgaccatca gcgggaccca ggctatggat     300
gaggctgact attactgtca ggcgtggtac agcagcacca tgtgtggtatt cggcggaggg     360
accaagctga ccgtcctagg tcagcccaag gctgccccct cggtcactct gttcccgccc     420
tcctctgagg agcttcaagc caacaaggcc acactggtgt gtctcataag tgacttctac     480
ccgggagccg tgacagtggc ctggaaggca gatagcagcc ccgtcaaggc gggagtggag     540
accaccacac cctccaaaca aagcaacaac aagtacgcgg ccagcagcta tctgagcctg     600
acgcctgaac agtggaagtc cacagaagc tacagctgcc aggtcacgca tgaagggagc     660
accgtggaga agacagtggc ccctacagaa tgttca                               696

<210> SEQ ID NO 265
<211> LENGTH: 232
<212> TYPE: PRT
<213> ORGANISM: Homo sapiens

<400> SEQUENCE: 265

Met Ala Trp Ile Pro Leu Phe Leu Gly Val Leu Ala Tyr Cys Thr Gly
1               5                   10                  15

Ser Val Ala Ser Tyr Glu Leu Thr Gln Pro Pro Ser Val Ser Val Ser
```

```
            20                  25                  30
Pro Gly Gln Thr Ala Ser Ile Thr Cys Ser Gly Asp Lys Met Gly Glu
        35                  40                  45

Arg Tyr Ala Cys Trp Tyr Gln Gln Lys Pro Gly Gln Ser Pro Ile Leu
    50                  55                  60

Val Ile Tyr Gln Asp Thr Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Tyr Ser Ser
            100                 105                 110

Thr Asn Val Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 266
<211> LENGTH: 1398
<212> TYPE: DNA
<213> ORGANISM: Homo sapiens

<400> SEQUENCE: 266
atggagtttg ggctgagctg ggttttcctc gttgctcttt taagaggtgt ccagtgtcag     60
gtgcagctgg tggagtctgg gggaggcgtg gtccagcctg gaggtccct gagactctcc    120 tgtgcagcgt ctggattcac cttcagtaac tatggcatgc actgggtccg ccaggctcca    180 ggcaagggc tggagtgggt ggcagttata tggtatgttg aagtaataa atactatgca     240 gactccgtga agggccgatt caccatctcc agagacaatt ccaagaacac gctgtatctg    300
caaatgaaca gcctgagagc cgaggacacg gctgtgtatt actgtgcgag agcccaggag    360
ggtatggccc ctgatgcttt tgatatctgg ggccaaggga caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
```

```
gtggaggtgc ataatgccaa gacaaagcca cggggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080 cagcccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa                                                 1398
```

<210> SEQ ID NO 267
<211> LENGTH: 466
<212> TYPE: PRT
<213> ORGANISM: Homo sapiens

<400> SEQUENCE: 267

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Met His Trp Val Arg Gln Ala Pro Gly Lys Gly Leu
    50                  55                  60

Glu Trp Val Ala Val Ile Trp Tyr Val Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Met Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285
```

```
Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 268
<211> LENGTH: 711
<212> TYPE: DNA
<213> ORGANISM: Mus musculus

<400> SEQUENCE: 268
atggagacag acacactcct gctatgggtg ctgctgctct gggttccagg ttccacaggt    60
aacatcgtgc tgacccaatc tccagcttct ttggctgtgt ctctagggca gagggccacc   120
atatcctgca gagccagtga aagtgttgat agttatggca atagttttat gcactggtac   180
cagcagaaac caggacagcc acccaaactc ctcatctatc ttgcatccaa cctagaatct   240
ggggtccctg ccaggttcag tggcagtggg tctaggacag acttcaccct caccattgat   300
cctgtggagg ctgatgatgc tgcaacctat tactgtcagc aaaataatga ggatcggacg   360
ttcggtggag gcaccaagct ggaaatcaaa cgggctgatg ctgcaccaac tgtatccatc   420
ttcccaccat ccagtgagca gttaacatct ggaggtgcct cagtcgtgtg cttcttgaac   480
aacttctacc ccaaagacat caatgtcaag tggaagattg atggcagtga acgacaaaat   540
ggcgtcctga acagttggac tgatcaggac agcaaagaca gcacctacag catgagcagc   600
accctcacgt tgaccaagga cgagtatgaa cgacataaca gctatacctg tgaggccact   660
cacaagacat caacttcacc cattgtcaag agcttcaaca ggaatgagtg t            711

<210> SEQ ID NO 269
<211> LENGTH: 237
<212> TYPE: PRT
<213> ORGANISM: Mus musculus

<400> SEQUENCE: 269

Met Glu Thr Asp Thr Leu Leu Leu Trp Val Leu Leu Leu Trp Val Pro
1               5                   10                  15
```

```
Gly Ser Thr Gly Asn Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Ala Ala Thr Tyr Tyr Cys
            100                 105                 110

Gln Gln Asn Asn Glu Asp Arg Thr Phe Gly Gly Gly Thr Lys Leu Glu
            115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
            195                 200                 205

Tyr Glu Arg His Asn Ser Tyr Thr Cys Glu Ala Thr His Lys Thr Ser
        210                 215                 220

Thr Ser Pro Ile Val Lys Ser Phe Asn Arg Asn Glu Cys
225                 230                 235

<210> SEQ ID NO 270
<211> LENGTH: 1419
<212> TYPE: DNA
<213> ORGANISM: Mus musculus

<400> SEQUENCE: 270
atgggttggc tgtggaactt gctattcctg atggcagctg cccaaagtgc ccaagcacag    60
atccagttgg tacagtctgg acctgagctg aagaagcctg gagagacagt caagatctcc   120
tgcaaggctt ctgggtatac cttcacaacc tatggaatga ctgggtgaa acaggctcca    180 ggaaagggtt taaagtggat gggctggata aacacctact ctggagtgcc aacatatgct   240
gatgacttca agggacggtt tgccttctct ttggaaacct ctgccagcac tgcctatttg   300
cagatcaaca acctcaaaaa tgaggacacg gctacatatt tctgtgcaag cttatggtac   360
tacggtaggg cctttgacta ctggggccaa ggcaccactc tcacagtctc ctcagccaaa   420
acaacagccc catcggtcta tccactggcc cctgtgtgtg aggtacaaac tggctcctcg   480
gtgactctag gatgcctggt caagggttat ttccctgagc agtgaccttg acctggaac   540 tctggatccc tgtccagtgg tgtgcacacc ttcccagctc tcctgcagtc tggcctctac   600
accctcagca gctcagtgac tgtaacctcg aacctggc ccagccagac catcacctgc     660
aatgtggccc acccggcaag cagcaccaaa gtggacaaga aaattgagcc cagagtgccc   720
ataacacaga acccctgtcc tccactcaaa gagtgtcccc catgcgcagc tccagacctc   780
ttgggtggac catccgtctt catcttccct ccaaagatca aggatgtact catgatctcc   840
```

-continued

```
ctgagcccca tggtcacatg tgtggtggtg gatgtgagcg aggatgaccc agacgtccag    900
atcagctggt ttgtgaacaa cgtggaagta cacacagctc agacacaaac ccatagagag    960
gattacaaca gtactctccg ggtggtcagt gccctcccca tccagcacca ggactggatg   1020
agtggcaagg agttcaaatg caaggtcaac aacagagccc tcccatcccc catcgagaaa   1080
accatctcaa acccagaggc cagtaagaa gctccacagg tatatgtctt gcctccacca    1140
gcagaagaga tgactaagaa agagttcagt ctgacctgca tgatcacagg cttcttacct   1200
gccgaaattg ctgtggactg gaccagcaat gggcgtacag agcaaaacta caagaacacc   1260
gcaacagtcc tggactctga tggttcttac ttcatgtaca gcaagctcag agtacaaaag   1320
agcacttggg aaagaggaag tcttttcgcc tgctcagtgg tccacgaggg tctgcacaat   1380
caccttacga ctaagaccat ctcccggtct ctgggtaaa                          1419
```

<210> SEQ ID NO 271
<211> LENGTH: 473
<212> TYPE: PRT
<213> ORGANISM: Mus musculus

<400> SEQUENCE: 271

```
Met Gly Trp Leu Trp Asn Leu Phe Leu Met Ala Ala Ala Gln Ser
1               5                   10                  15

Ala Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Thr Tyr Gly Met Ser Trp Val Lys Gln Ala Pro Gly Lys Gly Leu
        50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Ser Leu Trp Tyr Tyr Gly Arg Ala Phe Asp Tyr Trp
        115                 120                 125

Gly Gln Gly Thr Thr Leu Thr Val Ser Ser Ala Lys Thr Thr Ala Pro
    130                 135                 140

Ser Val Tyr Pro Leu Ala Pro Val Cys Gly Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Leu Leu Gln Ser Gly Leu Tyr Thr Leu Ser Ser Ser Val Thr Val
        195                 200                 205

Thr Ser Asn Thr Trp Pro Ser Gln Thr Ile Thr Cys Asn Val Ala His
    210                 215                 220

Pro Ala Ser Ser Thr Lys Val Asp Lys Lys Ile Glu Pro Arg Val Pro
225                 230                 235                 240

Ile Thr Gln Asn Pro Cys Pro Pro Leu Lys Glu Cys Pro Pro Cys Ala
                245                 250                 255

Ala Pro Asp Leu Leu Gly Gly Pro Ser Val Phe Ile Phe Pro Pro Lys
            260                 265                 270
```

| | | | | | | | | | | | |
|---|---|---|---|---|---|---|---|---|---|---|---|
|Ile|Lys|Asp|Val|Leu|Met|Ile|Ser|Leu|Ser|Pro|Met|Val|Thr|Cys|Val|
| | |275| | | |280| | | |285| |
|Val|Val|Asp|Val|Ser|Glu|Asp|Asp|Pro|Asp|Val|Gln|Ile|Ser|Trp|Phe|
| |290| | | | |295| | | | |300|
|Val|Asn|Asn|Val|Glu|Val|His|Thr|Ala|Gln|Thr|Gln|Thr|His|Arg|Glu|
|305| | | | |310| | | | |315| | | | |320|
|Asp|Tyr|Asn|Ser|Thr|Leu|Arg|Val|Val|Ser|Ala|Leu|Pro|Ile|Gln|His|
| | | | |325| | | | |330| | | | |335|
|Gln|Asp|Trp|Met|Ser|Gly|Lys|Glu|Phe|Lys|Cys|Lys|Val|Asn|Asn|Arg|
| | | |340| | | | |345| | | | |350|
|Ala|Leu|Pro|Ser|Pro|Ile|Glu|Lys|Thr|Ile|Ser|Lys|Pro|Arg|Gly|Pro|
| | | |355| | | | |360| | | | |365|
|Val|Arg|Ala|Pro|Gln|Val|Tyr|Val|Leu|Pro|Pro|Ala|Glu|Glu|Met|
| |370| | | | |375| | | | |380|
|Thr|Lys|Lys|Glu|Phe|Ser|Leu|Thr|Cys|Met|Ile|Thr|Gly|Phe|Leu|Pro|
|385| | | | |390| | | | |395| | | | |400|
|Ala|Glu|Ile|Ala|Val|Asp|Trp|Thr|Ser|Asn|Gly|Arg|Thr|Glu|Gln|Asn|
| | | | |405| | | | |410| | | | |415|
|Tyr|Lys|Asn|Thr|Ala|Thr|Val|Leu|Asp|Ser|Asp|Gly|Ser|Tyr|Phe|Met|
| | | |420| | | | |425| | | | |430|
|Tyr|Ser|Lys|Leu|Arg|Val|Gln|Lys|Ser|Thr|Trp|Glu|Arg|Gly|Ser|Leu|
| | |435| | | | |440| | | | |445|
|Phe|Ala|Cys|Ser|Val|Val|His|Glu|Gly|Leu|His|Asn|His|Leu|Thr|Thr|
| | |450| | | | |455| | | | |460|
|Lys|Thr|Ile|Ser|Arg|Ser|Leu|Gly|Lys|
|465| | | | |470|

<210> SEQ ID NO 272
<211> LENGTH: 711
<212> TYPE: DNA
<213> ORGANISM: Mus musculus

<400> SEQUENCE: 272

```
atggagacag acacactcct gctatgggtg ctgctgctct ggttccagg ttccacaggt      60
gacattgtgc tgacccaatc tccagcttct ttggctgtgt ctctagggca gagggccacc    120
atatcctgca gagccagtga aagtgttgat agttatggca atagttttat gcactggtac    180
cagcagaaac aggacagcc acccaaactc ctcatctatc gtgcatccaa ctagaatct     240
gggatccctg ccaggttcag tggcagtggg tctaggacag acttcaccct caccattaat    300
cctgtggagg ctgatgatgt tgcaacctat tactgtcacc aaagtaatga ggagtacacg    360
ttcggagggg ggaccaagct ggaaataaaa cgggctgatg ctgcaccaac tgtatccatc    420
ttcccaccat ccagtgagca gttaacatct ggaggtgcct cagtcgtgtg cttcttgaac    480
aacttctacc ccaaagacat caatgtcaag tggaagattg atggcagtga acgacaaaat    540
ggcgtcctga cagttggac tgatcaggac agcaaagaca gcacctacag catgagcagc    600
accctcacgt tgaccaagga cgagtatgaa cgacataaca gctatacctg tgaggccact    660
cacaagacat caacttcacc cattgtcaag agcttcaaca ggaatgagtg t             711
```

<210> SEQ ID NO 273
<211> LENGTH: 237
<212> TYPE: PRT
<213> ORGANISM: Mus musculus

<400> SEQUENCE: 273

| Met | Glu | Thr | Asp | Thr | Leu | Leu | Leu | Trp | Val | Leu | Leu | Leu | Trp | Val | Pro |
| 1 | | | | 5 | | | | | 10 | | | | | 15 | |

Gly Ser Thr Gly Asp Ile Val Leu Thr Gln Ser Pro Ala Ser Leu Ala
            20                25            30

Val Ser Leu Gly Gln Arg Ala Thr Ile Ser Cys Arg Ala Ser Glu Ser
      35              40            45

Val Asp Ser Tyr Gly Asn Ser Phe Met His Trp Tyr Gln Gln Lys Pro
 50               55            60

Gly Gln Pro Pro Lys Leu Leu Ile Tyr Arg Ala Ser Asn Leu Glu Ser
65            70            75            80

Gly Ile Pro Ala Arg Phe Ser Gly Ser Gly Ser Arg Thr Asp Phe Thr
            85            90            95

Leu Thr Ile Asn Pro Val Glu Ala Asp Asp Val Ala Thr Tyr Tyr Cys
          100            105          110

His Gln Ser Asn Glu Glu Tyr Thr Phe Gly Gly Gly Thr Lys Leu Glu
          115            120          125

Ile Lys Arg Ala Asp Ala Ala Pro Thr Val Ser Ile Phe Pro Pro Ser
     130            135            140

Ser Glu Gln Leu Thr Ser Gly Gly Ala Ser Val Val Cys Phe Leu Asn
145            150            155          160

Asn Phe Tyr Pro Lys Asp Ile Asn Val Lys Trp Lys Ile Asp Gly Ser
          165            170          175

Glu Arg Gln Asn Gly Val Leu Asn Ser Trp Thr Asp Gln Asp Ser Lys
        180            185            190

Asp Ser Thr Tyr Ser Met Ser Ser Thr Leu Thr Leu Thr Lys Asp Glu
          195            200          205

Tyr Glu Arg His Asn Ser Tyr Thr Cys Glu Ala Thr His Lys Thr Ser
     210            215            220

Thr Ser Pro Ile Val Lys Ser Phe Asn Arg Asn Glu Cys
225            230            235

<210> SEQ ID NO 274
<211> LENGTH: 1383
<212> TYPE: DNA
<213> ORGANISM: Mus musculus

<400> SEQUENCE: 274

| | | | | | |
|---|---|---|---|---|---|
| atgggttggc | tgtggaactt | gctattcctg | atggcagctg | cccaaagtgc | ccaagcacag | 60 |
| atccagttgg | tacagtctgg | acctgagctg | aagaagcctg | gagagacagt | caagatctcc | 120 |
| tgcaaggctt | ctgggtatac | cttcacaacc | tatggaatga | gctgggtgaa | acaggctcca | 180 |
| ggaaagggtt | taaagtggat | gggctggata | aatacctact | ctggagtgcc | aacatatgct | 240 |
| gatgacttca | aggacggttt | gccttctct | ttgaaacct | ctgccagcac | tgcctatttg | 300 |
| cagatcaaca | acctcaaaaa | tgaggacacg | gctacatatt | tctgtggaag | agaccactac | 360 |
| tacggggagt | tgcttactg | ggccaaggg | actctggtca | ctgtctctgc | agccaaaacg | 420 |
| acacccccat | ctgtctatcc | actggcccct | ggatctgctg | cccaaactaa | ctccatggtg | 480 |
| accctgggat | gcctggtcaa | gggctatttc | cctgagccag | tgacagtgac | ctggaactct | 540 |
| ggatccctgt | ccagcggtgt | gcacaccttc | ccagctgtcc | tgcagtctga | cctctacact | 600 |
| ctgagcagct | cagtgactgt | cccctccagc | acctggccca | gccagaccgt | cacctgcaac | 660 |
| gttgcccacc | cggccagcag | caccaaggtg | gacaagaaaa | ttgtgcccag | ggattgtggt | 720 |
| tgtaagcctt | gcatatgtac | agtcccagaa | gtatcatctg | tcttcatctt | cccccccaaag | 780 |

```
cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacga aaccccggga ggagcagatc aacagcactt tccgttcagt cagtgaactt    960
cccatcatgc accaggactg gctcaatggc aaggagttca atgcagggt caacagtgca    1020 gctttccctg cccccatcga aaaaccatc tccaaaacca aaggcagacc gaaggctcca    1080
caggtgtaca ccattccacc tcccaaggag cagatggcca aggataaagt cagtctgacc    1140
tgcatgataa caaacttctt ccctgaagac attactgtgg agtggcagtg gaatgggcag    1200
ccagcggaga actacaagaa cactcagccc atcatggaca cagatggctc ttacttcgtc    1260
tacagcaagc tcaatgtgca gaagagcaac tgggaggcag aaatactttt cacctgctct    1320
gtgttacatg agggcctgca caaccaccat actgagaaga gcctctccca ctctcctggt    1380
aaa                                                                 1383
```

<210> SEQ ID NO 275
<211> LENGTH: 461
<212> TYPE: PRT
<213> ORGANISM: Mus musculus

<400> SEQUENCE: 275

```
Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Gly Arg Asp His Tyr Tyr Gly Glu Val Ala Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Gln Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
```

|     |     |     |     | 260 |     |     |     |     | 265 |     |     |     |     | 270 |     |
| --- | --- | --- | --- | --- | --- | --- | --- | --- | --- | --- | --- | --- | --- | --- | --- |

Val Thr Cys Val Val Asp Ile Ser Lys Asp Asp Pro Glu Val Gln
                275                 280                 285

Phe Ser Trp Phe Val Asp Val Glu Val His Thr Ala Gln Thr Lys
        290                 295                 300

Pro Arg Glu Glu Gln Ile Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
    370                 375                 380

Asn Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
        435                 440                 445

His His Thr Glu Lys Ser Leu Ser His Ser Pro Gly Lys
    450                 455                 460

<210> SEQ ID NO 276
<211> LENGTH: 711
<212> TYPE: DNA
<213> ORGANISM: Mus musculus

<400> SEQUENCE: 276
atggagacag acacactcct gctatgggtg ctgctgctct gggttccagg ttccacaggt      60
gacattgtgc tgacccaatc tccagcttct ttggctgtgt ctctagggca gagggccacc     120
atatcctgca gagccagtga aagtgttgat agttttggca tagttttat gcactggtac     180 cagctgaaac aggacagcc acccaaactc ctcatctatc gtgcatccaa cctagaatct     240
gggatccctg ccaggttcag tggcagtggg tctaggacag acttcaccct caccattaat     300
cctgtggagg ctgatgatgt tgcaatttat tactgtcagc aaagtaatga ggagtacacg     360
ttcggagggg ggaccaagct ggaaataaaa cgggctgatg ctgcaccaac tgtatccatc     420
ttcccaccat ccagtgagca gttaacatct ggaggtgcct cagtcgtgtg cttcttgaac     480
aacttctacc ccaaagacat caatgtcaag tggaagattg atggcagtga acgacaaaat     540
ggcgtcctga acagttggac tgatcaggac agcaaagaca gcacctacag catgagcagc     600
accctcacgt tgaccaagga cgagtatgaa cgacataaca gctatacctg tgaggccact     660
cacaagacat caacttcacc cattgtcaag agcttcaaca ggaatgagtg t            711

<210> SEQ ID NO 277
<211> LENGTH: 237
<212> TYPE: PRT
<213> ORGANISM: Mus musculus

<400> SEQUENCE: 277

Met Glu Thr Asp Thr Leu Leu Leu Trp Val Leu Leu Leu Trp Val Pro

```
            1               5               10              15
Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Glu Ser
            35                  40                  45

Val Asp Ser Phe Gly Asn Ser Phe Met His Trp Tyr Gln Leu Lys Pro
        50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Ile Tyr Tyr Cys
            100                 105                 110

Gln Gln Ser Asn Glu Glu Tyr Thr Phe Gly Gly Gly Thr Lys Leu Glu
        115                 120                 125

Ile Lys Arg Ala Asp Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
210                 215                 220

Thr Ser Pro Ile Val Lys Ser Phe Asn Arg Asn Glu Cys
225                 230                 235
```

<210> SEQ ID NO 278
<211> LENGTH: 1383
<212> TYPE: DNA
<213> ORGANISM: Mus musculus

<400> SEQUENCE: 278

| | | | | | |
|---|---|---|---|---|---|
| atgggttggc | tgtggaactt | gctattcctg | atggcagctg | cccaaagtgc | ccaagcacag | 60 |
| atccagttgg | tacagtctgg | acctgagctg | aagaagcctg | gagagacagt | caagatctcc | 120 |
| tgcaaggctt | ctgggtatac | cttcacaacc | tatggaatga | gctgggtgaa | acaggctcca | 180 |
| ggaaagggtt | taaagtggat | gggctggata | aacacctcct | ctggagtgcc | aacatatgct | 240 |
| gatgacttca | tgggacggtt | tgccttctct | ttggaaacct | ctgccagcac | tgcctatttg | 300 |
| cagatcaaca | acctcaaaaa | tgaggacacg | gctacgtatt | tctgtgcaag | agaccgctac | 360 |
| tacggggagg | ttgcttactg | gggccaaggg | actctggtca | ccgtctctgc | agccaaaacg | 420 |
| acacccccat | ctgtctatcc | actggcccct | ggatctgctg | cccaaactaa | ctccatggtg | 480 |
| accctgggat | gcctggtcaa | gggctatttc | cctgagccag | tgacagtgac | ctggaactct | 540 |
| ggatccctgt | ccagcggtgt | gcacaccttc | ccagctgtcc | tgcagtctga | cctctacact | 600 |
| ctgagcagct | cagtgactgt | cccctccagc | acctggccca | gcgagaccgt | cacctgcaac | 660 |
| gttgcccacc | cggccagcag | caccaaggtg | gacaagaaaa | ttgtgcccag | ggattgtggt | 720 |
| tgtaagcctt | gcatatgtac | agtcccagaa | gtatcatctg | tcttcatctt | ccccccaaag | 780 |
| cccaaggatg | tgctcaccat | tactctgact | cctaaggtca | cgtgtgttgt | ggtagacatc | 840 |

```
agcaaggatg atcccgaggt ccagttcagc tggtttgtag atgatgtgga ggtgcacaca    900
gctcagacgc aaccccggga ggagcagttc aacagcactt tccgctcagt cagtgaactt    960
cccatcatgc atcaggactg gctcaatggc aaggagttca atgcagggt caacagtgca    1020 gctttccctg cccccatcga gaaaccatc tccaaaacca aggcagacc gaaggctcca    1080 caggtgtaca ccattccacc tcccaaggag cagatggcca aggataaagt cagtctgacc    1140
tgcatgataa cagacttctt ccctgaagac attactgtgg agtggcagtg gaatgggcag    1200
ccagcggaga actacaagaa cactcagccc atcatggaca cagatggctc ttacttcgtc    1260
tacagcaagc tcaatgtgca gaagagcaac tgggaggcag aaatacttt cacctgctct    1320 gtgttacatg agggcctgca caaccaccat actgagaaga gcctctccca ctctcctggt    1380
aaa                                                                  1383
```

<210> SEQ ID NO 279
<211> LENGTH: 461
<212> TYPE: PRT
<213> ORGANISM: Mus musculus

<400> SEQUENCE: 279

```
Met Gly Trp Leu Trp Asn Leu Leu Phe Leu Met Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Thr Ser Ser Gly Val Pro Thr Tyr Ala
65                  70                  75                  80

Asp Asp Phe Met Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Arg Tyr Tyr Gly Glu Val Ala Tyr Trp Gly
        115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270
```

Val Thr Cys Val Val Asp Ile Ser Lys Asp Asp Pro Glu Val Gln
            275                 280                 285

Phe Ser Trp Phe Val Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
            325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
            355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
            435                 440                 445

His His Thr Glu Lys Ser Leu Ser His Ser Pro Gly Lys
450                 455                 460

<210> SEQ ID NO 280
<211> LENGTH: 696
<212> TYPE: DNA
<213> ORGANISM: Rattus norvegicus

<400> SEQUENCE: 280
atggctccag tccaacttct agggcttttg ctgctctgcc tccgagccat gagatgtgac        60
atccagatga cccagtctcc ttcactcctg tcagcatctg tgggagacag agtcactctc       120
agctgcaaag caagtcagaa tatttacaag tacttaaact ggtatcagca aaagcttgga       180
gaagctccca aactcctgat atattataca aacagtttgc aaacgggcat cccatcaagg       240
ttcagtggca gtggatctgg tacagatttc acacttacca tcagcagcct gcagcctgaa       300
gatgttgcca catattactg ctatcagtat aacagtgggc cacgtttgg agctgggacc        360 aagctggaac tgaaacgggc tgatgctgca ccaactgtat ctatcttccc accatccacg       420
gaacagttag caactggagg tgcctcagtc gtgtgcctca tgaacaactt ctatcccaga       480
gacatcagtg tcaagtggaa gattgatggc actgaacgac agagatggtgt cctggacagt       540 gttactgatc aggacagcaa agacagcacg tacagcatga gcagcaccct tcgttgacc        600 aaggctgact atgaaagtca taacctctat acctgtgagg ttgttcataa gacatcatcc       660
tcacccgtcg tcaagagctt caacaggaat gagtgt                                  696

<210> SEQ ID NO 281
<211> LENGTH: 232
<212> TYPE: PRT
<213> ORGANISM: Rattus norvegicus

<400> SEQUENCE: 281

Met Ala Pro Val Gln Leu Leu Gly Leu Leu Leu Leu Cys Leu Arg Ala
1               5                   10                  15

Met Arg Cys Asp Ile Gln Met Thr Gln Ser Pro Ser Leu Leu Ser Ala
            20                  25                  30

Ser Val Gly Asp Arg Val Thr Leu Ser Cys Lys Ala Ser Gln Asn Ile
        35                  40                  45

Tyr Lys Tyr Leu Asn Trp Tyr Gln Gln Lys Leu Gly Glu Ala Pro Lys
50                  55                  60

Leu Leu Ile Tyr Tyr Thr Asn Ser Leu Gln Thr Gly Ile Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Val Ala Thr Tyr Tyr Cys Tyr Gln Tyr Asn Ser
            100                 105                 110

Gly Pro Thr Phe Gly Ala Gly Thr Lys Leu Glu Leu Lys Arg Ala Asp
        115                 120                 125

Ala Ala Pro Thr Val Ser Ile Phe Pro Pro Ser Thr Glu Gln Leu Ala
    130                 135                 140

Thr Gly Gly Ala Ser Val Val Cys Leu Met Asn Asn Phe Tyr Pro Arg
145                 150                 155                 160

Asp Ile Ser Val Lys Trp Lys Ile Asp Gly Thr Glu Arg Arg Asp Gly
                165                 170                 175

Val Leu Asp Ser Val Thr Asp Gln Asp Ser Lys Asp Ser Thr Tyr Ser
            180                 185                 190

Met Ser Ser Thr Leu Ser Leu Thr Lys Ala Asp Tyr Glu Ser His Asn
        195                 200                 205

Leu Tyr Thr Cys Glu Val Val His Lys Thr Ser Ser Pro Val Val
    210                 215                 220

Lys Ser Phe Asn Arg Asn Glu Cys
225                 230

<210> SEQ ID NO 282
<211> LENGTH: 1395
<212> TYPE: DNA
<213> ORGANISM: Rattus norvegicus

<400> SEQUENCE: 282
atgggcaggc ttacttcctc attcctgctg ctgattatcc ctgcatatgt cttgtctcag      60
gttactctga aagagtctgg ccctgggata ttgcagcctt cccagaccct cagtctgact     120
tgctctttct ctgggttttc actgagcact tctggtatat gtgtgagctg gattcgtcag     180
ccttcaggga agggtctgga gtggctggca actatttgtt gggaggatag taagggctac     240
aacccttctc tgaagaaccg gctcacaatc tccaaggaca cctccaacaa ccaagcattc     300
ctcaagatca ccagtgtgga cactgcagat accgccatat actactgtgc tcggcccctt     360
aactacggag ggtatagtga gctagaattg gattactggg gccaaggagt catggtcaca     420
gtctcctcag ctgaaacaac agccccatct gtctatccac tggctcctgg aactgctctc     480
aaaagtaact ccatggtgac cctgggatgc ctggtcaagg ctatttccc tgagccagtc      540 accgtgacct ggaactctgg agccctgtcc agcggtgtgc acaccttccc agctgtcctg     600
cagtctggac tctacactct caccagctca gtgactgtac cctccagcac ctggtccagc     660
caggccgtca cctgcaacgt agcccacccg ccagcagca ccaaggtgga caagaaaatt     720
gtgccaaggg aatgcaatcc ttgtggatgt acaggctcag aagtatcatc tgtcttcatc     780
ttccccccaa agaccaaaga tgtgctcacc atcactctga ctcctaaggt cacgtgtgtt     840

-continued

```
gtggtagaca ttagccagaa tgatcccgag gtccggttca gctggtttat agatgacgtg    900
gaagtccaca cagctcagac tcatgccccg gagaagcagt ccaacagcac tttacgctca    960
gtcagtgaac tccccatcgt gcaccgggac tggctcaatg caagacgtt caaatgcaaa    1020 gtcaacagtg gagcattccc tgccccatc gagaaaagca tctccaaacc cgaaggcaca    1080
ccacgaggtc cacaggtata caccatggcg cctcccaagg aagagatgac ccagagtcaa    1140
gtcagtatca cctgcatggt aaaaggcttc tatcccccag acatttatac ggagtggaag    1200
atgaacgggc agccacagga aaactacaag aacactccac ctacgatgga cacagatggg    1260
agttacttcc tctacagcaa gctcaatgta aagaaagaaa catggcagca gggaaacact    1320
ttcacgtgtt ctgtgctgca tgagggcctg cacaaccacc atactgagaa gagtctctcc    1380
cactctccgg gtaaa                                                     1395
```

<210> SEQ ID NO 283
<211> LENGTH: 465
<212> TYPE: PRT
<213> ORGANISM: Rattus norvegicus

<400> SEQUENCE: 283

```
Met Gly Arg Leu Thr Ser Ser Phe Leu Leu Ile Ile Pro Ala Tyr
1               5                   10                  15

Val Leu Ser Gln Val Thr Leu Lys Glu Ser Gly Pro Gly Ile Leu Gln
                20                  25                  30

Pro Ser Gln Thr Leu Ser Leu Thr Cys Ser Phe Ser Gly Phe Ser Leu
            35                  40                  45

Ser Thr Ser Gly Ile Cys Val Ser Trp Ile Arg Gln Pro Ser Gly Lys
        50                  55                  60

Gly Leu Glu Trp Leu Ala Thr Ile Cys Trp Glu Asp Ser Lys Gly Tyr
65                  70                  75                  80

Asn Pro Ser Leu Lys Asn Arg Leu Thr Ile Ser Lys Asp Thr Ser Asn
                85                  90                  95

Asn Gln Ala Phe Leu Lys Ile Thr Ser Val Asp Thr Ala Asp Thr Ala
            100                 105                 110

Ile Tyr Tyr Cys Ala Arg Pro Leu Asn Tyr Gly Gly Tyr Ser Glu Leu
        115                 120                 125

Glu Leu Asp Tyr Trp Gly Gln Gly Val Met Val Thr Val Ser Ser Ala
130                 135                 140

Glu Thr Thr Ala Pro Ser Val Tyr Pro Leu Ala Pro Gly Thr Ala Leu
145                 150                 155                 160

Lys Ser Asn Ser Met Val Thr Leu Gly Cys Leu Val Lys Gly Tyr Phe
                165                 170                 175

Pro Glu Pro Val Thr Val Thr Trp Asn Ser Gly Ala Leu Ser Ser Gly
            180                 185                 190

Val His Thr Phe Pro Ala Val Leu Gln Ser Gly Leu Tyr Thr Leu Thr
        195                 200                 205

Ser Ser Val Thr Val Pro Ser Ser Thr Trp Ser Ser Gln Ala Val Thr
    210                 215                 220

Cys Asn Val Ala His Pro Ala Ser Ser Thr Lys Val Asp Lys Lys Ile
225                 230                 235                 240

Val Pro Arg Glu Cys Asn Pro Cys Gly Cys Thr Gly Ser Glu Val Ser
                245                 250                 255

Ser Val Phe Ile Phe Pro Pro Lys Thr Lys Asp Val Leu Thr Ile Thr
            260                 265                 270
```

```
Leu Thr Pro Lys Val Thr Cys Val Val Asp Ile Ser Gln Asn Asp
            275                 280                 285

Pro Glu Val Arg Phe Ser Trp Phe Ile Asp Val Glu Val His Thr
    290                 295                 300

Ala Gln Thr His Ala Pro Glu Lys Gln Ser Asn Ser Thr Leu Arg Ser
305                 310                 315                 320

Val Ser Glu Leu Pro Ile Val His Arg Asp Trp Leu Asn Gly Lys Thr
                325                 330                 335

Phe Lys Cys Lys Val Asn Ser Gly Ala Phe Pro Ala Pro Ile Glu Lys
            340                 345                 350

Ser Ile Ser Lys Pro Glu Gly Thr Pro Arg Gly Pro Gln Val Tyr Thr
            355                 360                 365

Met Ala Pro Pro Lys Glu Glu Met Thr Gln Ser Gln Val Ser Ile Thr
    370                 375                 380

Cys Met Val Lys Gly Phe Tyr Pro Pro Asp Ile Tyr Thr Glu Trp Lys
385                 390                 395                 400

Met Asn Gly Gln Pro Gln Glu Asn Tyr Lys Asn Thr Pro Pro Thr Met
                405                 410                 415

Asp Thr Asp Gly Ser Tyr Phe Leu Tyr Ser Lys Leu Asn Val Lys Lys
                420                 425                 430

Glu Thr Trp Gln Gln Gly Asn Thr Phe Thr Cys Ser Val Leu His Glu
            435                 440                 445

Gly Leu His Asn His His Thr Glu Lys Ser Leu Ser His Ser Pro Gly
            450                 455                 460

Lys
465

<210> SEQ ID NO 284
<211> LENGTH: 17
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 284

Val Ile Xaa Tyr Xaa Xaa Ser Asn Lys Tyr Tyr Ala Asp Ser Val Lys
1               5                   10                  15

Gly

<210> SEQ ID NO 285
<211> LENGTH: 17
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
```

```
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 285

Trp Ile Xaa Ala Xaa Asn Gly Xaa Xaa Xaa Xaa Ala Xaa Xaa Xaa Gln
1               5                   10                  15

Xaa

<210> SEQ ID NO 286
<211> LENGTH: 12
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 286

Ala Gln Glu Gly Xaa Ala Pro Asp Ala Phe Asp Ile
1               5                   10

<210> SEQ ID NO 287
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 287

Gln Ala Trp Tyr Ser Ser Thr Asn Val Xaa
1               5                   10

<210> SEQ ID NO 288
<211> LENGTH: 10
<212> TYPE: PRT
<213> ORGANISM: Homo sapiens
<220> FEATURE:
<221> NAME/KEY: misc_feature
<222> LOCATION: (9)..(10)
<223> OTHER INFORMATION: Xaa can be any naturally occurring amino acid

<400> SEQUENCE: 288

Gln Ala Trp Asp Ser Ser Thr Ala Xaa Xaa
1               5                   10

<210> SEQ ID NO 289
<211> LENGTH: 11
<212> TYPE: PRT
<213> ORGANISM: Homo sapiens
<220> FEATURE:
<221> NAME/KEY: misc_feature
<222> LOCATION: (7)..(11)
<223> OTHER INFORMATION: Xaa can be any naturally occurring amino acid

<400> SEQUENCE: 289

Gln Ser Asp Tyr Ser Ser Xaa Xaa Xaa Xaa Xaa
1               5                   10

<210> SEQ ID NO 290
<211> LENGTH: 330
<212> TYPE: DNA
<213> ORGANISM: Homo sapiens
```

<400> SEQUENCE: 290

```
cagtctgtgc tgactcagcc accctcaacg tctgggaccc ccgggcagag ggtcaccatc      60
tcttgttctg gaagcaactc caacatcgga agtcaaactg ttaactggta ccagcaactc     120
ccaggaacgg cccccaaact cctcatcttt agtcatcatc accggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggtgtggta     300
ttcggcggag ggaccaaact gaccgtccta                                      330
```

<210> SEQ ID NO 291
<211> LENGTH: 110
<212> TYPE: PRT
<213> ORGANISM: Homo sapiens

<400> SEQUENCE: 291

```
Gln Ser Val Leu Thr Gln Pro Pro Ser Thr Ser Gly Thr Pro Gly Gln
1               5                   10                  15

Arg Val Thr Ile Ser Cys Ser Gly Ser Asn Ser Asn Ile Gly Ser Gln
            20                  25                  30

Thr Val Asn Trp Tyr Gln Gln Leu Pro Gly Thr Ala Pro Lys Leu Leu
        35                  40                  45

Ile Phe Ser His His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 292
<211> LENGTH: 375
<212> TYPE: DNA
<213> ORGANISM: Homo sapiens

<400> SEQUENCE: 292

```
gaggtgcagc tggtggagtc tgggggaggc ttggtaaagc ctggggggtc ccttagactc      60
tcctgtgcag cctctggatt cactttcagt gacgcctgga tgagctgggt ccgccaggct     120
ccagggaagg ggctggagtg ggttggccgt attaaaagca aaactgatgg tgggacaaca     180
gacttcgctg cacccgtgaa aggcagattc accatctcaa gagatgattc aaaaaacacg     240
ctgtatctgc aaatgaacag cctgaacacc gaggacacag cagtgtatta ctgtaccctca     300
tctcatagca gcgcctggta cggctacttc ggtatggacg tctggggcca agggaccacg     360
gtcaccgtct cctca                                                     375
```

<210> SEQ ID NO 293
<211> LENGTH: 125
<212> TYPE: PRT
<213> ORGANISM: Homo sapiens

<400> SEQUENCE: 293

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30
```

```
Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Phe Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Asn Thr Glu Asp Thr Ala Val Tyr
                 85                  90                  95

Tyr Cys Thr Ser Ser His Ser Ser Ala Trp Tyr Gly Tyr Phe Gly Met
                100                 105                 110

Asp Val Trp Gly Gln Gly Thr Thr Val Thr Val Ser Ser
            115                 120                 125

<210> SEQ ID NO 294
<211> LENGTH: 13
<212> TYPE: PRT
<213> ORGANISM: Homo sapiens

<400> SEQUENCE: 294

Ser Gly Ser Asn Ser Asn Ile Gly Ser Gln Thr Val Asn
 1               5                  10

<210> SEQ ID NO 295
<211> LENGTH: 7
<212> TYPE: PRT
<213> ORGANISM: Homo sapiens

<400> SEQUENCE: 295

Ser His His His Arg Pro Ser
 1               5

<210> SEQ ID NO 296
<211> LENGTH: 11
<212> TYPE: PRT
<213> ORGANISM: Homo sapiens

<400> SEQUENCE: 296

Ala Ala Trp Asp Asp Ser Leu Asn Gly Val Val
 1               5                  10

<210> SEQ ID NO 297
<211> LENGTH: 10
<212> TYPE: PRT
<213> ORGANISM: Homo sapiens

<400> SEQUENCE: 297

Gly Phe Thr Phe Ser Asp Ala Trp Met Ser
 1               5                  10

<210> SEQ ID NO 298
<211> LENGTH: 19
<212> TYPE: PRT
<213> ORGANISM: Homo sapiens

<400> SEQUENCE: 298

Arg Ile Lys Ser Lys Thr Asp Gly Gly Thr Thr Asp Phe Ala Ala Pro
 1               5                  10                  15

Val Lys Gly

<210> SEQ ID NO 299
<211> LENGTH: 14
```

<212> TYPE: PRT
<213> ORGANISM: Homo sapiens

<400> SEQUENCE: 299

Ser His Ser Ser Ala Trp Tyr Gly Tyr Phe Gly Met Asp Val
1               5                   10

<210> SEQ ID NO 300
<211> LENGTH: 330
<212> TYPE: DNA
<213> ORGANISM: Homo sapiens

<400> SEQUENCE: 300
cagtctgtgc tgactctgtc accctcagcg tctgggaccc ccgggcagag ggtcaccatc      60
tcttgttctg gaagcacctc caacatcgga agtaatactg taaattggtt ccagcagctc     120
ccaggaacgg cccccaaact cctcatcttt agtaataatc agcggccctc agggtccct     180 gaccgatttt ctgcctccaa gtctggcacc tcagcctccc tggccatcag tgggctccag     240
tctgaggatg aggctgatta ttactgtgca gcgtgggatg acagcctgaa tggtgtggta     300
ttcggcggag ggaccaagct gaccgtccta                                      330

<210> SEQ ID NO 301
<211> LENGTH: 110
<212> TYPE: PRT
<213> ORGANISM: Homo sapiens

<400> SEQUENCE: 301

Gln Ser Val Leu Thr Leu Ser Pro Ser Ala Ser Gly Thr Pro Gly Gln
1               5                   10                  15

Arg Val Thr Ile Ser Cys Ser Gly Ser Thr Ser Asn Ile Gly Ser Asn
                20                  25                  30

Thr Val Asn Trp Phe Gln Gln Leu Pro Gly Thr Ala Pro Lys Leu Leu
            35                  40                  45

Ile Phe Ser Asn Asn Gln Arg Pro Ser Gly Val Pro Asp Arg Phe Ser
        50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 302
<211> LENGTH: 375
<212> TYPE: DNA
<213> ORGANISM: Homo sapiens

<400> SEQUENCE: 302
gaggtgcagc tggtggagtc tgggggaggc ttggtaaagc ctgggggtc ccttagactc       60 tcctgtgcag cctctggaat cactttcagt aacgcctgga tgagctgggt ccgccaggct     120
ccagggaagg ggctggagtg ggttggccgt atcaaaagca agactgatga tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300
tctgatagca gcggctggta cggctactac ggtatggacg tctggggcca agggaccacg     360
gtcaccgtct cctca                                                      375

<210> SEQ ID NO 303
<211> LENGTH: 125
<212> TYPE: PRT
<213> ORGANISM: Homo sapiens

<400> SEQUENCE: 303

Glu Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ser Asp Ser Ser Gly Trp Tyr Gly Tyr Tyr Gly Met
            100                 105                 110

Asp Val Trp Gly Gln Gly Thr Thr Val Thr Val Ser Ser
        115                 120                 125

<210> SEQ ID NO 304
<211> LENGTH: 13
<212> TYPE: PRT
<213> ORGANISM: Homo sapiens

<400> SEQUENCE: 304

Ser Gly Ser Thr Ser Asn Ile Gly Ser Asn Thr Val Asn
1               5                   10

<210> SEQ ID NO 305
<211> LENGTH: 7
<212> TYPE: PRT
<213> ORGANISM: Homo sapiens

<400> SEQUENCE: 305

Ser Asn Asn Gln Arg Pro Ser
1               5

<210> SEQ ID NO 306
<211> LENGTH: 11
<212> TYPE: PRT
<213> ORGANISM: Homo sapiens

<400> SEQUENCE: 306

Ala Ala Trp Asp Asp Ser Leu Asn Gly Val Val
1               5                   10

<210> SEQ ID NO 307
<211> LENGTH: 10
<212> TYPE: PRT
<213> ORGANISM: Homo sapiens

<400> SEQUENCE: 307

Gly Ile Thr Phe Ser Asn Ala Trp Met Ser
1               5                   10

<210> SEQ ID NO 308
<211> LENGTH: 19

<212> TYPE: PRT
<213> ORGANISM: Homo sapiens

<400> SEQUENCE: 308

Arg Ile Lys Ser Lys Thr Asp Asp Gly Thr Thr Asp Tyr Ala Ala Pro
1               5                   10                  15

Val Lys Gly

<210> SEQ ID NO 309
<211> LENGTH: 14
<212> TYPE: PRT
<213> ORGANISM: Homo sapiens

<400> SEQUENCE: 309

Ser Asp Ser Ser Gly Trp Tyr Gly Tyr Tyr Gly Met Asp Val
1               5                   10

<210> SEQ ID NO 310
<211> LENGTH: 330
<212> TYPE: DNA
<213> ORGANISM: Homo sapiens

<400> SEQUENCE: 310
cagtctgtgc tgactcagcc accctcagcg tctgggaccc ccgggcagag ggtcaccatc      60
tcttgttttg gaagcagctc aacatcgga agtaattctg taaactggta ccagcagctc     120
ccaggaacgg cccccaaact cctcatcttt agtaatgatc agcggccctc aggggtccct     180
gaccgattct ctgggtccaa gtctggcacc tcagattccc tggccatcag tgggctccag     240
tctgaggatg aagctgatta ttactgtgca gcatgggatg acagcctgaa tggtgtggta     300
ttcggcggag ggaccaagct gaccgtccta                                      330

<210> SEQ ID NO 311
<211> LENGTH: 110
<212> TYPE: PRT
<213> ORGANISM: Homo sapiens

<400> SEQUENCE: 311

Gln Ser Val Leu Thr Gln Pro Pro Ser Ala Ser Gly Thr Pro Gly Gln
1               5                   10                  15

Arg Val Thr Ile Ser Cys Phe Gly Ser Ser Asn Ile Gly Ser Asn
            20                  25                  30

Ser Val Asn Trp Tyr Gln Gln Leu Pro Gly Thr Ala Pro Lys Leu Leu
        35                  40                  45

Ile Phe Ser Asn Asp Gln Arg Pro Ser Gly Val Pro Asp Arg Phe Ser
50                  55                  60

Gly Ser Lys Ser Gly Thr Ser Asp Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 312
<211> LENGTH: 375
<212> TYPE: DNA
<213> ORGANISM: Homo sapiens

<400> SEQUENCE: 312
gaggtgcagc tggtggagtc tgggggaggc ttggtaaagc ctggggggtc ccttagactc      60

```
tcctgtgcag cctctggatt cactttcagt aatgcctgga tgagctgggt ccgccaggct      120
ccagggaagg ggctggagtg ggttggccgt attaaaagca aaactgatgg tgggacaaca      180
gactacgctg ctcccgtgaa aggcagattc accatctcaa gagatgattc aaaagacacg      240
ctgtatctgc aaatgaacag cctgaaaacc gaggacacac ccgtgtatta ctgtaccaca      300
tctgatagca gcggctggtt cgggtactac ggaatggacg tctggggcca agggaccacg      360
gtcaccgtct cctca                                                       375
```

<210> SEQ ID NO 313
<211> LENGTH: 125
<212> TYPE: PRT
<213> ORGANISM: Homo sapiens

<400> SEQUENCE: 313

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
            20                  25                  30
Trp Met Ser Trp Val Arg Gln Ala Pro Gly Lys Gly Leu Glu Trp Val
        35                  40                  45
Gly Arg Ile Lys Ser Lys Thr Asp Gly Gly Thr Thr Asp Tyr Ala Ala
    50                  55                  60
Pro Val Lys Gly Arg Phe Thr Ile Ser Arg Asp Asp Ser Lys Asp Thr
65                  70                  75                  80
Leu Tyr Leu Gln Met Asn Ser Leu Lys Thr Glu Asp Thr Ala Val Tyr
                85                  90                  95
Tyr Cys Thr Thr Ser Asp Ser Ser Gly Trp Phe Gly Tyr Tyr Gly Met
            100                 105                 110
Asp Val Trp Gly Gln Gly Thr Thr Val Thr Val Ser Ser
        115                 120                 125

<210> SEQ ID NO 314
<211> LENGTH: 13
<212> TYPE: PRT
<213> ORGANISM: Homo sapiens

<400> SEQUENCE: 314

Phe Gly Ser Ser Ser Asn Ile Gly Ser Asn Ser Val Asn
1               5                   10

<210> SEQ ID NO 315
<211> LENGTH: 7
<212> TYPE: PRT
<213> ORGANISM: Homo sapiens

<400> SEQUENCE: 315

Ser Asn Asp Gln Arg Pro Ser
1               5

<210> SEQ ID NO 316
<211> LENGTH: 11
<212> TYPE: PRT
<213> ORGANISM: Homo sapiens

<400> SEQUENCE: 316

Ala Ala Trp Asp Asp Ser Leu Asn Gly Val Val
1               5                   10

```
<210> SEQ ID NO 317
<211> LENGTH: 10
<212> TYPE: PRT
<213> ORGANISM: Homo sapiens

<400> SEQUENCE: 317

Gly Phe Thr Phe Ser Asn Ala Trp Met Ser
1               5                   10

<210> SEQ ID NO 318
<211> LENGTH: 19
<212> TYPE: PRT
<213> ORGANISM: Homo sapiens

<400> SEQUENCE: 318

Arg Ile Lys Ser Lys Thr Asp Gly Gly Thr Thr Asp Tyr Ala Ala Pro
1               5                   10                  15

Val Lys Gly

<210> SEQ ID NO 319
<211> LENGTH: 14
<212> TYPE: PRT
<213> ORGANISM: Homo sapiens

<400> SEQUENCE: 319

Ser Asp Ser Ser Gly Trp Phe Gly Tyr Tyr Gly Met Asp Val
1               5                   10

<210> SEQ ID NO 320
<211> LENGTH: 330
<212> TYPE: DNA
<213> ORGANISM: Homo sapiens

<400> SEQUENCE: 320
cagtctgtgc tgactcagcc accctcaacg tctgggaccc ccgggcagag ggtcaccatc     60
tcttgttttg gaagcaactc caacatcgga agtcaaactg ttaactggta ccagcaactc    120
ccaggaacgg cccccaaact cctcatcttt agtcatcatc accggccctc aggggtccct    180
gaccgattct ctggctccaa gtctggcacc tcagcctccc tggccatcag tgggctccag    240
tctgaggatg aggctgatta ttactgtgca acatgggatg acagcctgaa tggtgtggta    300
ttcggcggag ggaccaaact gaccgtccta                                     330

<210> SEQ ID NO 321
<211> LENGTH: 110
<212> TYPE: PRT
<213> ORGANISM: Homo sapiens

<400> SEQUENCE: 321

Gln Ser Val Leu Thr Gln Pro Pro Ser Thr Ser Gly Thr Pro Gly Gln
1               5                   10                  15

Arg Val Thr Ile Ser Cys Phe Gly Ser Asn Ser Asn Ile Gly Ser Gln
            20                  25                  30

Thr Val Asn Trp Tyr Gln Gln Leu Pro Gly Thr Ala Pro Lys Leu Leu
        35                  40                  45

Ile Phe Ser His His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Ser Leu
                85                  90                  95
```

Asn Gly Val Val Phe Gly Gly Gly Thr Lys Leu Thr Val Leu
            100                 105                 110

<210> SEQ ID NO 322
<211> LENGTH: 375
<212> TYPE: DNA
<213> ORGANISM: Homo sapiens

<400> SEQUENCE: 322
gaggtgcagc tggtggagtc tgggggaggc ttggtaaagc ctggggggtc ccttagactc      60
tcctgtgcag cctctggatt cactttcagt gacgcctgga tgagctgggt ccgccaggct     120
ccagggaagg gactggggtg ggttggccgt attaaaagca aaactgatgg tgggacaaca     180
gacttcgctg cacccgtgaa aggcagattc accatctcaa gagatgattc aaaaaacacg     240
ctgtatctgc aaatgaacag cctgaaaacc gaggacacag ccgtgtatta ctgtacctca     300
tctcatagca gcgcctggta cggctacttc ggtatggacg tctggggcca agggaccacg     360
gtcaccgtct cctca                                                      375

<210> SEQ ID NO 323
<211> LENGTH: 125
<212> TYPE: PRT
<213> ORGANISM: Homo sapiens

<400> SEQUENCE: 323

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Ser Trp Val Arg Gln Ala Pro Gly Lys Gly Leu Gly Trp Val
        35                  40                  45

Gly Arg Ile Lys Ser Lys Thr Asp Gly Gly Thr Thr Asp Phe Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ser Ser His Ser Ser Ala Trp Tyr Gly Tyr Phe Gly Met
            100                 105                 110

Asp Val Trp Gly Gln Gly Thr Thr Val Thr Val Ser Ser
        115                 120                 125

<210> SEQ ID NO 324
<211> LENGTH: 13
<212> TYPE: PRT
<213> ORGANISM: Homo sapiens

<400> SEQUENCE: 324

Phe Gly Ser Asn Ser Asn Ile Gly Ser Gln Thr Val Asn
1               5                   10

<210> SEQ ID NO 325
<211> LENGTH: 7
<212> TYPE: PRT
<213> ORGANISM: Homo sapiens

<400> SEQUENCE: 325

Ser His His His Arg Pro Ser
1               5

<210> SEQ ID NO 326
<211> LENGTH: 11
<212> TYPE: PRT
<213> ORGANISM: Homo sapiens

<400> SEQUENCE: 326

Ala Thr Trp Asp Asp Ser Leu Asn Gly Val Val
1               5                   10

<210> SEQ ID NO 327
<211> LENGTH: 10
<212> TYPE: PRT
<213> ORGANISM: Homo sapiens

<400> SEQUENCE: 327

Gly Phe Thr Phe Ser Asp Ala Trp Met Ser
1               5                   10

<210> SEQ ID NO 328
<211> LENGTH: 19
<212> TYPE: PRT
<213> ORGANISM: Homo sapiens

<400> SEQUENCE: 328

Arg Ile Lys Ser Lys Thr Asp Gly Gly Thr Thr Asp Phe Ala Ala Pro
1               5                   10                  15

Val Lys Gly

<210> SEQ ID NO 329
<211> LENGTH: 14
<212> TYPE: PRT
<213> ORGANISM: Homo sapiens

<400> SEQUENCE: 329

Ser His Ser Ser Ala Trp Tyr Gly Tyr Phe Gly Met Asp Val
1               5                   10

<210> SEQ ID NO 330
<211> LENGTH: 330
<212> TYPE: DNA
<213> ORGANISM: Homo sapiens

<400> SEQUENCE: 330
cagtctgccc tgactcagcc tgcctccgtg tctgggtctc ctggacagtc gatcaccatc      60
tcctgcactg gaaccagcag taatgttggg agttataacc ttgtctcctg gtaccaacag     120
cacccaggca agcccccaa actcatgatt tctgaggtca gtaagcggcc ctcaggactt      180
tctaatcgct tctctggctc caagtctggc aacacggcct ccctgacaat ctctgggctc     240
caggctgagg acgaggctga ttattactgc tgctcatatg caggtagtag cactttaata     300
ttcggcggag ggaccaagct gaccgtccta                                       330

<210> SEQ ID NO 331
<211> LENGTH: 110
<212> TYPE: PRT
<213> ORGANISM: Homo sapiens

<400> SEQUENCE: 331

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Ser Tyr

```
                20                  25                  30
Asn Leu Val Ser Trp Tyr Gln Gln His Pro Gly Lys Ala Pro Lys Leu
            35                  40                  45

Met Ile Ser Glu Val Ser Lys Arg Pro Ser Gly Leu Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Ile Phe Gly Gly Gly Thr Lys Leu Thr Val Leu
            100                 105                 110

<210> SEQ ID NO 332
<211> LENGTH: 360
<212> TYPE: DNA
<213> ORGANISM: Homo sapiens

<400> SEQUENCE: 332
caggtgcagc tacagcagtg gggcgcagga ccgttgaagc cttcggagac cctgtccctc      60
acctgcgctg tctataatgg gtccttcagt ggttactact ggagctggat ccgccagccc     120
ccagggaagg ggctggaatg gattggggat atcaatcata gtggaaacac caagtacaac     180
ccgtccctca gagtcgagt caccatatca gtagacacgt ccaagaatca gttctccctg     240
aagctgagct ctgtgaccgc cgcggacacg gctgtgtatt actgtgcgag aggcgatttt     300
tggagtggtt ttgactggtt cgaccccctgg ggccagggaa ccctggtcac cgtctcctca    360

<210> SEQ ID NO 333
<211> LENGTH: 120
<212> TYPE: PRT
<213> ORGANISM: Homo sapiens

<400> SEQUENCE: 333

Gln Val Gln Leu Gln Gln Trp Gly Ala Gly Pro Leu Lys Pro Ser Glu
1               5                   10                  15

Thr Leu Ser Leu Thr Cys Ala Val Tyr Asn Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Asp Ile Asn His Ser Gly Asn Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asp Phe Trp Ser Gly Phe Asp Trp Phe Asp Pro Trp Gly Gln
            100                 105                 110

Gly Thr Leu Val Thr Val Ser Ser
        115                 120

<210> SEQ ID NO 334
<211> LENGTH: 14
<212> TYPE: PRT
<213> ORGANISM: Homo sapiens

<400> SEQUENCE: 334

Thr Gly Thr Ser Ser Asp Val Gly Ser Tyr Asn Leu Val Ser
1               5                   10
```

<210> SEQ ID NO 335
<211> LENGTH: 7
<212> TYPE: PRT
<213> ORGANISM: Homo sapiens

<400> SEQUENCE: 335

Glu Gly Ser Lys Arg Pro Ser
1               5

<210> SEQ ID NO 336
<211> LENGTH: 10
<212> TYPE: PRT
<213> ORGANISM: Homo sapiens

<400> SEQUENCE: 336

Cys Ser Tyr Ala Gly Ser Ser Thr Leu Ile
1               5                   10

<210> SEQ ID NO 337
<211> LENGTH: 10
<212> TYPE: PRT
<213> ORGANISM: Homo sapiens

<400> SEQUENCE: 337

Gly Gly Ser Phe Ser Gly Tyr Tyr Trp Ser
1               5                   10

<210> SEQ ID NO 338
<211> LENGTH: 16
<212> TYPE: PRT
<213> ORGANISM: Homo sapiens

<400> SEQUENCE: 338

Glu Ile Asn His Ser Gly Ser Thr Asn Tyr Asn Pro Ser Leu Lys Ser
1               5                   10                  15

<210> SEQ ID NO 339
<211> LENGTH: 12
<212> TYPE: PRT
<213> ORGANISM: Homo sapiens

<400> SEQUENCE: 339

Gly Asp Phe Trp Ser Gly Phe Asp Trp Phe Asp Pro
1               5                   10

<210> SEQ ID NO 340
<211> LENGTH: 330
<212> TYPE: DNA
<213> ORGANISM: Homo sapiens

<400> SEQUENCE: 340
cagtctgccc tgactcagcc tgcctccgtg tctgggtctc ctggacagtc gatcaccatc      60
tcctgcactg gaaccagcag taatgttggg acttataaac ttgtctcctg gtaccaacag     120
cacccaggca agccccccaa actcatgatt tctgaggtca gtaagcggcc ctcaggactt     180
tctaatcgct tctctggctc caagtctggc aacacggcct ccctgacaat ctctgggctc     240
caggctgagg acgaggctga ttattactgc tcctcatatg caggtgatag cactttggta     300
ttcggcggag ggaccaagct gaccgtccta                                      330

<210> SEQ ID NO 341
<211> LENGTH: 110

```
<212> TYPE: PRT
<213> ORGANISM: Homo sapiens

<400> SEQUENCE: 341

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Thr Tyr
            20                  25                  30

Lys Leu Val Ser Trp Tyr Gln Gln His Pro Gly Lys Ala Pro Lys Leu
        35                  40                  45

Met Ile Ser Glu Val Ser Lys Arg Pro Ser Gly Leu Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Asp
                85                  90                  95

Ser Thr Leu Val Phe Gly Gly Gly Thr Lys Leu Thr Val Leu
            100                 105                 110

<210> SEQ ID NO 342
<211> LENGTH: 359
<212> TYPE: DNA
<213> ORGANISM: Homo sapiens

<400> SEQUENCE: 342
caggtgcacc tacagcagtg gggcgcagga ccgttgaagc cttcggagac cctgtccctc      60
acctgcgctg tctacaatgg gtccttcagt ggttactatt ggagctggat ccgccagccc     120
ccagggaagg ggctggattg gattgggat atcaatcata gtggaaacac caagtacaac     180
ccgtccctca agagtcgagt caccatatca gtagacacgg ccaagaatca gttctccctg     240
aagctgagtt ctgtgaccgc cgcggacacg gctgtgtatt actgtgcgag aggcgatttt     300
tggagtggtt ttgactggtt cgaccccctgg ggccagggaa ccctggtcac cgtctcctc     359

<210> SEQ ID NO 343
<211> LENGTH: 120
<212> TYPE: PRT
<213> ORGANISM: Homo sapiens

<400> SEQUENCE: 343

Gln Val His Leu Gln Gln Trp Gly Ala Gly Pro Leu Lys Pro Ser Glu
1               5                   10                  15

Thr Leu Ser Leu Thr Cys Ala Val Tyr Asn Gly Ser Phe Ser Gly Tyr
            20                  25                  30

Tyr Trp Ser Trp Ile Arg Gln Pro Pro Gly Lys Gly Leu Asp Trp Ile
        35                  40                  45

Gly Asp Ile Asn His Ser Gly Asn Thr Lys Tyr Asn Pro Ser Leu Lys
    50                  55                  60

Ser Arg Val Thr Ile Ser Val Asp Thr Ala Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asp Phe Trp Ser Gly Phe Asp Trp Phe Asp Pro Trp Gly Gln
            100                 105                 110

Gly Thr Leu Val Thr Val Ser Ser
            115                 120
```

<210> SEQ ID NO 344
<211> LENGTH: 14
<212> TYPE: PRT
<213> ORGANISM: Homo sapiens

<400> SEQUENCE: 344

Thr Gly Thr Ser Ser Asn Val Gly Thr Tyr Lys Leu Val Ser
1               5                   10

<210> SEQ ID NO 345
<211> LENGTH: 7
<212> TYPE: PRT
<213> ORGANISM: Homo sapiens

<400> SEQUENCE: 345

Glu Val Ser Lys Arg Pro Ser
1               5

<210> SEQ ID NO 346
<211> LENGTH: 10
<212> TYPE: PRT
<213> ORGANISM: Homo sapiens

<400> SEQUENCE: 346

Ser Ser Tyr Ala Gly Asp Ser Thr Leu Val
1               5                   10

<210> SEQ ID NO 347
<211> LENGTH: 10
<212> TYPE: PRT
<213> ORGANISM: Homo sapiens

<400> SEQUENCE: 347

Asn Gly Ser Phe Ser Gly Tyr Tyr Trp Ser
1               5                   10

<210> SEQ ID NO 348
<211> LENGTH: 16
<212> TYPE: PRT
<213> ORGANISM: Homo sapiens

<400> SEQUENCE: 348

Asp Ile Asn His Ser Gly Asn Thr Lys Tyr Asn Pro Ser Leu Lys Ser
1               5                   10                  15

<210> SEQ ID NO 349
<211> LENGTH: 12
<212> TYPE: PRT
<213> ORGANISM: Homo sapiens

<400> SEQUENCE: 349

Gly Asp Phe Trp Ser Gly Phe Asp Trp Phe Asp Pro
1               5                   10

<210> SEQ ID NO 350
<211> LENGTH: 330
<212> TYPE: DNA
<213> ORGANISM: Homo sapiens

<400> SEQUENCE: 350
cagtctgccc tgactcagcc tgcctccgtg tctgggtctc ctggacagtc gatcaccatc        60
tcctgcactg gaaccagcag taatgttggg agttataacc ttgtctcctg gtaccaacaa       120
cacccaggca aagcccccaa actcatgctt tctgaggtca gtaagcggcc ctcaggactt       180

```
tctagtcgct tctctggctc caagtctggc gacacggcct ccctgacaat ctctgggctc    240
caggctgagg acgaggctga ttattactgc tgctcatatg caggtagtag cactttggta    300
ttcggcggag ggaccaagct gaccgtccta                                    330
```

<210> SEQ ID NO 351  
<211> LENGTH: 110  
<212> TYPE: PRT  
<213> ORGANISM: Homo sapiens

<400> SEQUENCE: 351

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Ser Tyr
            20                  25                  30

Asn Leu Val Ser Trp Tyr Gln Gln His Pro Gly Lys Ala Pro Lys Leu
        35                  40                  45

Met Leu Ser Glu Val Ser Lys Arg Pro Ser Gly Leu Ser Ser Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Val Phe Gly Gly Gly Thr Lys Leu Thr Val Leu
            100                 105                 110
```

<210> SEQ ID NO 352  
<211> LENGTH: 360  
<212> TYPE: DNA  
<213> ORGANISM: Homo sapiens

<400> SEQUENCE: 352

```
caggtgcagc tacagcagtg gggcgcagga ccgttgaagc cttcggagac cctgtccctc     60
acctgcgctg tctatggtgg gtccttcagt ggttactact ggagctggat ccgccagccc    120
ccagggaagg ggctggaatg gattggggat atcaatcata gtggaaacac caagtacaac    180
ccgtccctca agagtcgagt caccatatca gtagacacgt ccaagaatca gttctccctg    240
aagctgaact ctgtgaccgc cgcggacacg gctgtgtatt actgtgcgag aggcgatttt    300
tggagtggtt ttgactggtt cgaccccctgg ggccagggaa ccctggtcac cgtctcttct    360
```

<210> SEQ ID NO 353  
<211> LENGTH: 120  
<212> TYPE: PRT  
<213> ORGANISM: Homo sapiens

<400> SEQUENCE: 353

```
Gln Val Gln Leu Gln Gln Trp Gly Ala Gly Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Asp Ile Asn His Ser Gly Asn Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
```

```
                    85                  90                  95
Arg Gly Asp Phe Trp Ser Gly Phe Asp Trp Phe Asp Pro Trp Gly Gln
            100                 105                 110

Gly Thr Leu Val Thr Val Ser Ser
        115                 120

<210> SEQ ID NO 354
<211> LENGTH: 14
<212> TYPE: PRT
<213> ORGANISM: Homo sapiens

<400> SEQUENCE: 354

Thr Gly Thr Ser Ser Asn Val Gly Ser Tyr Asn Leu Val Ser
1               5                   10

<210> SEQ ID NO 355
<211> LENGTH: 7
<212> TYPE: PRT
<213> ORGANISM: Homo sapiens

<400> SEQUENCE: 355

Glu Val Ser Lys Arg Pro Ser
1               5

<210> SEQ ID NO 356
<211> LENGTH: 10
<212> TYPE: PRT
<213> ORGANISM: Homo sapiens

<400> SEQUENCE: 356

Cys Ser Tyr Ala Gly Ser Ser Thr Leu Val
1               5                   10

<210> SEQ ID NO 357
<211> LENGTH: 10
<212> TYPE: PRT
<213> ORGANISM: Homo sapiens

<400> SEQUENCE: 357

Gly Gly Ser Phe Ser Gly Tyr Tyr Trp Ser
1               5                   10

<210> SEQ ID NO 358
<211> LENGTH: 16
<212> TYPE: PRT
<213> ORGANISM: Homo sapiens

<400> SEQUENCE: 358

Asp Ile Asn His Ser Gly Asn Thr Lys Tyr Asn Pro Ser Leu Lys Ser
1               5                   10                  15

<210> SEQ ID NO 359
<211> LENGTH: 12
<212> TYPE: PRT
<213> ORGANISM: Homo sapiens

<400> SEQUENCE: 359

Gly Asp Phe Trp Ser Gly Phe Asp Trp Phe Asp Pro
1               5                   10

<210> SEQ ID NO 360
<211> LENGTH: 330
<212> TYPE: DNA
<213> ORGANISM: Homo sapiens
```

<400> SEQUENCE: 360

```
cagtctgccc tgactcagcc tgcctccgtg tctgggtctc ctggacagtc gatcaccatc    60
tcctgcactg gaaccagcag taatgttggg agttataacc ttgtctcctg gtaccaaaag   120
cacccaggca aagcccccaa actcatgatt tctgaggtca gtaagcggcc ctcaggactt   180
tctaatcgct tctctggctc caagtctggc aacacggcct ccctgacaat ctctgggctc   240
caggctgagg acgaggctga ttattactgc tgctcatatg caggtagtag tactttggta   300
ttcggcggag ggaccaaact gaccgtccta                                    330
```

<210> SEQ ID NO 361
<211> LENGTH: 110
<212> TYPE: PRT
<213> ORGANISM: Homo sapiens

<400> SEQUENCE: 361

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Ser Tyr
            20                  25                  30

Asn Leu Val Ser Trp Tyr Gln Lys His Pro Gly Lys Ala Pro Lys Leu
        35                  40                  45

Met Ile Ser Glu Val Ser Lys Arg Pro Ser Gly Leu Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Val Phe Gly Gly Gly Thr Lys Leu Thr Val Leu
            100                 105                 110

<210> SEQ ID NO 362
<211> LENGTH: 360
<212> TYPE: DNA
<213> ORGANISM: Homo sapiens

<400> SEQUENCE: 362

```
caggtgcagc tacagcagtg gggcgcagga ccgttgaagc cttcggagac cctgtccctc    60
acctgcgctg tctatggtgg gtccttcagt ggttactact ggagctggat ccgccagccc   120
ccagggaagg gctggaatg gattggggat atcaatcata gtggaaacac caagtacaac   180
ccgtccctca gagtcgagt caccatatca gtagacacgt ccaaaaatca tttctcctg    240 aagctgagtt ctgtgaccgc cgcggacacg gctgtgtatt actgtgcaag aggcgatttt   300
tggagtggtt ttgactggtt cgaccctgg ggccaggaa ccctggtcac cgtctcctca    360
```

<210> SEQ ID NO 363
<211> LENGTH: 120
<212> TYPE: PRT
<213> ORGANISM: Homo sapiens

<400> SEQUENCE: 363

Gln Val Gln Leu Gln Gln Trp Gly Ala Gly Pro Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile

```
                    35                  40                  45
Gly Asp Ile Asn His Ser Gly Asn Thr Lys Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Gly Asp Phe Trp Ser Gly Phe Asp Trp Phe Asp Pro Trp Gly Gln
            100                 105                 110

Gly Thr Leu Val Thr Val Ser Ser
            115                 120

<210> SEQ ID NO 364
<211> LENGTH: 14
<212> TYPE: PRT
<213> ORGANISM: Homo sapiens

<400> SEQUENCE: 364

Thr Gly Thr Ser Ser Asn Val Gly Ser Tyr Asn Leu Val Ser
1               5                   10

<210> SEQ ID NO 365
<211> LENGTH: 7
<212> TYPE: PRT
<213> ORGANISM: Homo sapiens

<400> SEQUENCE: 365

Glu Val Ser Lys Arg Pro Ser
1               5

<210> SEQ ID NO 366
<211> LENGTH: 10
<212> TYPE: PRT
<213> ORGANISM: Homo sapiens

<400> SEQUENCE: 366

Cys Ser Tyr Ala Gly Ser Ser Thr Leu Val
1               5                   10

<210> SEQ ID NO 367
<211> LENGTH: 10
<212> TYPE: PRT
<213> ORGANISM: Homo sapiens

<400> SEQUENCE: 367

Gly Gly Ser Phe Ser Gly Tyr Tyr Trp Ser
1               5                   10

<210> SEQ ID NO 368
<211> LENGTH: 16
<212> TYPE: PRT
<213> ORGANISM: Homo sapiens

<400> SEQUENCE: 368

Asp Ile Asn His Ser Gly Asn Thr Lys Tyr Asn Pro Ser Leu Lys Ser
1               5                   10                  15

<210> SEQ ID NO 369
<211> LENGTH: 11
<212> TYPE: PRT
<213> ORGANISM: Homo sapiens

<400> SEQUENCE: 369
```

Gly Asp Phe Trp Ser Gly Phe Asp Trp Phe Asp
1               5                   10

<210> SEQ ID NO 370
<211> LENGTH: 330
<212> TYPE: DNA
<213> ORGANISM: Homo sapiens

<400> SEQUENCE: 370
cagtctgccc tgactcagcc tgcctccgtg tctgggtctc ctggacagtc gatcaccatc      60
tcctgcactg gaaccagcag taatgttggg acttataaac ttgtctcctg gtaccaacag     120
cacccagaca agcccccaa actcattatt tctgaggtca gtaagcggcc ctcaggactt      180
tctaatcgct tctctggctc caagtctggc aacacggcct ccctgacaat ctctgggctc     240
caggctgagg acgaggttga ttattactgc tcctcatatg caggtgatag cactttggta     300
ttcggcggag ggaccaagct gaccgtccta                                      330

<210> SEQ ID NO 371
<211> LENGTH: 110
<212> TYPE: PRT
<213> ORGANISM: Homo sapiens

<400> SEQUENCE: 371

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Thr Tyr
                20                  25                  30

Lys Leu Val Ser Trp Tyr Gln Gln His Pro Asp Lys Ala Pro Lys Leu
            35                  40                  45

Ile Ile Ser Glu Val Ser Lys Arg Pro Ser Gly Leu Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Val Asp Tyr Tyr Cys Ser Ser Tyr Ala Gly Asp
                85                  90                  95

Ser Thr Leu Val Phe Gly Gly Gly Thr Lys Leu Thr Val Leu
            100                 105                 110

<210> SEQ ID NO 372
<211> LENGTH: 360
<212> TYPE: DNA
<213> ORGANISM: Homo sapiens

<400> SEQUENCE: 372
caggtgcacc tacagcagtg gggcgcagga ccgttgaagc cttcggagac cctgtccctc      60
acctgcgctg tctataatgg gtccttcagt ggttactact ggagctggat ccgccagccc     120
ccagggaagg ggctggaatg gattggggat atcaatcata gtggaaacac caagtacaac     180
ccgtccctca gagtcgagt caccatatca gtagacacgg ccaagaatca gttctccctg     240
aagctgagtt ctgtgaccgc cgcggacacg gctgtgtatt actgtgcgag aggcgatttt     300
tggagtggtt ttgactggtt cgaccccctgg ggccagggaa ccctggtcac cgtctcctcc    360

<210> SEQ ID NO 373
<211> LENGTH: 120
<212> TYPE: PRT
<213> ORGANISM: Homo sapiens

<400> SEQUENCE: 373

Gln Val His Leu Gln Gln Trp Gly Ala Gly Pro Leu Lys Pro Ser Glu
1               5                   10                  15

Thr Leu Ser Leu Thr Cys Ala Val Tyr Asn Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Asp Ile Asn His Ser Gly Asn Thr Lys Tyr Asn Pro Ser Leu Lys
    50                  55                  60

Ser Arg Val Thr Ile Ser Val Asp Thr Ala Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asp Phe Trp Ser Gly Phe Asp Trp Phe Asp Pro Trp Gly Gln
            100                 105                 110

Gly Thr Leu Val Thr Val Ser Ser
        115                 120

<210> SEQ ID NO 374
<211> LENGTH: 14
<212> TYPE: PRT
<213> ORGANISM: Homo sapiens

<400> SEQUENCE: 374

Thr Gly Thr Ser Ser Asn Val Gly Thr Tyr Lys Leu Val Ser
1               5                   10

<210> SEQ ID NO 375
<211> LENGTH: 7
<212> TYPE: PRT
<213> ORGANISM: Homo sapiens

<400> SEQUENCE: 375

Glu Val Ser Lys Arg Pro Ser
1               5

<210> SEQ ID NO 376
<211> LENGTH: 11
<212> TYPE: PRT
<213> ORGANISM: Homo sapiens

<400> SEQUENCE: 376

Cys Ser Ser Tyr Ala Gly Asp Ser Thr Leu Val
1               5                   10

<210> SEQ ID NO 377
<211> LENGTH: 10
<212> TYPE: PRT
<213> ORGANISM: Homo sapiens

<400> SEQUENCE: 377

Asn Gly Ser Phe Ser Gly Tyr Tyr Trp Ser
1               5                   10

<210> SEQ ID NO 378
<211> LENGTH: 16
<212> TYPE: PRT
<213> ORGANISM: Homo sapiens

<400> SEQUENCE: 378

Asp Ile Asn His Ser Gly Asn Thr Lys Tyr Asn Pro Ser Leu Lys Ser

<210> SEQ ID NO 379
<211> LENGTH: 11
<212> TYPE: PRT
<213> ORGANISM: Homo sapiens

<400> SEQUENCE: 379

Gly Asp Phe Trp Ser Gly Phe Asp Trp Phe Asp
1               5                   10

<210> SEQ ID NO 380
<211> LENGTH: 330
<212> TYPE: DNA
<213> ORGANISM: Homo sapiens

<400> SEQUENCE: 380
cagtctgccc tgactcagcc tgcctccgtg tctgggtctc ctggacagtc gatcaccatc     60
tcctgcactg gaaccagcag taatgttggg acttataagc ttgtctcctg gtaccaacaa    120
cacccaggca agccccccaa actcatgatt tctgaggtca gtaagcggcc ctcaggactt    180
tctaatcgct tctctggctc caagtctggc aacacggcct ccctgacaat ctctgggctc    240
caggctgagg acgaggctga ttattactgc tcctcatatg caggtgatag cactttgata    300
gtcggcggag ggaccaagct gaccgtccta                                     330

<210> SEQ ID NO 381
<211> LENGTH: 110
<212> TYPE: PRT
<213> ORGANISM: Homo sapiens

<400> SEQUENCE: 381

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Val Gly Thr Tyr
            20                  25                  30

Lys Leu Val Ser Trp Tyr Gln Gln His Pro Gly Lys Ala Pro Lys Leu
        35                  40                  45

Met Ile Ser Glu Val Ser Lys Arg Pro Ser Gly Leu Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Asp
                85                  90                  95

Ser Thr Leu Ile Val Gly Gly Gly Thr Lys Leu Thr Val Leu
            100                 105                 110

<210> SEQ ID NO 382
<211> LENGTH: 360
<212> TYPE: DNA
<213> ORGANISM: Homo sapiens

<400> SEQUENCE: 382
caggtgcacc tacaacagtg gggcgcagga ccgttgaagc cttcggagac cctgtccctc     60
acctgcgctg tctataatgg gtccttcagt ggttactact ggagctggat ccgccagccc    120
ccagggaagg ggctggaatg gattgggat atcaatcata gtggaaacac caagtacaac    180
ccgtccctca gagtcgagt caccatatca gtagacacgg ccaagaatca gttctccctg    240
aagctgaatt ctgtgaccgc cgcggacacg gctgtgtatt actgtgcgag aggcgatttt    300

```
tggagtggtt ttgactggtt cgacccctgg ggccagggaa ccctggtcac cgtctcttca    360
```

<210> SEQ ID NO 383
<211> LENGTH: 120
<212> TYPE: PRT
<213> ORGANISM: Homo sapiens

<400> SEQUENCE: 383

```
Gln Val His Leu Gln Gln Trp Gly Ala Gly Pro Leu Lys Pro Ser Glu
1               5                   10                  15

Thr Leu Ser Leu Thr Cys Ala Val Tyr Asn Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Asp Ile Asn His Ser Gly Asn Thr Lys Tyr Asn Pro Ser Leu Lys
    50                  55                  60

Ser Arg Val Thr Ile Ser Val Asp Thr Ala Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Asp Phe Trp Ser Gly Phe Asp Trp Phe Asp Pro Trp Gly Gln
            100                 105                 110

Gly Thr Leu Val Thr Val Ser Ser
        115                 120
```

<210> SEQ ID NO 384
<211> LENGTH: 14
<212> TYPE: PRT
<213> ORGANISM: Homo sapiens

<400> SEQUENCE: 384

```
Thr Gly Thr Ser Ser Asn Val Gly Thr Tyr Lys Leu Val Ser
1               5                   10
```

<210> SEQ ID NO 385
<211> LENGTH: 7
<212> TYPE: PRT
<213> ORGANISM: Homo sapiens

<400> SEQUENCE: 385

```
Glu Val Ser Lys Arg Pro Ser
1               5
```

<210> SEQ ID NO 386
<211> LENGTH: 11
<212> TYPE: PRT
<213> ORGANISM: Homo sapiens

<400> SEQUENCE: 386

```
Cys Ser Ser Tyr Ala Gly Asp Ser Thr Leu Ile
1               5                   10
```

<210> SEQ ID NO 387
<211> LENGTH: 10
<212> TYPE: PRT
<213> ORGANISM: Homo sapiens

<400> SEQUENCE: 387

```
Asn Gly Ser Phe Ser Gly Tyr Tyr Trp Ser
1               5                   10
```

<210> SEQ ID NO 388
<211> LENGTH: 16
<212> TYPE: PRT
<213> ORGANISM: Homo sapiens

<400> SEQUENCE: 388

Asp Ile Asn His Ser Gly Asn Thr Lys Tyr Asn Pro Ser Leu Lys Ser
1               5                   10                  15

<210> SEQ ID NO 389
<211> LENGTH: 12
<212> TYPE: PRT
<213> ORGANISM: Homo sapiens

<400> SEQUENCE: 389

Gly Asp Phe Trp Ser Gly Phe Asp Trp Phe Asp Pro
1               5                   10

<210> SEQ ID NO 390
<211> LENGTH: 333
<212> TYPE: DNA
<213> ORGANISM: Homo sapiens

<400> SEQUENCE: 390
cagtctgtgc tgacgcagcc gccctcagtg tctggggccc cagggcagag ggtcaccatc      60
tcctgcactg ggagcagctc caacatcggg gcaggttatg gtgtatactg gtaccagcag     120
cttccaggaa cagcccccaa actcctcatc tatggtcaca acaatcggcc ctcaggggtc     180
cctgaccgat tctctggctc caagtctgac acctcagcct ccctggccat cactgggctc     240
caggctgaag atgaggctga ttattactgc cagtcctatg acagcaacct gattggttct     300
gtcttcggaa ctgggaccaa ggtcaccgtc cta                                  333

<210> SEQ ID NO 391
<211> LENGTH: 111
<212> TYPE: PRT
<213> ORGANISM: Homo sapiens

<400> SEQUENCE: 391

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val Tyr Trp Tyr Gln Gln Leu Pro Gly Thr Ala Pro Lys Leu
        35                  40                  45

Leu Ile Tyr Gly His Asn Asn Arg Pro Ser Gly Val Pro Asp Arg Phe
    50                  55                  60

Ser Gly Ser Lys Ser Asp Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Asn
                85                  90                  95

Leu Ile Gly Ser Val Phe Gly Thr Gly Thr Lys Val Thr Val Leu
            100                 105                 110

<210> SEQ ID NO 392
<211> LENGTH: 351
<212> TYPE: DNA
<213> ORGANISM: Homo sapiens

<400> SEQUENCE: 392

```
caggttcagc tggtgcagtc tggagctgag gtgaaggaac ctggggcctc agtgaaggtc    60
tcctgcaagg cttctggtta cacctttacc agctatggtg tcagctgggt gcgacaggcc   120
cctggacaag ggcttgagtg gatgggatgg atcagcgctt acaatggtaa cacactctat   180
gcacagcacc tcctgggcag agtcaccatg accacagaca catccacgag cacagcctac   240
atggagctga ggagcctgag atctgacgac acggccgtat attattgtgc gagagaggat   300
ttggggatgg gtgactactg gggccaggga accctggtca ccgtctcctc a            351
```

<210> SEQ ID NO 393
<211> LENGTH: 117
<212> TYPE: PRT
<213> ORGANISM: Homo sapiens

<400> SEQUENCE: 393

Gln Val Gln Leu Val Gln Ser Gly Ala Glu Val Lys Glu Pro Gly Ala
1               5                   10                  15

Ser Val Lys Val Ser Cys Lys Ala Ser Gly Tyr Thr Phe Thr Ser Tyr
            20                  25                  30

Gly Val Ser Trp Val Arg Gln Ala Pro Gly Gln Gly Leu Glu Trp Met
        35                  40                  45

Gly Trp Ile Ser Ala Tyr Asn Gly Asn Thr Leu Tyr Ala Gln His Leu
    50                  55                  60

Leu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asp Leu Gly Met Gly Asp Tyr Trp Gly Gln Gly Thr Leu
            100                 105                 110

Val Thr Val Ser Ser
        115

<210> SEQ ID NO 394
<211> LENGTH: 14
<212> TYPE: PRT
<213> ORGANISM: Homo sapiens

<400> SEQUENCE: 394

Thr Gly Ser Ser Ser Asn Ile Gly Ala Gly Tyr Gly Val Tyr
1               5                   10

<210> SEQ ID NO 395
<211> LENGTH: 7
<212> TYPE: PRT
<213> ORGANISM: Homo sapiens

<400> SEQUENCE: 395

Gly His Asn Asn Arg Pro Ser
1               5

<210> SEQ ID NO 396
<211> LENGTH: 11
<212> TYPE: PRT
<213> ORGANISM: Homo sapiens

<400> SEQUENCE: 396

Gln Ser Tyr Asp Ser Asn Leu Ile Gly Ser Val
1               5                   10

<210> SEQ ID NO 397

```
<211> LENGTH: 10
<212> TYPE: PRT
<213> ORGANISM: Homo sapiens

<400> SEQUENCE: 397

Gly Tyr Thr Phe Thr Ser Tyr Gly Val Ser
1               5                   10

<210> SEQ ID NO 398
<211> LENGTH: 17
<212> TYPE: PRT
<213> ORGANISM: Homo sapiens

<400> SEQUENCE: 398

Trp Ile Ser Ala Tyr Asn Gly Asn Thr Leu Tyr Ala Gln His Leu Leu
1               5                   10                  15

Gly

<210> SEQ ID NO 399
<211> LENGTH: 8
<212> TYPE: PRT
<213> ORGANISM: Homo sapiens

<400> SEQUENCE: 399

Glu Asp Leu Gly Met Gly Asp Tyr
1               5

<210> SEQ ID NO 400
<211> LENGTH: 362
<212> TYPE: PRT
<213> ORGANISM: Homo sapiens

<400> SEQUENCE: 400

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
                20                  25                  30

His Leu Thr Ala Val Ser Ser Pro Ala Pro Gly Thr Pro Ala Phe Trp
            35                  40                  45

Val Ser Gly Trp Leu Gly Pro Gln Gln Tyr Leu Ser Tyr Asn Ser Leu
        50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
                100                 105                 110

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
        130                 135                 140

Leu Lys Gln Gly Thr Trp Gly Gly Asp Trp Pro Glu Ile Ser Gln Arg
145                 150                 155                 160

Trp Gln Gln Gln Asp Lys Ala Ala Asn Lys Glu Leu Thr Phe Leu Leu
                165                 170                 175

Phe Ser Cys Pro His Arg Leu Arg Glu His Leu Glu Arg Gly Arg Gly
                180                 185                 190

Asn Leu Glu Trp Lys Glu Pro Pro Ser Met Arg Leu Lys Ala Arg Pro
            195                 200                 205
```

Ser Ser Pro Gly Phe Ser Val Leu Thr Cys Ser Ala Phe Ser Phe Tyr
    210                 215                 220

Pro Pro Glu Leu Gln Leu Arg Phe Leu Arg Asn Gly Leu Ala Ala Gly
225                 230                 235                 240

Thr Gly Gln Gly Asp Phe Gly Pro Asn Ser Asp Gly Ser Phe His Ala
                245                 250                 255

Ser Ser Ser Leu Thr Val Lys Ser Gly Asp Glu His His Tyr Cys Cys
            260                 265                 270

Ile Val Gln His Ala Gly Leu Ala Gln Pro Leu Arg Val Glu Leu Glu
        275                 280                 285

Ser Pro Ala Lys Ser Ser Val Leu Val Val Gly Ile Val Ile Gly Val
    290                 295                 300

Leu Leu Leu Thr Ala Ala Ala Val Gly Gly Ala Leu Leu Trp Arg Arg
305                 310                 315                 320

Met Arg Ser Gly Leu Pro Ala Pro Trp Ile Ser Leu Arg Gly Asp Asp
                325                 330                 335

Thr Gly Val Leu Leu Pro Thr Pro Gly Glu Ala Gln Asp Ala Asp Leu
                340                 345                 350

Lys Asp Val Asn Val Ile Pro Ala Thr Ala
                355                 360

<210> SEQ ID NO 401
<211> LENGTH: 990
<212> TYPE: DNA
<213> ORGANISM: Homo sapiens

<400> SEQUENCE: 401

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990
```

<210> SEQ ID NO 402
<211> LENGTH: 330
<212> TYPE: PRT
<213> ORGANISM: Homo sapiens

<400> SEQUENCE: 402

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 403
<211> LENGTH: 978
<212> TYPE: DNA
<213> ORGANISM: Homo sapiens

<400> SEQUENCE: 403
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180

```
ggactctact ccctcagcag cgtggtgacc gtgccctcca gcaacttcgg cacccagacc      240
tacacctgca acgtagatca caagcccagc aacaccaagg tggacaagac agttgagcgc      300
aaatgttgtg tcgagtgccc accgtgccca gcaccacctg tggcaggacc gtcagtcttc      360
ctcttccccc caaacccaag gacaccctca tgatctccc ggaccctga ggtcacgtgc        420 gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac tcccatgct ggactccgac      840 ggctccttct cctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaa                                                   978

<210> SEQ ID NO 404
<211> LENGTH: 326
<212> TYPE: PRT
<213> ORGANISM: Homo sapiens

<400> SEQUENCE: 404

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
```

```
                225                 230                 235                 240
Gln Val Ser Leu Thr Cys Leu Val Lys Gly Phe Tyr Pro Ser Asp Ile
                    245                 250                 255

Ala Val Glu Trp Glu Ser Asn Gly Gln Pro Glu Asn Asn Tyr Lys Thr
                    260                 265                 270

Thr Pro Pro Met Leu Asp Ser Asp Gly Ser Phe Phe Leu Tyr Ser Lys
                    275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 405
<211> LENGTH: 321
<212> TYPE: DNA
<213> ORGANISM: Homo sapiens

<400> SEQUENCE: 405
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 406
<211> LENGTH: 107
<212> TYPE: PRT
<213> ORGANISM: Homo sapiens

<400> SEQUENCE: 406

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 407
<211> LENGTH: 318
<212> TYPE: DNA
<213> ORGANISM: Homo sapiens

<400> SEQUENCE: 407
ggtcagccca aggccaaccc cactgtcact ctgttcccgc cctcctctga ggagctccaa      60
```

```
gccaacaagg ccacactagt gtgtctgatc agtgacttct acccgggagc tgtgacagtg      120
gcctggaagg cagatggcag ccccgtcaag gcgggagtgg agaccaccaa accctccaaa      180
cagagcaaca caagtacgc ggccagcagc tacctgagcc tgacgcccga gcagtggaag       240
tcccacagaa gctacagctg ccaggtcacg catgaaggga gcaccgtgga agacagtg        300 gccctacag aatgttca                                                     318

<210> SEQ ID NO 408
<211> LENGTH: 106
<212> TYPE: PRT
<213> ORGANISM: Homo sapiens

<400> SEQUENCE: 408

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 409
<211> LENGTH: 318
<212> TYPE: DNA
<213> ORGANISM: Homo sapiens

<400> SEQUENCE: 409
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tatctgagcc tgacgcctga gcagtggaag      240
tcccacagaa gctacagctg ccaggtcacg catgaaggga gcaccgtgga agacagtg       300 gccctacag aatgttca                                                    318

<210> SEQ ID NO 410
<211> LENGTH: 106
<212> TYPE: PRT
<213> ORGANISM: Homo sapiens

<400> SEQUENCE: 410

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 411
<211> LENGTH: 318
<212> TYPE: DNA
<213> ORGANISM: Homo sapiens

<400> SEQUENCE: 411
ggtcagccca aggctgcccc ctcggtcact ctgttcccac cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac ccctccaaa    180 caaagcaaca caagtacgc ggccagcagc tacctgagcc tgacgcctga gcagtggaag    240
tcccacaaaa gctacagctg ccaggtcacg catgaaggga gcaccgtgga agacagtg    300 gcccctacag aatgttca                                                 318

<210> SEQ ID NO 412
<211> LENGTH: 106
<212> TYPE: PRT
<213> ORGANISM: Homo sapiens

<400> SEQUENCE: 412

Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 413
<211> LENGTH: 318
<212> TYPE: DNA
<213> ORGANISM: Homo sapiens

<400> SEQUENCE: 413
ggtcagccca aggctgcccc atcggtcact ctgttcccgc cctcctctga ggagcttcaa    60
gccaacaagg ccacactggt gtgcctgatc agtgacttct acccgggagc tgtgaaagtg   120
gcctggaagg cagatggcag cccgtcaac acgggagtgg agaccaccac ccctccaaa    180 cagagcaaca caagtacgc ggccagcagc tacctgagcc tgacgcctga gcagtggaag    240
tcccacagaa gctacagctg ccaggtcacg catgaaggga gcaccgtgga agacagtg    300 gcccctgcag aatgtgca                                                 318

```
<210> SEQ ID NO 414
<211> LENGTH: 106
<212> TYPE: PRT
<213> ORGANISM: Homo sapiens

<400> SEQUENCE: 414

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ala
            100                 105

<210> SEQ ID NO 415
<211> LENGTH: 318
<212> TYPE: DNA
<213> ORGANISM: Homo sapiens

<400> SEQUENCE: 415
ggtcagccca aggctgcccc ctcggtcact ctgttcccac cctcctctga ggagcttcaa       60
gccaacaagg ccacactggt gtgtctcgta agtgacttct acccgggagc cgtgacagtg      120
gcctggaagg cagatggcag ccccgtcaag gtgggagtgg agaccaccaa accctccaaa      180
caaagcaaca acaagtatgc ggccagcagc tacctgagcc tgacgcccga gcagtggaag      240
tcccacagaa gctacagctg ccgggtcacg catgaaggga gcaccgtgga agacagtg        300 gcccctgcag aatgctct                                                    318

<210> SEQ ID NO 416
<211> LENGTH: 106
<212> TYPE: PRT
<213> ORGANISM: Homo sapiens

<400> SEQUENCE: 416

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

ANTI-HEPCIDIN ANTIBODIES AND METHODS OF USE

CROSS-REFERENCE TO RELATED APPLICATIONS

This application is a national stage application under 35 U.S.C. 371 of International Application No. PCT/US2009/002606, having an international filing date of 28 Apr. 2009, which claims the benefit of U.S. Provisional Application No. 61/049,687, filed 01 May 2008, which is hereby incorporated by reference in its entirety.

SEQUENCE LISTING

The present application is being filed along with a Sequence Listing in electronic ASCII ".txt" format. The Sequence Listing is provided as a file entitled "A-1419-US-PCT_SeqList.txt" and was created on 28 Apr. 2009. The text file is 295,945 bytes in size. The information in the electronic format of the Sequence Listing is incorporated herein by reference in its entirety.

FIELD OF THE INVENTION

The invention relates to hepcidin, hepcidin antagonists (including antibodies that bind hepcidin) and their ability to modulate hepcidin activity.

BACKGROUND OF THE INVENTION

Iron is an essential trace element required for growth and development of all living organisms. Iron content in mammals is regulated by controlling iron absorption, iron recycling, and release of iron from the cells in which it is stored. Iron is absorbed predominantly in the duodenum and upper jejunum by enterocytes. A feedback mechanism exists that enhances iron absorption in individuals who are iron deficient, and that reduces iron absorption in individuals with iron overload (Andrews, *Ann. Rev. Genomics Hum. Genet.*, 1:75 (2000); Philpott, *Hepatology*, 35:993 (2002); Beutler et al., *Drug-Metab. Dispos.*, 29:495 (2001)). Iron is recycled from degraded red cells by reticuloendothelial macrophages in bone marrow, hepatic Kupffer cells and spleen. Iron release is controlled by ferroportin, a major iron export protein located on the cell surface of enterocytes, macrophages and hepatocytes, the main cells capable of releasing iron into plasma. Hepcidin binds to ferroportin and decreases its functional activity by causing it to be internalized from the cell surface and degraded. (Nemeth et al., *Science*, 306:2090-3, 2004; De Domenico et al., *Mol. Biol. Cell.*, 18:2569-2578, 2007).

Hepcidin is an important regulator of iron homeostasis (Philpott, Hepatology, 35:993 (2002); Nicolas et al., *Proc. Natl. Acad. Sci. USA,* 99:4396 (2002)). High levels of human hepcidin result in reduced iron levels, and vice versa. Mutations in the hepcidin gene which result in lack of hepcidin activity are associated with juvenile hemochromatosis, a severe iron overload disease (Roetto et al., *Nat. Genet.,* 33:21-22, 2003). Studies in mice have demonstrated a role of hepcidin in control of normal iron homeostasis (Nicolas et al., *Nat. Genet.,* 34:97-101, 2003; Nicolas et al., *Proc. Natl. Acad. Sci. USA,* 99:4596-4601, 2002; Nicolas et al., *Proc. Natl. Acad. Sci. USA,* 98:8780-8785, 2001.).

In addition, data is accumulating implicating hepcidin in iron sequestration during inflammation (See, e.g., Weinstein et al., *Blood,* 100:3776-36781, 2002; Kemna et al., *Blood,* 106:1864-1866, 2005; Nicolas et al., *J. Clin. Invest.,* 110: 1037-1044, 2002; Nemeth et al., *J. Clin. Invest.,* 113:1271-1276, 2004; Nemeth et al., *Blood,* 101:2461-2463, 2003 and Rivera et al., *Blood,* 105:1797-1802, 2005). Hepcidin gene expression has been observed to be robustly upregulated after inflammatory stimuli, such as infections, which induce the acute phase response of the innate immune systems of vertebrates. In mice, hepcidin gene expression was shown to be upregulated by lipopolysaccharide (LPS), turpentine, Freund's complete adjuvant, and adenoviral infections. Hepcidin expression is induced by the inflammatory cytokine interleukin-6 (IL-6). A strong correlation between hepcidin expression and anemia of inflammation was also found in patients with chronic inflammatory diseases, including bacterial, fungal, and viral infections.

Human hepcidin, a 25 amino acid peptide with anti-microbial and iron-regulating activity, was discovered independently by two groups investigating novel anti-microbial peptides. (Krause et al., *FEBS Lett.,* 480:147 (2000); Park et al., *J. Biol. Chem.,* 276:7806 (2001)). It has also been referred to as LEAP-1 (liver-expressed antimicrobial peptide). A hepcidin cDNA encoding an 83 amino acid pre-propeptide in mice and an 84 amino acid pre-propeptide in rat and human were subsequently identified in a search for liver specific genes that were regulated by iron (Pigeon et al., *J. Biol. Chem.,* 276: 7811 (2001)). The 24 residue N-terminal signal peptide is first cleaved to produce pro-hepcidin, which is then further processed to produce mature hepcidin, found in both blood and urine. In human urine, the predominant form contains 25 amino acids, although shorter 22 and 20 amino acid peptides are also present.

The mature peptide is notable for containing eight cysteine residues linked as four disulfide bridges. The structure of hepcidin was studied by Hunter et al., *J. Biol. Chem.,* 277: 37597-37603 (2002), by NMR using chemically synthesized hepcidin with an identical HPLC retention time to that of native hepcidin purified from urine. Hunter et al. reported their determination that hepcidin folded into a hairpin loop structure containing a vicinal disulfide bond (C1-C8, C2-C7, C3-C6, C4-C5). See also Lauth et al., *J. Biol. Chem.,* 280: 9272-9282 (2005). However, as discovered and disclosed in copending U.S. patent application Ser. No. 12/022,515, incorporated by reference herein in its entirety, the structure of hepcidin was determined to have a disulfide bond connectivity different than noted above.

U.S. Patent Application Publication Nos. 2003/0187228, 2004/0096987, 2004/0096990, 2005/0148025, 2006/0019339, 2005/0037971 and 2007/0224186; U.S. Pat. Nos. 7,232,892 and 7,294,690 and International Publication No. WO 02/98444 discuss hepcidin antibodies.

SUMMARY OF THE INVENTION

Various embodiments of the invention provide antibodies, including monoclonal antibodies that specifically bind human hepcidin, methods of producing such antibodies, methods of using such antibodies for detecting hepcidin, pharmaceutical formulations including such antibodies, methods of preparing the pharmaceutical formulations, and methods of treating patients with the pharmaceutical formulations, including combination therapy with erythropoiesis stimulators as described below. Nucleic acids encoding such antibodies, vectors and recombinant host cells comprising such nucleic acids, and methods of producing such antibodies are also provided.

In some embodiments, an isolated antibody is provided that binds to human hepcidin of SEQ ID NO: 9 with an affinity $K_D$ of less than about $10^{-8}$M that exhibits at least one of the properties selected from the group consisting of: (a) at least about a 50-fold higher $K_D$ at a pH of about 5.5 or about 6 compared to its $K_D$ for said hepcidin at a pH of about 7.4; (b) at least about a 5-fold faster clearance of said hepcidin compared to antibody 1S1; and (c) an off rate of about $6\times10^{-2}$ $s^{-1}$ or higher at about pH 5.5 or about pH 6. Alternatively, or in addition to one or more of the foregoing properties, the antibody exhibits at least one of the properties selected from the group consisting of: (a) reduces the level of total human hepcidin in serum by at least about 20%, 30%, 40%, 50%, 60%, 70%, 80% or 90% in a C57BL/6 mouse about 24 hours after the administration to said mouse of (i) a 1 mg doses of said antibody and (ii) a pre-complexed single dose of 3.7 µg of human hepcidin with a 1 mg dose of said antibody; (b) reduces the level of total human hepcidin in serum in a mouse by at least about 20%, 30%, 40%, 50%, 60%, 70%, 80% or 90% about 24 hours after said mouse is administered a single dose of 3.7 µg of human hepcidin, wherein said hepcidin is administered three days after said mouse is pre-dosed with said antibody; (c) results in a greater than about 50% reduction in overall accumulation of total serum hepcidin in mice treated with said antibody compared to antibody 1S1; and (d) results in at least about a 2-fold higher intracellular accumulation of hepcidin in FcRn transfected HEK293 cells incubated with said antibody compared to antibody 1S1.

In some embodiments, an isolated antibody is provided that binds to human hepcidin of SEQ ID NO: 9 with an affinity $K_D$ of less than about $10^{-8}$M, wherein said antibody increases circulating iron level or Tsat in a mouse overexpressing human hepcidin for at least 1 day, at least 2, at least 3, at least 4, at least 5, at least 6, at least 7, at least 8, at least 9, at least 10, at least 11 days or more after a single dose of antibody.

In some embodiments, an isolated antibody is provided that binds to human hepcidin of SEQ ID NO: 9, with an affinity $K_D$ of at least $10^{-8}$M, wherein said antibody is obtained by: (a) replacing an amino acid in the heavy or light chain of said antibody with a histidine; (b) screening the antibody obtained in (a) for differential pH binding; (c) replacing another amino acid in the heavy or light chain of said antibody with a histidine; and (d) screening said antibody for having at least one of the properties selected from the group consisting of: (i) at least about 50-1000 fold higher $K_D$ at about pH 5.5 or about pH 6 compared to its $K_D$ for said hepcidin at about pH 7.4; and (ii) an off rate of about $6\times10^{-2}$ $s^{-1}$ or higher at about pH 5.5 or about pH 6.

In some embodiments, an antibody described herein decreases iron in ferroportin expressing cells stimulated with 50 ng/mL hepcidin at an $EC_{50}$ of about 20 nM or less; and/or increases the level in a subject of one of at least hemoglobin or hematocrit, or both; and/or increases in a subject one of at least the red blood cell count, the red blood cell hemoglobin content or the red blood cell mean cell volume of red blood cell count, or any combinations thereof; and/or increases in a subject one of at least the reticulocyte count, the reticulocyte hemoglobin content or the reticulocyte mean cell volume of reticulocyte count, or any combinations thereof; and/or inhibits the iron-regulating activity of hepcidin.

In some embodiments, the antibody comprises an amino acid sequence at least 90% identical to SEQ ID NO: 170 or to SEQ ID NO: 168, said polypeptide comprising at least one amino acid sequence selected from the group consisting of SEQ ID NOs: 171-176, and any sequences comprising at least one amino acid change to any of SEQ ID NOs: 171-176. In one aspect, the antibody comprises SEQ ID NOs: 171-173. In another aspect, the antibody comprises SEQ ID NOs: 174-176.

In some embodiments, an antibody described herein comprises an amino acid sequence at least 90% identical to SEQ ID NO: 333 or to SEQ ID NO: 331, said polypeptide comprising at least one amino acid sequence selected from the group consisting of SEQ ID NOs: 334-349, and any sequences comprising at least one amino acid change to any of SEQ ID NOs: 334-349. In one aspect, an antibody described herein comprises SEQ ID NOs: 334-346. In another aspect, an antibody described herein comprises SEQ ID NOs: 347-349.

In some embodiments, an antibody described herein comprises an amino acid sequence at least 90% identical to SEQ ID NO: 343 or to SEQ ID NO: 341, said polypeptide comprising at least one amino acid sequence selected from the group consisting of SEQ ID NOs: 344-349, and any sequences comprising at least one amino acid change to any of SEQ ID NOs: 344-349. In one aspect, an antibody described herein comprises SEQ ID NOs: 344-346. In another aspect, an antibody described herein comprises SEQ ID NOs: 347-349.

In some embodiments, an antibody described herein comprises an amino acid sequence at least 90% identical to SEQ ID NO: 353 or to SEQ ID NO: 351, said polypeptide comprising at least one amino acid sequence selected from the group consisting of SEQ ID NOs: 354-359, and any sequences comprising at least one amino acid change to any of SEQ ID NOs: 354-359. In one aspect, an antibody described herein comprises SEQ ID NOs: 354-356. In another aspect, an antibody described herein comprises SEQ ID NOs: 357-359.

In some embodiments, an antibody described herein comprises an amino acid sequence at least 90% identical to SEQ ID NO: 363 or to SEQ ID NO: 361, said polypeptide comprising at least one amino acid sequence selected from the group consisting of SEQ ID NOs: 364-369, and any sequences comprising at least one amino acid change to any of SEQ ID NOs: 364-369. In one aspect, an antibody described herein comprises SEQ ID NOs: 364-366. In another aspect, an antibody described herein comprises SEQ ID NOs: 367-369.

In some embodiments, an antibody described herein comprises an amino acid sequence at least 90% identical to SEQ ID NO: 373 or to SEQ ID NO: 37, said polypeptide comprising at least one amino acid sequence selected from the group consisting of SEQ ID NOs: 374-379, and any sequences comprising at least one amino acid change to any of SEQ ID NOs: 374-379. In one aspect, an antibody described here comprises SEQ ID NOs: 374-376. In another aspect, an antibody described herein comprises SEQ ID NOs: 377-379.

In some embodiments, an antibody described herein comprises an amino acid sequence at least 90% identical to SEQ ID NO: 383 or to SEQ ID NO: 381, said polypeptide comprising at least one amino acid sequence selected from the group consisting of SEQ ID NOs: 384-389, and any sequences comprising at least one amino acid change to any of SEQ ID NOs: 384-389. In one aspect, an antibody described herein comprises SEQ ID NOs: 384-386. In another aspect, an antibody described herein comprises comprising SEQ ID NOs: 387-389.

In some embodiments, an antibody described herein comprises an amino acid sequence at least 90% identical to SEQ ID NO: 393 or to SEQ ID NO: 391, said polypeptide comprising at least one amino acid sequence selected from the group consisting of SEQ ID NOs: 394-399, and any sequences comprising at least one amino acid change to any of SEQ ID NOs: 394-399. In one aspect, an antibody described herein comprises SEQ ID NOs: 394-396. In another aspect, an antibody described herein comprises comprising SEQ ID NOs: 397-399.

In some embodiments, an antibody described here comprises an amino acid sequence of SEQ ID NO: 170 wherein at least one, two, three or all four of the amino acids at positions 52, 57, 99 and 107 of said amino acid sequence are replaced with a histidine. Such an antibody may further comprise SEQ ID NO: 168. In other embodiments, the antibody comprises an amino acid sequence of SEQ ID NO: 168 wherein at least one or both of the amino acids at positions 27 and 89 of said amino acid sequence are replaced with a histidine. Such an antibody may further comprise SEQ ID NO: 170. Optionally, any of the foregoing modified SEQ ID NO: 170 and any of the foregoing modified SEQ ID NO: 168 may be combined in an antibody. In one embodiment, the amino acids at positions 57 and 107 of SEQ ID NO: 170 are both replaced with a histidine. In another embodiment, the amino acid at position 107 of SEQ ID NO: 170 and the amino acid at position 27 of SEQ ID NO: 168 are both replaced with a histidine. In another embodiment, the amino acid at position 107 of SEQ ID NO: 170 and the amino acid at position 89 of SEQ ID NO: 168 are both replaced with a histidine. In yet another embodiment, the amino acids at positions 99 and 107 of SEQ ID NO: 170 are both replaced with a histidine.

Any of the foregoing antibodies may be a monoclonal antibody, or a chimeric, humanized, or human antibody. In some embodiments, the antibody is an IgG isotype, such as an IgG1, IgG2, IgG3 or IgG4 isotype.

In another aspect, embodiments of the invention include an isolated nucleic acid molecule comprising a nucleotide sequence that encodes any of the foregoing antibodies, an expression vector comprising any of the isolated nucleic acid molecules, operably linked to a regulatory control sequence, host cells comprising such isolated nucleic acid molecules or vectors, and methods of using such host cells to produce an antibody. Such production methods comprise culturing the host cell under suitable conditions such that the nucleic acid is expressed to produce the antibody, and optionally recovering the antibody from the host cell or culture medium. In a related embodiment, an isolated antibody or agent produced by the aforementioned method is provided.

Embodiments described herein include a composition that contains any of the foregoing antibodies, e.g. in a therapeutically effective amount, and a pharmaceutically acceptable carrier, diluent or excipient. In a related aspect, embodiments of the invention include a method of treating a disorder of iron homeostasis in a subject in need thereof by administering any of the foregoing antibodies or compositions, e.g., in a therapeutically effective amount. Exemplary disorders of iron homeostasis include anemia, sepsis, anemia of inflammation, anemia of cancer, chemotherapy induced anemia, chronic inflammatory anemia, congestive heart failure, end stage renal disorder, chronic kidney disease (stage I, II, III, IV or V), iron deficiency anemia, a disorder of iron homeostasis, ferroportin disease, hemochromatosis, diabetes, inflammation, rheumatoid arthritis, arteriosclerosis, tumors, vasculitis, systemic lupus erythematosus, hemoglobinopathies, and red blood cell disorders. In related aspects, embodiments of the invention provide methods of treating a human with an elevated level of hepcidin, or methods of treating a human with anemia, by administering any of the foregoing antibodies or compositions, e.g. in a therapeutically effective amount. Also provided are uses of any of the foregoing antibodies in preparation of a medicament for treating any of the foregoing subjects or conditions.

It is understood that co-administration methods involving administration of antibodies with a second therapeutic agent, as described herein, encompass not only the use of the antibody in preparation of a medicament for co-administration with the second therapeutic agent, but also the use of the second therapeutic agent in preparation of a medicament for co-administration with the antibody.

In some embodiments, the mammal is a human suffering from a condition selected from the group consisting of African iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, *H. pyelori* infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperteritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

In some embodiments, methods of treating anemia are provided, in which a human administered any of the foregoing antibodies or compositions and an erythropoiesis stimulator. Exemplary erythropoiesis stimulators include erythropoietin, erythropoietin variants and peptides or antibodies that bind and activate erythropoietin receptor. Other exemplary erythropoiesis stimulators include human erythropoietin of SEQ ID NO: 72 or darbepoetin alfa of SEQ ID NO: 73. Exemplary forms of anemia that may be treated according to such methods include anemia of inflammation, anemia of cancer, chemotherapy induced anemia, iron deficiency anemia, a disorder of iron homeostasis, ferroportin disease, or anemia resulting from kidney disease. Also provided are methods of treating a mammal with anemia that is hyporesponsive, or even resistant, to therapy with an erythropoiesis stimulator, comprising administering a therapeutically effective amount of an antibody that specifically binds human hepcidin. Any of the foregoing methods may also include administering iron to the subject.

The foregoing summary is not intended to define every aspect of the invention, and additional aspects are described in other sections, such as the Detailed Description. The entire document is intended to be related as a unified disclosure, and it should be understood that all combinations of features described herein may be contemplated, even if the combination of features are not found together in the same sentence, or paragraph, or section of this document.

In addition to the foregoing, the invention can include, as an additional aspect, all embodiments of the invention narrower in scope in any way than the variations defined by specific paragraphs herein. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It should also be understood that when describing a range of values, the characteristic being described could be an individual value found within the range. For example, "a pH from about pH 4 to about pH 6," could be, but is not limited to, pH 4, 4.2, 4.6, 5.1 5.5 etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH. In some embodiments, when the term "about" is used, it means the recited number plus or minus 5%, 10%, 15% or more of that recited number. The actual variation intended is determinable from the context. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE FIGURES

FIGS. 1A-F show the off-rates for antibodies 1S1, 1S3, 2.7, 18B11, 23F11 and 26F11.

FIG. 2 shows murine anti-hepcidin antibody 2.7's functional ability to drive down intracellular iron concentrations in a beta-lactamase iron-response assay.

FIG. 3 shows the ability of human anti-hepcidin antibodies 18B11, 23F11 and 24E4 to drive down intracellular iron concentrations in a beta-lactamase iron-response assay FIGS. 4A-B demonstrate that an anti-hepcidin antibody neutralizes human hepcidin injected into mice.

FIGS. 5A-E demonstrate that antibody neutralization of human hepcidin virally expressed mice restores normal early red cell characteristics.

FIGS. 7A-B demonstrate that treatment with antibody 18B11 leads to significant reduction in total hepcidin levels.

FIGS. 11A-C shows that neutralization of hepcidin by anti-hepcidin antibody treatment restores responsiveness to erythropoietin in human hepcidin knock-in mice with anemia of inflammation.

FIG. 14A shows a decision tree of iron indices and disease states for assessment of a patient, in the absence of hepcidin measurement.

DETAILED DESCRIPTION OF THE INVENTION

Figure 1D:
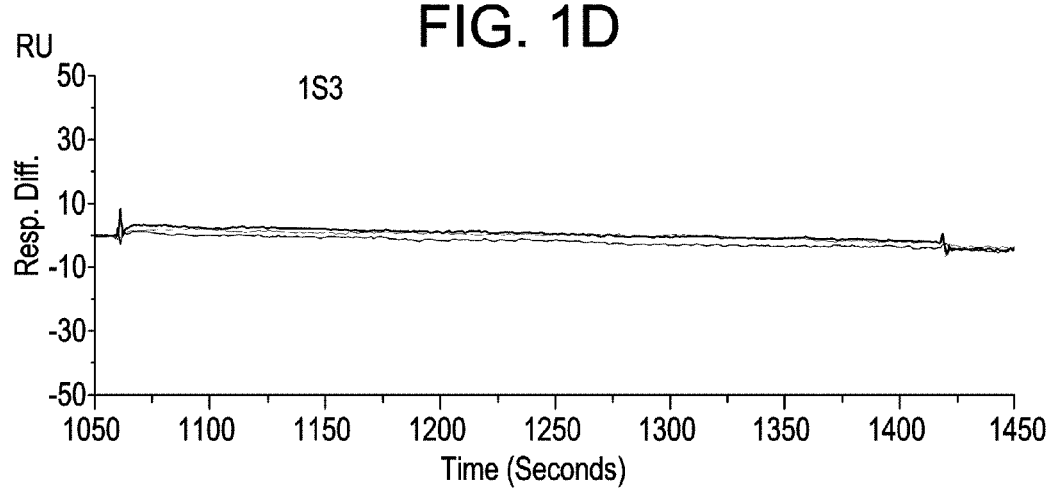

Described herein are antibodies that exhibit one or more properties that are associated with enhanced target antigen clearance from the circulation. Normally, antibodies are internalized into cells and then recycled back into circulation via a pathway involving the receptor FcRn (SEQ ID NO: 400). See, e.g., Prabhat et al., *Proc. Nat'l Acad. Sci.*, 104(14): 5889-5894 (2007). Antibodies (either alone or complexed with antigen) are internalized into the acidified endosomes of the cells. Some of these antibodies in the acidified endosomes then bind to FcRn, which then recycles the antibodies and any associated antigen back out of the cell. Antibodies and/or antigen which did not bind to FcRn are transported to the lysosomes where they are degraded.

Antibodies are provided herein that exhibit differential pH binding to an antigen at a pH below about 7.4, as well as improved methods of treatment using such antibodies. For example, in some embodiments, such antibodies bind to antigen with at least about 50-fold to 1000-fold or more reduced binding affinity at a pH of about 5.5 or about 6 compared to a pH of about 7.4 (as measured by a 50-fold to 1000-fold or higher relative $K_D$ at pH of about 5.5 or about 6 compared to at a pH of about 7.4). In some embodiments, the antibodies exhibit rapid off-rate for antigen of about $6 \times 10^{-2}$ $s^{-1}$ or higher, or about $1 \times 10^{-1}$ $s^{-1}$ or higher. Such antibodies are expected to bind antigen in circulation but tend to release the antigen in acidified endosomes at a pH of about 5.5 or about 6. The greater release of antigen in acidified lysosomes is associated with greater degradation of the target antigen and enhanced clearance of antigen. Another property may be greater recycling of free antibodies (unbound to antigen) into circulation to bind to additional antigen. In contrast, antibodies that do not release their antigen are more frequently recycled into circulation as an antibody-antigen complex, resulting in the inability of the antibody to bind to and ultimately clear additional antigen from circulation.

Also provided are antibodies that produce increased, e.g., at least 1.5-fold or 2-fold, intracellular accumulation of target antigen and/or enhanced clearance of antigen from circulation and/or reduced accumulation of circulating antigen, as well as improved methods of treatment using such antibodies. Other properties of such antibodies may include prevention of build-up of antibody-antigen complexes in circulation, making more recycled free antibody available to bind antigen than conventional antibodies, better potency, and reduced dose and/or frequency of administration to achieve therapeutic effectiveness.

Target antigens can include soluble antigens that have a relatively high level of production and/or a short half-life in circulation of about 24 hours or less, or about 18, 12, 8, 4, 3, 2, or 1 hour or less, or about 45, 30, or 15 minutes or less. Antibodies will generally bind to the target antigen with a $K_D$ in the range of $1 \times 10^{-6}$ M or less, or ranging down to $10^{-16}$ M or lower, (e.g., about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about $10^{-15}$, about $10^{-16}$ or less), where lower $K_D$ indicates better affinity.

Also provided are methods of screening for antibodies with desired properties comprising identifying an antibody that exhibits differential pH binding to an antigen at a pH below about 7.4, and optionally demonstrating that the antibody exhibits enhanced target antigen clearance relative to an antibody of similar or better binding affinity that does not exhibit differential pH binding, and/or optionally demonstrating that the antibody exhibits increased intracellular accumulation of target antigen and/or reduced accumulation of circulating antigen relative to an antibody of similar or better binding affinity that does not exhibit differential pH binding.

In another aspect, methods of treatment are provided that involve administering therapeutically effective amounts of antibodies with the above-described properties, optionally also involving detecting circulating blood level of a target antigen before or concurrent with said administration, and detecting circulating blood level of said target antigen after said administration, e.g. about 24 hours, 2 days, 3, 4, 5, 6, 7 days, or 2 weeks after said administration.

Hepcidin is a good target antigen for antibodies that exhibit the properties described herein. Hepcidin has a relatively short half-life (Rivera et al., Blood, 106:2196-2199, 2005). The human hepcidin gene encodes an 84 residue pre-propeptide (SEQ ID NO: 8). The corresponding cDNA and genomic sequences are set forth in SEQ ID NOs: 7 and 100, respectively. The 24-residue N-terminal signal peptide (residues 1-24 of SEQ ID NO: 8) is first cleaved to produce prohepcidin, which is then further processed by cleavage of the prodomain (residues 25-59 of SEQ ID NO: 8) to produce the 25-residue mature hepcidin (residues 60-84 of SEQ ID NO: 8, set forth in SEQ ID NO: 9). In addition to the primary 25 amino acid form, further N-terminally truncated forms that are 20 or 22 amino acids in length can be identified in urine (20 amino acids, SEQ ID NO: 96; and 22 amino acids, SEQ ID NO: 98). Mature human hepcidin contains eight cysteine residues, which are referred to herein sequentially as C1 through C8 (numbered from the N-terminus to the C-terminus).

In some embodiments, the antibodies described herein bind to mature, correctly folded, bioactive human hepcidin in which disulfide bonds are formed between C1-C8, C2-C4, C3-C6 and C5-C7, with the desired affinity. In some embodiments, the antibodies inhibit the iron-regulating activity of hepcidin. In some embodiments, the monoclonal antibody decreases intracellular iron concentration and/or increases circulating iron concentration at an $EC_{50}$ of about $10^{-8}$ M or less, or about 20 nM or less. In some embodiments, the antibody exhibits the property in mammals of increasing red blood cell count (number) or hemoglobin or hematocrit levels, and/or normalizing reticulocyte count, reticulocyte mean cell volume and/or reticulocyte hemoglobin content, increases circulating iron level or Tsat in a mouse overexpressing human hepcidin for at least 1, 2, 3, 4, 5, 6, 7, 8, 9, 10 or 11 days or longer after a single dose of the antibody.

Anti-Hepcidin Antibodies and Specific Binding Agents

The term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)$_2$, Fv, single chain antibodies, diabodies), and recombinant peptides comprising the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

In some embodiments, the antibodies described herein exhibit differential pH binding to an antigen. The term "differential pH binding" as used herein refers to an antibody that binds to its antigen with high affinity (lower $K_D$) at a pH of about 7.4 but binds to the antigen with a lower affinity (higher $K_D$) at a lower pH. An antibody that exhibits a $K_D$ that is at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000-fold or more higher for its antigen at a pH more acidic than a pH of about 7.4 (e.g., a pH of about 7.0, about 6.5, about 6.0, about 5.5, about 5.0 or about 4.5) is specifically contemplated.

The term "binding affinity" or "affinity" as used herein refers to the equilibrium dissociation constant ($K_D$) associated with each antigen-antibody interaction. In some embodiments, the antibodies described herein exhibit desirable properties such as binding affinity as measured by $K_D$ for hepcidin in the range of $1 \times 10^{-6}$ M or less, or ranging down to $10^{-16}$ M or lower, (e.g., about $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ M or less) at about pH 7.4, where lower $K_D$ indicates better affinity. Optionally the antibody further exhibits a $K_D$ for hepcidin at least 50-1000 fold higher (less binding affinity) at about pH 5.5 or about pH 6 compared to at a pH of about 7.4. The equilibrium dissociation constant can be determined in solution equilibrium assay using BIAcore and/or KinExA, such as described in Examples 3 and 4.

The binding affinity is directly related to the ratio of the kinetic off-rate (generally reported in units of inverse time, e.g. seconds$^{-1}$) divided by the kinetic on-rate (generally reported in units of concentration per unit time, e.g. M/s). Off-rate analysis can estimate the interaction that occurs in vivo, since a slow off-rate would predict a greater degree of interaction over long period of time. In some embodiments, the antibodies described herein exhibit an off-rate of about $6 \times 10^{-2} s^{-1}$ or higher, or about $1 \times 10^{-1} s^{-1}$ or higher (faster off-rate) at about pH 5.5 or about pH 6. Optionally, the antibody also exhibits an off rate of $1 \times 10^{-3} s^{-1}$ or less (slower off-rate) at about pH 7.4. In other embodiments, the antibodies described herein exhibit an off-rate (measured in $s^{-1}$) that is at least about 10-fold, 20, 30, 40, 50, 60, 70, 80, 90 or 100-fold higher at about pH 5.5 or about pH 6 compared to the off-rate at about pH 7.4.

In other embodiments, the antibodies described herein exhibit specificity for or specifically bind to human hepcidin. As used herein, an antibody is "specific for" or "specifically binds" human hepcidin when it has a significantly higher binding affinity for, and consequently is capable of distinguishing, human hepcidin compared to other unrelated proteins in different families. In some embodiments, such antibodies may also cross-react with hepcidin of other species, such as murine, rat, or primate hepcidin; while in other embodiments, the antibodies bind only to human or primate hepcidin and not significantly to rodent hepcidin. In some embodiments, antibodies bind to human and cynomologous monkey hepcidin but not significantly to rodent hepcidin. In some embodiments, antibodies specific for hepcidin cross-react with other proteins in the same family, while in other embodiments, the antibodies distinguish hepcidin from other related family members, including defensins or mouse hepc2.

In some embodiments, the antibodies exhibit "enhanced target antigen clearance", meaning they produce a faster or greater reduction in circulating blood levels of total target antigen. For example, enhanced antigen clearance compared to an antibody that does not exhibit differential pH binding can be measured by comparing blood levels of target antigen at a certain time point, e.g. about 12, 24, 36, 48, or 72 hours after administration of antibody. Enhanced antigen clearance will result in greater reduction in blood level at the same time point. Alternatively, for example, enhanced antigen clearance can be measured by comparing the time period required to reduce target antigen to, e.g., 25%, 50%, 75% or 90% of its blood level prior to administration of antibody. Enhanced antigen clearance will result in a shorter time period to achieve such reduction. As yet another alternative, enhanced antigen clearance is indicated by greater internalization of target antigens into cells expressing FcRn, as measured by intracellular accumulation of target antigen.

In yet other embodiments, the monoclonal antibodies inhibit (or neutralize) hepcidin iron-regulating activity, in vitro and or in vivo. Such hepcidin-neutralizing antibodies are therapeutically useful for hepcidin-related disorders or disorders of iron homeostasis. Hepcidin neutralizing activity can be measured through a number of markers, for example, ferritin/iron levels, red blood cell count, red blood cell characteristics (hemoglobin content and/or cell volume), early red blood cell characteristics (reticulocyte numbers, hemoglobin content or cell volume) (Clinical Hematology, third edition, Lippincott, Williams and Wilkins; editor Mary L. Turgeon, 1999) ferroportin internalization, or iron transport. In one embodiment, the monoclonal antibody decreases intracellular iron concentration at an $EC_{50}$ of about $10^{-8}$ M or less and/or increases circulating iron concentration.

In some embodiments, a monoclonal antibody as described herein antagonizes the effect of human hepcidin or inhibits hepcidin iron-regulating activity. In some embodiments, a monoclonal antibody as described herein exerts an effect at an $EC_{50}$ of about $1 \times 10^{-8}$ M or less, or about $1 \times 10^{-7}$ M or less. For example, an antibody may decrease the intracellular iron level in a cell at an $EC_{50}$ of about $1 \times 10^{-8}$ M or less, or may reduce ferritin expression at an $EC_{50}$ of about $1 \times 10^{-8}$ M or less, as determined by a ferritin assay. In other embodiments, a monoclonal antibody as described herein may reduce free serum hepcidin levels by at least about 20%, by at least about 30%, by at least about 40%, by at least about 50%, by at least about 60%, by at least about 70%, by at least about 80%, or by at least about 90%. In other embodiments, a monoclonal antibody as described herein may increase red blood cell count (number), red blood cell mean cell volume or red blood cell hemoglobin content, increase hemoglobin, increase hematocrit, increase Tsat, increase circulating (or serum) iron levels, and/or increase or normalize reticulocyte count, reticulocyte mean cell volume, reticulocyte hemoglobin content or reticulocyte numbers.

In some embodiments, the invention contemplates: 1) a monoclonal antibody that retains any one, two, three, four, five, or six of CDRH1, CDRH2, CDRH3, CDRL1, CDRL2 or CDRL3 of any of antibody Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11, optionally including one or two mutations in such CDR(s), wherein the antibody exhibits differential pH binding, and/or rapid off rate (e.g., $6 \times 10^{-2} s^{-1}$ or higher) at a pH of about 5.5 or about 6, and/or enhanced hepcidin clearance; 2) a monoclonal antibody that retains all of CDRH1, CDRH2, CDRH3, or the heavy chain variable region of any of antibody Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11, optionally including one or two mutations in such CDR(s), wherein the antibody exhibits differential pH binding, and/or rapid off rate (e.g., $6 \times 10^{-2} s^{-1}$ or higher) at a pH of about 5.5 or about 6, and/or enhanced hepcidin clearance; 3) a monoclonal antibody that retains all of CDRL1, CDRL2, CDRL3, or the light chain variable region of any of antibody Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11, optionally including one or two mutations in such CDR(s), wherein the antibody exhibits differential pH binding, and/or rapid off rate (e.g., $6 \times 10^{-2} s^{-1}$ or higher) at a pH of about 5.5 or about 6, and/or enhanced hepcidin clearance; 4) a monoclonal antibody that binds to the same epitope of mature human hepcidin as antibody Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11, e.g. as determined through X-ray crystallography, or a conformational epitope comprising an amino acid within amino acids 1-5 of SEQ ID NO: 9 and/or an amino acid within a loop formed by amino acids 10-13 of SEQ ID NO: 9 and/or an amino acid within a loop formed by amino acids 14-22 of SEQ ID NO: 9, wherein the antibody exhibits differential pH binding, and/or rapid off rate (e.g., $6 \times 10^{-2}$ s$^{-1}$ or higher) at a pH of about 5.5 or about 6, and/or enhanced hepcidin clearance; 5) a monoclonal antibody that competes with antibody Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11 for binding to mature human hepcidin by more than about 75%, more than about 80%, or more than about 81%, 82%, 83%, 84%, 85%, 86%, 87%, 88%, 89%, 90%, 91%, 92%, 93%, 94% or 95% (e.g., assessed by competitive ELISA or Biacore or by other methods known in the art), wherein the antibody exhibits differential pH binding, and/or rapid off rate (e.g., $6 \times 10^{-2}$ s$^{-1}$ or higher) at a pH of about 5.5 or about 6, and/or enhanced hepcidin clearance; 6) a monoclonal antibody that specifically binds to human hepcidin of SEQ ID NO: 9 with an affinity $K_D$ (equilibrium dissociation constant) for hepcidin in the range of $1 \times 10^{-8}$ M or less, or ranging down to $10^{-16}$ M or lower, (e.g., about $10^{-8}$, $10^{-9}$, $10^{-10}$, $10^{-11}$, $10^{-12}$, $10^{-13}$, $10^{-14}$, $10^{-15}$, $10^{-16}$ M or less) as measured by BIAcore or KinExA and that exhibits at least one, two, three or more of the properties selected from the group consisting of: i) differential pH binding as shown by at least about 50-1000 fold lower affinity (or higher $K_D$) at a pH of about 5.5 or about 6 compared to at about pH 7.4; ii) at least about 5, 6, 7, 8, 9, or 10-fold faster clearance of said hepcidin compared to antibody 1S1; iii) a rapid off rate as measured by, e.g., an off-rate of about $6 \times 10^{-2}$ s$^{-1}$ or higher at about pH 5.5 or about pH 6, or an off-rate of about $1 \times 10^{-1}$ s$^{-1}$ or higher at about pH 5.5 or about pH 6, or an off rate of at least about 10-fold, 20, 30, 40, 50, 60, 70, 80, 90 or 100-fold higher at about pH 5.5 or about 6 compared to the off-rate at about pH 7.4; iv) reduces the level of total human hepcidin in serum by at least about 90% in a C57BL/6 mouse about 24 hours after the administration to said mouse of (i) a 1 mg dose of said antibody and (ii) a pre-complexed single dose of 3.7 µg of human hepcidin with a 1 mg dose of said antibody; v) reduces the level of total human hepcidin in serum in a mouse by at least about 90% about 24 hours after said mouse is administered a single dose of 3.7 µg of human hepcidin, wherein said hepcidin is administered three days after said mouse is pre-dosed with said antibody; vi) produces at least about 1.5-fold or 2-fold higher intracellular accumulation of human hepcidin in FcRn-transfected HEK293 cells compared to antibody 1S1; vii) results in a greater than about 50% reduction in overall accumulation of total serum hepcidin in mice treated with said antibody compared to antibody 1S1, e.g., at about 24 hours; and/or viii) increases circulating iron level or Tsat in a mouse expressing hepcidin for at least about 1 day, at least 2, at least 3, at least 4, at least 5, at least 6, at least 7, at least 8, at least 9, at least 10, at least 11 days or more after a single dose of the antibody.

In some embodiments, an antibody described herein exhibits differential pH binding as shown by at least about 50-1000 fold lower affinity (higher $K_D$) at a pH of about 5.5 or about 6 compared to at about pH 7.4 and also exhibits (1) at least about 5, 6, 7, 8, 9, or 10-fold faster clearance of said hepcidin compared to antibody 1S1; and/or (2) a rapid off rate of, e.g., about $6 \times 10^{-2}$ s$^{-1}$ or higher at about pH 5.5 or about pH 6; and/or (3) reduces the level of total human hepcidin in serum by at least about 90% in a C57BL/6 mouse about 24 hours after the administration to said mouse of (i) a 1 mg dose of said antibody and (ii) a pre-complexed single dose of 3.7 µg of human hepcidin with a 1 mg dose of said antibody; and/or (4) reduces the level of total human hepcidin in serum in a mouse by at least about 90% about 24 hours after said mouse is administered a single dose of 3.7 µg of human hepcidin, wherein said hepcidin is administered three days after said mouse is pre-dosed with said antibody; and/or (5) further produces at least about 1.5-fold or 2-fold higher intracellular accumulation of human hepcidin in FcRn-transfected HEK293 cells compared to antibody 1S1; and/or (6) results in a greater than about 50% reduction in overall accumulation of total serum hepcidin in mice treated with said antibody compared to antibody 1S1; and/or (7) increases circulating iron level or Tsat in a mouse expressing hepcidin for at least about 1 day, at least 2, at least 3, at least 4, at least 5, at least 6, at least 7, at least 8, at least 9, at least 10, at least 11 days or more after a single dose of the antibody.

In some embodiments, an antibody described herein exhibits at least about 5, 6, 7, 8, 9, or 10-fold faster clearance of said hepcidin compared to antibody 1S1 and also (1) reduces the level of total human hepcidin in serum by at least about 90% in a C57BL/6 mouse about 24 hours after the administration to said mouse of (i) a 1 mg dose of said antibody and (ii) a pre-complexed single dose of 3.7 µg of human hepcidin with a 1 mg dose of said antibody; and/or (2) reduces the level of total human hepcidin in serum in a mouse by at least about 90% about 24 hours after said mouse is administered a single dose of 3.7 µg of human hepcidin, wherein said hepcidin is administered three days after said mouse is pre-dosed with said antibody; and/or (3) produces at least about 1.5-fold or 2-fold higher intracellular accumulation of human hepcidin in FcRn-transfected HEK293 cells compared to antibody 1S1; and/or (4) results in a greater than about 50% reduction in overall accumulation of total serum hepcidin in mice treated with said antibody compared to antibody 1S1 and/or (5) increases circulating iron level or Tsat in a mouse expressing hepcidin for at least about 1 day, at least 2, at least 3, at least 4, at least 5, at least 6, at least 7, at least 8, at least 9, at least 10, at least 11 days or more after a single dose of the antibody.

In some embodiments, the antibody exhibits a rapid off-rate, e.g., about $6 \times 10^{-2}$ s$^{-1}$ or higher at about pH 5.5 or about pH 6 and also (1) reduces the level of total human hepcidin in serum by at least about 90% in a C57BL/6 mouse about 24 hours after the administration to said mouse of (i) a 1 mg dose of said antibody and (ii) a pre-complexed single dose of 3.7 µg of human hepcidin with a 1 mg dose of said antibody; and/or (2) reduces the level of total human hepcidin in serum in a mouse by at least about 90% about 24 hours after said mouse is administered a single dose of 3.7 µg of human hepcidin, wherein said hepcidin is administered three days after said mouse is pre-dosed with said antibody; and/or (3) produces at least about 1.5-fold or 2-fold higher intracellular accumulation of human hepcidin in FcRn-transfected HEK293 cells compared to antibody 1S1; and/or (4) results in a greater than about 50% reduction in overall accumulation of total serum hepcidin in mice treated with said antibody compared to antibody 1S1; and/or (5) increases circulating iron level or Tsat in a mouse expressing hepcidin for at least about 1 day, at least 2, at least 3, at least 4, at least 5, at least 6, at least 7, at least 8, at least 9, at least 10, at least 11 days or more after a single dose of the antibody.

In some embodiments, an antibody described herein reduces the level of total human hepcidin in serum in a mouse by at least about 90% about 24 hours after said mouse is administered a single dose of 3.7 µg of human hepcidin, wherein said hepcidin is administered three days after said mouse is pre-dosed with said antibody, and also (1) produces at least about 1.5-fold or 2-fold higher intracellular accumulation of human hepcidin in FcRn-transfected HEK293 cells compared to antibody 1S1; and/or (2) results in a greater than about 50% reduction in overall accumulation of total serum hepcidin in mice treated with said antibody compared to antibody 1S1; and/or (3) increases circulating iron level or Tsat in a mouse expressing hepcidin for at least about 1 day, at least 2, at least 3, at least 4, at least 5, at least 6, at least 7, at least 8, at least 9, at least 10, at least 11 days or more after a single dose of the antibody.

In some embodiments, an antibody described herein produces at least about 1.5-fold or 2-fold higher intracellular accumulation of human hepcidin in FcRn-transfected HEK293 cells compared to antibody 1S1 and also results in a greater than about 50% reduction in overall accumulation of total serum hepcidin in mice treated with said antibody compared to antibody 1S1; and/or increases circulating iron level or Tsat in a mouse expressing hepcidin for at least about 1 day, at least 2, at least 3, at least 4, at least 5, at least 6, at least 7, at least 8, at least 9, at least 10, at least 11 days or more after a single dose of the antibody.

In another aspect, methods are provided for modifying antibodies that lack properties such as differential pH binding and/or enhanced target antigen clearance) to produce antibodies that exhibit such properties. The antibody can be an anti-hepcidin antibody produced by such methods. In some embodiments, residues in the CDRs and/or residues that according to three-dimensional modeling are predicted to be most affected by introduction of an amino acid with a pKa in the range of pH of about 5.5 to about 7.4 are mutated by the introduction of such an amino acid, e.g. histidine. Histidine is an amino acid that is sensitive to pH shifts from 7.4 to 6.0, as the imidazole side chain of histidine has a pKa just over 6, which may vary slightly higher or lower depending on the environment of the amino acid. Upon a change in pH from about 7.4 to a lower pH of about 6.0 or 5.5, for example, the mutated antibody may undergo an allosteric conformational change that would disrupt antigen-antibody interaction.

Candidate residues for mutation include residues that are directed contact sites with antigen or sites that contribute to the formation of charge-charge interactions along the antibody-antigen binding interface. Other candidate residues include residues within conserved regions of the antibody. Yet other candidate residues include framework residues that are at least 10% surface exposed and within 4.5 Å of a CDR residue. Additional candidate residues include those selected by visual inspection of a 3-dimensional structural model for amino acids in proximity to the CDRs or selected framework residues. Histidine or other desired amino acids can be mutated at single or multiple positions within the amino acid sequence. For example, mutations which produce some differential pH binding effect as single mutations can be combined as double, triple or more multiple mutations. Antibodies that have been mutated in such a manner are then screened for differential pH binding and then can be further screened for other properties.

In one aspect, at least one, two, three, four, five, six or more residues in the heavy chain variable region of said antibody are deleted and replaced with a histidine residue. In another aspect, at least one, two, three, four, five, six or more residues in the light chain variable region of said antibody are deleted and replaced with a histidine residue. In some aspects, at least one residue from the light chain variable region of said antibody and at least one residue from the heavy chain variable region of said antibody is replaced with a histidine residue. In one embodiment, at least one residue in the heavy chain variable region at a position selected from the group consisting of 52, 57, 99 and 107 of SEQ ID NO: 170 is replaced with a histidine residue. In another embodiment, at least one residue in the light chain variable region at a position selected from the group consisting of 27 and 89 of SEQ ID NO: 168 is replaced with a histidine residue. In another embodiment, the amino acids at positions 57 and 107 of the heavy chain variable region of SEQ ID NO: 170 are replaced with a histidine residue. In another embodiment, the amino acids at position 107 of the heavy chain variable region of SEQ ID NO: 170 and position 27 of the light chain variable region of SEQ ID NO: 168 are replaced with a histidine. In another embodiment, the amino acid at position 107 of the heavy chain variable region of SEQ ID NO: 170 and the amino acid at position 89 of the light chain variable region of SEQ ID NO: 168 is replaced with a histidine. In another embodiment, the amino acid at positions 99 and 107 of the heavy chain variable region of SEQ ID NO: 170 are replaced with a histidine.

In one embodiment, the antibody comprises at least one, two, three, four, five or all of the amino acid sequences selected from the group consisting of SEQ ID NOs: 16-21 (Ab 43). In another embodiment, the antibody comprises at least one, two, three, four, five or all of the amino acid sequences selected from the group consisting of SEQ ID NOs: 28-33 (2.7 CDRs). In another embodiment, the antibody comprises at least one, two, three, four, five or all of the amino acid sequences selected from the group consisting of SEQ ID NOs: 40-45 (2.41 CDRs). In yet another embodiment, the antibody comprises at least one, two, three, four, five or all of the amino acid sequences selected from the group consisting of SEQ ID NOs: 52-57 (R9 CDRs). In another embodiment, the antibody comprises at least one, two, three, four, five or all of the amino acid sequences selected from the group consisting of SEQ ID NOs: 111-116 (1C9 CDRs). In another embodiment, the antibody comprises at least one, two, three, four, five or all of the amino acid sequences selected from the group consisting of SEQ ID NOs: 121-126 (3B3 CDRs). In yet another embodiment, the antibody comprises at least one, two, three, four, five or all of the amino acid sequences selected from the group consisting of SEQ ID NOs: 131-136 (4E1 CDRs). In another embodiment, the antibody comprises at least one, two, three, four, five or all of the amino acid sequences selected from the group consisting of SEQ ID NOs: 141-146 (7A3 CDRs). In another embodiment, the antibody comprises at least one, two, three, four, five or all of the amino acid sequences selected from the group consisting of SEQ ID NOs: 151-156 (9D12 CDRs). In another embodiment, the antibody comprises at least one, two, three, four, five or all of the amino acid sequences selected from the group consisting of SEQ ID NOs: 161-166 (12B9 CDRs). In yet another embodiment, the antibody comprises at least one, two, three, four, five or all of the amino acid sequences selected from the group consisting of SEQ ID NOs: 171-176 (15E1 CDRs). In another embodiment, the antibody comprises at least one, two, three, four, five or all of the amino acid sequences selected from the group consisting of SEQ ID NOs: 334-339 (18B11 CDRs). In another embodiment, the antibody comprises at least one, two, three, four, five or all of the amino acid sequences selected from the group consisting of SEQ ID NOs: 314-319 (18D8 CDRs). In another embodiment, the antibody comprises at least one, two, three, four, five or all of the amino acid sequences selected from the group consisting of SEQ ID NOs: 344-349 (19B8 CDRs). In another embodiment, the antibody comprises at least one, two, three, four, five or all of the amino acid sequences selected from the group consisting of SEQ ID NOs: 324-329 (19C1 CDRs). In yet another embodiment, the antibody comprises at least one, two, three, four, five or all of the amino acid sequences selected from the group consisting of SEQ ID NOs: 294-299

(19D12 CDRs). In another embodiment, the antibody comprises at least one, two, three, four, five or all of the amino acid sequences selected from the group consisting of SEQ ID NOs: 304-309 (19H6 CDRs). In another embodiment, the antibody comprises at least one, two, three, four, five or all of the amino acid sequences selected from the group consisting of SEQ ID NOs: 354-359 (20E12 CDRs). In another embodiment, the antibody comprises at least one, two, three, four, five or all of the amino acid sequences selected from the group consisting of SEQ ID NOs: 364-369 (22F12 CDRs). In another embodiment, the antibody comprises at least one, two, three, four, five or all of the amino acid sequences selected from the group consisting of SEQ ID NOs: 374-379 (22H10 CDRs). In another embodiment, the antibody comprises at least one, two, three, four, five or all of the amino acid sequences selected from the group consisting of SEQ ID NOs: 384-389 (23A11 CDRs). In yet another embodiment, the antibody comprises at least one, two, three, four, five or all of the amino acid sequences selected from the group consisting of SEQ ID NOs: 181-186 (23F11 CDRs). In another embodiment, the antibody comprises at least one, two, three, four, five or all of the amino acid sequences selected from the group consisting of SEQ ID NOs: 394-399 (24E4 CDRs). In another embodiment, the antibody comprises at least one, two, three, four, five or all of the amino acid sequences selected from the group consisting of SEQ ID NOs: 191-196 (26F11 CDRs). In another embodiment, the antibody comprises at least one, two, three, four, five or all of the amino acid sequences selected from the group consisting of SEQ ID NOs: 203-205 and 131-133 (1S1 CDRs). In another embodiment, the antibody comprises at least one, two, three, four, five or all of the amino acid sequences selected from the group consisting of SEQ ID NOs: 214-216 and 144-146 (1S2 CDRs). In yet another embodiment, the antibody comprises at least one, two, three, four, five or all of the amino acid sequences selected from the group consisting of SEQ ID NOs: 225-227 and 164-166 (1S3 CDRs). In another embodiment, the antibody comprises at least one, two, three, four, five or all of the amino acid sequences selected from the group consisting of SEQ ID NOs: 236-238 and 174-176 (1S4 CDRs). In another embodiment, the antibody comprises at least one, two, three, four, five or all of the amino acid sequences selected from the group consisting of SEQ ID NOs: 247-249 and 184-186 (1S5 CDRs).

In some embodiments, the antibody comprises all three light chain CDRs, all three heavy chain CDRs, or all six CDRs. In some embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous.

Consensus CDRs may also be used. In one embodiment, the antibody comprises one or more of the amino acid sequences set forth in SEQ ID NO: 74 (XASNLES), SEQ ID NO: 75 (XQSNEE) and SEQ ID NO: 76 (QQXNEX), SEQ ID NO: 28 (RASESVDSYGNSFMH), SEQ ID NO: 77 (WINTXSGVPTYADDFXG), SEQ ID NO: 78 (XXYYGX*A*Y), SEQ ID NO: 19 (TYGMS), SEQ ID NO: 284 (VIXYXXSNKYYADSVKG), SEQ ID NO: 285 (WIXAXNGXXXXAXXXQX), SEQ ID NO: 286 (AQEGXAP-DAFDI), SEQ ID NO: 287 (QAWYSSTNVX), SEQ ID NO: 288 (QAWDSSTAXX), SEQ ID NO: 289 (QSDYSSXXX**), wherein X is any amino acid and * can be absent or any amino acid.

In yet another embodiment, the antibody comprises the light and/or heavy chain variable region of an antibody, e.g., SEQ ID NO: 15 (Ab43 heavy chain variable region), and/or SEQ ID NO: 13 (Ab43 light chain variable region); SEQ ID NO: 27 (2.7 heavy chain variable region), and/or SEQ ID NO: 25 (2.7 light chain variable region); SEQ ID NO: 39 (2.41 heavy chain variable region), and/or SEQ ID NO: 37 (2.41 light chain variable region); or SEQ ID NO: 51 (R9 heavy chain variable region), and/or SEQ ID NO: 49 (R9 light chain variable region), SEQ ID NO: 110 (1C9 heavy chain variable region) and/or SEQ ID NO: 108 (1C9 light chain variable region); or SEQ ID NO: 120 (3B3 heavy chain variable region) and/or SEQ ID NO: 118 (3B3 light chain variable region); SEQ ID NO: 130 (4E1 heavy chain variable region) and/or SEQ ID NO: 128 (4E1 light chain variable region); or SEQ ID NO: 140 (7A3 heavy chain variable region) and/or SEQ ID NO:138 (7A3 light chain variable region); or SEQ ID NO: 150 (9D12 heavy chain variable region) and/or SEQ ID NO: 148 (9D12 light chain variable region); SEQ ID NO: 160 (12B9 heavy chain variable region), and/or SEQ ID NO: 158 (12B9 light chain variable region); SEQ ID NO: 170 (15E1 heavy chain variable region) and/or SEQ ID NO: 168 (15E1 light chain variable region); SEQ ID NO: 333 (18B11 heavy chain variable region) and/or SEQ ID NO: 331 (18B11 light chain variable region); SEQ ID NO: 313 (18D8 heavy chain variable region) and/or SEQ ID NO: 311 (18D8 light chain variable region); SEQ ID NO: 343 (19B8 heavy chain variable region) and/or SEQ ID NO: 341 (19B8 light chain variable region); SEQ ID NO: 323 (19C1 heavy chain variable region) and/or SEQ ID NO: 321 (19C1 light chain variable region); SEQ ID NO: 293 (19D12 heavy chain variable region) and/or SEQ ID NO: 291 (19D12 light chain variable region); SEQ ID NO: 303 (19H6 heavy chain variable region) and/or SEQ ID NO: 301 (191-16 light chain variable region); SEQ ID NO: 353 (20E12 heavy chain variable region) and/or SEQ ID NO: 351 (20E12 light chain variable region); SEQ ID NO: 363 (22F12 heavy chain variable region) and/or SEQ ID NO: 361 (22F12 light chain variable region); SEQ ID NO: 373 (22H10 heavy chain variable region) and/or SEQ ID NO: 371 (22H10 light chain variable region); SEQ ID NO: 383 (23A11 heavy chain variable region) and/or SEQ ID NO: 381 (23A11 light chain variable region); SEQ ID NO: 180 (23F11 heavy chain variable region) and/or SEQ ID NO: 178 (23F11 light chain variable region); 393 (24E4 heavy chain variable region) and/or SEQ ID NO: 391 (24E4 light chain variable region); SEQ ID NO: 190 (26F11 heavy chain variable region) and/or SEQ ID NO: 188 (26F11 light chain variable region); or SEQ ID NO: 202 (1S1 heavy chain variable region) and/or SEQ ID NO: 128 (1S1 light chain variable region); SEQ ID NO: 213 (1S2 light chain variable region) and/or SEQ ID NO: 140 (1S2 heavy chain variable region); SEQ ID NO: 224 (1S3 light chain variable region) and/or SEQ ID NO: 160 (1S3 heavy chain variable region); SEQ ID NO: 235 (1S4 light chain variable region) and/or SEQ ID NO: 170 (1S4 heavy chain variable region; or SEQ ID NO: 246 (1S5 light chain variable region) and/or SEQ ID NO: 190 (1S5 heavy chain variable region).

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to an amino acid sequence selected from the group consisting of SEQ ID NOs:

(Ab43 heavy chain variable region), 27 (2.7 heavy chain variable region), 39 (2.41 heavy chain variable region), 51 (R9 heavy chain variable region), 110 (1C9 heavy chain variable region), 120 (3B3 heavy chain variable region), 130 (4E1 heavy chain variable region), 140 (7A3 heavy chain variable region), 150 (9D12 heavy chain variable region), 160 (12B9 heavy chain variable region), 170 (15E1 heavy chain variable region), 333 (18B11 heavy chain variable region), 313 (18D8 heavy chain variable region), 343 (19B8 heavy chain variable region), 323 (19C1 heavy chain variable region), 293 (19D12 heavy chain variable region), 303 (19H6 heavy chain variable region), 353 (20E12 heavy chain variable region), 363 (22F12 heavy chain variable region), 373 (22H10 heavy chain variable region), 383 (23A11 heavy chain variable region), 180 (23F11 heavy chain variable region), 393 (24E4 heavy chain variable region), 190 (26F11 heavy chain variable region), 202 (1S1 heavy chain variable region), 13 (Ab43 light chain variable region), 25 (2.7 light chain variable region), 37 (2.41 light chain variable region), 49 (R9 light chain variable region), 108 (1C9 light chain variable region), 118 (3B3 light chain variable region), 128 (4E1 light chain variable region), 138 (7A3 light chain variable region), 148 (9D12 light chain variable region), 158 (12B9 light chain variable region), 168 (15E1 light chain variable region), 331 (18B11 light chain variable region), 311 (18D8 light chain variable region), 341 (19B8 light chain variable region), 321 (19C1 light chain variable region), 291 (19D12 light chain variable region), 301 (19H6 light chain variable region), 351 (20E12 light chain variable region), 361 (22F12 light chain variable region), 371 (22H10 light chain variable region), 381 (23A11 light chain variable region), 178 (23F11 light chain variable region), 391 (24E4 light chain variable region), 188 (26F11 light chain variable region), 213 (1S2 light chain variable region), 224 (1S3 light chain variable region), 235 (1S4 light chain variable region), 246 (1S5 light chain variable region), the polypeptide further comprising at least one or more of the amino acid sequences set forth in SEQ ID NOs: 16-21 (Ab43 CDRs), 28-33 (2.7CDRs), 40-45 (2.41 CDRs), 52-57 (R9 CDRs), 111-116 (1C9 CDRs), 121-126 (3B3 CDRs), 131-136 (4E1 CDRs), 141-146 (7A3 CDRs), 151-156 (9D12 CDRs), 161-166 (12B9 CDRs), 171-176 (15E1 CDRs), 334-339 (18B11 CDRs), 314-319 (18D8 CDRs), 344-349 (19B8 CDRs), 324-329 (19C1 CDRs), 294-299 (19D12 CDRs), 304-309 (19H6 CDRs), 354-359 (20E12 CDRs), 364-369 (22F12 CDRs), 374-379 (22H10 CDRs), 384-389 (23A11 CDRs), 181-186 (23F11 CDRs), 394-399 (24E4 CDRs), 191-196 (26F11 CDRs), 203-205 (1S1 light chain CDRs) and 131-133 (1S1 heavy chain CDRs), 214-216 (1S2 heavy chain CDRs) and 144-146 (1S2 light chain CDRs), 225-227 (1S3 heavy chain CDRs) and 164-166 (1S3 light chain CDRs), 236-238 (1S4 heavy chain CDRs) and 174-176 (1S4 light chain CDRs), 247-249 (1S5 heavy chain CDRs) and 184-186 (1S5 light chain CDRs). In any of the foregoing embodiments, the polypeptide includes a sequence comprising one or two modifications to any of the amino acid sequences set forth in SEQ ID NOs: 16-21 (Ab43 CDRs), 28-33 (2.7CDRs), 40-45 (2.41 CDRs), 52-57 (R9CDRs), 111-116 (1C9 CDRs), 121-126 (3B3 CDRs), 131-136 (4E1 CDRs), 141-146 (7A3 CDRs), 151-156 (9D12 CDRs), 161-166 (12B9 CDRs), 171-176 (15E1 CDRs), 334-339 (18B11 CDRs), 314-319 (18D8 CDRs), 343-349 (1988 CDRs), 324-329 (19C1 CDRs), 294-299 (19D12 CDRs), 304-309 (19H6 CDRs), 354-359 (20E12 CDRs), 364-369 (22F12 CDRs), 374-379 (22H10 CDRs), 384-389 (23A11 CDRs), 181-186 (23F11 CDRs), 394-399 (24E4 CDRs), 191-196 (26F11 CDRs), 203-205 (1S1 light chain CDRs) and 131-133 (1S1 heavy chain CDRs), 214-216 (1S2 heavy chain CDRs) and 144-146 (1S2 light chain CDRs), 225-227 (1S3 heavy chain CDRs) and 164-166 (1S3 light chain CDRs), 236-238 (1S4 heavy chain CDRs) and 174-176 (1S4 light chain CDRs), 247-249 (1S5 heavy chain CDRs) and 184-186 (1S5 light chain CDRs).

In some embodiments, the antibody comprises the heavy chain variable region of any of antibodies Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11 and optionally comprises a constant region selected from the group consisting of a human IgG1 heavy chain constant region (SEQ ID NOs: 401-402) and a human IgG2 heavy chain constant region (SEQ ID NOs: 403-404). In some embodiments, the antibody comprises the light chain variable region of any of antibodies Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4, and 26F11 and optionally comprises a human kappa light chain constant region (SEQ ID NOs: 405-406). In another embodiment, the antibody comprises the light chain variable region of any of antibodies Ab43, 2.7, 2.41, R9, 1C9, 1S1, 1S2, 1S3, 1S4, 1S5, 3B3; 4E1, 7A3, 9D12, 12B9, 15E1, 18B11, 18D8, 19B8, 19C1, 19D12, 19H6, 20E12, 22F12, 22H10, 23A11, 23F11, 24E4 and 26F11 and optionally comprises a constant region selected from the group consisting of a human lambda light chain constant region type C1 (SEQ ID NOs: 407-408), a human lambda light chain constant region type C2 (SEQ ID NOs: 409-410), a human lambda light chain constant region type C3 (SEQ ID NOs: 411-412), a human lambda light chain constant region type C6 (SEQ ID NOs: 413-414) and a human lambda light chain constant region type C7 (SEQ ID NO: 415-416).

The cDNA and amino acid sequences for the full length light and heavy chains of each of antibodies 1C9, 3B3, 4E1, 7A3, 9D12, 12B9, 15E1, 23F11 and 26F11 are also provided. The cDNA sequences encoding the full length light chain of antibodies 1C9, 3B3, 4E1, 7A3, 9D12, 12B9, 15E1, 123F11, 26F11, 1S2, 1S3, 1S4 and 1S5, including the constant region, are set forth in SEQ ID NOs: 197, 208, 219, 230, 241, 252, 256, 260, 264, 217, 228, 239 and 250, respectively. The amino acid sequences of the full length light chain of antibodies 1C9, 3B3, 4E1, 7A3, 9D12, 12B9, 15E1, 23F11, 26F11, 1S2, 1S3, 1S4 and 1S5, including the constant region, are set forth in SEQ ID NOs: 198 (of which residues 1-20 correspond to the signal peptide and the remainder is the mature polypeptide), 209 (of which residues 1-19 correspond to the signal peptide and the remainder is the mature polypeptide), 220 (of which residues 1-20 correspond to the signal peptide and the remainder is the mature polypeptide), 231 (of which residues 1-20 correspond to the signal peptide and the remainder is the mature polypeptide), 242 (of which residues 1-19 correspond to the signal peptide and the remainder is the mature polypeptide), 253 (of which residues 1-20 correspond to the signal peptide and the remainder is the mature polypeptide), 257 (of which residues 1-20 correspond to the signal peptide and the remainder is the mature polypeptide), 261 (of which residues 1-19 correspond to the signal peptide and the remainder is the mature polypeptide), 265 (of which residues 1-19 correspond to the signal peptide and the remainder is the mature polypeptide), 218 (of which residues 1-22 correspond to the signal peptide and the remainder is the mature polypeptide), 229 (of which residues 1-22 correspond to the signal peptide and the remainder is the mature polypeptide), 240 (of which residues 1-22 correspond to the signal peptide and the remainder is the mature polypeptide) and 251 (of which residues 1-22 correspond to the signal peptide and the remainder is the mature polypeptide), respectively.

The cDNA sequences encoding the full length heavy chain of antibodies 1C9, 3B3, 4E1, 7A3, 9D12, 12B9, 15E1, 23F11, 26F11 and 1S1, including the constant region, are set forth in SEQ ID NOs: 199, 210, 221, 232, 243, 254, 258, 262, 266 and 206, respectively. The amino acid sequences of the full length heavy chain of antibodies 1C9, 3B3, 4E1, 7A3, 9D12, 12B9, 15E1, 23F11, 26F11 and 1S1, including the constant region, are set forth in SEQ ID NOs: 200 (of which residues 1-19 correspond to the signal peptide and the remainder is the mature polypeptide), 211 (of which residues 1-19 correspond to the signal peptide and the remainder is the mature polypeptide), 222 (of which residues 1-19 correspond to the signal peptide and the remainder is the mature polypeptide), 233 (of which residues 1-19 correspond to the signal peptide and the remainder is the mature polypeptide), 244 (no signal peptide), 255 (of which residues 1-19 correspond to the signal peptide and the remainder is the mature polypeptide), 259 (of which residues 1-19 correspond to the signal peptide and the remainder is the mature polypeptide), 263 (of which residues 1-20 correspond to the signal peptide and the remainder is the mature polypeptide), 267 (of which residues 1-19 correspond to the signal peptide and the remainder is the mature polypeptide) and 207 (of which residues 1-19 correspond to the signal peptide and the remainder is the mature polypeptide), respectively.

In some embodiments of the invention, antibodies comprise amino acids 20-467 of SEQ ID NO: 207 (1S1 heavy chain) and amino acids 21-234 of SEQ ID NO: 220 (1S1 light chain); or amino acids 20-466 of SEQ ID NO: 233 (1S2 heavy chain) and amino acids 23-234 of SEQ ID NO: 218 (1S2 light chain); or amino acids 20-466 of SEQ ID NO: 255 (1S3 heavy chain) and amino acids 23-234 of SEQ ID NO: 229 (1S3 light chain); or amino acids 20-466 of SEQ ID NO: 259 (1S4 heavy chain) and wherein amino acids 23-234 of SEQ ID NO: 240 (1S4 light chain); or amino acids 20-466 of SEQ ID NO: 267 (1S5 heavy chain) and amino acids 23-234 of SEQ ID NO: 251 (1S5 light chain).

The term "monoclonal antibody" as used herein refers to an antibody, as that term is defined herein, obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab', F'(ab)$_2$, Fv, single chain antibodies, diabodies), maxibodies, nanobodies, and recombinant peptides comprising the foregoing as long as they exhibit the desired biological activity, or variants or derivatives thereof. Humanizing or modifying antibody sequence to be more human-like is described in, e.g., Jones et al., Nature 321:522 525 (1986); Morrison et al., Proc. Natl. Acad. Sci., U.S.A., 81:6851 6855 (1984); Morrison and 01, Adv. Immunol., 44:65 92 (1988); Verhoeyer et al., Science 239:1534 1536 (1988); Padlan, Molec. Immun., 28:489 498 (1991); Padlan, Molec. Immunol., 31(3):169 217 (1994); and Kettleborough, C. A. et al., Protein Engineering., 4(7):773 83 (1991); Co, M. S., et al. (1994), J. Immunol. 152, 2968-2976); Studnicka et al., Protein Engineering 7: 805-814 (1994); each of which is incorporated herein by reference in its entirety. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. Patent Application Publication Nos. 2003/0194404, 2003/0031667 or 2002/0199213; each incorporated herein by reference in its entirety.

An "isolated" antibody refers to an antibody, as that term is defined herein, that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody, or more than 99% by weight, (2) to a degree sufficient to obtain at least 15 residues of N-terminal or internal amino acid sequence, or (3) to homogeneity by SDS-PAGE under reducing or nonreducing conditions using Coomassie blue or silver stain. Isolated naturally occurring antibody includes the antibody in situ within recombinant cells since at least one component of the antibody's natural environment will not be present. Ordinarily, however, isolated antibody will be prepared by at least one purification step.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

Allotypes are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)). Even a single CDR may recognize and bind antigen, although with a lower affinity than the entire antigen binding site containing all of the CDRs.

An alternative definition of residues from a hypervariable "loop" is described by Chothia et al., J. Mol. Biol., 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact immunoglobulin, e.g., an antigen binding or variable region of the intact antibody, and include multispecific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a VH domain) (Ward et al., Nature, 341:544-546, 1989), complementarity determining region (CDR) fragments, single-chain antibodies (scFv, containing VH and VL domains on a single polypeptide chain) (Bird et al., Science, 242:423-426, 1988, and Huston et al., Proc. Natl. Acad. Sci., USA 85:5879-5883, 1988, optionally including a polypeptide linker; and optionally multispecific, Gruber et al., J. Immunol., 152: 5368 (1994)), single chain antibody fragments, diabodies (VH and VL domains on a single polypeptide chain that pair with complementary VL and VH domains of another chain) (EP 404,097; WO 93/11161; and Holliger et al., Proc. Natl. Acad. Sci., USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), linear antibodies (tandem Fd segments (VH-CH1-VH-CH1) (Zapata et al., Protein Eng., 8(10):1057-1062 (1995)); chelating recombinant antibodies (crAb, which can bind to two adjacent epitopes on the sane antigen) (Neri et al., J Mol Biol., 246:367-73, 1995), bibodies (bispecific Fab-scFv) or tribodies (trispecific Fab-(scFv)(2)) (Schoonjans et al., J. Immunol. 165:7050-57, 2000; Willems et al., J. Chromatogr. B. Analyt. Technol. Biomed. Life Sci., 786:161-76, 2003), intrabodies (Biocca, et al., EMBO J., 9:101-108, 1990; Colby et al., Proc. Natl. Acad. Sci. USA, 101:17616-21, 2004) which may also comprise cell signal sequences which retain or direct the antibody intracellularly (Mhashilkar et al, EMBO J., 14:1542-51, 1995; Wheeler et al., FASEB J., 17:1733-5, 2003), transbodies (cell-permeable antibodies containing a protein transduction domain (PTD) fused to scFv (Heng et al., Med Hypotheses., 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (U.S. Patent Application Publication 2003/0133939 and US Patent Application Publication 2003/0118592), an antigen-binding-domain immunoglobulin fusion protein, a camelized antibody (in which VH recombines with a constant region that contains hinge, CH1, CH2 and CH3 domains) (Desmyter et al., J. Biol. Chem., 276: 26285-90, 2001; Ewert et al., Biochemistry, 41:3628-36, 2002; U.S. Patent Application Publication Nos. 2005/0136049 and 2005/0037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "variant" refers to a polypeptide sequence of an antibody that contains at least one amino acid substitution, deletion, or insertion in the variable region or the portion equivalent to the variable region, provided that the variant retains the desired binding affinity or biological activity. In addition, the antibodies as described herein may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9):6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "modification" includes but is not limited to, one or more amino acid change (including substitutions, insertions or deletions); chemical modifications that do not interfere with hepcidin-binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) will retain the binding properties of unmodified molecules.

The term "derivative" refers to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives will retain the binding properties of underivatized molecules.

Methods for making bispecific or other multispecific antibodies are known in the art and include chemical cross-linking, use of leucine zippers (Kostelny et al., *J. Immunol* 148:1547-1553, 1992); diabody technology (Hollinger et al., *Proc. Natl. Acad. Sci. USA*, 90:6444-48, 1993); scFv dimers (Gruber et al., *J. Immunol.*, 152: 5368, 1994), linear antibodies (Zapata et al., *Protein Eng.*, 8:1057-62, 1995); and chelating recombinant antibodies (Neri et al., *J. Mol. Biol.*, 246: 367-73, 1995).

Thus, a variety of compositions comprising one, two, and/or three CDRs of a heavy chain variable region or a light chain variable region of an antibody may be generated by techniques known in the art.

Recombinant Production of Antibodies

Isolated nucleic acids encoding monoclonal antibodies described herein are also provided, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

Relevant amino acid sequence from an immunoglobulin of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies).

Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, e.g., membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al., (1977) *Proc. Natl. Acad. Sci. USA*, 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

Once isolated, the DNA may be operably linked to expression control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells (i.e., a multicellular organism). Prokaryotic host cells include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris*, *Schizosaccharomyces pombe*; *Kluyveromyces*, *Yarrowia*; *Candida*; *Trichoderma reesia*; *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Host cells for the expression of glycosylated polypeptide or antibody can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of polypeptide or antibody from such cells has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *Proc. Natl. Acad. Sci. USA*, 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, *Biol. Reprod.*, 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., *Annals N.Y. Acad. Sci.*, 383: 44-68 (1982)); MRC 5 cells or FS4 cells; or mammalian myeloma cells.

Host cells are transformed or transfected with the above-described nucleic acids or vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antibodies.

The host cells used to produce an antibody described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.*, 58: 44 (1979), Barnes et al., *Anal. Biochem.*, 102: 255 (1980), U.S. Pat. Nos. 4,767,704; 4,657,866; 4,927,762; 4,560,655; or 5,122,469; WO 90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody can be purified using, for example, hydroxylapatite chromatography, cation or anion exchange chromatography, or affinity chromatography, using the antigen of interest or protein A or protein G as an affinity ligand. Protein A can be used to purify antibodies that are based on human γ1, γ2, or γ4 heavy chains (Lindmark et al., *J. Immunol. Meth.* 62: 1-13 (1983)). Protein G is recommended for all mouse isotypes and for human γ3 (Guss et al., *EMBO J.* 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Chimeric and Humanized Antibodies

Because chimeric or humanized antibodies are less immunogenic in humans than the parental rodent monoclonal antibodies, they can be used for the treatment of humans with far less risk of anaphylaxis. Thus, these antibodies are contemplated in therapeutic applications that involve in vivo administration to a human.

For example, a murine antibody on repeated in vivo administration in man either alone or as a conjugate will bring about an immune response in the recipient, sometimes called a HAMA response (Human Anti Mouse Antibody). The HAMA response may limit the effectiveness of the pharmaceutical if repeated dosing is required. The immunogenicity of the antibody may be reduced by chemical modification of the antibody with a hydrophilic polymer such as polyethylene glycol or by using the methods of genetic engineering to make the antibody binding structure more human like.

The phrase "chimeric antibody," as used herein, refers to an antibody containing sequence derived from two different antibodies which typically originate from different species. Most typically, chimeric antibodies comprise variable Ig domains of a rodent monoclonal antibody fused to human constant Ig domains. Such antibodies can be generated using standard procedures known in the art (See Morrison, S. L., et al. (1984) "Chimeric Human Antibody Molecules; Mouse Antigen Binding Domains with Human Constant Region Domains," *Proc. Natl. Acad. Sci. USA*, 81, 6841-6855; and, Boulianne, G. L., et al, *Nature* 312, 643-646. (1984)). Although some chimeric monoclonal antibodies have proved less immunogenic in humans, the rodent variable Ig domains can still lead to a significant human anti-rodent response.

The phrase "humanized antibody" refers to an antibody derived from a non-human antibody, typically a rodent monoclonal antibody. Alternatively, a humanized antibody may be derived from a chimeric antibody.

Humanized antibodies may be achieved by a variety of methods including, for example: (1) grafting the non-human complementarity determining regions (CDRs) onto a human framework and constant region (a process referred to in the art as humanizing through "CDR grafting"), or, alternatively, (2) transplanting the entire non-human variable domains, but "cloaking" them with a human-like surface by replacement of surface residues (a process referred to in the art as "veneering"). These methods are disclosed in, e.g., Jones et al., Nature 321:522 525 (1986); Morrison et al., *Proc. Natl. Acad. Sci., USA,* 81:6851 6855 (1984); Morrison and Oi, *Adv. Immunol.,* 44:65 92 (1988); Verhoeyer et al., *Science* 239: 1534 1536 (1988); Padlan, *Molec. Immun.* 28:489 498 (1991); Padlan, *Molec. Immunol.* 31(3):169 217 (1994); and Kettleborough, C. A. et al., *Protein Eng.* 4(7):773 83 (1991) each of which is incorporated herein by reference in its entirety.

CDR grafting involves introducing one or more of the six CDRs from the mouse heavy and light chain variable Ig domains into the appropriate framework regions of a human variable Ig domain. This technique (Riechmann, L., et al., *Nature* 332, 323 (1988)), utilizes the conserved framework regions (FR1-FR4) as a scaffold to support the CDR loops which are the primary contacts with antigen. A significant disadvantage of CDR grafting, however, is that it can result in a humanized antibody that has a substantially lower binding affinity than the original mouse antibody, because amino acids of the framework regions can contribute to antigen binding, and because amino acids of the CDR loops can influence the association of the two variable Ig domains. To maintain the affinity of the humanized monoclonal antibody, the CDR grafting technique can be improved by choosing human framework regions that most closely resemble the framework regions of the original mouse antibody, and by site-directed mutagenesis of single amino acids within the framework or CDRs aided by computer modeling of the antigen binding site (e.g., Co, M. S., et al. (1994), *J. Immunol.* 152, 2968-2976).

One method of humanizing antibodies comprises aligning the non-human heavy and light chain sequences to human heavy and light chain sequences, selecting and replacing the non-human framework with a human framework based on such alignment, molecular modeling to predict the conformation of the humanized sequence and comparing to the conformation of the parent antibody. This process is followed by repeated back mutation of residues in the CDR region which disturb the structure of the CDRs until the predicted conformation of the humanized sequence model closely approximates the conformation of the non-human CDRs of the parent non-human antibody. Such humanized antibodies may be further derivatized to facilitate uptake and clearance, e.g., via Ashwell receptors (See, e.g., U.S. Pat. Nos. 5,530,101 and 5,585,089).

A number of humanizations of mouse monoclonal antibodies by rational design have been reported (See, for example, U.S. Patent Application Publication No. 2002/0091240 published Jul. 11, 2002, WO 92/11018 and U.S. Pat. Nos. 5,693, 762, 5,766,866).

Human Engineered™ Antibodies

The phrase "Human Engineered™ antibody" refers to an antibody derived from a non-human antibody, typically a rodent monoclonal antibody or possibly a chimeric antibody. Human Engineering™ of antibody variable domains has been described by Studnicka [See, e.g., Studnicka et al. U.S. Pat. No. 5,766,886; Studnicka et al. *Protein Engineering,* 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding; (2) moderate risk changes are those that would further reduce immunogenicity, but have a greater chance of affecting antigen binding or protein folding; (3) high risk residues are those that are important for binding or for maintaining antibody structure and carry the highest risk that antigen binding or protein folding will be affected. Due to the three-dimensional structural role of prolines, modifications at prolines are generally considered to be at least moderate risk changes, even if the position is typically a low risk position.

Variable regions of the light and heavy chains of a rodent antibody can be Human Engineered™ by substituting human amino acids at positions determined to be unlikely to adversely effect either antigen binding or protein folding, but likely to reduce immunogenicity in a human environment. Although any human variable region can be used, including an individual VH or VL sequence or a human consensus VH or VL sequence or an individual or consensus human germline sequence, generally a human sequence with highest identity or homology to the rodent sequence is used to minimize the number of substitutions. The amino acid residues at any number of the low risk positions, or at all of the low risk positions, can be changed. For example, at each low risk position where the aligned murine and human amino acid residues differ, an amino acid modification is introduced that replaces the rodent residue with the human residue. In addition, the amino acid residues at any number or all of the moderate risk positions can be changed. In some embodiments, all of the low and moderate risk positions are changed from rodent to human sequence.

Synthetic genes containing modified heavy and/or light chain variable regions are constructed and linked to human γ heavy chain and/or kappa light chain constant regions. Any human heavy chain and light chain constant regions of any class or subclass may be used in combination with the Human Engineered™ antibody variable regions.

Antibodies from Transgenic Animals Engineered to Contain Human Immunoglobulin Loci Antibodies to hepcidin can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. Transgenic non-primate mammalian hosts capable of mounting an immune response to an immunogen, wherein the antibodies have primate constant and/or variable regions, and wherein the endogenous immunoglobulin encoding loci are substituted or inactivated have also been discussed. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein.

See also Jakobovits et al., *Proc. Natl. Acad. Sci. USA*, 90:2551 (1993); Jakobovits et al., *Nature*, 362:255-258 (1993); Bruggermann et al., Year in Immuno., 7:33 (1993); and U.S. Pat. Nos. 5,591,669, 5,589,369, 5,545,807; and U.S. Patent Application Publication No. 2002/0199213. U.S. Patent Application Publication No. 2003/0092125 describes methods for biasing the immune response of an animal to the desired epitope. Human antibodies may also be generated by in vitro activated B cells (see U.S. Pat. Nos. 5,567,610 and 5,229,275).

Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, *Proc. Natl. Acad. Sci. USA*, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol.*, 222:581-597 (1991); U.S. Pat. Nos. 5,565,332 and 5,573,905; Clackson, T., and Wells, J. A., *TIBTECH*, 12, 173-184 (1994)). In particular, in vitro selection and evolution of antibodies derived from phage display libraries has become a powerful tool (See Burton, D. R., and Barbas III, C. F., *Adv. Immunol.*, 57, 191-280 (1994); and, Winter, G., et al., *Annu. Rev. Immunol.*, 12, 433-455 (1994); U.S. Patent Application Publication No. 2002/0004215 and WO92/01047; U.S. Patent Application Publication No. 2003/0190317 published Oct. 9, 2003 and U.S. Pat. Nos. 6,054,287; 5,877,293.

Watkins, "Screening of Phage-Expressed Antibody Libraries by Capture Lift," *Methods in Molecular Biology, Antibody Phage Display: Methods and Protocols*, 178: 187-193, and U.S. Patent Application Publication No. 2003/0044772 published Mar. 6, 2003 describes methods for screening phage-expressed antibody libraries or other binding molecules by capture lift, a method involving immobilization of the candidate binding molecules on a solid support.

Antibody Fragments

As noted above, antibody fragments comprise a portion of an intact full length antibody, or an antigen binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science 242:423-426, 1988, and Huston et al., Proc. Natl. Acad. Sci. USA 85:5879-5883, 1988). An Fd fragment consists of the $V_H$ and $C_H1$ domains.

Additional antibody fragments include a domain antibody (dAb) fragment (Ward et al., Nature 341:544-546, 1989) which consists of a $V_H$ domain.

"Linear antibodies" comprise a pair of tandem Fd segments ($V_H$-$C_H1$-$V_H$-$C_H1$) which form a pair of antigen binding regions. Linear antibodies can be bispecific or monospecific (Zapata et al., Protein Eng., 8:1057-62 (1995)).

A "minibody" consisting of scFv fused to CH3 via a peptide linker (hingeless) or via an IgG hinge has been described in Olafsen, et al., Protein Eng. Des. Sel., 2004 April; 17(4): 315-23.

The term "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001).

Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain. Classical $V_H$-only fragments are difficult to produce in soluble form, but improvements in solubility and specific binding can be obtained when framework residues are altered to be more $VH_H$-like. (See, e.g., Reichman, et al., J. Immunol. Methods, 1999, 231:25-38.) Camelized $V_{HH}$ domains have been found to bind to antigen with high affinity (Desmyter et al., J. Biol. Chem. 276:26285-90, 2001) and possess high stability in solution (Ewert et al., Biochemistry 41:3628-36, 2002). Methods for generating antibodies having camelized heavy chains are described in, for example, in U.S. Patent Application Publication Nos. 2005/0136049 and 2005/0037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., Cancer Research 64:2853-57, 2004). A nanobody library may be generated from an immunized dromedary as described in Conrath et al., (Antimicrob Agents Chemother, 45: 2807-12, 2001).

Intrabodies are single chain antibodies which demonstrate intracellular expression and can manipulate intracellular protein function (Biocca, et al., EMBO J. 9:101-108, 1990; Colby et al., Proc Natl Acad Sci USA. 101:17616-21, 2004). Intrabodies, which comprise cell signal sequences which retain the antibody contruct in intracellular regions, may be produced as described in Mhashilkar et al (EMBO J 14:1542-51, 1995) and Wheeler et al. (FASEB J. 17:1733-5. 2003). Transbodies are cell-permeable antibodies in which a protein transduction domains (PTD) is fused with single chain variable fragment (scFv) antibodies Heng et al., (Med Hypotheses., 64:1105-8, 2005).

Further contemplated are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent Application Publication No. 2003/0133939 and US Patent Application Publication No. 2003/0118592.

Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Additionally, the anti-hepcidin antibodies disclosed herein can also be constructed to fold into multivalent forms, which may improve binding affinity, specificity and/or increased half-life in blood. Multivalent forms of anti-hepcidin antibodies can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., Hum Antibodies Hybridomas 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments have also been described in the literature. For example, bispecific or trispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., *Bio/Technology* 10:163-167 (1992); Shalaby et al., *J. Exp. Med.*, 175:217-225 (1992)).

Shalaby et al., *J. Exp. Med.*, 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific or multispecific antibody fragments directly from recombinant cell culture have also been described. For example, bispecific antibodies have been produced using leucine zippers, e.g. GCN4. (See generally Kostelny et al., *J. Immunol.* 148(5): 1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

Diabodies, described above, are one example of a bispecific antibody. See, for example, Hollinger et al., *Proc. Natl. Acad. Sci. USA,* 90:6444-6448 (1993). Bivalent diabodies can be stabilized by disulfide linkage.

Stable monospecific or bispecific Fv tetramers can also be generated by noncovalent association in (scFv$_2$)$_2$ configuration or as bis-tetrabodies. Alternatively, two different scFvs can be joined in tandem to form a bis-scFv.

Another strategy for making bispecific antibody fragments by the use of single-chain Fv (sFv) dimers has also been reported. See Gruber et al., *J. Immunol.* 152: 5368 (1994).

One approach has been to link two scFv antibodies with linkers or disulfide bonds (Mallender and Voss, *J. Biol. Chem.,* 269:199-2061994, WO 94/13806, and U.S. Pat. No. 5,989,830, the disclosures of which are incorporated herein by reference in their entireties).

Alternatively, the bispecific antibody may be a "linear antibody" produced as described in Zapata et al. *Protein Eng.* 8(10):1057-1062 (1995). Briefly, these antibodies comprise a pair of tandem Fd segments ($V_H$-$C_H1$-$V_H$-$C_H1$) which form a pair of antigen binding regions. Linear antibodies can be bispecific or monospecific.

Antibodies with more than two valencies are also contemplated. For example, trispecific antibodies can be prepared. (Tutt et al., *J. Immunol* 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol.* 246:367-73, 1995).

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

In yet another method, dimers, trimers, and tetramers are produced after a free cysteine is introduced in the parental protein. A peptide-based cross linker with variable numbers (two to four) of maleimide groups was used to cross link the protein of interest to the free cysteines (Cochran et al., Immunity 12(3): 241-50 (2000), the disclosure of which is incorporated herein in its entirety).

Specific Binding Agents

Other hepcidin-specific binding agents can be prepared, for example, based on CDRs from an antibody or by screening libraries of diverse peptides or organic chemical compounds for peptides or compounds that exhibit the desired binding properties for human hepcidin. Hepcidin specific binding agent include peptides containing amino acid sequences that are at least 80%, 81%, 82%, 83%, 84%, 85%, 86%, 87%, 88%, 89%, 90%, 91%, 92%, 93%, 94%, 95%, 96%, 97%, 98%, 99% or more identical to one or more CDRs of murine antibody Ab43 (SEQ ID NOs: 16-21); murine antibody 2.7 (SEQ ID NOs: 28-33); murine antibody 2.41 (SEQ ID NOs: 40-45), rat antibody R9 (SEQ ID NOs: 52-57) or human antibody 1C9 (SEQ ID NOs: 111-116), human antibody 3B3 (SEQ ID NOs: 121-126), human antibody 4E1 (SEQ ID NOs: 131-136), human antibody 7A3 (SEQ ID NOs: 141-46), human antibody 9D12 (SEQ ID NOs: 151-156), human antibody 12B9 (SEQ ID NOs: 161-166), human antibody 15E1 (SEQ ID NOs: 171-176), human antibody 18B11 (SEQ ID NOs: 334-339), human antibody 18D8 (SEQ ID NOs: 314-319), human antibody 19B8 (SEQ ID NOs: 343-349), human antibody 19C1 (SEQ ID NOs: 324-329), human antibody 19D12 (SEQ ID NOs: 294-299), human antibody 19H6 (SEQ ID NOs: 304-309), human antibody 20E12 (SEQ ID NOs: 353-359), human antibody 22F12 (SEQ ID NOs: 363-369), human antibody 22H10 (SEQ ID NOs: 373-379), human antibody 23A11 (SEQ ID NOs: 383-389), human antibody 23F11 (SEQ ID NOs: 181-186), human antibody 24E4 (SEQ ID NOs: 393-399), human antibody 26F11 (SEQ ID NOs: 191-196), or human antibody 1S1 (SEQ ID NOs: 203-205 and 131-133) or human antibody 1S2 (SEQ ID NOs: 214-216 and 144-146) or human antibody 1S3 (SEQ ID NOs:

225-227 and 164-166) or human antibody 1S4 (SEQ ID NOs: 236-238 and 174-176) or human antibody 1S5 (SEQ ID NO: 247-249 and 184-186.

Hepcidin-specific binding agents also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example, the carboxyl terminus may be capped with an amino group, cysteines may be cappe, or amino acid residues may substituted by moieties other than amino acid residues (see, e.g., Bhatnagar et al., *J. Med. Chem.,* 39: 3814-9 (1996), and Cuthbertson et al., *J. Med. Chem.,* 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, *Ann. Rev. Biophys. Biomol. Struct.,* 26: 401-24 (1997). Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of for example, a desired molecule in between two consecutive amino acids, optionally joined by a suitable linker.

The development of hepcidin peptibodies is also contemplated. The interaction of a protein ligand with its receptor often takes place at a relatively large interface. However, as demonstrated for human growth hormone and its receptor, only a few key residues at the interface contribute to most of the binding energy. Clackson et al., *Science* 267: 383-6 (1995). The bulk of the protein ligand merely displays the binding epitopes in the right topology or serves functions unrelated to binding. Thus, molecules of only "peptide" length (generally 2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

Phage display technology has emerged as a powerful method in identifying such peptide agonists and antagonists. See, for example, Scott et al. *Science,* 249: 386 (1990); Devlin et al., *Science* 249: 404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). In peptide phage display libraries, random peptide sequences can be displayed by fusion with coat proteins of filamentous phage. The displayed peptides can be affinity-eluted against an antibody-immobilized extracellular domain of a receptor, if desired. The retained phage may be enriched by successive rounds of affinity purification and repropagation. The best binding peptides may be sequenced to identify key residues within one or more structurally related families of peptides. See, e.g., Cwirla et al., *Science* 276: 1696-9 (1997), in which two distinct families were identified. The peptide sequences may also suggest which residues may be safely replaced by alanine scanning or by mutagenesis at the DNA level. Mutagenesis libraries may be created and screened to further optimize the sequence of the best binders. Lowman, *Ann. Rev. Biophys. Biomol. Struct.,* 26: 401-24 (1997).

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al., *Nature Biotech* 15: 1266-70 (1997). These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA. See, for example, Roberts and Szostak, *Proc. Natl. Acad. Sci. USA,* 94: 12297-303 (1997). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, *Curr. Opin. Biotechnol.,* 3: 355-62 (1992).

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. See, e.g., Cortese et al., *Curr. Opin. Biotech.,* 7: 616-21 (1996). Peptide libraries are now being used most often in immunological studies, such as epitope mapping. See Kreeger, *The Scientist,* 10(13):19-20 (1996).

Sources for compounds that may be screened for ability to bind to or modulate (i.e., increase or decrease) the activity of the hepcidin polypeptides described herein include (1) inorganic and organic chemical libraries, (2) natural product libraries, and (3) combinatorial libraries comprised of either random or mimetic peptides, oligonucleotides or organic molecules.

Chemical libraries may be readily synthesized or purchased from a number of commercial sources, and may include structural analogs of known compounds or compounds that are identified as "hits" or "leads" via natural product screening.

The sources of natural product libraries are microorganisms (including bacteria and fungi), animals, plants or other vegetation, or marine organisms, and libraries of mixtures for screening may be created by: (1) fermentation and extraction of broths from soil, plant or marine microorganisms or (2) extraction of the organisms themselves. Natural product libraries include polyketides, non-ribosomal peptides, and (non-naturally occurring) variants thereof. For a review, see *Science* 282:63-68 (1998).

Combinatorial libraries are composed of large numbers of peptides, oligonucleotides or organic compounds and can be readily prepared by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opin. Biotechnol.* 8:701-707 (1997). For reviews and examples of peptidomimetic libraries, see Al-Obeidi et al., *Mol. Biotechnol.*, 9(3):205-23 (1998); Hruby et al., *Curr. Opin. Chem. Biol.*, 1(1):114-19 (1997); Dorner et al., *Bioorg. Med. Chem.*, 4(5):709-15 (1996) (alkylated dipeptides).

Hepcidin-specific binding agents also include scaffolding proteins, as described by Hays et al. *Trends In Biotechnology*, 23(10):514-522 (2005), herein incorporated by reference in its entirety, and Avimer protein technology, as described in U.S. Publication Nos. 2006-0286603 and 2006-0223114, both herein incorporated by reference in their entireties.

Screening Methods for Antibodies or Specific Binding Agents

Methods of identifying antibodies or specific binding agents which bind hepcidin and/or which cross-block exemplary antibodies described herein, and/or which inhibit hepcidin activity are also provided.

Antibodies or specific binding agents may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety.

To initially screen for antibodies or specific binding agents which bind to the desired epitope on the target antigen, a routine cross-blocking assay such as that described in Antibodies, A Laboratory Manual, Cold Spring Harbor Laboratory, Ed Harlow and David Lane (1988), can be performed. Routine competitive binding assays may also be used, in which the unknown antibody is characterized by its ability to inhibit binding of target to a target-specific antibody described herein. Intact antigen, fragments thereof such as the extracellular domain, or linear epitopes can be used. Epitope mapping is described in Champe et al., *J. Biol. Chem.* 270: 1388-1394 (1995). Competitive binding assays may also be used to determine the off-rate of an antibody-antigen interaction. For example, one example of a competitive binding assay is a radioimmunoassay comprising the incubation of labeled antigen (e.g., $^3$H or $^{125}$I), or fragment or variant thereof, with the antibody of interest in the presence of increasing amounts of unlabeled antigen, and the detection of the antibody bound to the labeled antigen. The binding off-rates can be determined from the data by scatchard plot analysis.

In one variation of an in vitro binding assay, method is provided comprising (a) contacting an immobilized hepcidin with a candidate antibody or specific binding agent and (b) detecting binding of the candidate antibody or specific binding agent to the hepcidin. In an alternative embodiment, the candidate antibody or specific binding agent is immobilized and binding of hepcidin is detected. Immobilization is accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin moiety. Detection of binding can be accomplished (i) using a radioactive label on the compound that is not immobilized, (ii) using a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known and routinely practiced in the art.

In some embodiments, antibodies or specific binding agents that inhibit or neutralize human hepcidin activity may be identified by contacting hepcidin with the antibody (or specific binding agent), comparing hepcidin activity in the presence and absence of the test antibody (or specific binding agent), and determining whether the presence of the antibody (or specific binding agent) decreases activity of the hepcidin. The biological activity of a particular antibody, or specific binding agent, or combination of antibodies or specific binding agents, may be evaluated in vivo using a suitable animal model, including any of those described herein.

In some embodiments, high throughput screening (HTS) assays to identify antibodies that interact with or inhibit biological activity (i.e., inhibit phosphorylation, dimerization, ligand induced-receptor activation, or intracellular signaling, etc.) of target antigen are also contemplated. HTS assays permit screening of large numbers of compounds in an efficient manner. Cell-based HTS systems are contemplated to investigate the interaction between target antigen and its binding partners. HTS assays are designed to identify "hits" or "lead compounds" having the desired property, from which modifications can be designed to improve the desired property.

In another embodiment, high throughput screening for antibody fragments or CDRs with 1, 2, 3 or more modifications to amino acids within the CDRs having suitable binding affinity to a target antigen polypeptide is employed.

Production of Antibody Variants and Derivatives

The anti-hepcidin antibodies disclosed herein can readily be modified by techniques well-known to one of ordinary skill in the art. Potential mutations include insertion, deletion or substitution of one or more residues. In some embodiment, insertions or deletions are in the range of about 1 to 5 amino acids, in the range of about 1 to 3 amino acids, or in the range of about 1 or 2 amino acids.

Deletion variants are polypeptides wherein at least one amino acid residue of any amino acid sequence is removed. Deletions can be effected at one or both termini of the protein, or with removal of one or more residues within (i.e., internal to) the polypeptide. Methods for preparation of deletion variants are routine in the art. See, e.g., Sambrook et al. (1989) Molecular Cloning: A Laboratory Guide, Vols 1-3, Cold Spring Harbor Press, the disclosure of which is incorporated herein by reference in its entirety.

Amino acid sequence insertions include amino- and/or carboxyl-terminal fusions ranging in length from one residue to polypeptides containing hundreds or more residues, as well as internal sequence insertions of one or more amino acids. As with any of the different variant types described herein, insertional variants can be designed such that the resulting polypeptide retains the same biological properties or exhibits a new physical, chemical and/or biological property not associated with the parental polypeptide from which it was derived. Methods for preparation of insertion variants are also routine and well known in the art (Sambrook et al., supra).

Fusion proteins comprising a polypeptide comprising an anti-hepcidin antibody described herein, and a heterologous polypeptide, are a specific type of insertion variant contemplated herein. Nonlimiting examples of heterologous polypeptides which can be fused to polypeptides of interest include proteins with long circulating half-life, such as, but not limited to, immunoglobulin constant regions (e.g., Fc region); marker sequences that permit identification of the polypeptide of interest; sequences that facilitate purification of the polypeptide of interest; and sequences that promote formation of multimeric proteins.

Methods of making antibody fusion proteins are well known in the art. See, e.g., U.S. Pat. No. 6,306,393, the disclosure of which is incorporated herein by reference in its entirety. In certain embodiments, fusion proteins are produced which may include a flexible linker, which connects the chimeric scFv antibody to the heterologous protein moiety. Appropriate linker sequences are those that do not affect the ability of the resulting fusion protein to be recognized and bind the epitope specifically bound by the V domain of the protein (see, e.g., WO 98/25965, the disclosure of which is incorporated herein by reference in its entirety).

Substitution variants are those in which at least one residue in the polypeptide amino acid sequence is removed and a different residue is inserted in its place. Modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. In certain embodiments, substitution variants are designed, i.e., one or more specific (as opposed to random) amino acid residues are substituted with a specific amino acid residue. Typical changes of these types include conservative substitutions and/or substitution of one residue for another based on similar properties of the native and substituting residues.

Conservative substitutions are shown in Table 1. The most conservative substitution is found under the heading of "preferred substitutions." If such substitutions result in no change in biological activity, then more substantial changes may be introduced and the products screened.

TABLE 1

| Original | Exemplary | Preferred Residue Substitutions |
|---|---|---|
| Ala (A) | val; leu; ile | val |
| Arg (R) | lys; gln; asn | lys |
| Asn (N) | gln; his; asp, lys; gln | arg |
| Asp (D) | glu; asn | glu |
| Cys (C) | ser; ala | ser |
| Gln (Q) | asn; glu | asn |
| Glu (E) | asp; gln | asp |

TABLE 1-continued

| Original | Exemplary | Preferred Residue Substitutions |
|---|---|---|
| Gly (G) | ala | |
| His (H) | asn; gln; lys; arg | |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Amino acid residues which share common side-chain properties are often grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Antibody Variants

In certain instances, antibody variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which antibody amino acid residues are important for epitope recognition and binding, alanine scanning mutagenesis can be performed to produce substitution variants. See, for example, Cunningham et al., *Science*, 244:1081-1085 (1989), the disclosure of which is incorporated herein by reference in its entirety. In this method, individual amino acid residues are replaced one-at-a-time with an alanine residue and the resulting anti-hepcidin antibody is screened for its ability to bind its specific epitope relative to the unmodified antibody. Modified antibodies with reduced binding capacity are sequenced to determine which residue was changed, indicating its significance in binding or biological properties.

Substitution variants of antibodies can be prepared by affinity maturation wherein random amino acid changes are introduced into the parent antibody sequence. See, for example, Ouwehand et al., Vox Sang 74 (Suppl 2):223-232, 1998; Rader et al., *Proc. Natl. Acad. Sci. USA* 95:8910-8915, 1998; Dall'Acqua et al., *Curr. Opin. Struct. Biol.*, 8:443-450, 1998, the disclosures of which are incorporated herein by reference in their entireties. Affinity maturation involves preparing and screening the anti-hepcidin antibodies, or variants thereof and selecting from the resulting variants those that have modified biological properties, such as increased binding affinity relative to the parent anti-hepcidin antibody. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of M13 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., *J. Mol. Biol.* 260, 359-68, 1996), and saturation mutagenesis (Nishimiya et al., *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA*. 102:8466-71, 2005). Nonstochastic techniques often use alanine-scanning or site-directed mutagenesis to generate limited collections of specific muteins. Some methods are described in further detail below.

Affinity maturation via panning methods—Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA*. 97:2029-34, 2000).

Look-through mutagenesis—Look-through mutagenesis (LTM) (Rajpal et al., *Proc Natl Acad Sci USA*. 102:8466-71, 2005) provides a method for rapidly mapping the antibody-binding site. For L™, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error prone PCR—Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol. Biol. 226:889-96, 1992). After the mutation cycles, clones with improved affinity for the antigen are selected using routine methods in the art.

Techniques utilizing gene shuffling and directed evolution may also be used to prepare and screen anti-hepcidin antibodies, or variants thereof, for desired activity. For example, Jermutus et al., Proc Natl Acad Sci USA., 98(1):75-80 (2001) showed that tailored in vitro selection strategies based on ribosome display were combined with in vitro diversification by DNA shuffling to evolve either the off-rate or thermodynamic stability of scFvs; Fermer et al., Tumour Biol. 2004 January-April; 25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

Antibody with Modified Carbohydrate

Antibody variants can also be produced that have a modified glycosylation pattern relative to the parent antibody, for example, adding or deleting one or more of the carbohydrate moieties bound to the specific binding agent or antibody, and/or adding or deleting one or more glycosylation sites in the specific binding agent or antibody.

Glycosylation of polypeptides, including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a specific binding agent or antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a specific binding agent or antibody by inserting or substituting one or more serine or threonine residues to the sequence of the original specific binding agent or antibody.

Altered Effector Function

Cysteine residue(s) may be removed or introduced in the Fc region of an antibody or Fc-containing polypeptide, thereby eliminating or increasing interchain disulfide bond formation in this region. A homodimeric specific binding agent or antibody thus generated may have improved internalization capability and/or increased complement-mediated cell killing and antibody-dependent cellular cytotoxicity (ADCC). See Caron et al., *J. Exp. Med.*, 176:1191-1195 (1992) and Shopes, B., *J. Immunol.* 148: 2918-2922 (1992). Homodimeric specific binding agents or antibodies may also be prepared using heterobifunctional cross-linkers as described in Wolff et al., *Cancer Research*, 53:2560-2565 (1993). Alternatively, a specific binding agent or antibody can be engineered which has dual Fc regions and may thereby have enhanced complement lysis and ADCC capabilities. See Stevenson et al., *Anti-Cancer Drug Design* 3:219-230 (1989).

It has been shown that sequences within the CDR can cause an antibody to bind to MHC Class II and trigger an unwanted helper T-cell response. A conservative substitution can allow the specific binding agent or antibody to retain binding activity yet reduce its ability to trigger an unwanted T-cell response. It is also contemplated that one or more of the N-terminal 20 amino acids of the heavy or light chain are removed.

In some embodiments, production of antibody molecules are contemplated with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 2004 Sep. 5; 87(5):614-22). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol. Immunol. 1989 December; 26(12):1113-23). Some host cell strains, e.g. Lec13 or rat hybridoma YB2/0 cell line naturally produce antibodies with lower fucosylation levels. Shields et al., J Biol. Chem. 2002 Jul. 26; 277(30):26733-40; Shinkawa et al., J Biol. Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat. Biotechnol. 1999 February; 17(2): 176-80. It has been predicted that the absence of only one of the two fucose residues may be sufficient to increase ADCC activity. (Ferrara et al., J Biol. Chem. 2005 Dec. 5).

Other Covalent Modifications

Covalent modifications of a polypeptide, or antibody are also included within the scope of this invention. They may be made by chemical synthesis or by enzymatic or chemical cleavage of the polypeptide or antibody, if applicable. Other types of covalent modifications can be introduced by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. In some embodiments, para-bromophenacyl bromide also is useful; and the reaction is performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R-N.dbd.C.dbd.N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the specific binding agent or antibody. These procedures are advantageous in that they do not require production of the polypeptide or antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the polypeptide or antibody may be accomplished chemically or enzymatically. Chemical deglycosylation requires exposure of the specific binding agent or antibody to the compound trifluoromethanesulfonic acid, or an equivalent compound. This treatment results in the cleavage of most or all sugars except the linking sugar (N-acetylglucosamine or N-acetylgalactosamine), while leaving the specific binding agent or antibody intact. Chemical deglycosylation is described by Hakimuddin, et al., Arch. Biochem. Biophys., 259: 52 (1987) and by Edge et al., Anal. Biochem., 118: 131 (1981). Enzymatic cleavage of carbohydrate moieties on a specific binding agent or antibody can be achieved by the use of a variety of endo- and exo-glycosidases as described by Thotakura et al., Meth. Enzymol., 138: 350 (1987).

Another type of covalent modification of an anti-hepcidin antibody described herein comprises linking the polypeptide, specific binding agent or antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Diagnostic Methods for Hepcidin-Related Disorders and Monitoring of Therapy with Anti-Hepcidin Antibodies In another aspect, a method is provided of detecting human hepcidin in a sample, comprising contacting a sample from a human with any of the aforementioned antibodies under conditions that allow binding of the antibody to human hepcidin, and detecting the bound antibody. In one embodiment, a first antibody to hepcidin is immobilized on a solid support, as a capture reagent, and a second antibody to hepcidin is used as a detection reagent. In a related aspect, the amount of hepcidin in the sample is quantitated by measuring the amount of the bound antibody. The detection methods can be used in a variety of diagnostic, prognostic and monitoring methods, including methods of diagnosing a hepcidin-related disorder, methods of differentiating an inflammatory disease from a non-inflammatory disease and methods of monitoring therapy with an anti-hepcidin antibody. In such methods, a level of hepcidin above a certain threshold is correlated with the presence of hepcidin-related disorder, such as hepcidin-related anemia, while a level below said threshold indicates that the patient is unlikely to have hepcidin-related disorder. Similarly, a level of hepcidin above a certain threshold is correlated with the presence of an inflammatory disease, while a level below said threshold indicates that the patient is unlikely to have an inflammatory disease. In some embodiments, such methods will diagnose patients having iron deficiency anemia, anemia of inflammation or mixed anemia. For monitoring of therapy aimed at suppressing hepcidin levels, a level of hepcidin below a certain threshold indicates that the dose of hepcidin antibody is therapeutically effective, and a level above said threshold indicates that the dose of hepcidin antibody is not therapeutically effective.

Also provided are methods for diagnosing hepcidin-related disorders, such as hepcidin-related anemia, or other diseases of hepcidin excess or hepcidin deficiency, and for monitoring the effectiveness of therapy for such a disease, including therapy with an anti-hepcidin antibody described herein. To determine the presence or absence of hepcidin-related anemia, a biological sample from a patient is contacted with one or more of the anti-hepcidin antibodies disclosed herein under conditions and for a time sufficient to allow immunocomplexes to form. Immunocomplexes formed between an anti-hepcidin antibody and hepcidin in the biological sample are then detected. The amount of hepcidin in the sample is quantitated by measuring the amount of the immunocomplex formed between the antibody and hepcidin. Within certain methods, a biological sample is isolated from a patient and is incubated with one or more of the anti-hepcidin antibodies disclosed herein, and the level of the antibody-hepcidin complex above a certain threshold is correlated with the presence of hepcidin-related anemia, and a level below said threshold indicates that the patient is unlikely to have hepcidin-related anemia. For example, a level within the normal range indicates the patient is unlikely to have hepcidin-related anemia. Normal range of serum hepcidin is generally less than 10 ng/ml when determined by certain assays, i.e., mass spectrometry techniques described in co-owned U.S. patent application Ser. No. 11/880,313 and International Publication No. WO 2008/011158, the disclosures of which are incorporated herein by reference in their entirety, but will vary depending on the assay and depending on the subset of population tested.

Also provided are methods for differentiating an inflammatory disease from a non-inflammatory disease. To determine the presence or absence of an inflammatory disease, a biological sample from a patient is contacted with one or more of the anti-hepcidin antibodies disclosed herein under conditions and for a time sufficient to allow immunocomplexes to form. Various immunoassays known in the art can be used, including but are not limited to: competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. Antibodies: A Laboratory Manual (1988) by Harlow & Lane or more recent editions; Immunoassays: A Practical Approach, Oxford University Press, Gosling, J. P. (ed.) (2001) or more recent editions; and/or Current Protocols in Molecular Biology (Ausubel et al.), which is regularly updated. Examples of such assays usually involve the antibody attached to a surface or matrix, patient serum added and time allowed for a complex to form; suitable washing procedures to remove unbound complex, followed by either the addition of a second antibody to allow detection of the complex (a sandwich ELISA) or a detectable version of hepcidin to detect free hepcidin binding sites on the antibody surface (a competition ELISA). The level of hepcidin, as detected by the foregoing methods, above a certain threshold is correlated with the presence of an inflammatory disease, and a level below said threshold indicates that the patient is unlikely to have an inflammatory disease. A patient is unlikely to have an inflammatory disease when the hepcidin level is within the normal range. A patient is likely to have an inflammatory disease when the hepcidin level exceeds the normal range, for example 20 ng/ml, in particular, when the level is between 20 and 1000 ng/ml. Exemplary hepcidin-related inflammatory diseases include anemia of cancer, anemia of chronic disease, anemia of inflammation, chemotherapy-induced anemia, chronic kidney disease (stage I, II, III, IV or V), end stage renal disease, chronic renal failure congestive heart failure, cancer, rheumatoid arthritis, systemic lupus erythematosus, Crohn's disease, *H. pylori* infection or other bacterial infections, hepatitis C, HIV, and other viral illnesses, arteriosclerosis, atherosclerosis, cirrhosis of the liver, pancreatitis, sepsis, vasculitis, iron-deficiency, hypochromic microcytic anemia and conditions with hepcidin excess.

Within other methods, a biological sample obtained from a patient is tested for the level of hepcidin. The biological sample is incubated with one or more of the anti-hepcidin antibodies disclosed herein under conditions and for a time sufficient to allow immunocomplexes to form. Immunocomplexes formed between the hepcidin and antibodies in the biological sample that specifically bind to the hepcidin are then detected. A biological sample for use within such methods may be any sample obtained from a patient that is expected to contain hepcidin. Suitable biological samples include blood, sera, plasma, urine and bone marrow. Suitable antibodies include antibodies from human cells, rodent, rabbit, goat, camel, or any other species.

The biological sample is incubated with antibodies in a reaction mixture under conditions and for a time sufficient to permit immunocomplexes to form between hepcidin and antibodies that are immunospecific for hepcidin. For example, a biological sample and one or more anti-hepcidin antibodies may be incubated at 4° C. for 24-48 hours.

Following the incubation, the reaction mixture is tested for the presence of immuno-complexes. Detection of immuno-complexes formed between an anti-hepcidin antibody and hepcidin present in the biological sample may be accomplished by a variety of known techniques, such as radioimmunoassays (RIA) and enzyme linked immunosorbent assays (ELISA). Suitable assays are well known in the art and are amply described in the scientific and patent literature (Harlow and Lane, 1988). Assays that may be used include, but are not limited to, the double monoclonal antibody sandwich immunoassay technique (U.S. Pat. No. 4,376,110); monoclonal-polyclonal antibody sandwich assays (Wide L., "Solid Phase Antigen-Antibody Systems," *Radioimmunoassay Methods: European Workshop Sep.* 15-17 1970 Edinburgh, Kirkham and Hunter, eds., (Churchill Livingston, Edenburgh, (1971)) pp. 405-412; the "western blot" method (U.S. Pat. No. 4,452, 901); immunoprecipitation of labeled ligand (Brown et al., *J. Biol. Chem.* 4980-4983m 1980); enzyme-linked immunosorbent assays; immunocytochemical techniques, including the use of fluorochromes (Brooks et al., *Clin. Exp. Immunol.*, 39: 477, 1980); and neutralization of activity (Bowen-Pope et al., *Science*, 226:701-703, 1984). Other immunoassays include, but are not limited to, those described in U.S. Pat. Nos. 3,850, 752; 3,901,654; 3,935,074; 3,984,533; 3,996,345; 4,034,074; and 4,098,876.

For detection purposes, an anti-hepcidin antibody may either be labeled or unlabeled. Unlabeled antibodies may be used in agglutination assays or in combination with labeled detection reagents that bind to the immunocomplexes (e.g., anti-immunoglobulin, protein G, Protein A or a lectin and secondary antibodies, or antigen-binding fragments thereof, capable of binding to the antibodies that specifically bind to the hepcidin). If the anti-hepcidin antibody is labeled, the reporter group may be any suitable reporter group known in the art, including radioisotopes, fluorescent groups (e.g. fluorescein or rhodamine), luminescent groups, enzymes, biotin and dye particles. Labels that are themselves directly detectable include fluorescent or luminescent dyes, metals or metal chelates, electrochemical labels, radionuclides (e.g., 32P, 14C, 125I, 3H, or 131I), magnetic labels or beads (e.g., DYNABEADS), paramagnetic labels, or colorimetric labels (e.g., colloidal gold, colored glass or plastic beads). Such detectable labels may be directly conjugated to the anti-hepcidin antibody or detection reagent or may be associated with a bead or particle that is attached to the anti-hepcidin antibody or detection reagent. Labels that are detectable through binding of a labeled specific binding partner include biotin, digoxigenin, maltose, oligohistidine, 2,4-dinitrobenzene, phenylarsenate, ssDNA, or dsDNA). Indirect labels that can be indirectly detected by their production of a detectable reaction product include various enzymes well known in the art, such as alkaline phosphatase, horseradish peroxidase, β-galactosidase, xanthine oxidase, glucose oxidase or other saccharide oxidases, or luciferases, which cleave appropriate substrate to form a colored or fluorescent reaction product.

Within certain assays, an unlabeled anti-hepcidin antibody is immobilized on a solid support, for use as a "capture agent" (or reagent) that captures the hepcidin within a biological sample. The solid support may be any material known to those of ordinary skill in the art to which the antibody may be attached. For example, the solid support may be a test well in a microtiter plate or a nitrocellulose or other suitable membrane. Alternatively, the support may be a tube, bead, particle or disc, such as glass, fiberglass, latex or a plastic material such as polyethylene, polypropylene, polystyrene or polyvinylchloride or a porous matrix. Other materials include agarose, dextran, polyacrylamide, nylon, Sephadex, cellulose or polysaccharides. The support may also be a magnetic particle or a fiber optic sensor, such as those disclosed, for example, in U.S. Pat. No. 5,359,681. The immobilized anti-hepcidin antibody may be a polyclonal antibody, or one or more monoclonal antibodies such as those described herein, or a combination of polyclonal and one or more monoclonal antibodies. The antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is contemplated. In such cases, adsorption may be achieved by contacting the anti-hepcidin antibody, in a suitable buffer, with the solid support for a suitable amount of time. The contact time varies with temperature, but is typically between about 1 hour and about 1 day. In general, contacting a well of a plastic microtiter plate (including polystyrene or polyvinylchloride) with an amount of peptide ranging from about 10 ng to about 10 μg, about 100 ng to about 1 μs, is sufficient to immobilize an adequate amount of peptide.

Following immobilization, the remaining protein binding sites on the support are typically blocked. Any suitable blocking agent known to those of ordinary skill in the art, including bovine serum albumin, Tween™ 20™ (Sigma Chemical Co., St. Louis, Mo.), heat-inactivated normal goat serum (NGS), or BLOTTO (buffered solution of nonfat dry milk which also contains a preservative, salts, and an antifoaming agent) can be used. The support is then incubated with a biological sample suspected of containing hepcidin. The sample can be applied neat, or, more often, it can be diluted, usually in a buffered solution which contains a small amount (0.1%-5.0% by weight) of protein, such as BSA, NGS, or BLOTTO. In general, an appropriate contact time (i.e., incubation time) is a period of time that is sufficient to detect the presence of antibody or an antigen binding fragment that is immunospecific for the hepcidin within a sample containing hepcidin. In some embodiments, the contact time is sufficient to achieve a level of binding that is at least about 95% of that achieved at equilibrium between bound and unbound antibody or antibody fragment. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween™ 20. A detection reagent that binds to the hepcidin in the immunocomplexes (formed by binding of the capture agent and the hepcidin from the sample) may then be added. Such detection reagent may be a polyclonal antibody, or one or more monoclonal antibodies such as those described herein, or a combination of polyclonal and one or more monoclonal antibodies such as those described herein or a Fab fraction of any antibody. The detection reagent may be directly labeled, i.e., comprises at least a first detectable label or "reporter" molecule. Alternatively, the detection reagent may be an unlabeled anti-hepcidin antibody. This unlabeled anti-hepcidin (primary) antibody is then detected by the binding of a labeled secondary antibody or reagent to the primary antibody. For example, if the primary antibody is a murine immunoglobulin, the secondary antibody may be a labeled anti-murine immunoglobulin antibody. Similarly, if the primary antibody is a rabbit immunoglobulin, the secondary antibody may be a labeled anti-rabbit immunoglobulin antibody.

The detection reagent is incubated with the immunocomplex for an amount of time sufficient to detect the bound antibody or antigen binding fragment thereof. An appropriate amount of time may generally be determined by assaying the level of binding that occurs over a period of time. Unbound label or detection reagent is then removed and bound label or detection reagent is detected using a suitable assay or analytical instrument. The method employed for detecting the reporter group depends upon the nature of the reporter group. For radioactive labels, scintillation counting or autoradiographic methods are generally appropriate. Spectroscopic methods may be used to detect dyes, luminescent or chemiluminescent moieties and various chromogens, fluorescent labels and such like. Biotin may be detected using avidin, coupled to a different reporter group (commonly a radioactive or fluorescent group or an enzyme). Enzyme reporter groups (including horseradish peroxidase, β-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from an individual with a normal level of hepcidin) indicates the presence of a disorder associated with expression of hepcidin.

In alternative embodiments, the sample and detection reagent may be contacted simultaneously with the capture agent, rather than sequentially added. In yet another alternative, the sample and detection reagent may be pre-incubated together, then added to the capture agent. Other variations are readily apparent to one of ordinary skill in the art.

In another embodiment, the amount of hepcidin present in a sample is determined by a competitive binding assay. Competitive binding assays rely on the ability of a labeled standard (e.g., a hepcidin polypeptide, or an immunologically reactive portion thereof) to compete with the test sample analyte (a hepcidin polypeptide) for binding with a limited amount of an anti-hepcidin antibody. Following separation of free and bound hepcidin, the hepcidin is quantitated by relating ratio of bound/unbound hepcidin to known standards. The amount of a hepcidin polypeptide in the test sample is inversely proportional to the amount of standard that becomes bound to the antibodies. To facilitate determining the amount of standard that becomes bound, the antibodies typically are immobilized on a solid support so that the standard and analyte that are bound to the antibodies may conveniently be separated from the standard and analyte which remain unbound. Thus, in such embodiments, also contemplated is contacting a biological sample with labeled mature hepcidin (or a labeled fragment thereof that retains the antigenicity of hepcidin) and an antibody that binds to mature hepcidin, and detecting the amount of antibody-labeled hepcidin complex formed.

Preparation of conjugates to solid supports or detectable labels often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, whereas pyridyl disulfides react with sulfhydryls to produce mixed disulfides. The pyridyl disulfide product is cleavable. Imidoesters are also very useful for protein-protein cross-links.

Heterobifunctional cross-linkers possess two or more different reactive groups that allow for sequential conjugations with specific groups of proteins, minimizing undesirable polymerization or self-conjugation. Heterobifunctional reagents are also used when modification of amines is problematic. Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups. A variety of heterobifunctional cross-linkers, each combining different attributes for successful conjugation, are commercially available. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

As described in copending U.S. patent application Ser. No. 12/022,515, the disclosure of which is incorporated by reference herein in its entirety, it is the level of mature hepcidin (amino acids 60-84 of SEQ ID NO: 8) rather than the level of prohepcidin (amino acids 25-84 of SEQ ID NO: 8) which is diagnostic for certain disease states such as anemia of inflammation and anemia of cancer. Thus, in one preferred embodiment, antibody(ies) that bind to mature, properly folded, hepcidin (SEQ ID NO: 9) are used as both capture agent and detection reagent. Antibodies that bind to the naturally occurring N-terminally truncated versions (e.g. lacking up to two or up to five of the N-terminal amino acids of mature hepcidin) may also be used. Various combinations of capture agent and detection reagent are contemplated. For example, the capture agent may be a monoclonal antibody that binds to a first epitope of mature hepcidin and the detection reagent may be a different monoclonal antibody that binds to a second epitope of mature hepcidin. In some embodiments, antibodies specific for different epitopes of hepcidin are used, in order to minimize competition or interference between the capture agent and detection reagent. Alternatively, the capture agent may be a polyclonal antibody that binds to mature hepcidin and the detection reagent may be a monoclonal antibody. As yet another alternative, the capture agent may be a monoclonal antibody that binds to mature hepcidin and the detection reagent may be a polyclonal antibody. In any of the preceding embodiments, either the capture agent or the detection reagent may be a combination of a polyclonal and a monoclonal antibody.

In some embodiments, a mature-hepcidin-specific monoclonal antibody is used as either the capture agent or detection reagent or both. A mature-hepcidin-specific antibody does not bind prohepcidin at all, or binds to prohepcidin with such low affinity that the antibody can differentiate mature hepcidin from prohepcidin. For example, such a monoclonal antibody may bind to the N-terminus of mature hepcidin, or it may bind an epitope of mature hepcidin that is not detectable in prohepcidin (e.g. due to masking by the prodomain).

In embodiments utilizing a monoclonal antibody that binds to an epitope present in both mature hepcidin and prohepcidin, an optional further refinement is contemplated. The amount of mature hepcidin alone is determined by subtracting the amount of prohepcidin present in the sample from the amount of total hepcidin (prohepcidin plus mature hepcidin) present in the same sample. The amount of prohepcidin can be determined by using prohepcidin-specific polyclonal and/or monoclonal antibodies in techniques like those described above. A prohepcidin-specific antibody does not bind mature hepcidin at all, or binds to mature hepcidin with such low affinity that the antibody can differentiate prohepcidin from mature hepcidin. For example, such antibodies may bind to a linear or conformational epitope present uniquely in the prodomain of hepcidin (amino acids 25-59 of SEQ ID NO: 8). In such embodiments, the amount of total hepcidin and prohepcidin may be determined sequentially or simultaneously. Because prohepcidin is rapidly degraded in serum to hepcidin, in some embodiments furin inhibitors are added to the biological sample in order to prevent or reduce degradation of prohepcidin.

In some embodiments utilizing a monoclonal antibody that binds to the 25-amino acid mature hepcidin, the monoclonal antibody does not bind the degradation products (i.e., hepcidin-22 and hepcidin-20).

In one embodiment of a simultaneous assay for detecting total hepcidin and prohepcidin, the capture agent is an antibody that binds to an epitope present in both mature hepcidin and prohepcidin, and two detection reagents are applied simultaneously. The first detection reagent is a labeled antibody that binds to an epitope present in both mature hepcidin and prohepcidin and the second detection reagent is a differently labeled prohepcidin-specific antibody. For example, the first detection reagent is labeled with a fluorescent dye detectable at a first wavelength while the second detection reagent is labeled with a fluorescent dye detectable at a second wavelength. Thus, in such an example, the capture agent will bind total hepcidin (mature hepcidin plus prohepcidin) in the sample, the first detection reagent will detect the amount of total hepcidin, and the second detection reagent will detect the amount of prohepcidin. Subtracting the amount of prohepcidin from amount of the total hepcidin will yield the amount of mature hepcidin. In other alternative embodiments, two different capture agents may be used: a first capture agent that binds to an epitope present in both mature hepcidin and prohepcidin, and a second capture agent that is a prohepcidin-specific antibody, optionally with a detection reagent that binds an epitope present in both mature hepcidin and prohepcidin.

Other embodiments for carrying out simultaneous assays are well known in the art, including the multiplex system described, e.g., in Khan et al., *Clin. Vaccine Immunol.*, 13(1) 45-52 (January 2006) involving differentially coded sets of fluorescent microbeads. Other embodiments for performing multiple simultaneous assays on a single surface include surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and capillary devices (see, e.g., U.S. Pat. No. 6,019,944). In these embodiments, each discrete surface location has a different antibody that immobilizes a different analyte for detection at each location. Surfaces can alternatively have one or more discrete particles (e.g., microparticles or nanoparticles) immobilized at discrete locations of a surface, of which each set of particles contains a different capture agent for a different analyte.

Complementary antibody pairs (antibodies that bind to different epitopes on hepcidin such that the pairs are suitable for use in sandwich assays) were difficult to identify. Use of complementary pairs that minimize competition or interference can increase sensitivity of the assay by 20-fold to 50-fold. In some embodiments, the immunoassays described herein are capable of measuring hepcidin levels ranging from 0.01 ng/mL to 10 µg/mL.

Antibody pairs suitable for use in sandwich immunoassays include the following: (1) when one antibody of the pair is an antibody binds to the same epitope as antibody is 1S1, or competes with antibody 1S1 for binding to mature human hepcidin of SEQ ID NO: 9 by at least about 75%, 80%, 85%, 90% or more, a suitable second antibody may be: (a) an antibody that binds to the same epitope as antibody is 23F11, or competes with antibody 23F11 for binding to mature human hepcidin of SEQ ID NO: 9 by at least about 75%, 80%, 85%, 90% or more; or (b) an antibody that binds to the same epitope as antibody is 15E1, or competes with antibody 15E1 for binding to mature human hepcidin of SEQ ID NO: 9 by at least about 75%, 80%, 85%, 90% or more; or (c) an antibody that binds to the same epitope as antibody is 12B9, or competes with antibody 12B9 for binding to mature human hepcidin of SEQ ID NO: 9 by at least about 75%, 80%, 85%, 90% or more; (2) when one antibody of the pair is an antibody that binds to the same epitope as antibody 12B9 or competes with antibody 12B9 for binding to mature human hepcidin of SEQ ID NO: 9 by at least about 75%, 80%, 85%, 90% or more, a suitable second antibody may be: (a) an antibody that binds to the same epitope as antibody 18D8, or competes with antibody 18D8 for binding to mature human hepcidin of SEQ ID NO: 9 by at least about 75%, 80%, 85%, 90% or more, or (b) an antibody that binds to the same epitope as antibody 19C1, or competes with antibody 19C1 for binding to mature human hepcidin of SEQ ID NO: 9 by at least about 75%, 80%, 85%, 90% or more, or (c) an antibody that binds to the same epitope as antibody 19D12, or competes with antibody 19D12 for binding to mature human hepcidin of SEQ ID NO: 9 by at least about 75%, 80%, 85%, 90% or more, or (d) an antibody that binds to the same epitope as antibody 19H6, or competes with antibody 19H6 for binding to mature human hepcidin of SEQ ID NO: 9 by at least about 75%, 80%, 85%, 90% or more; or (e) an antibody that binds to the same epitope as antibody 1S1 or competes with antibody 1S1 for binding to mature human hepcidin of SEQ ID NO: 9 by at least about 75%, 80%, 85%, 90% or more; or (3) when one antibody o the pair is an antibody that binds to the same epitope as antibody 23F11, or competes with antibody 23F11 for binding to mature human hepcidin of SEQ ID NO: 9 by at least about 75%, 80%, 85%, 90% or more, a suitable second antibody may be: (a) an antibody that binds to the same epitope as antibody 18D8, or competes with antibody 18D8 for binding to mature human hepcidin of SEQ ID NO: 9 by at least about 75%, 80%, 85%, 90% or more, or (b) an antibody that binds to the same epitope as antibody 19C1, or competes with antibody 19C1 for binding to mature human hepcidin of SEQ ID NO: 9 by at least about 75%, 80%, 85%, 90% or more, or (c) an antibody that binds to the same epitope as antibody 19D12, or competes with antibody 19D12 for binding to mature human hepcidin of SEQ ID NO: 9 by at least about 75%, 80%, 85%, 90% or more, or (d) an antibody that binds to the same epitope as antibody 19H6, or competes with antibody 19H6 for binding to mature human hepcidin of SEQ ID NO: 9 by at least about 75%, 80%, 85%, 90% or more; or (e) an antibody that binds to the same epitope as antibody 1S1 or competes with antibody 4E1 for binding to mature human hepcidin of SEQ ID NO: 9 by at least about 75%, 80%, 85%, 90% or more; or (f) an antibody that binds to the same epitope as antibody 3B3 or competes with antibody 3B3 for binding to mature human hepcidin of SEQ ID NO: 9 by at least about 75%, 80%, 85%, 90% or more; (4) when one antibody of the pair is an antibody binds to the same epitope as antibody 15E1, or competes with antibody 15E1 for binding to mature human hepcidin of SEQ ID NO: 9 by at least about 75%, 80%, 85%, 90% or more, a suitable second antibody may be: (a) an antibody that binds to the same epitope as antibody 1S1, or competes with antibody 1S1 for binding to mature human hepcidin of SEQ ID NO: 9 by at least about 75%, 80%, 85%, 90% or more.

In some embodiments, methods for monitoring the effectiveness of therapy with an anti-hepcidin antibody include monitoring changes in the level of hepcidin in a sample, or in an animal such as a human patient. Methods in which hepcidin levels are monitored may comprise (a) incubating a first biological sample, obtained from a patient prior to a therapy with one or more of the anti-hepcidin antibodies disclosed herein, wherein the incubation is performed under conditions and for a time sufficient to allow immunocomplexes to form; (b) detecting immunocomplexes formed between the hepcidin in the biological sample and antibodies or antigen binding fragments that specifically bind hepcidin; and optionally (c) repeating steps (a) and (b) using a second biological sample taken from the patient at later time, such as for example, following therapy with one or more of the anti-hepcidin antibodies disclosed herein; and (d) comparing the number of immunocomplexes detected in the first and second biological samples.

Other monitoring methods include measuring (a) the blood (e.g., serum or plasma) circulating level of complexes between hepcidin and the therapeutic agent, and optionally (b) the amount of free hepcidin present in circulation. For example, complexes between hepcidin and therapeutic antibody can be detected using an anti-human Fc antibody that binds to the therapeutic antibody part of the complex and an Fab fragment of a "pairing" anti-hepcidin antibody that binds to the hepcidin part of the complex. Alternatively, an anti-idiotypic antibody can be used in place of the anti-human Fc antibody. As another alternative, an anti-hepcidin antibody containing a non-human Fc (e.g. a human Fc is replaced with murine Fc) can be used in place of the Fab fragment.

As another example, free hepcidin can be detected after removing hepcidin-therapeutic antibody complexes from the biological sample, using either an anti-human Fc antibody or an anti-idiotypic antibody that has been immobilized on a solid support. The amount of free hepcidin which remains unbound to the solid support is then measured. This level of free hepcidin may reflect the effectiveness of the therapeutic antibody in removing available circulating hepcidin.

A biological sample for use within such methods may be any sample obtained from a patient that would be expected to contain hepcidin. Exemplary biological samples include blood, plasma, sera, urine and bone marrow. A first biological sample may be obtained prior to initiation of therapy or part way through a therapy regime. The second biological sample should be obtained in a similar manner, but at a time following additional therapy. The second biological sample may be obtained at the completion of, or part way through, therapy, provided that at least a portion of therapy takes place between the isolation of the first and second biological samples.

Incubation and detection procedures for both samples may generally be performed as described above. A decrease in the number of immunocomplexes in the second sample relative to the first sample indicates a decrease in hepcidin levels and reflects successful therapy. Free serum hepcidin may also be analyzed in a similar manner, and a decrease in free serum hepcidin indicates successful therapy.

Hepcidin-related disorders, inflammatory diseases, and diseases or disorders of iron homeostasis for which the diagnostic or monitoring methods may be useful include but are not limited to african iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, H. pyelori infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hepcidin deficiency, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, FIFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

Methods of setting an appropriate threshold for diagnosis of the disease states described herein and prognostic monitoring as described herein are well known in the art. By way of example, levels of hepcidin in a fluid sample from a sufficient representative number of normal subjects (e.g. healthy population without the condition to be detected) are analyzed relative to the hepcidin level from a sufficient representative number of diseased subjects (e.g. population confirmed to have the disease or condition) using the same protocols. A threshold cutoff can be determined that differentiates most of the normal population from most of the diseased population. Alternatively, useful end point values for negative, uncertain and positive results can be determined from the data. For example, a normal range (indicative of a negative result) can be determined, which includes hepcidin of most of the normal population but which exclude almost all of the diseased population. Correspondingly, a range indicative of a positive result can be determined, which includes hepcidin of most of the diseased population but which exclude almost all of the normal population. Similarly, a threshold differentiating hepcidin levels in a population suffering from anemia of inflammation from hepcidin levels in a population suffering from iron deficiency anemia can be determined. Useful endpoint values may indicate that the patient is suffering from anemia of inflammation, iron deficiency anemia or mixed anemia. Appropriate endpoint values for the threshold may be determined to optimize the desired specificity or sensitivity, and may also take account of overall medical and epidemiological factors. Factors to be considered include the clinical objective of the laboratory test and whether it is necessary to have a high positive predictive value, or a high negative predictive value, as well as prevalence of the disease in the test population.

Therapeutic Uses for Anti-Hepcidin Antibodies

Also provided is the use of anti-hepcidin antibodies described herein that specifically bind human hepcidin, to treat subjects in need thereof. In some embodiments, the subject may be at risk of or suffering from an elevated level of hepcidin, a hepcidin-related disorder, a disorder of iron homeostasis, or anemia.

As used herein, "treatment" or "treat" refers to both prophylactic treatment of a subject at risk of, or having a predisposition toward, a disease or disorder, and to therapeutic treatment of a subject suffering from a disease or disorder.

Administration of a therapeutic agent in a prophylactic method can occur prior to the manifestation of symptoms of an undesired disease or disorder, such that the disease or disorder is prevented or, alternatively, delayed in its progression. Thus, when used in conjunction with prophylactic methods, the term "therapeutically effective" means that, after treatment, a fewer number of subjects (on average) develop the undesired disease or disorder or progress in severity of symptoms.

When used in conjunction with therapeutic methods involving administration of a therapeutic agent after the subject manifests symptoms of a disease or disorder, the term "therapeutically effective" means that, after treatment, one or more signs or symptoms of the disease or disorder is ameliorated or eliminated.

"Mammal" for purposes of treatment refers to any animal classified as a mammal, including humans, domestic and farm animals, and zoo, sports, or pet animals, such as dogs, horses, cats, cows, etc. In some embodiments, the mammal is human.

As used herein, a "hepcidin-related disorder" refers to a condition caused by or associated with an abnormal level of hepcidin (e.g., hepcidin excess or hepcidin deficiency relative to the degree of anemia or iron stored) which disrupts iron homeostasis. A disruption in iron homeostasis can in turn result in secondary diseases such as anemia. Acute or chronic inflammatory conditions can result in upregulation of hepcidin expression, which can result in decreased circulating iron levels, which can cause anemia or worsen existing anemia. Exemplary hepcidin-related inflammatory diseases include anemia of cancer, anemia of chronic disease, anemia of inflammation, chemotherapy-induced anemia, chronic kidney disease (stage I, II, III, IV or V), end stage renal disease, chronic renal failure congestive heart failure, cancer, rheumatoid arthritis, systemic lupus erythematosus, Crohn's disease, H. pylori infection or other bacterial infections, hepatitis C, HIV, and other viral illnesses, arteriosclerosis, atherosclerosis, cirrhosis of the liver, pancreatitis, sepsis, vasculitis, iron-deficiency, hypochromic microcytic anemia and conditions with hepcidin excess.

As used herein, the phrase "disease (or disorder) of iron homeostasis" refers to a condition in which a subject's iron levels require modulation. It includes hepcidin-related disorders; conditions not associated with elevated levels of hepcidin that nevertheless would benefit from inhibition of hepcidin activity, such as a disruption in iron homeostasis not caused by hepcidin; diseases where aberrant iron absorption, recycling, metabolism or excretion causes a disruption in normal iron blood levels or tissue distribution; diseases where iron dysregulation is a consequence of another disease or condition, such as inflammation, cancer or chemotherapy; diseases or disorders resulting from abnormal iron blood levels or tissue distribution; and diseases or disorders that can be treated by modulating iron levels or distribution. Nonlimiting examples of such diseases or disorders of iron homeostasis, hepcidin-related disorders and inflammatory conditions which can result in hepcidin excess include african iron overload, alpha thalassemia, Alzheimer's disease, anemia, anemia of cancer, anemia of chronic disease, anemia of inflammation, arteriosclerosis or atherosclerosis (including coronary artery disease, cerebrovascular disease or peripheral occlusive arterial disease), ataxias, ataxias related to iron, atransferrinemia, cancer, ceruloplasmin deficiency, chemotherapy-induced anemia, chronic renal/kidney disease (stage I, II, III, IV or V), including end stage renal disease or chronic renal/kidney failure, cirrhosis of liver, classic hemochromatosis, collagen-induced arthritis (CIA), conditions with hepcidin excess (elevated hepcidin), congenital dyserythropoietic anemia, congestive heart failure, Crohn's disease, diabetes, disorders of iron biodistribution, disorders of iron homeostasis, disorders of iron metabolism, ferroportin disease, ferroportin mutation hemochromatosis, folate deficiency, Friedrich's ataxia, funicular myelosis, gracile syndrome, H. pyelori infection or other bacterial infections, Hallervordan Spatz disease, hemochromatosis, hemochromatosis resulting from mutations in transferrin receptor 2, hemoglobinopathies, hepatitis, hepatitis (Brock), hepatitis C, hepatocellular carcinoma, hereditary hemochromatosis, HIV or other viral illnesses, Huntington's disease, hyperferritinemia, hypochromic microcytic anemia, hypoferremia, insulin resistance, iron deficiency anemia, iron deficiency disorders, iron overload disorders, iron-deficiency conditions with hepcidin excess, juvenile hemochromatosis (HFE2), multiple sclerosis, mutation in transferrin receptor 2, HFE, hemojuvelin, ferroportin or other genes of iron metabolism, neonatal hemochromatosis, neurodegenerative diseases related to iron, osteopenia, osteoporosis pancreatitis, Pantothenate kinase-associated neurodegeneration, Parkinson's disease, pellagra, pica, porphyria, porphyria cutanea tarda, pseudoencephalitis, pulmonary hemosiderosis, red blood cell disorders, rheumatoid arthritis, sepsis, sideroblastic anemia, systemic lupus erythematosus, thalassemia, thalassemia intermedia, transfusional iron overload, tumors, vasculitis, vitamin B6 deficiency, vitamin B12 deficiency, and/or Wilson's disease.

Non-inflammatory conditions which are implicated in a disruption of iron regulation include, but are not limited to, vitamin B6 deficiency, vitamin B12 deficiency, folate deficiency, pellagra, funicular myelosis, pseudoencephalitis, Parkinson's disease (Fasano et al., *J. Neurochem.* 96:909 (2006) and Kaur et al., *Ageing Res. Rev.,* 3:327 (2004)), Alzheimer's disease, coronary heart disease, osteopenia and osteoporosis (Guggenbuhl et al., *Osteoporos. Int.* 16:1809 (2005)), hemoglobinopathies and other disorders of red cell metabolism (Papanikolaou et al., *Blood* 105:4103 (2005)), and peripheral occlusive arterial disease.

Various other iron indices and their normal ranges of concentrations are listed in Table 2.

TABLE 2

| Iron Index | Normal Level (Range) |
| --- | --- |
| Serum iron | 50-170 µg/dL |
| Hemoglobin | 11.5-18 g/dL |
| Hematocrit | 37-54% |
| Red blood cell count (RBC) | $4.6\text{-}6.2 \times 10^{12}$ cells/L (men) |
|  | $4.25\text{-}5.4 \times 10^{12}$ cells/L (women) |
| Mean Corpuscular Hemoglobin (MCH) | 27-32 pg |
| Mean Corpuscular Hemoglobin Concentration (MCHC) | 32-36% |
| Mean Corpuscular Volume (MCV) | 80-96 fL |
| Red Cell Distribution Width (RDW) | 11.5-14.5% (electrical impedence method) or 10.2-11.8% (laser light method) |
| Reticulocyte count | $18\text{-}158 \times 10^9$ cells/L (0.8-2.5% in men; 0.8-4% in women) |
| Total Iron Binding Capacity (TIBC) | 250-450 µg/dL |
| Transferrin Iron Saturation Percentage (Tsat) | 15-50% |
| Ferritin | 12-120 µg/L |
| Folate | 3-16 ng/mL (serum) and 130-628 ng/mL (red blood cell) |
| Vitamin B12 | 200-900 pg/ml |

A patient's iron index level outside of the normal ranges listed in Table 2 indicates that the patient may benefit from treatment with an anti-hepcidin antibody described herein. Since hepcidin plays a key role in iron homeostasis, hepcidin levels and activity will correlate to a disruption of iron homeostasis and/or iron indices. Elevated hepcidin levels correlate with serum iron levels below the normal ranges indicated in Table 2, low hemoglobin, and hematocrit, reduced or normal Tsat and high or normal ferritin values, and elevated inflammatory status as measured by C-reactive protein (CRP) elevation or other markers of inflammation.

As used herein, the phrase "therapeutically effective amount" of an anti-hepcidin antibody described herein refers to an amount that results in the desired therapeutic effect (i.e. that provides "therapeutic efficacy"). Exemplary therapeutic effects include increased circulating iron levels or increased iron availability, increased red blood cell count, increased red blood cell mean cell volume, increased red blood cell hemoglobin content, increased hemoglobin (e.g., increased by ≥0.5 g/dL), increased hematocrit, increased Tsat, increased reticulocyte count, increased or normalized reticulocyte mean cell volume, increased reticulocyte hemoglobin content, or reduced free hepcidin levels in serum or plasma, or normalization of any of the parameters described above. Returning such a parameter to its normal range is not required for therapeutic efficacy; for example, a measurable change (increase or reduction) in the direction of normal can be considered to be a desired therapeutic effect by a clinician. When applied to an individual active ingredient, administered alone, the term refers to that ingredient alone. When applied to a combination, the term refers to combined amounts of the active ingredients that result in the therapeutic effect, whether administered in combination, serially or simultaneously. For example, in aspects where the anti-hepcidin antibody is administered in conjunction with an enrythropoiesis stimulator, a therapeutically effective amount is meant to refer to the combined amount that increases or normalizes any of the parameters stated above.

Figure 14B:
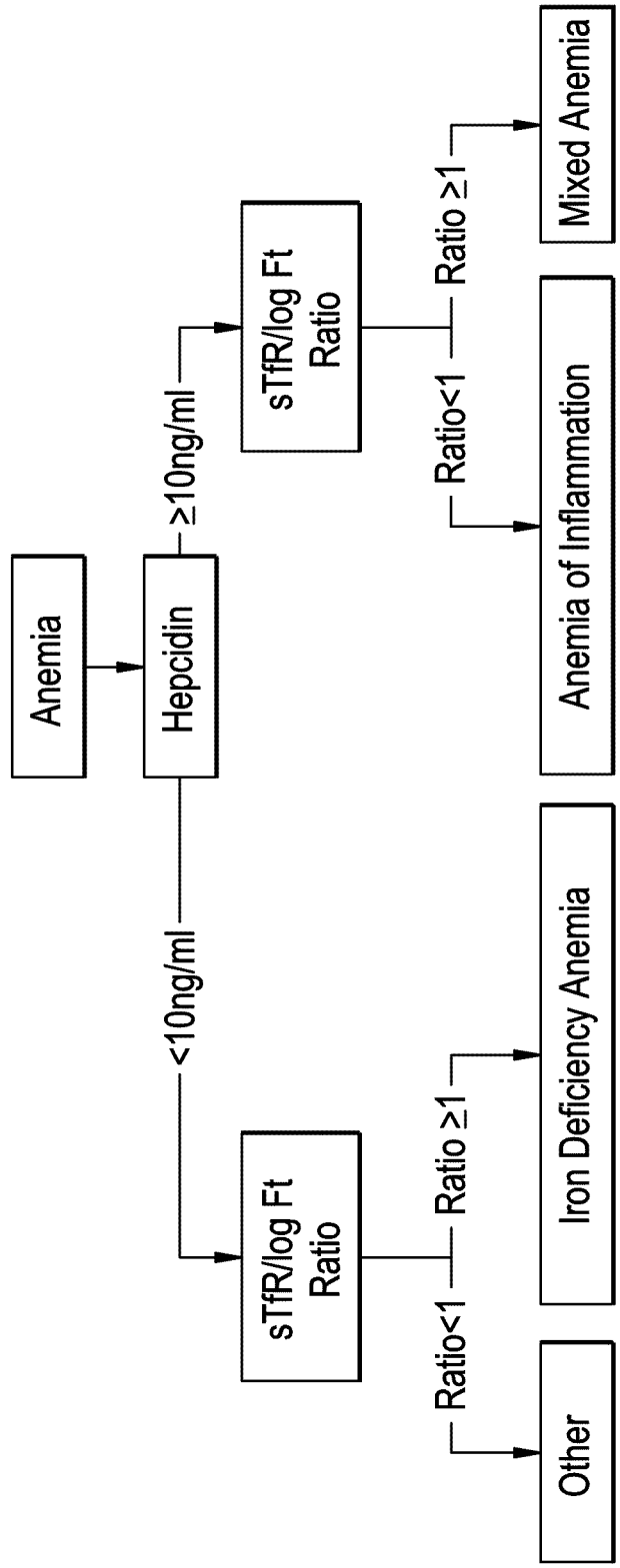
FIG. 14B shows a theoretical decision tree for assessment of a patient using measurement of hepcidin levels.

In order to facilitate the diagnosis of patients, decision trees, such as that of FIG. 14B, can be used to interpret the level of the hepcidin, and which is used to assist the user or interpreter in determining a course of treatment and the significance of the concentration reading. Hepcidin values are predicted to be elevated in patients with inflammation iron overload and ferroportin disease and suppressed in patients with hemochromatosis, hemoglobinopathies, and other red cell disorders. The decision tree of FIG. 14B shows how measurement of hepcidin levels simplifies diagnosis and/or assessment of a patient suspected of having iron metabolism disorders. FIG. 14A shows the decision tree assessment without a measurement of hepcidin levels.

The compositions for and methods of treatment described herein may utilize one or more anti-hepcidin antibodies described herein used singularly or in combination with other therapeutic agents to achieve the desired effects.

Combination Therapy

It may be further advantageous to mix two or more antibodies together (which bind to the same or different target antigens) or to co-administer an antibody described herein with a second therapeutic agent to provide still improved efficacy. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments, the methods described herein include the administration of single antibodies, as well as combinations, or "cocktails", of different antibodies. Such antibody cocktails may have certain advantages inasmuch as they contain antibodies which exploit different effector mechanisms. Such antibodies in combination may exhibit synergistic therapeutic effects.

Combination therapy using an anti-hepcidin antibody described herein and an erythropoiesis stimulator is specifically contemplated. In various embodiments, anti-hepcidin antibodies and erythropoiesis stimulators can be used to improve treatment of a patient with anemia. In particular, patients who are hypo-responsive to, including unresponsive or resistant to, erythropoiesis stimulator therapy, such as erythropoietin or analogs thereof (Epoetin alfa, Epoetin beta, darbepoetin alfa), among others, will benefit from co-treatment with an anti-hepcidin antibody described herein. In one embodiment, combination therapy includes treatment with at least one antibody that binds to human hepcidin and at least one erythropoiesis stimulator.

Combination therapy using an anti-hepcidin antibody and an iron chelator to redistribute iron stores in the body is also contemplated. An iron chelator is an agent capable of binding iron and removing it from a tissue or from circulation. Examples include deferoxamine (Desferal®) and deferasirox (Exjade®), and deferiprone (1,2-dimethyl-3-hydroxypyridin-4-one). In some embodiments, anti-hepcidin antibodies and erythropoiesis stimulators can be used to improve treatment of a patient an iron loading disorder secondary to transfusion-dependent iron overload, or have an iron maldistribution disorder such as Friedreich's ataxia.

As used herein, "erythropoiesis stimulator" means a chemical compound that directly or indirectly causes activation of the erythropoietin receptor, for example, by binding to and causing dimerization of the receptor or by stimulating endogenous erythropoietin expression. Erythropoiesis stimulators include erythropoietin and variants, analogs, or derivatives thereof that bind to and activate erythropoietin receptor; antibodies that bind to erythropoietin receptor and activate the receptor; or peptides that bind to and activate erythropoietin receptor; or small organic chemical compounds, optionally less than about 1000 Daltons in molecular weight, that bind to and activate erythropoietin receptor. Erythropoiesis stimulators include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), mimetic antibodies and HIF inhibitors (see U.S. Patent Application Publication No. 2005/0020487, the disclosure of which is incorporated by reference in its entirety). Exemplary erythropoiesis stimulators include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547, 933; 5,618,698; 5,621,080; 5,756,349; 5,767,078; 5,773,569; 5,955,422; 5,830,851; 5,856,298; 5,986,047; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/ 084477; WO 2003/094858; WO 2004/002417; WO 2004/ 002424; WO 2004/009627; WO 2004/024761; WO 2004/ 033651; WO 2004/035603; WO 2004/043382; WO 2004/ 101600; WO 2004/101606; WO 2004/101611; WO 2004/ 106373; WO 2004/018667; WO 2005/001025; WO 2005/ 001136; WO 2005/021579; WO 2005/025606; WO 2005/ 032460; WO 2005/051327; WO 2005/063808; WO 2005/ 063809; WO 2005/070451; WO 2005/081687; WO 2005/ 084711; WO 2005/103076; WO 2005/100403; WO 2005/ 092369; WO 2006/50959; WO 2006/02646; WO 2006/ 29094; and U.S. Patent Application Publication Nos.: US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; US 2006/0111279.

Erythropoietin includes, but is not limited to, a polypeptide comprising the amino acid sequence as set forth in SEQ ID NO: 72. Amino acids i through 165 of SEQ ID NO: 72 constitute the mature protein of any molecules designated as an epoetin, e.g., epoetin alfa, epoetin beta, epoetin delta, epoetin omega, epoetin iota, epoetin gamma, epoetin zeta, and the like. Additionally, an epoetin also includes any of the aforementioned epoetin which are chemically modified, e.g., with one or more water-soluble polymers such as, e.g., polyethylene glycol (including PEG-EPO-beta). Also contemplated are analogs of erythropoietin, with 65%, 70%, 75%, 80%, 85%, 90%, 91%, 92%, 93%, 94%, 95%, 96%, 97%, 98%, or 99% identity to SEQ ID NO: 72 still retaining erythropoietic activity.

Exemplary sequences, manufacture, purification and use of recombinant human erythropoietin are described in a number of patent publications, including but not limited to Lin U.S. Pat. No. 4,703,008 and Lai et al. U.S. Pat. No. 4,667,016, each of which is incorporated herein by reference in its entirety. Darbepoetin is a hyperglycosylated erythropoietin analog having five changes in the amino acid sequence of rHuEPO which provide for two additional carbohydrate chains. More specifically, darbepoetin alfa contains two additional N-linked carbohydrate chains at amino acid residues 30 and 88 of SEQ ID NO: 73. Exemplary sequences, manufacture, purification and use of darbepoetin and other erythropoietin analogs are described in a number of patent publications, including Strickland et al., WO 91/05867, Elliott et al., WO 95/05465, Egrie et al., WO 00/24893, and Egrie et al. WO 01/81405, each of which is incorporated herein by reference in its entirety. Derivatives of naturally occurring or analog polypeptides include those which have been chemically modified, for example, to attach water soluble polymers (e.g., pegylated), radionuclides, or other diagnostic or targeting or therapeutic moieties.

The term "erythropoietic activity" means activity to stimulate erythropoiesis as demonstrated in an in vivo assay, for example, the exhypoxic polycythemic mouse assay. See, e.g., Cotes and Bangham, *Nature* 191:1065 (1961).

Administration and Preparation of Pharmaceutical Formulations

In another aspect, pharmaceutical compositions are provided comprising a therapeutically effective amount of any of the antibodies described herein and a pharmaceutically acceptable sterile carrier, diluent or excipient. Also provided is the use of such antibodies in preparation of a medicament for treatment of a human with an elevated level of hepcidin, a hepcidin-related disorder, a disorder of iron homeostasis or an anemia. It is understood that co-administration methods involving administration of antibodies with a second therapeutic agent, as described herein, encompass not only the use of the antibody in preparation of a medicament for co-administration with the second therapeutic agent, but also the use of the second therapeutic agent in preparation of a medicament for co-administration with the antibody.

In some embodiments, the anti-hepcidin antibodies or specific binding agents used in the practice of a method described herein may be formulated into pharmaceutical compositions comprising a carrier suitable for the desired delivery method. Suitable carriers include any material which, when combined with an anti-hepcidin antibody or specific binding agent, retains the high-affinity binding of hepcidin and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antibody concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antibody may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antibody, may be included in the formulation. Exemplary tonicity agents include polyols, such as mannitol, sucrose or trehalose. In some embodiments, the aqueous formulation is isotonic, although hypertonic or hypotonic solutions may be suitable. Exemplary concentrations of the polyol in the formulation may range from about 1% to about 15% w/v.

A surfactant may also be added to the antibody formulation to reduce aggregation of the formulated antibody and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antibody, buffer, polyol and surfactant) and is essentially free of one or more preservatives, such as benzyl alcohol, phenol, m-cresol, chlorobutanol and benzethonium C1. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antoxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the anti-hepcidin antibody are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation contains an isotonic buffer such as a phosphate, acetate, or TRIS buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5-5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antibodies are also contemplated. Methods to make suspensions and crystal forms are known to one of skill in the art.

The formulations to be used for in vivo administration must be sterile. In some embodiments, the compositions described herein may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, *Journal of Parenteral Science and Technology*, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, *Drug Development and Industrial Pharmacy*, Volume 18, Numbers 11 and 12, pages 1311-1354 (1992).

Excipients have been noted in some cases to act as stabilizers for freeze-dried products; Carpenter et al., *Developments in Biological Standardization*, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In some embodiments, the formulations described herein may be designed to be short-acting, fast-releasing, long-acting, or sustained-releasing as described herein. Thus, the pharmaceutical formulations may also be formulated for controlled release or for slow release.

Therapeutically effective amounts of a composition will vary and depend on the severity of the disease and the weight and general state of the subject being treated, but generally range from about 1.0 µg/kg to about 100 mg/kg body weight, or about 10 µg/kg to about 30 mg/kg, or about 0.1 mg/kg to about 10 mg/kg or about 1 mg/kg to about 10 mg/kg per application. Administration can be daily, on alternating days, weekly, twice a month, monthly or more or less frequently, as necessary depending on the response to the disorder or condition and the subject's tolerance of the therapy. Maintenance dosages over a longer period of time, such as 4, 5, 6, 7, 8, 10 or 12 weeks or longer may be needed until a desired suppression of disorder symptoms occurs, and dosages may be adjusted as necessary. The progress of this therapy is easily monitored by conventional techniques and assays.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The anti-hepcidin antibody or specific binding agent is administered by any suitable means, either systemically or locally, including via parenteral, subcutaneous, intraperitoneal, intrapulmonary, and intranasal, and, if desired for local treatment, intralesional administration. Parenteral routes include intravenous, intraarterial, intraperitoneal, epidural, intrathecal administration. In addition, the specific binding agent or antibody is suitably administered by pulse infusion, particularly with declining doses of the specific binding agent or antibody. In some embodiments, the dosing is given by injections, e.g., intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. In some embodiments, the specific binding agent or antibody described herein is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), or a dose ranging from 0.1 to 45 mg/kg, 0.1 to 15 mg/kg or 0.1 to 10 mg/kg at a frequency of 2 or 3 times per week, or up to 45 mg/kg once a month.

Diagnostic and Therapeutic Kits

In another related aspect, kits for treating a disorder associated with elevated hepcidin levels, or a hepcidin-related disorder, or a disorder of iron homeostasis, or a mammal with anemia, are also provided. In one embodiment, the kit includes (a) an anti-hepcidin antibody, and (b) an erythropoiesis stimulator, and optionally, iron. In another embodiment, the kit includes an anti-hepcidin antibody and a label attached to or packaged with the container, the label describing use of the anti-hepcidin antibody with an erythropoiesis stimulator. In yet another embodiment, the kit includes an erythropoiesis stimulator and a label attached to or packaged with the container, the label describing use of the erythropoiesis stimulator with an anti-hepcidin antibody. Also provided is the use of an anti-hepcidin antibody in preparation of a medicament for administration with an erythropoiesis stimulator, as well as use of an erythropoiesis stimulator in preparation of a medicament for administration with an anti-hepcidin antibody. In any of these kits or uses, the anti-hepcidin antibody and the erythropoiesis stimulator can be in separate vials or can be combined together in a single pharmaceutical composition. In yet another embodiment, an anti-hepcidin antibody or erythropoiesis stimulator, or both, can be combined with iron in a single pharmaceutical composition or can be in separate vials.

As a matter of convenience, an antibody disclosed herein can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic reagents and kits comprising one or more such reagents for use in a variety of diagnostic assays, including for example, immunoassays such as ELISA (sandwich-type or competitive format). In some embodiments, such kits may include at least a first peptide (optionally a properly folded mature hepcidin standard as described herein), or a first antibody or antigen binding fragment described herein, a functional fragment thereof, or a cocktail thereof, and means for signal generation. The kit's components may be pre-attached to a solid support, or may be applied to the surface of a solid support when the kit is used. In some embodiment, the signal generating means may come pre-associated with an antibody described herein or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In some embodiments, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods described herein.

Also provided is a kit comprising an anti-hepcidin antibody described herein and an erythropoiesis stimulator packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating a disorder associated with elevated hepcidin levels and comprises an anti-hepcidin antibody and an erythropoiesis stimulator. The kit may optionally further include iron for oral or parenteral, e.g. intravenous, administration. In another aspect, the kit comprises an anti-hepcidin antibody and a label attached to or packaged with the container describing use of the anti-hepcidin antibody with an erythropoiesis stimulator. In yet another aspect, the kit comprises an erythropoiesis stimulator and a label attached to or packaged with the container describing use of the erythropoiesis stimulator with an anti-hepcidin antibody. In certain embodiments, an anti-hepcidin antibody and an erythropoiesis stimulator, and optionally the iron, are in separate vials or are combined together in the same pharmaceutical composition. In yet another aspect, an anti-hepcidin antibody described herein is combined with iron in a single pharmaceutical composition. In yet another embodiment, the erythropoiesis stimulator is combined with iron in a single pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and diagnostic kits disclosed herein may also be prepared that comprise at least one of the antibody, peptide, antigen binding fragment, or polynucleotide disclosed herein and instructions for using the composition as a diagnostic reagent or therapeutic agent. Containers for use in such kits may typically comprise at least one vial, test tube, flask, bottle, syringe or other suitable container, into which one or more of the diagnostic and/or therapeutic composition(s) may be placed, and suitably aliquoted. Where a second therapeutic agent is also provided, the kit may also contain a second distinct container into which this second diagnostic and/or therapeutic composition may be placed. Alternatively, a plurality of compounds may be prepared in a single pharmaceutical composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the diagnostic or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In related embodiments, also provided is a processor, a computer readable memory, and a routine stored on the computer readable memory and adapted to be executed on the processor to perform any of the methods described herein, and/or to generate as output the detected level of hepcidin and a threshold or range of threshold levels considered "normal", such that levels outside the "normal" range correlate with one or more of the conditions as described herein. In some embodiments, computer readable media containing programs or routines to perform similar functions are also provided. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

Non-Therapeutic Uses for Anti-Hepcidin Antibodies

The antibodies disclosed herein may be used as affinity purification agents for target antigen or in diagnostic assays for target antigen, e.g., detecting its expression in specific cells, tissues, or serum. The antibodies may also be used for in vivo diagnostic assays. Generally, for these purposes the antibody is labeled with a radionuclide (such as $^{111}$In, $^{99}$Tc, $^{14}$C, $^{131}$I, $^{125}$I, $^{3}$H, $^{32}$P or $^{35}$S) so that the site can be localized using immunoscintigraphy.

The antibodies disclosed herein may be employed in any known assay method, such as competitive binding assays, direct and indirect sandwich assays, such as ELISAs, and immunoprecipitation assays. Zola, Monoclonal Antibodies: A Manual of Techniques, pp. 147-158 (CRC Press, Inc. 1987). The antibodies may also be used for immunohistochemistry, to label cell samples using methods known in the art.

EXAMPLES

Example 1

Preparation of Anti-Human Hepcidin Monoclonal Antibodies

Monoclonal antibodies can be prepared by various procedures generally as described in copending U.S. patent application Ser. No. 12/022,515, incorporated by reference herein in its entirety. For example, Xenomouse™ IgG2κλ and IgG4κλ mice were immunized with KLH-conjugated human hepcidin (SEQ ID NO: 9) using standard methods. 23,040 IgG2 supernatants and 11,520 IgG4 supernatants were screened at a single concentration against biotinylated human hepcidin anchored to a plate. From this screen 617 IgG2 and 1013 IgG4 supernatants were tested for binding to both human and mouse biotinylated hepcidin using an antibody capture ELISA in which the amount of antibody captured was limited to minimize the effect of concentration differences between supernatants. Top-ranking samples (70 IgG2 and 110 IgG4) were further characterized in a bridging ELISA which measures solution-phase hepcidin-antibody binding over a range of antibody concentrations. This assay provided a relative affinity ranking of antibody binding.

Supernatants from each of the IgG2 and IgG4 panels were designated as follows: 1C9 (SEQ ID NOs: 107-116), 3B3 (SEQ ID NOs: 117-126), 4E1 (SEQ ID NOs: 127-136), 7A3 (SEQ ID NOs: 137-146), 9D12 (SEQ ID NOs: 147-156), 12B9 (SEQ ID NOs: 157-166), 15E1 (SEQ ID NOs: 167-176), 18D8 (SEQ ID NOs: 310-319), 19C1 (SEQ ID NOs: 320-329), 19D12 (SEQ ID NOs: 290-299), 19H6 (SEQ ID NOs: 300-309), 23F11 (SEQ ID NOs: 177-186), 26F11 (SEQ ID NOs: 187-196), 18B11 (SEQ ID NOs: 331-339), 19B8 (SEQ ID NOs: 341-349), 20E12 (SEQ ID NOs: 351-359), 22F12 (SEQ ID NOs: 361-369), 22H10 (SEQ ID NOs: 371-379), 23A11 (SEQ ID NOs: 381-389) and 24E4 (SEQ ID NOs: 391-399).

Generally, the binding affinities of these antibodies to human hepcidin were determined by BIAcore, which were then confirmed by KinExA if the $K_D$ as estimated by BIAcore was below 100 pM. The binding affinity of antibody 18B11, however, was determined by KinExA without the BIAcore assay. The $K_D$ for the lead antibodies were in the range of between 1 μM and more than 400 μM.

Relative species cross-reactivity and binding to Hepc20 (SEQ ID NO: 96) was determined by competition ELISA. 18B11 was observed to be cross-reactive with cynomolgus monkey hepcidin and not-significantly cross-reactive with mouse hepcidin. Antibody 18B11 competes with antibody 23F11 for binding to human hepcidin.

Example 2

Generation and Selection of Human Antibodies with Certain Pharmacokinetic Properties 2,522 hepcidin-specific antibodies were screened for differential binding profiles to human hepcidin at pH 7.4 and pH 6.0 by ELISA. 50 μL of Neutravidin (Pierce) at 8 μg/mL in 1×PBS was coated upon a Nunc Maxisorp 384-well plate, and incubated at 37° C. for 1 hr. After blocking the wells with 0.1% BSA/PBS/0.05% Tween20 for 1 hour at room temperature, plates were washed six times with PBS/0.05% Tween20. 25 μL of mono-biotinylated hepcidin at 50 ng/mL in 0.1% BSA/PBS/0.05% Tween20 was added to the 384-well plate, and incubated at room temperature for 1 hour. The plates were next washed six times with PBS/0.05% Tween20. Starting hepcidin antibody concentrations were normalized to 1 μg/mL for pH 5.5 and 6.0 conditions and to 100 ng/mL for pH 7.4 conditions. The hepcidin antibodies were serially diluted 3-fold in PBS/1% NFDM pH 7.4 and 4-fold in PBS/1% NFDM pH 6.0 and 5.5. The dilutions and titrations were performed in polypropylene 96-well dilution plates, and then were transferred in duplicate to a Neutravidin-coated 384-well plate. The biotinylated hepcidin and antibodies were incubated for 2 hours at room temperature. The plate was next washed six times with PBS/0.05% Tween20. 25 μL of goat anti-huIgG-horseradish peroxidase at a 1:7000 dilution in 0.1% BSA/PBS/0.05% Tween20 was next added to each well of the assay plate. The plate was finally washed six times in PBS/0.05% Tween20. Enhanced K-Blue 3,3',5,5'-Tetramethylbenzidine (TMB) Substrate (Neogen) was added and the reaction stopped using 1 M $H_3PO_4$ after 10 minutes of incubation at room temperature. The absorption was measured at 450 nm on a plate reader. Binding data were analyzed by non-linear regression analysis (sigmoidal dose-response, variable slope) to generate $EC_{50}$ values using GraphPad Prism® software. From this screen 243 antibodies demonstrated a >2-fold difference in binding at pH 7.4 versus pH 6.0. The top 32 well supernatants were rescreened for a third time over a range of antibody dilutions at pH 7.4 and pH 6.0. Antibodies 18B11, 19B8, 20E12, 22C11, 22F12, 22H10, 23A11, 24E4 and 25H6 were selected for subcloning.

The binding affinities of these antibodies to human hepcidin were determined by KinExA and the off-rates were determined by BIAcore. At a 1:250 dilution, all of the antibodies tested demonstrated an about 10-fold reduction in affinity for hepcidin at pH 6 compared to pH 7.4.

Example 3

Engineering of Antibody with Differential pH Binding

Introduction of one or more histidine residues in the light and/or heavy variable region of an antibody can provide antibodies that exhibit differential pH binding to its antigen. Histidine is the amino acid most sensitive to pH shifts from 7.4 to 6.0, as the imidazole side chain of histidine has a pKa just over 6, varying higher or lower depending on the environment of the amino acid. This technique can be applied to any anti-hepcidin antibodies, including those described herein.

A crystal structure model of the Fv portion of the anti-hepcidin antibody 15E1 was prepared. Using this structure model, all 62 CDR residues of antibody 15E1, using the Kabat definition, were selected for mutation, along with framework residues that were at least 10% exposed and within 4.5 Å of a CDR residue, resulting in an additional 31 residues for mutation. Additional positions were selected for mutation by visual inspection of the structure model for amino acids in proximity to the CDRs or selected framework residues. The encoding DNA was mutated to provide histidine mutations at single or multiple positions within the amino acid sequence. Mutations which produced some pH differential binding effect as single mutations can be combined as double, triple or more multiple mutations. The histidine mutations displayed collectively below were engineered at any one or more amino acids in which the "Mutants" sequence identifies a change to a histidine in the following diagram:

```
                             11111111111                     22
15E1 Light           SYELTQPPSVSVSPGQTATITCSGDKLGERYACWYQQRPGQSPVLVIYQD 15E1 Light Mutants   HHHLHHPPSVSVSPGQTATIHCHHHHHHHHHHHWYQQRPGQSPHLVIHHH 22222                        3333333333
15E1 Light           SKRPSGIPERFSGSNSGNTATLTISGTQAMDEADYFCQAWYSSTNVLFGG 15E1 Light Mutants   HHHHHHHHHRFHHHHHHHHATLTISGTQAMDEADYFCHHHHHHHHHHFGG 15E1 Light           GTKLTVLGQP 15E1 Light Mutants   GTKLTVLGQP 11111                  2
15E1 Heavy           QVQLVESGGGVVQPGRSLRLSCAASGFTFSSYGMHWVRQAPGKGLEWVAV 15E1 Heavy Mutants   QHQLVESGGGVVQPGRSLRLSCAASGHHFHHHHHHWVRQAPGKGLHHVAH 2222222222222222                          33
15E1 Heavy           IWYAESNKYYADSVKGRFTISRDNSKNTLYLQMNSLRAEDTAVYYCARAQ 15E1 Heavy Mutants   HHHHHHHHHHHHHHHHHFHIHRHHSKNTLYLQMNSLHAEDTAVYYCARHH 333333333
15E1 Heavy           EGIAPDAFDIWGQGTMVTVSS 15E1 Heavy Mutants   HHHHHHHHHHGQGTMVTVSS
```

Expression of Mutant Constructs

Mutations were introduced into wild-type constructs in vector pTT5 (heavy and light chains on separate vectors) using a Quickchange II kit (Stratagene #200523) and were transiently transfected into 293-6E cells (NRCC).

Light Chain Mutation

S1H
Y2H
E3H
T5H
Q6H
T21H
S23H
G24H
D25H
K26H
L27H
G28H
E29H
R30H
Y31H
A32H
C33H
V44H
Y48H
Q49H
D50H
S51H
K52H
R53H
P54H
S55H
G56H
I57H
P58H
E59H
S62H
G63H
S64H
N65H
S66H
G67H
N68H
T69H
Q88H
A89H
W90H
Y91H
S92H
S93H
T94H
N95H
V96H
L97H

Heavy Chain Mutation

V2H
F27H
T28H
S30H
S31H
Y32H
G33H
M34H
E46H
W47H
V50H
I51H
W52H

Y53H
A54H
E55H
S56H
N57H
K58H
Y59H
Y60H
A61H
D62H
S63H
V64H
K65H
G66H
R67H
T69H
S71H
D73H
N74H
R87H
A99H
Q100H
E101H
G102H
I103H
A104H
P105H
D106H
A107H
F108H
D109H
I110H
W111H

KinExA Solution Equilibrium Binding Analysis for Antibodies 15E1, 15E1 Variants and 18B11 to Binding to Human Hepc.

SA-Sepharose beads were pre-coated with biotinylated human hepcidin (SEQ ID NO: 9) and blocked with BSA according to manufacturer's instructions. Antibodies and hepcidin were diluted in PBS/0.1% BSA/0.05% NaN$_3$ buffer. Fixed concentrations of antibodies 15E1, 15E1 W52H, 15E1 A99H, 15E1 N521-1, 15E1 A107H and 18B11 were incubated with various concentrations of human hepcidin at room temperature for 8 hours before being run through the human hepcidin-coated beads. The amount of the bead-bound antibody was quantified by fluorescently (Cy5)-labeled goat anti-murine-IgG (H+L) antibody (Jackson Immuno Research, West Grove, Pa.). The binding signal is proportional to the concentration of free antibody at equilibrium. Dissociation equilibrium constant ($K_D$) was obtained from nonlinear regression of the competition curves using a dual-curve one-site homogeneous binding model (KinExATM Pro software). The results are set forth below in Table 3.

TABLE 3

| Antibody | $K_D$ | $K_D$ range |
| --- | --- | --- |
| 18B11 | 7.4 nM | 2-23.4 nM |
| 15E1 (wild type) | 37 pM | 13-75 pM |
| 15E1 A107H | 31 pM | 13-58 pM |
| 15E1 A99H | >10 nM | N/A |
| 15E1 N57H | 3 nM | 1.6-4.7 nM |
| 15E1 W52H | 1.7 | 5.8-16.5 nM |

Differential pH binding of the antibodies listed above in Table 3 was then determined by ELISA. 50 μL of Neutravidin (Pierce) at 8 μg/mL in 1×PBS was coated upon a Nunc Maxisorp 384-well plate, and incubated at 37° C. for 1 hr. After blocking the wells with 0.1% BSA/PBS/0.05% Tween20 for 1 hour at room temperature, plates were washed six times with PBS/0.05% Tween20. 25 μL of mono-biotinylated hepcidin at 50 ng/mL in 0.1% BSA/PBS/0.05% Tween20 was added to the 384-well plate, and incubated at room temperature for 1 hour. The plates were next washed six times with PBS/0.05% Tween20. Starting hepcidin antibody concentrations were normalized to 1 μg/mL for pH 5.5 and 6.0 conditions and to 100 ng/mL for pH 7.4 conditions. The hepcidin antibodies were serially diluted 3-fold in PBS/1% NFDM pH 7.4 and 4-fold in PBS/1% NFDM pH 6.0 and 5.5. The dilutions and titrations were performed in polypropylene 96-well dilution plates, and then were transferred in duplicate to a Neutravidin-coated 384-well plate. The biotinylated hepcidin and antibodies were incubated for 2 hours at room temperature. The plate was next washed six times with PBS/0.05% Tween20. 25 μL it of goat anti-huIgG-horseradish peroxidase at a 1:7000 dilution in 0.1% BSA/PBS/0.05% Tween20 was next added to each well of the assay plate. The plate was finally washed six times in PBS/0.05% Tween20. Enhanced K-Blue 3,3',5,5'-Tetramethylbenzidine (TMB) Substrate (Neogen) was added and the reaction stopped using 1 M H$_3$PO$_4$ after 10 minutes of incubation at room temperature. The absorption was measured at 450 nm on a plate reader. Binding data were analyzed by non-linear regression analysis (sigmoidal dose-response, variable slope) to generate EC$_{50}$ values using GraphPad Prism® software. Single mutations of wild type 15E1 that produced at least 1.5 fold increase in EC50 as the pH was lowered to 6.0 included L$_{27}$H (light chain), A89H (light chain), W52H (heavy chain), N57H (heavy chain), A99H (heavy chain), and A107H (heavy chain). Double combinations of these mutants were made. Multiple mutants of wild type 15E1 with at least a 5.5 fold increase in EC50 as the pH was lowered to 6.0 included A107H (heavy chain)/A89H (light chain), A107H (heavy chain)/L27H (light chain), A107H (heavy chain)/N57H (heavy chain), and A107H (heavy chain)/A99H (heavy chain). Representative results are set forth in Table 4 below.

TABLE 4

| | EC50 ng/mL | | |
| --- | --- | --- | --- |
| Sample | pH 7.4 | pH 6.0 | pH 5.5 |
| 18B11 | 2.7 | 244.1 | NC |
| 15E1 (wild type) | 2.3 | 2.3 | 2.3 |
| 15E1 L27H | 4.5 | 6.5 | 8 |
| 15E1 A89H | 5.4 | 10.6 | 12 |
| 15E1 W52H | 4.5 | 5.8 | 17 |
| 15E1 N57H | 1.8 | 4 | 3.2 |
| 15E1 A99H | 4.1 | 10.7 | 29.1 |
| 15E1 A107H | 2 | 3.6 | 3.7 |
| 15E1 N57H A107H | 7.3 | 75.6 | NC |
| 15E1 A99H A107H | 3.0 | 5.5 | 16.1 |
| 15E1 A107H A89H | 6.0 | 34.7 | NC |
| 15E1 A107H L27H | 4.3 | 19.3 | 316 |

Results indicated that antibody 18B11 demonstrated a 2-log lower apparent binding affinity and that 15E1 N57H A107H demonstrated a 1-log lower apparent binding affinity for hepcidin at pH 6.0 compared to pH 7.4.

Example 4

Off-Rate Binding Analysis for Human Antibody 18B11

Off-rate analysis of dissociation at different pHs was also performed. A slow off-rate is expected to predict increased binding interaction over a longer period of time, while a faster off-rate is expected to predict decreased binding interaction.

For example, a faster off-rate at lower pH is expected to predict greater release of antigen at lower pH. Solution equilibrium binding analysis was performed using BIAcore to study the off-rates of antibodies 1S1, 1S3, 2.7, 18B11, 23F11 and 26F11 with recombinant human hepcidin (SEQ ID NO: 9).

Preparation of Biacore Chip Surfaces

Immobilization of recombinant human hepcidin (rhu-Hepc) to a BIAcore sensor chip surface was performed according to manufacturer's instructions at a flow rate 10 µL/min of running buffer (DPBS: Dulbecco's Phosphate Buffer Salinel X, no CaCl or MgCl, with 0.005% Biacore surfactant P-20). The carboxylated matrix of the sensor chip was first activated with a 60 µL injection of a mixture containing 0.2 M EDC(N-ethyl-N-(dimethylamine-propyl)carbodiimide in water, from BIAcore) and 0.05M NHS (N-hydroxysuccinimide in water, from Biacore). 55 µL of recombinant human hepcidin (1 µg/ml in 10 mM Na-acetate pH4.0) was injected to immobilize onto the sensor chip. The excess reactive groups of the sensor chip were deactivated with an injection of 60 µL of ethanolamine (1.0M, from Biacore).

BIAcore Analysis

Figure 1E:
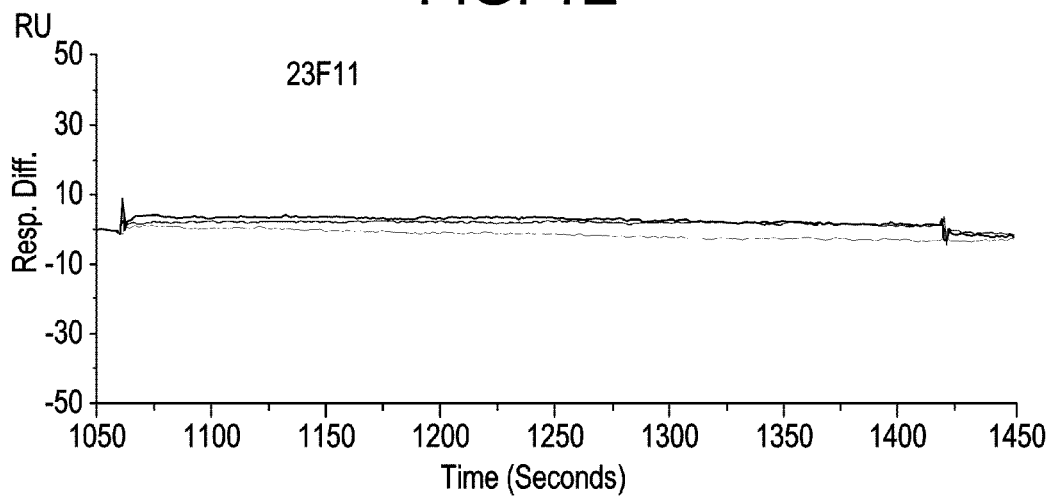
Figure 1F:
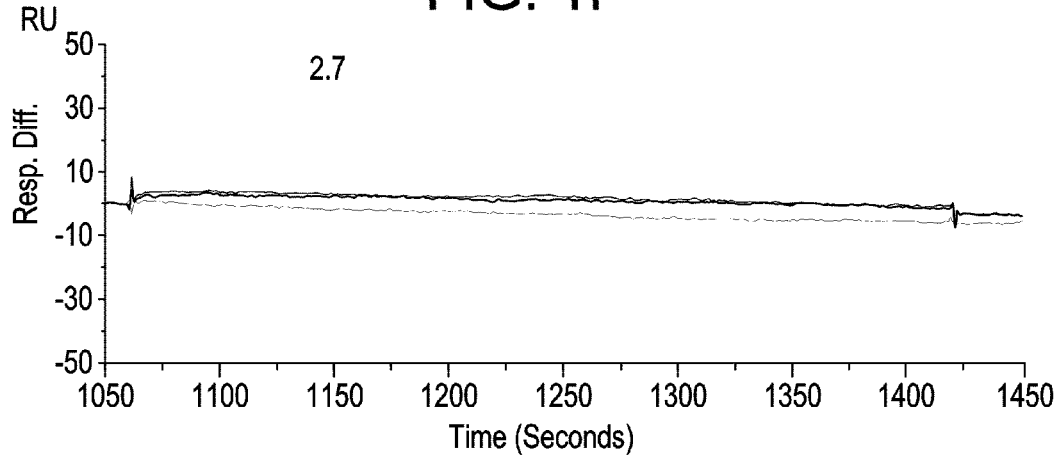

After rhuHepc was immobilized on the CM5 chip with low density, 50 nM of antibodies 1S1, 1S3, 2.7, 18B11, 23F11 and 26F11 were injected over and bound the rhuHepc surface at pH 7.4. Dissociation buffers with pH 7.4, pH6 and pH 5.5 were run over the bound surface. The dissociation curves were obtained. Results indicated that antibody 18B11 demonstrated a significant difference in off rate at pH 7.4 (>1× $10^{-2}$) compared to pH 5.5. The other antibodies tested did not demonstrate a significant difference in off rate at pH 7.4, 6.0 or 5.5. See FIG. 1.

Example 5

In Vitro Hepcidin Activity in an Iron-Responsive B-Lactamase Assay can be Neutralized by Anti-Hepcidin Antibodies Hepcidin causes ferroportin to be internalized and removed from the cell surface, thus inhibiting release of iron and raising intracellular iron concentrations. The effect of anti-human hepcidin antibodies on this hepcidin-mediated iron sequestration was evaluated in vitro. A 293 cell line containing a doxycycline-inducible ferroportin (Fpn) expression construct as well as a beta-lactamase (BLA) expression construct containing one copy of the 5' iron response element (IRE) from ferritin having the following nucleotide sequence:

(SEQ ID NO: 103)
```
tcggccccgcctcctgccaccgcagattggccgctagccctccccgagc gccctgcctccgagggccggcgcaccataaaagaagccgcctagccac gtcccctcgcagttcggcggtcccgcgggtctgtctcttgcttcaacag tgtttggacggaacagatccggggactctcttccagcctccgaccgccc tccgatttcctctccgcttgcaacctccgggaccatcttctcggccatc tcctgcttctgggacctgccagcaccgttttttgtggttagctccttctt gccaacc
```
that regulates mRNA translation was constructed. These 293/Fpn/BLA cells, taken from a 70-80% confluent culture, were plated at $2.8 \times 10^5$ cells/mL in DMEM (Invitrogen Cat# 11965) 5% FBS (Invitrogen. Cat# 10099-141) PSQ (Invitrogen Cat# 10378-016), 90 µL/well (25,000 cells/well) in Bio-Coat Poly-D Lysine coated plates (Becton-Dickinson Cat# 35-6640) and incubated at 37C with 5% $CO_2$. At the end of the same day, a solution of assay medium (DMEM 5% FBS PSQ) with 100 ug/mL doxycycline was made, 10 µL/well of it added to the plate, and the plate incubated overnight or for at least 20 hours. The next day, media was removed from the wells and replaced with premade mixes of DMEM 5% FBS PSQ, 2.5 µg/mL ferric citrate, 50 ng/mL synthetic human hepcidin and serial dilutions of the antibodies (24E4, 23F11, 18B11, 2.7, 2.41, and Ab43), all prepared in a 96-well polypropylene deep-well block plate immediately before addition to the assay plate. Mixtures were added at 100 µL/well and incubated overnight at 37C, 5% $CO_2$ in a cell culture incubator. Plates were then removed from the incubator and equilibrated to room temperature for 10 minutes before adding 20 µL/well of the prepared Invitrogen Gene-Blazer CCF4 A/M development reagent (Invitrogen Kit# K1085) and incubating for 90 minutes in the dark. Development reagent was also added to 16 wells of a control assay plate without cells containing 100 µL assay medium (DMEM 5% FBS PSQ) and incubated for the same time. Blue & Green fluorescence signals were then read on an Envision Multilabel Reader (Perkin-Elmer Inc.) by exciting at 409 nm and reading emissions at 447 nm (blue) and 520 nm (green). The results are depicted in FIGS. 2 and 3. It was determined that mAb 43, 2.7, 2.41, 18B11, 23F11, 24E4 decreased intracellular concentration of iron at an $EC_{50}$ of $1.380 \times 10^{-8}$, $1.700 \times 10^{-8}$, $1.636 \times 10^{-8}$, $2.0 \times 10^{-8}$, $2.3 \times 10^{-9}$ and $5.0 \times 10^{-9}$, respectively.

Example 6

Anti-Hepcidin Antibodies Neutralize Human Hepcidin in Mice

Figure 4A:
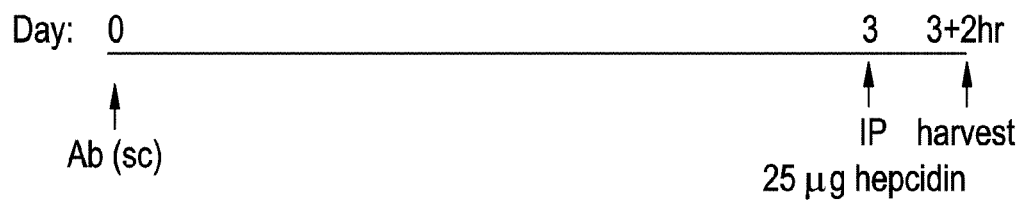
Figure 4B:
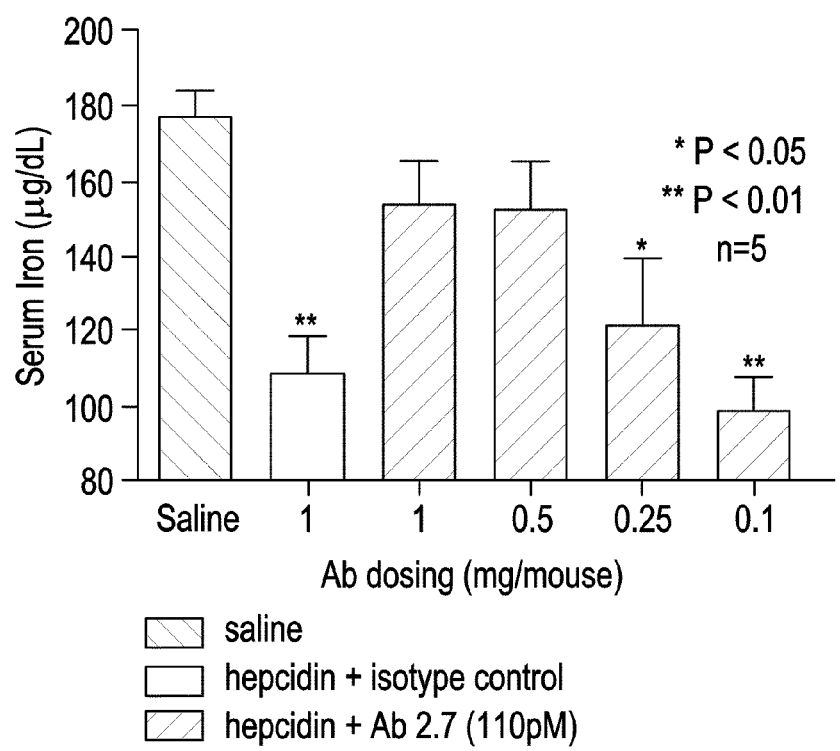

Activity of anti-human hepcidin antibodies was evaluated in vivo in mice that were administered human hepcidin in an amount sufficient to generate a hypoferremic response. On day 0, female C57BL/6 mice were injected subcutaneously with a murine monoclonal antibody (Ab2.7) directed against human hepcidin. Control mice received murine IgG1 as an isotypic control. At day 3, the mice received a single intraperitoneal injection of 25 µg E. coli-derived recombinant human Hepcidin (rhHepc). Serum iron levels were analyzed two hours later. Control animals treated with saline had normal serum iron levels, while animals treated with hepcidin and an isotype control antibody showed hypoferremia. Results are set forth in FIG. 4B. Both 1 mg and 0.5 mg of mAb2.7 provided statistically significant protection from the hypoferremic response. Although a reduction in hypoferremia was observed at the 0.25 mg dose of Ab 2.7, the lower doses (0.25 and 0.1 mg) were defined as non-neutralizing doses. Statistics represent ANOVA with a Dunnett's post-hoc test comparing all groups against the saline control.

Example 7

Figure 5A:
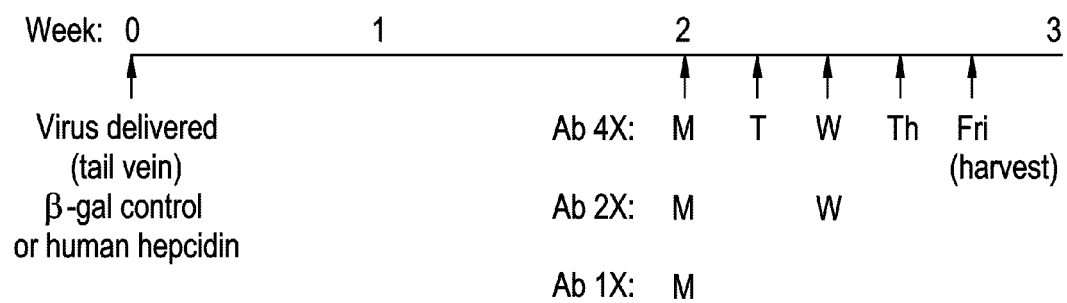

Antibody Neutralization of AAV-Delivered Hepcidin Restores Normal Early Red Blood Cell Characteristics AAV-mediated human hepcidin expression in mice produces a microcytic, hypochromic anemia consistent with iron deprivation. The activity of anti-human hepcidin antibodies was evaluated in vivo in these mice overexpressing human hepcidin. Male C57B1/6 mice were injected with AAV ($1.5 \times 10^{12}$ particles/mouse, I.V.) containing expression cassettes for either human hepcidin or beta-galactosidase (β-gal) as a negative control. The mice were left for two weeks to allow constitutive production of huHepc before being treated with 1 mg/mouse of Ab 2.7 or isotype control (muIgG1) at various dosing frequencies (1×, 2× and 4× per week) as shown in FIG. 5A. Blood was drawn on the fifth day for serum iron levels and determination of early red blood cell (reticulocyte) characteristics (reticulocyte count, reticulocyte hemoglobin content (CHr), and reticulocyte mean cell volume (Retic. MCV))

Results are set forth in FIGS. 5B-5E. Serum iron levels were restored to normal in mice receiving 4× dosing of Ab2.7 but not isotype control. All mice receiving Ab2.7 showed increased reticulocyte production. The reticulocyte hemoglobin content (CHr) was normal in mice given the 4× and 2× dosing of Ab 2.7, but hypochromicity is still seen in groups with 1× dosing, or the isotype control group. Treatment with Ab2.7 at the 4× and 2× dose restored normal volume to reticulocytes (Retic. MCV) but microcytosis was still present in the 1× and isotype control groups. Statistical comparisons to β-gal injected animals with isotype control treatment were determined to look for restoration of normal red cell characteristics (ANOVA with Dunnett's post-hoc test).

In another experiment, the activity of anti-human hepcidin antibodies 1S1, 18B11 and 24E4 was evaluated in vivo in mice overexpressing human hepcidin. C57B1/6 mice (4 weeks of age) were obtained from Charles River Laboratories. On Week 0, mice (n=5 per group) were injected via the tail vein with AAV containing human hepcidin (hHepc) or green fluorescence protein (GFP) as an expression control. Mice were maintained for 2 weeks after viral introduction to allow for protein expression before treatment with antibody. Mice were treated with either 1 mg or 0.5 mg of each antibody 1S1, 18B11 and 24E4 (subcutaneous injection, 0.2 ml/mouse in PBS) on Days 14 and 16 following viral introduction. Blood was collected on Day 18, and response to antibody administration was measured as a change in reticulocyte characteristics (reticulocyte cellular hemoglobin content) using an ADVIA 2120 Hematology Analyzer (Bayer Corporation, Tarrytown, N.Y.). Total serum hepcidin levels (free and bound) were measured by ELISA to determine the degree of complex formation. All results were expressed as the mean±standard error of the mean. ANOVA and a Dunnett's post test using Graphpad Prism software v4.0 (San Diego, Calif.) assessed statistical significance of differences (* denotes $p<0.05$, and ** denotes $p<0.01$ compared to AAV-hHepc+isotype control group).

Figure 6A:
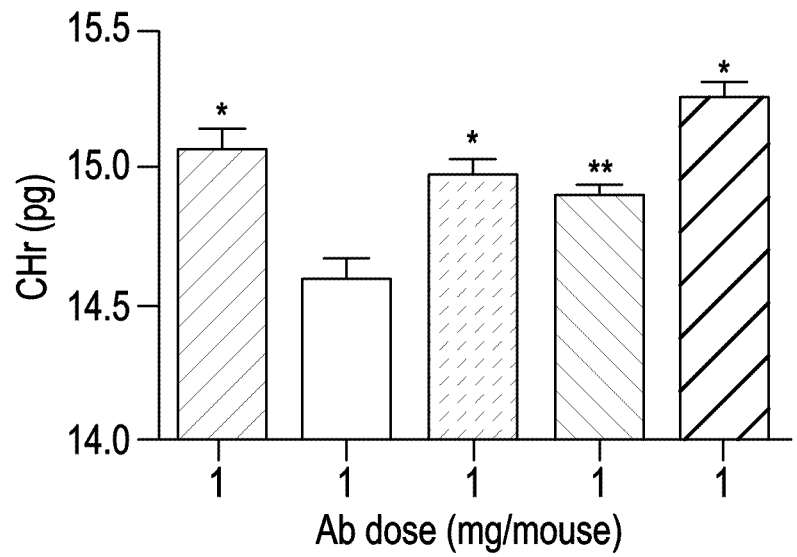
FIGS. 6A-B demonstrate that treatment with antibody 18B11 restored normal early red cell characteristics.
Figure 6B:
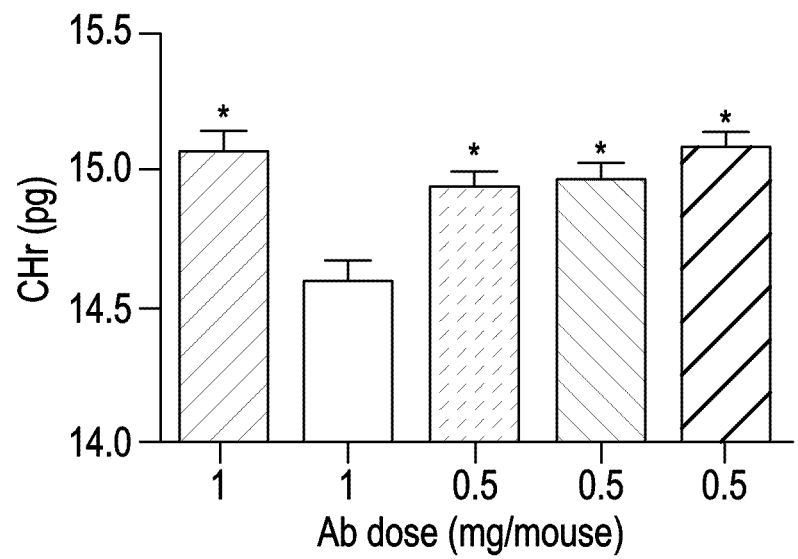

After 18 days, the reticulocytes in the AAV-hHepc+isotype treated control mice had reduced hemoglobin content (CHr), rendering them hypochromic. Animals treated with anti-hepcidin antibodies 1S1, 18B11 or 24E4 at either 1 mg or 0.5 mg/mouse had normal CHr values as compared to AAV-GFP control mice, indicating that these antibodies are efficacious in this model in restoring normal early red cell characteristics. See FIGS. 6A and 6B.

Results indicated that mice treated with the 1 mg dose of antibody 18B11 had a 10-fold reduction in total serum hepcidin compared to animals treated with antibody 1S1 or antibody 24E4 (FIG. 7A). Similar results were obtained at the 0.5 mg/mouse dose (FIG. 7B). The markedly reduced amount of total hepcidin seen with antibody 18B11, is consistent with hepcidin clearance through endosomes.

Example 8

Viral Hepcidin Over-Expression Results in Hypo-Responsiveness to Erythropoietin

The following Example investigated the role of hepcidin and anti-hepcidin antibodies in erythropoietin hypo-responsive mice.

Figure 8:
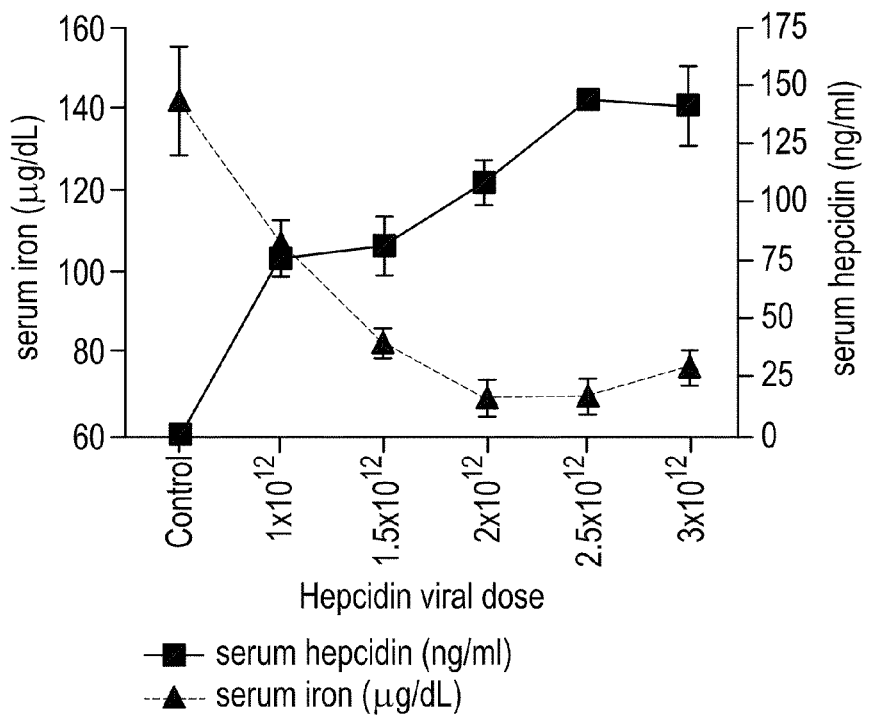
FIG. 8 shows a titration of adenovirus-associated virus (AAV)-mediated hepcidin expression and resulting serum iron concentrations.

Titration of AAV-mediated human hepcidin expression in mice causes an increase in serum hepcidin levels and dose-dependent hypoferremia, as shown in FIG. 8. Doses of AAV-human hepcidin were selected that gave an erythropoietin resistant phenotype and expressed levels of hepcidin in a similar range to that detected in cancer patient samples in previous studies (as described in co-pending co-owned U.S. patent application Ser. No. 11/880,313 and International Publication No. WO 2008/011158, the disclosures of which are incorporated herein by reference in their entirety). Male C57BL/6 mice were injected with AAV expressing human hepcidin or GFP as an expression control (n=4 per group). The mice were injected through the tail vein (human hepcidin, from $1 \times 10^{12}$ to $3 \times 10^{12}$ particles/mouse; GFP $3 \times 10^{12}$ particles/mouse). Protein expression was allowed to develop for two weeks prior to harvest. At two weeks, serum was collected from the mice and iron and hepcidin levels were determined. Results are reported in FIG. 8.

Figure 9:
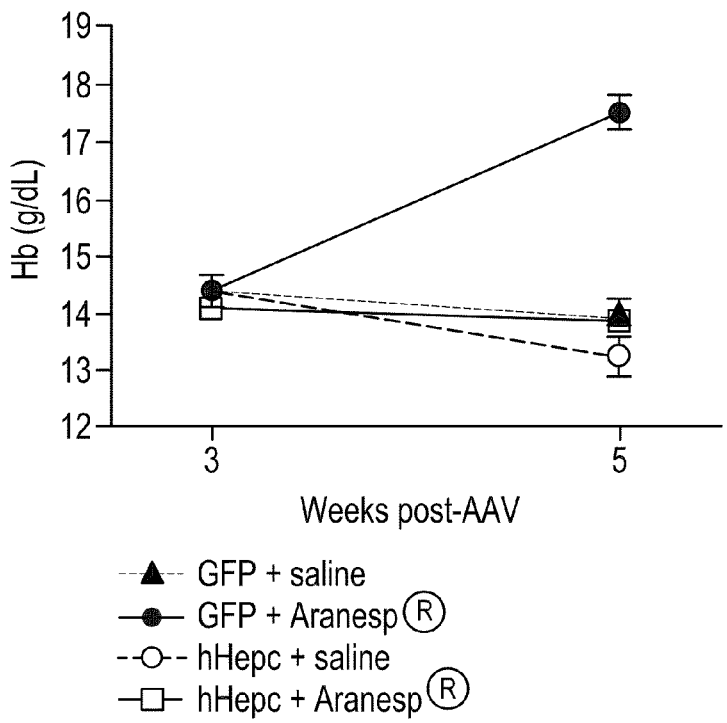
FIG. 9 shows that viral overexpression of hepcidin causes hypo-responsiveness to erythropoietin.

In order to evaluate hepcidin's effect on erythropoietin resistance, male C57BL/6 mice were injected with AAV ($3 \times 10^{12}$ particles/mouse, hepatic portal vein delivery) containing expression cassettes for either human hepcidin or GFP as a negative control (n=5 per group). The mice were left for three weeks to allow constitutive production of human hepcidin, and then bled to determine baseline hemoglobin (Hb) levels. The mice were treated with darbepoetin alfa (100 μkg/mouse) or saline as a negative control at four weeks. At five weeks, hemoglobin levels were again measured. Results are shown in FIG. 9. Mice over-expressing human hepcidin are resistant to high doses of darbepoetin alfa. Resistance to darbepoetin alfa demonstrates that elevated hepcidin levels are sufficient to cause hypo-responsiveness to erythropoetin.

Example 9

Figure 10A:
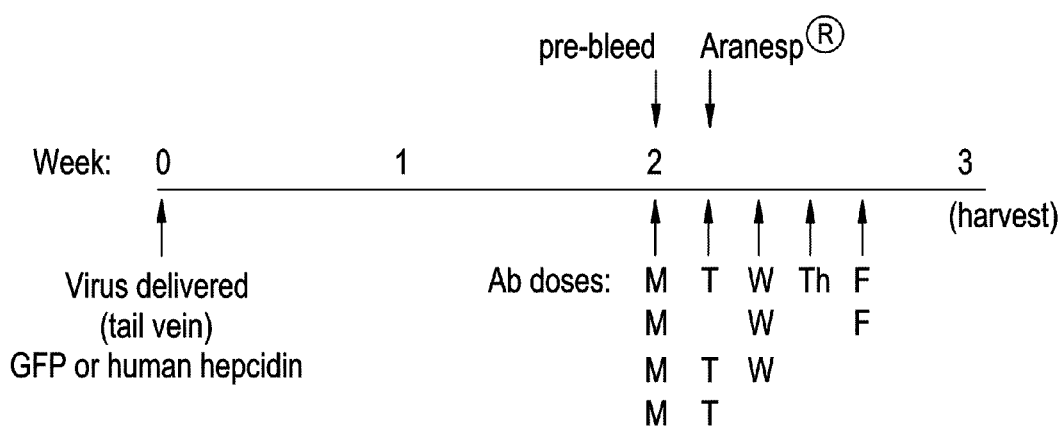
FIGS. 10A-E demonstrate that an anti-hepcidin antibody restores responsiveness to erythropoietin in mice virally over-expressing hepcidin.

Combination Therapy with Hepcidin Antibody and an Erythropoiesis Stimulator in a Viral Hepcidin Over-Expression Model Treating mice that possessed an erythropoetin resistant phenotype with an anti-hepcidin antibody restored responsiveness to treatment with darbepoetin alfa. Male C57BL/6 mice were injected with AAV ($5 \times 10^{12}$ particles/mouse, I.V.) containing genes coding for either human hepcidin or GFP as an expression control (n=5 per group). After allowing two weeks to establish constitutive protein expression, mice were bled to determine baseline hemoglobin (Hb) levels, then treated with Ab 2.7 (1 mg/mouse) or isotype control at various dose frequencies. On the day after the first dose, they were treated with darbepoetin alfa (100 μg/kg, subcutaneous). A schematic of the dosing schedule appears in FIG. 10A.

Figure 10B:
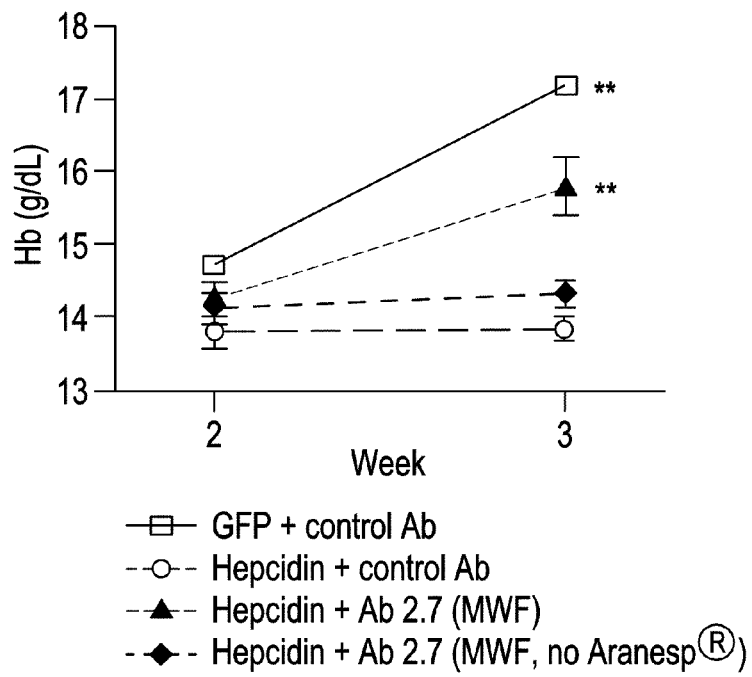
Figure 10C:
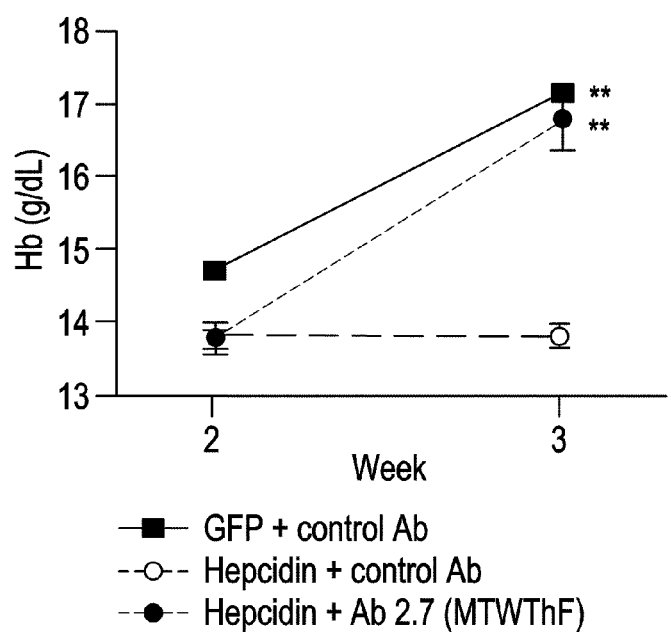
Figure 10D:
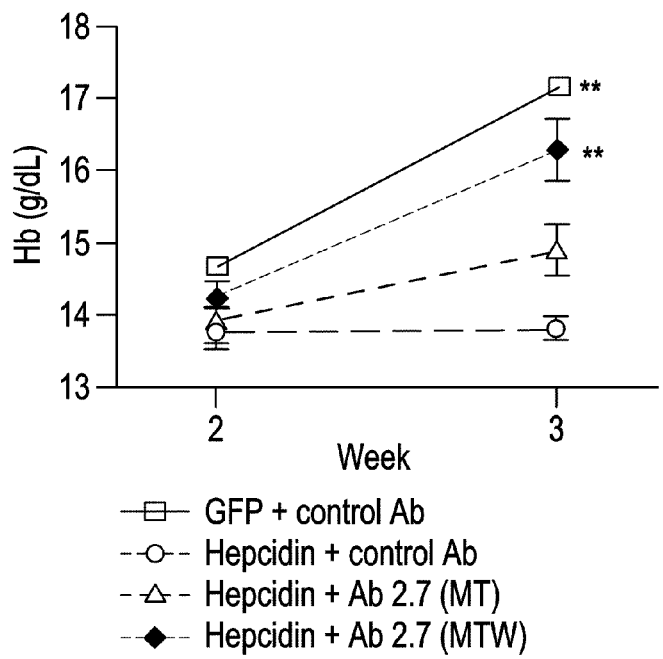
Figure 10E:
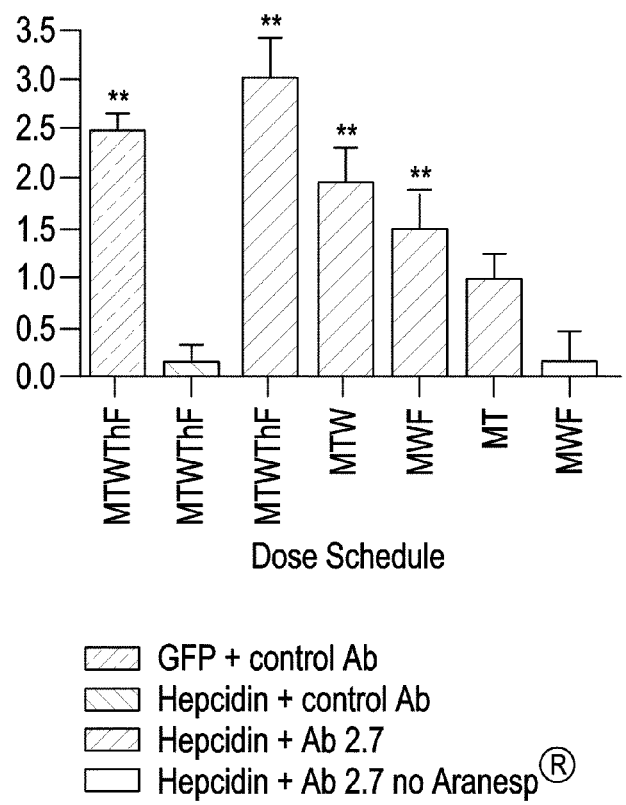

Neutralization of hepcidin restores responsiveness to darbepoetin alfa. Monday-Wednesday-Friday dosing of the antibody led to a partial response to darbepoetin alfa treatment as measured by an increase in Hb levels; a cohort with the same antibody dosing without darbepoetin alfa treatment showed no rise in Hb levels. (See FIG. 10B) A maximal response to darbepoetin alfa was achieved in mice receiving daily (Monday through Friday) dosing of Ab 2.7. (See FIG. 10C) Two and three doses of antibody in combination with darbepoetin alfa treatment led to a partial response, as measured by Hb levels. (See FIG. 10D) Antibody dose and proximity of antibody dose to darbepoetin alfa treatment affected overall Hb response to anti-hepcidin antibody treatment, as shown in FIG. 10E (results varying from the control where $p<0.01$ by ANOVA with Dunnett's post-hoc test are noted with double asterisks). Thus, antibody-mediated neutralization of hepcidin was shown to be an effective treatment for anemia caused by elevated hepcidin levels.

Example 10

Combination Therapy with an Anti-Hepicin Antibody and Erythropoiesis Stimulator in a Mouse Model of Inflammatory Anemia Combination therapy with an anti-hepcidin antibody and an erythropoiesis stimulator was also evaluated in a murine inflammatory anemia model as follows.

Mice were generated such that murine hepcidin 1 was knocked out and replaced with human hepcidin. Female mice, both homozygous for human hepcidin expression and wild-type littermate controls, were injected with *Brucella abortus* ($2\times10^8$ particles/mouse, I.P.) on day 0 and then bled on day 6 to assess hemoglobin levels. The mice were then treated with either Antibody 2.7 or an isotype control antibody (1 mg/mouse/day) on days 6 through 9. Darbepoetin alfa was administered (100 µg/kg/mouse) on day 7, and Hb levels evaluated on day 13. A schematic of the protocol is shown in FIG. 11A.

Wild-type control mice which still possessed the mouse hepcidin 1 gene did not respond to darbepoetin alfa either with or without Ab 2.7. (See FIG. 11B) Human knock-in mice treated with Antibody 2.7 exhibited a restored responsiveness to darbepoetin alfa treatment, as shown by the maintenance of stable hemoglobin levels. (See FIG. 11C).

These results demonstrate that anti-hepcidin antibodies can be used to neutralize hepcidin under conditions of hepcidin excess and restore responsiveness to erythropoietic agents in hepcidin-mediated anemias such as the anemia of inflammation.

Example 11

Measurement of Hepcidin Level in Patients

The level of hepcidin in human patients was measured by spectrometry techniques as previously described in co-pending co-owned U.S. patent application Ser. No. 11/880,313 and International Publication No. WO 2008/011158, the disclosures of each of these applications are incorporated herein by reference in their entirety. The method is reproduced below.

Samples from patients suffering from anemia of cancer (obtained from ProteoGenex) or volunteers (control) were collected. 100 µL of each sample, serum blanks and calibration standards consisting of seven non-zero concentrations in duplicates (10, 25, 50, 100, 250, 500, 1000 ng/mL) were extracted by SPE using an Oasis HLB mElution 96-well plate (Waters, Milford, Mass.). Washing solvent was 30% methanol/water with a pH of about 10 adjusted with ammonium hydroxide. Elution solvent was 90% methanol/water solution with a pH of about 5 adjusted with acetic acid. The SPE plate was activated with 500 µL methanol and conditioned with 500 µL water, then 100 µl, serum sample and 200 µL internal standard were loaded onto the elution plate, washed with 350 µL water and 350 µL washing solvent. Elution was done using 100 µL elution solvent and diluted with 100 µL water. The resulting 200 µL eluate was analyzed by LC-MS/MS.

20 µl of each extracted sample was injected onto a Polaris C18A, 5 µm HPLC column (2.1×50 mm, Varian). The LC flow rate was set to 300 µl/min. The HPLC mobile phase A was 5:95 methanol/water, and mobile phase B was 95:5 methanol/water, both containing 0.1% formic acid. The gradient conditions were set as follows: 0-0.1 min, isocratic 2% B/98% A; 2% B to 95% B at 0.1-4.5 min; 95% B at 4.5-4.9 min; 95% B to 2% B at 4.9-5.0 min; 5.0-6.0 min, isocratic 2% B.

A Sciex API4000 triple quadrupole mass spectrometer from Applied Biosystems (Foster City, Calif.) with Turbo ESI source was used for hepcidin detection in MRM mode with ion transition of m/z 930.60 to m/z 110.15. Quantification was achieved by comparing the ratio of the LC peak areas of the hepcidin and the internal standard to the ratios obtained from a series of standards where the amounts of hepcidin and internal standard were known.

Figure 12:
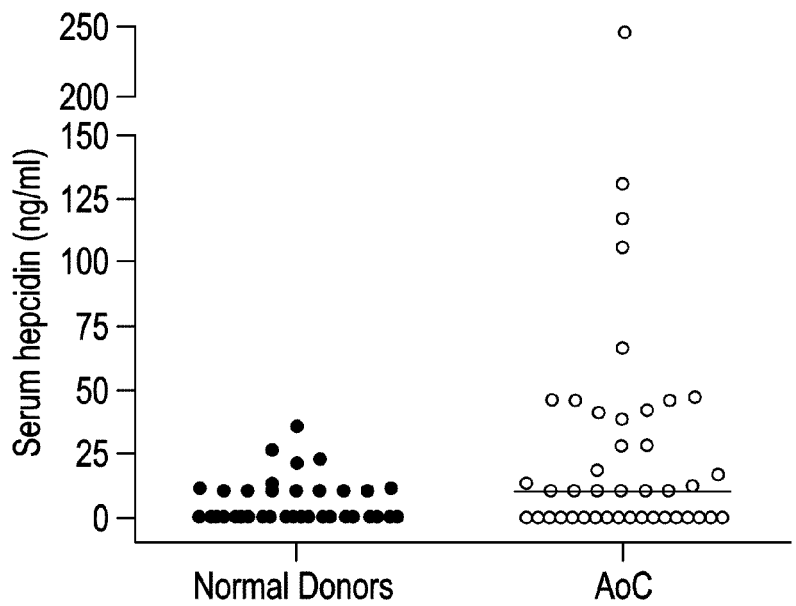
FIG. 12 demonstrates that hepcidin levels are elevated in anemia of cancer patients (AoC) and not in normal patients.

This experiment allowed for the determination of the serum levels of hepcidin in a control population presumed to contain a large number of healthy individuals as well as the serum level of hepcidin from patients suffering anemia of cancers (AoC). The results are shown in FIG. 12.

Figure 13:
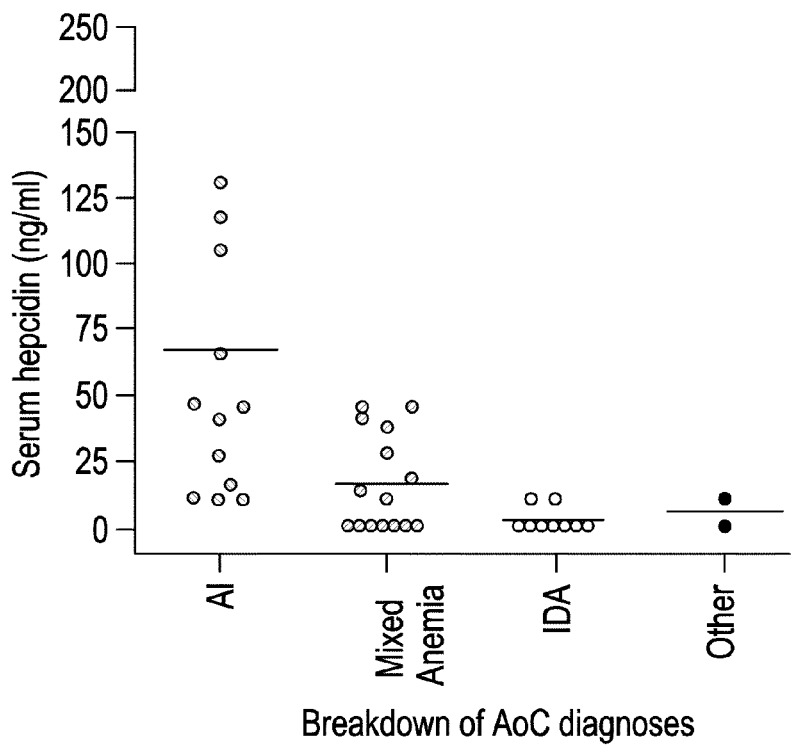
FIG. 13 demonstrates that hepcidin levels correlate with diagnosis of inflammatory anemia and not iron deficiency anemia.

Each patient's sample was then analyzed for other iron index concentrations to determine whether a patient had inflammation or iron deficiency anemia (FIG. 13). The parameters were measured as follows: serum iron, UIBC, ferritin, and CRP were measured on an Olympus AU400 clinical laboratory analyzer using standard procedures; sTfR was measured using a standard ELISA method (R&D systems).

As described in copending U.S. patent application Ser. No. 12/022,515, incorporated by reference herein in its entirety, prohepcidin levels measured using the DRG prohepcidin ELISA kit, however, do not correlate with the mature hepcidin levels of the patients, nor do prohepcidin levels correlate with the inflammatory status of patients. Hepcidin, but not prohepcidin, shows a relationship with CRP in anemia of cancer patients, and can therefore be used as a marker of inflammation.

Distinguishing the anemia of inflammation (AI) from iron deficiency anemia (IDA) and mixed anemia (components of both AI and IDA) is complicated since most of the commonly used lab parameters are influenced by acute phase responses. A ratio utilizing soluble transferrin receptor (sTfR) and ferritin (Ft) values has been described in the literature as a means to provide a more accurate diagnosis. See Punnonen et al., *Blood*, 89:1052-57, 1997. Anemia of inflammation is characterized by a low sTfR/log Ft quotient (values less than one), while a high ratio is indicative of IDA. Hence, the sTfR/log Ft ratio may serve as an accurate predictor of the three conditions when combined with an inflammatory marker to aid diagnosis of mixed anemia from absolute IDA.

Hepcidin levels are strongly related to sTfR/log Ft levels in AoC patients (r=−0.6407; P<0.0001), thus aiding patient diagnosis.

Figure 15A:
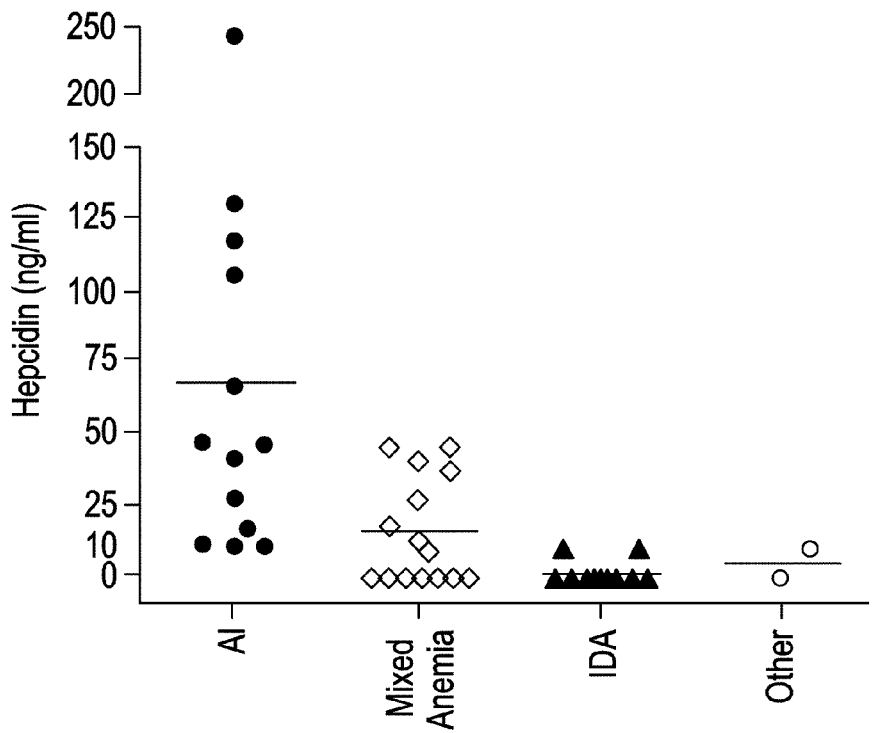
FIGS. 15A-B show prohepcidin concentration measured by a sandwich immunoassay, demonstrating that prohepcidin is not detectable in serum.
Figure 15B:
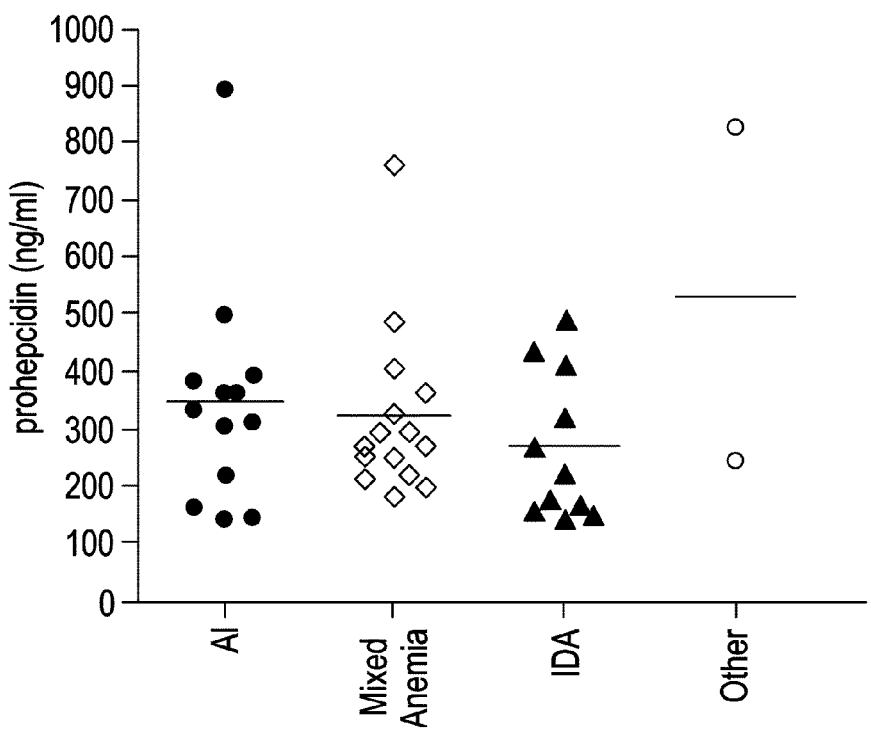

Using a decision tree combining CRP as a marker of inflammation and sTfR/logFt, anemia of cancer patients could be sub-divided into those with AI, with mixed anemia, with IDA and with an anemia of unknown origin, designated 'other' (FIG. 14A). Patients with elevated hepcidin levels were all observed to have either AI or a mixed anemia. (FIG. 15). Patients with low or absent hepcidin levels were observed to have either IDA or anemia of unknown origin. Hepcidin levels, as measured by the antibody-based immunoassay methods described in copending U.S. patent application Ser. No. 12/022,515, incorporated by reference herein in its entirety, or the mass spectrometry-based method quantitation method described in co-pending co-owned U.S. patent application Ser. No. 11/880,313 and International Publication No. WO 2008/011158, the disclosures of which are incorporated herein by reference in their entirety, and discussed in detail above, can be used to diagnose inflammatory anemia.

Example 12

Monoclonal Antibodies in a Sandwich Immunoassay for Hepcidin

The following Example describes a sandwich immunoassay to determine hepcidin levels in a sample.

Figure 16:
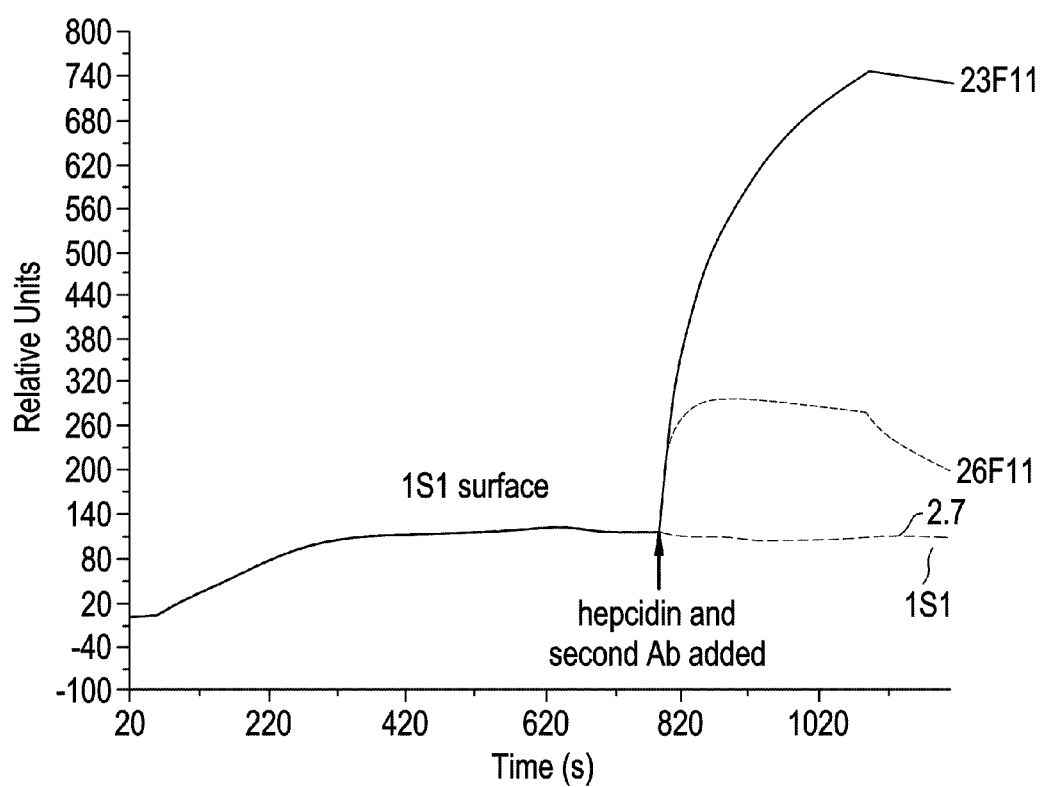
FIG. 16 shows results of a Biacore experiment demonstrating that two monoclonal antibodies can bind to hepcidin at once.

Using Biacore analysis, a surface coated with antibody 1S1 was tested for the concurrent binding of hepcidin and another antibody (FIG. 16). Immobilization of anti-Hepc antibody 1S1 to the sensor chip surface was performed according to manufacturer's instructions using a continuous flow of 0.005% P-20/PBS buffer. Briefly, carboxyl groups on the sensor chip surfaces were activated by injecting 60 µL of a mixture containing 0.2 M N-ethyl-N'-(dimethylaminopropyl)carbodiimide (EDC) and 0.05 M N-hydroxysuccinimide (NHS). This was followed by injecting 1S1 diluted in 10 mM acetate, pH 4.0 at concentrations between 20 µg/mL. Excess reactive groups on the surfaces were deactivated by injecting 60 µL of 1 M ethanolamine. Final immobilized levels were 5,000-6,000 resonance units (RU) for the Ab 1S1 surface. A blank, mock-coupled reference surface was also prepared on the sensor chip. 20 nM E. coli-derived human hepcidin was injected over and bound to the 1S1 antibody surface. Then 50 nM antibody 2.7, 23F11, 26F11, and 1S1 were injected over the hepcidin/1S1 surface. After the antibody injection, the surfaces were regenerated by injecting 10 mM HCl pH 2.0.

There was a high selectivity of binding in the form of complexes. The murine antibody 2.7, which was used in the competitive assay above, was not able to form a sandwich pair with 1S1, and 26F11 showed markedly lower ability to bind to hepcidin concurrently with 1S1 than did 23F11.

Figure 17:
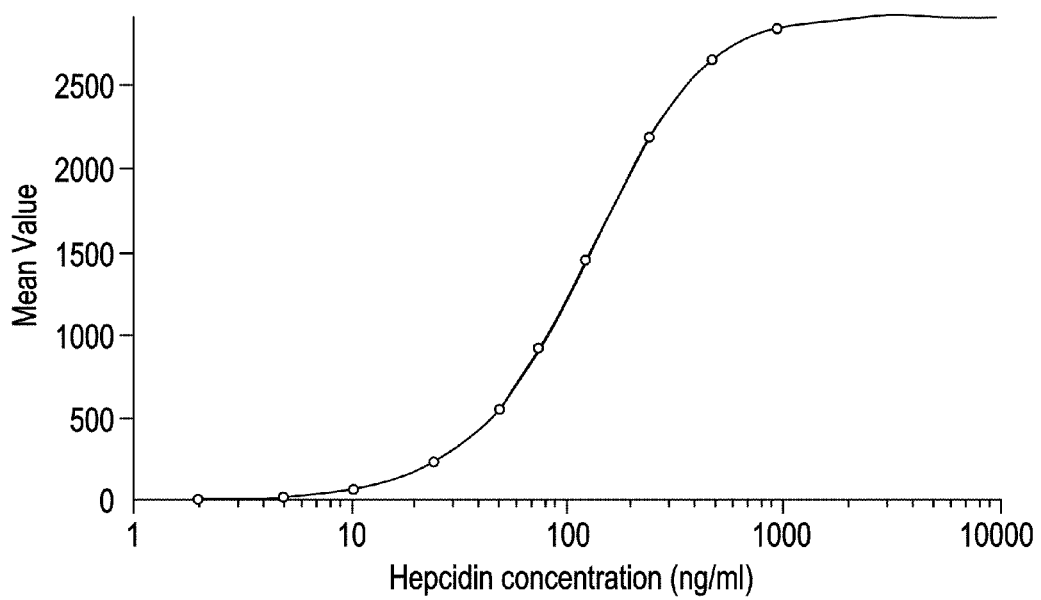
FIG. 17 demonstrates that a sandwich ELISA can be constructed with monoclonal antibodies raised against mature hepcidin.

When 1S1 and 23F11 were assembled into a sandwich ELISA format, the sensitivity of the immunoassay for detecting hepcidin levels was improved by 50-fold. As shown in FIG. 17, the assay proved capable of measuring levels of hepcidin in normal sera after a 50-fold pre-dilution step. The axis represents the hepcidin levels pre-dilution.

Example 13

Competitive Binding Assay

The following Example describes a competitive binding assay to determine hepcidin levels. In one protocol, unlabeled hepcidin present in serum competes with biotinylated hepcidin for binding to an anti-hepcidin antibody (e.g., Antibody 2.7).

Figure 18:
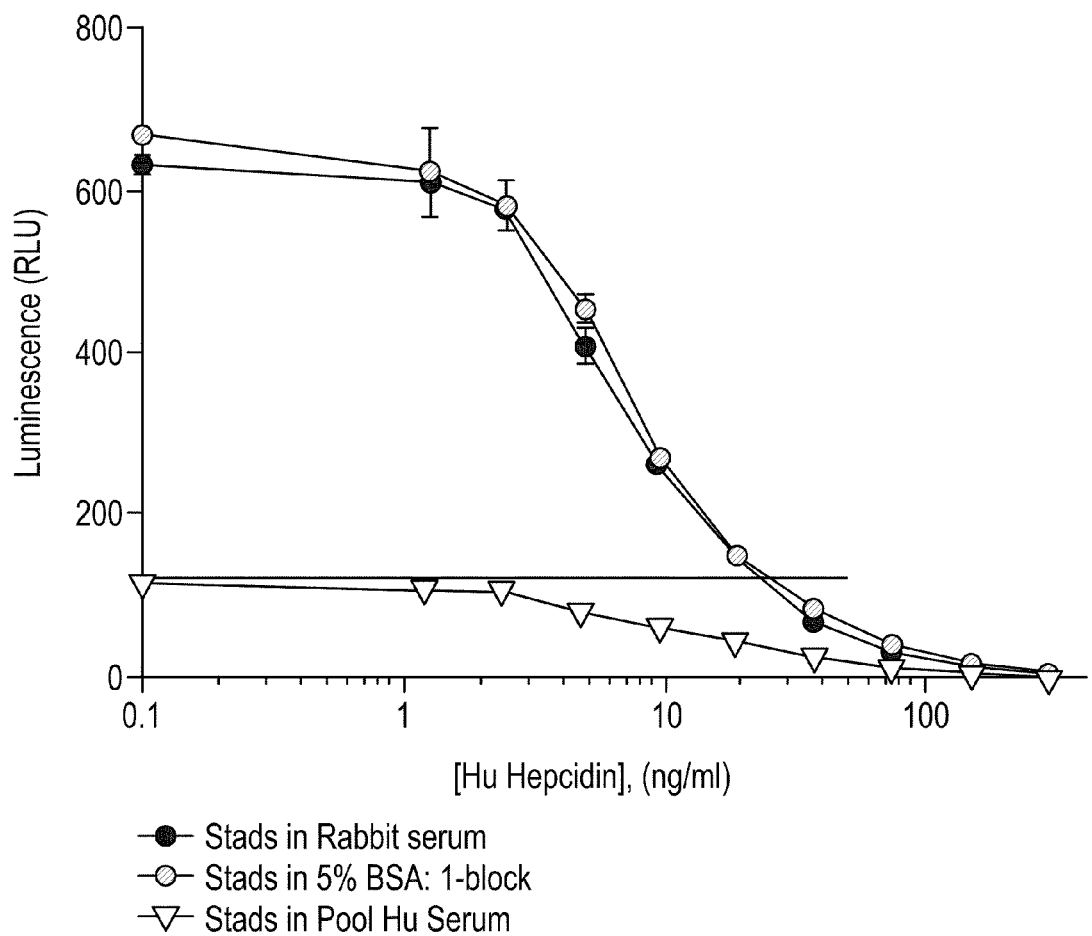
FIG. 18 shows the concentration of hepcidin present in buffer, rabbit serum and pooled human serum as determined by a competitive binding assay.

Hepcidin levels were determined using hepcidin standards of varying concentrations (from 1.4-300 ng/ml) spiked into buffer (5% BSA:I-block), rabbit serum, or pooled human serum. Hepcidin was added to equal volumes of 40 ng/mL of Ab2.7 and incubated for 120 minutes. 25 µl/well of mixed solution was added to Black half area plates coated with 1-2 µg/mL GxM capture antibody. 25 µL/well of biotinylated hepcidin was added at 0.25 nM. The plate was covered with plate film sealer and incubated at room temperature (25° C.) on a plate shaker at around <200 RPM for around 60 minutes. The plate was washed and then 50 µL/well of Poly horseradish peroxidase amplification reagent at 1:2000 was added. The plate was allowed to sit for 30 minutes and was then washed with a plate washer using PBS or KPL buffer 6 times. The plate was patted dry and a luminescent substrate (Femto or Pico) was quickly added. The plate was read with luminometer (ex: Lmax 340) for 1 second using Femto or Pico Substrate. Results indicated that hepcidin was measurable at a concentration range of 1-100 ng/ml in both the rabbit serum and buffer. (FIG. 18).

Figure 19:
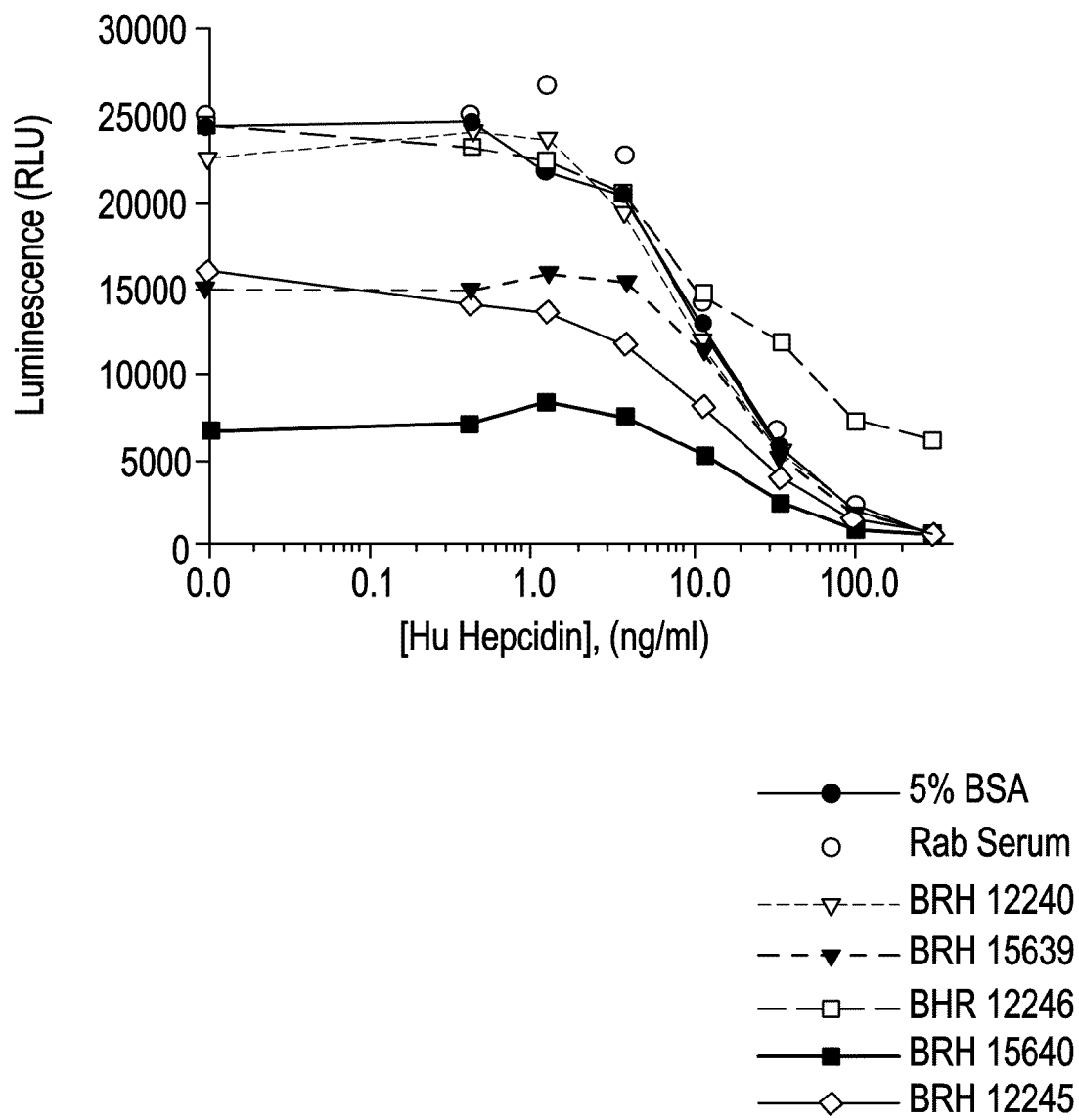
FIG. 19 shows the measurement of hepcidin in human sera.

Pooled human serum appeared to have an existing hepcidin level of greater than 20 ng/ml. It was determined that the levels of hepcidin varied substantially in human sera, over the range of 1-30 ng/ml for various randomly selected sera (FIG. 19).

Figure 20:
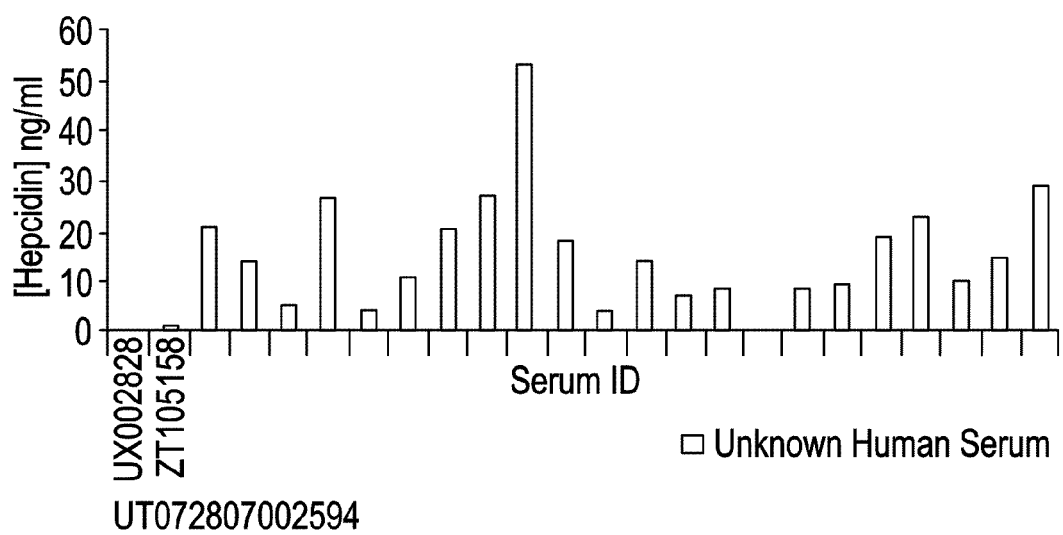
FIG. 20 shows the concentration of hepcidin present in normal human sera using a competitive binding assay.

Using hepcidin standards in rabbit serum determined above, 24 random sera from normal human subjects was tested. The hepcidin levels varied from undetectable to over 50 ng/ml. See FIG. 20. These values were at variance with the results from the levels of hepcidin measured through the mass spectrometry-based quantitation method described in co-pending co-owned U.S. patent application Ser. No. 11/880,313 and International Publication No. WO 2008/011158, the disclosures of which are incorporated herein by reference in their entirety, which generally gave much lower values.

Example 14

Pharmacokinetic Study of Antibody Following Single Dose of Antibody-Hepcidin Complex C57 BL/6 mice were pre-dosed with either the control antibody or antibodies 1S1 or 18B11 on Day 0 as a single intraperitoneal injection at a dose of 1 mg/mouse to ensure that the antibody concentration was above the antibody $K_D$. On Day 1, the mice were dosed with an antibody-hepcidin complex (i.e., either 1S1-hepcidin complex or 18B11-hepcidin complex). Urine samples for determination of hepcidin concentrations were collected prior to hepcidin administration and at 1 hour, 24 and 96 hours antibody-hepcidin complex administration. The results are set forth in Table 5 below.

TABLE 5

| Time (hours) | 1S1 Hepcidin Concentration | 18B11 Hepcidin Concentration |
| --- | --- | --- |
| 1 | Not detectable | 20 ng/mL |
| 24 | Not detectable | Not detectable |
| 96 | Not detectable | Not detectable |

Figure 21:
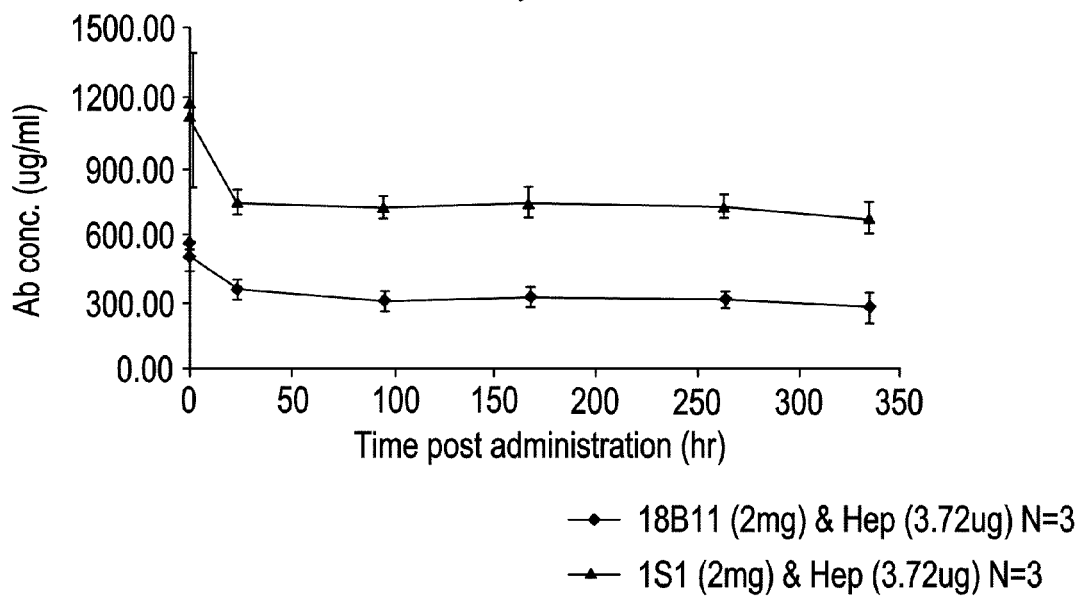
FIG. 21 shows the serum antibody concentration of antibodies 1S1 and 18B11 after administration of antibody-hepcidin complexes at various timepoints.
Figure 22:
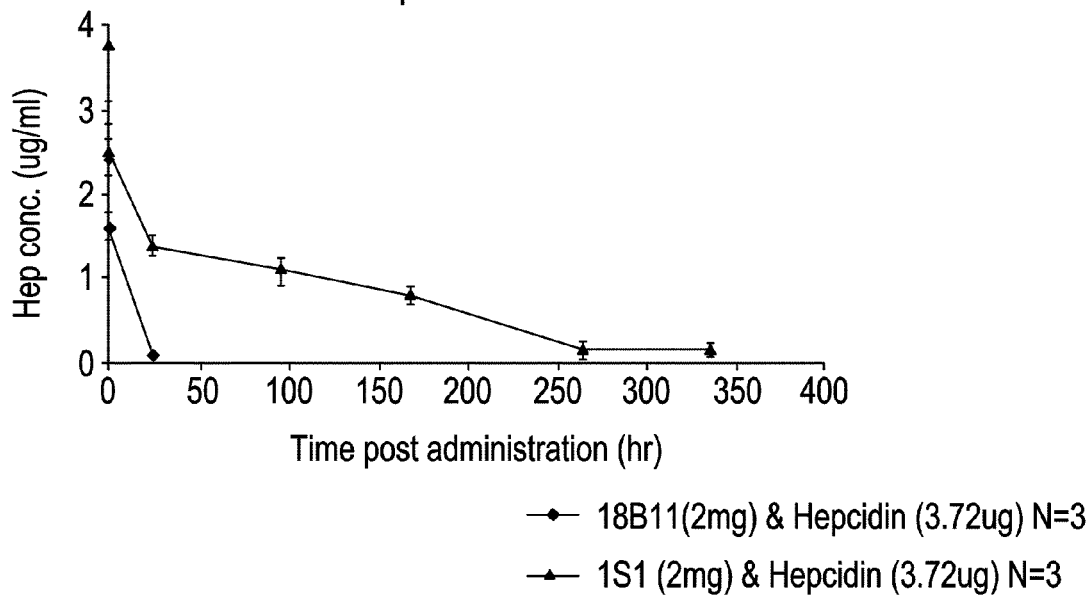
FIG. 22 shows the serum hepcidin concentration after administration of antibody-antigen complexes at various timepoints.

Serum samples for determination of serum antibody and serum hepcidin concentrations were collected at 5 minutes, 1 hour, 24 hours, 96 hours, 168 hours, 264 hours and 336 hours after administration of the antibody-hepcidin complex. Serum antibody and hepcidin concentrations were calculated by ELISA and the results are set forth in FIGS. 21 and 22, respectively. Results indicated that the concentration of serum hepcidin at the 5-minute timepoint in mice that received the 18B11-hepcidin complex was lower compared to the 1S1-hepcidin complex. Interestingly, hepcidin was not detectable after 24 hours in mice that received the 18B11-hepcidin complex, while mice treated with the 1S1-hepcidin complex still had detectable levels of serum hepcidin at 168 hours.

Example 15

Figure 23:
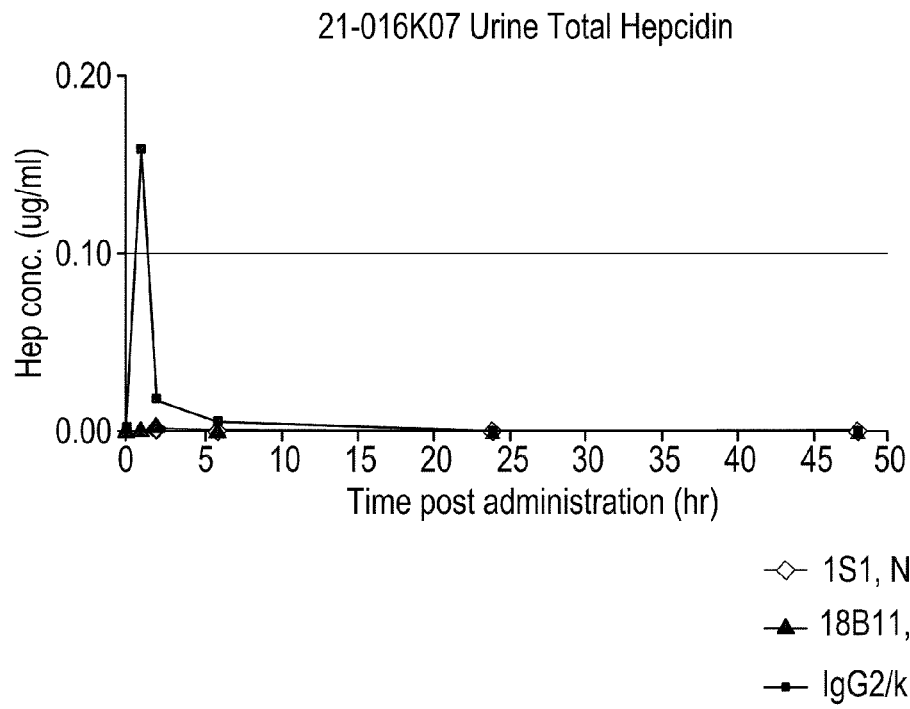
FIG. 23 shows the total urine hepcidin concentration mice pre-dosed with antibody 1S1 or 18B11 at various time points.

Pharmacokinetic Study of Antibodies Following Single Dose of Free Hepcidin to Mice C57 BL/6 mice were pre-dosed with either the control antibody or antibodies 1S1 or 18B11 on Day 0 as a single intraperitoneal injection at a dose of 1 mg/mouse. On Day 1, the mice were predosed with the antibodies as a single intravenous injection at a dose of 1 mg/mouse. On Day 4, human hepcidin (3.72 µg/mouse) was administered to the mice by intravenous injection. Urine samples for determination of hepcidin concentrations were collected prior to hepcidin administration and at 1 hour, 6 hours and 24 hours post-hepcidin administration. Results indicated that hepcidin was not detected in mice pre-dosed with either 1S1 or 18B11. See FIG. 23.

Figure 24:
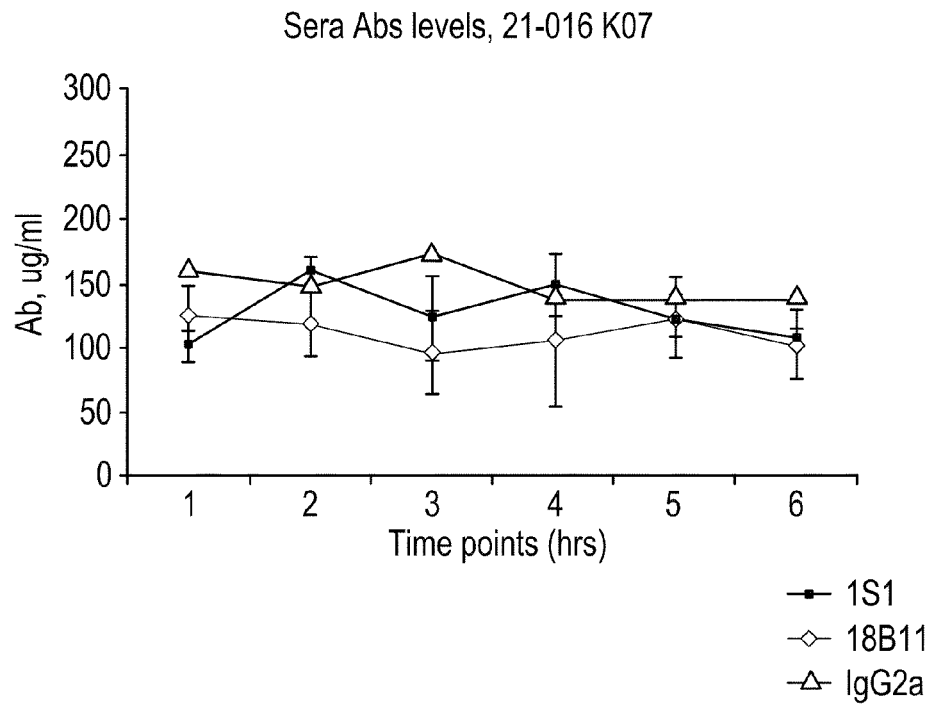
FIG. 24 shows the serum hepcidin concentration after administration of antibodies 18B11 and 1S1 at various timepoints.
Figure 25:
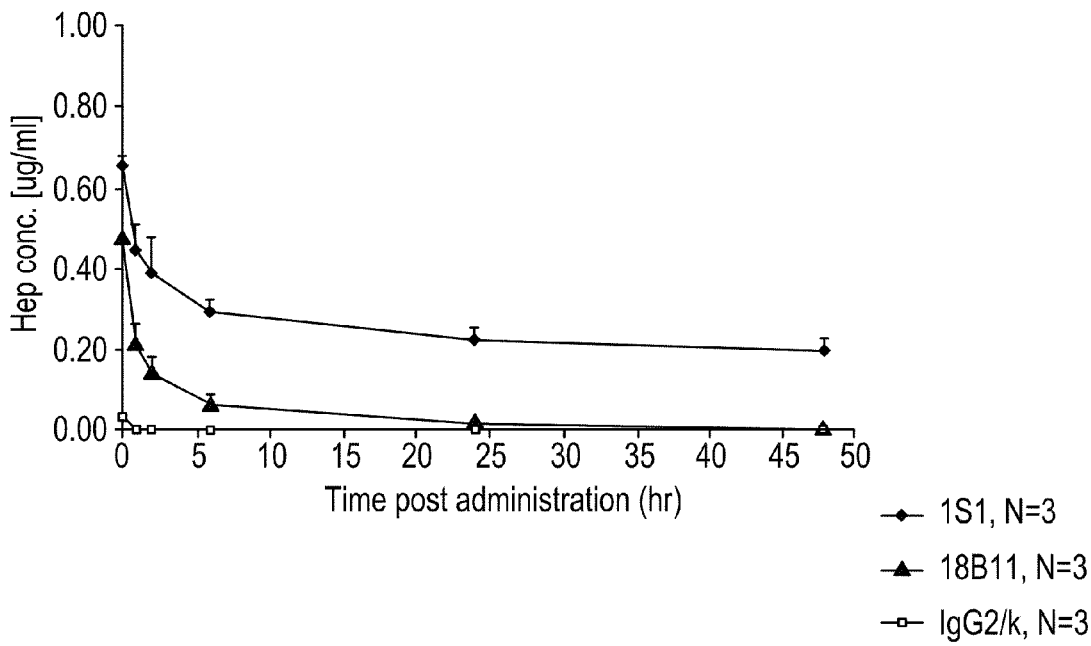
FIG. 25 shows the serum hepcidin concentration in mice pre-dosed with antibody 1S1 and 18B11 at various timepoints.

Serum samples for determination of antibody 1S1 or 18B11 and hepcidin concentrations were collected at 5 minutes, 1 hour, 24 hours, 96 hours, 168 hours, 264 hours and 336 hours after administration of the hepcidin. Serum antibody and hepcidin concentrations were calculated by ELISA and the results are set forth in FIGS. 24 and 25, respectively. Results indicated that antibody 18B11 cleared all detectable serum hepcidin by 24 hours, while hepcidin levels stabilized in mice treated with antibody 1S1.

Example 16

Figure 26:
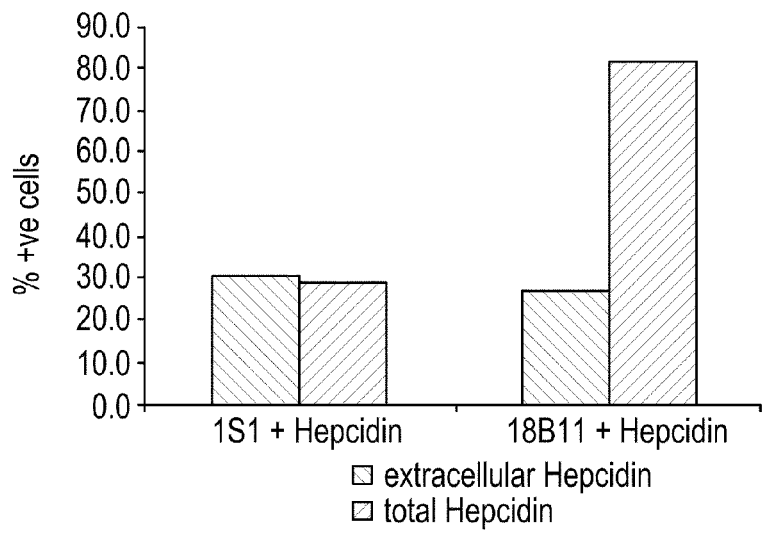
FIG. 26 demonstrates that antibody 18B11 causes an accumulation of intracellular hepcidin.

Detection of Hepcidin Intracellular Accumulation by Antibodies Contacted with Cells Expressing FCRN FcRn is the salvage receptor involved in recycling antibodies by rescuing them from endosomal degradation. This Example examined the effect of antibodies on relative levels of intracellular hepcidin compared to total hepcidin, providing an indication of the internalization and subsequent degradation of hepcidin by cells expressing FcRn. Alexa-647 labeled 1S1 or 18B11 antibodies were complexed with excess of biotinylated-hepcidin by incubation for 10 minutes at room temperature. Free hepcidin was removed using spin-columns. 293T/FcRn cells were incubated with the antibody-hepcidin complexes for 6 hours at 37° C., 5% $CO_2$ in 0% FBS medium. At the end of the incubation cells were harvested in cold FACs buffer (PBS 2% FBS). Cells from each group were either fixed only (detection of extracellular hepcidin) or fixed and permeabilized (detection of total hepcidin) using R&D's CytoFix and CytoPerm reagents. All samples were stained with SA-PE and read on FACS. Results indicated that antibody 18B11 caused greater intracellular accumulation of hepcidin compared to antibody 1S1. See FIG. 26. Of the total hepcidin detected in association with cells contacted with 1S1, all of the hepcidin was extracellular. Of the total hepcidin detected in association with cells contacted with 181311, only about one-third of the hepcidin was extracellular and the remainder was intracellular.

For the sake of completeness of disclosure, all patent documents and literature articles cited herein are expressly incorporated in this specification by reference in their entireties.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed:

1. An isolated antibody comprising SEQ ID NOs: 334-339 wherein the antibody binds to human hepcidin of SEQ ID NO: 9 with an affinity $K_D$ of less than about $10^{-8}$ M and which exhibits at least one of the properties selected from the group consisting of:
   (a) at least about a 50-fold higher $K_D$ at a pH of about 5.5 compared to its $K_D$ for said hepcidin at a pH of about 7.4;
   (b) at least about a 5-fold faster clearance of said hepcidin compared to antibody 1S1 having the heavy chain variable region of SEQ ID NO: 202 and the light chain variable region of SEQ ID NO: 128; and
   (c) an off rate of about $6 \times 10^{-2}$ s$^{-1}$ or higher at about pH 5.5.

2. An isolated antibody comprising the amino acid sequence SEQ ID NOs: 334-339 that binds to human hepcidin of SEQ ID NO: 9, with an affinity $K_D$ of at least $10^{-8}$ M and said antibody has at least about a 50-fold higher $K_D$ at about pH 5.5 compared to its $K_D$ for said hepcidin at about pH 7.4 or said antibody has an off rate of about $6 \times 10^{-2}$ s$^{-1}$ or higher at about pH 5.5, wherein said antibody is obtained by:
   (a) replacing an amino acid in the heavy or light chain of said antibody with a histidine;
   (b) screening the antibody obtained in (a) for differential pH binding;
   (c) replacing another amino acid in the heavy or light chain of said antibody with a histidine; and
   (d) screening said antibody for having at least one of the properties selected from the group consisting of:
      (i) at least about 50-fold higher $K_D$ at about pH 5.5 compared to its $K_D$ for said hepcidin at about pH 7.4; and
      (ii) an off rate of about $6 \times 10^{-2}$ s$^{-1}$ or higher at about pH 5.5.

* * * * *